United States Patent
Rohlff et al.

(10) Patent No.: US 9,228,023 B2
(45) Date of Patent: Jan. 5, 2016

(54) ANTI-ROR1 ANTIBODIES AND METHODS OF USE FOR TREATMENT OF CANCER

(75) Inventors: Christian Rohlff, Abingdon (GB); Alasdair Stamps, Abingdon (GB); Jonathan Alexander Terrett, San Jose, CA (US)

(73) Assignee: Oxford Biotherapeutics Ltd., Abington, Oxon (GB)

( * ) Notice: Subject to any disclaimer, the term of this patent is extended or adjusted under 35 U.S.C. 154(b) by 13 days.

(21) Appl. No.: 13/823,999

(22) PCT Filed: Oct. 3, 2011

(86) PCT No.: PCT/US2011/054645
§ 371 (c)(1),
(2), (4) Date: Jun. 3, 2013

(87) PCT Pub. No.: WO2012/045085
PCT Pub. Date: Apr. 5, 2012

(65) Prior Publication Data
US 2013/0251723 A1  Sep. 26, 2013

Related U.S. Application Data

(60) Provisional application No. 61/388,694, filed on Oct. 1, 2010, provisional application No. 61/482,554, filed on May 4, 2011.

(51) Int. Cl.
| | |
|---|---|
| A61K 39/395 | (2006.01) |
| A61P 35/00 | (2006.01) |
| C07K 16/40 | (2006.01) |
| C07K 16/00 | (2006.01) |
| C07K 16/28 | (2006.01) |

(52) U.S. Cl.
CPC ............. *C07K 16/40* (2013.01); *C07K 16/005* (2013.01); *C07K 16/2803* (2013.01); *C07K 2317/24* (2013.01); *C07K 2317/55* (2013.01); *C07K 2317/56* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| 8,212,009 B2 | 7/2012 | Kipps et al. |
| 2013/0273073 A1 | 10/2013 | Kipps et al. |

FOREIGN PATENT DOCUMENTS

| EP | 2316491 A1 | 5/2011 |
| WO | WO 2005/100605 A1 | 10/2005 |
| WO | WO 2007/051077 A2 | 5/2007 |
| WO | WO 2007/146957 A2 | 12/2007 |
| WO | WO 2008/076868 A2 | 6/2008 |
| WO | WO 2008/103849 A2 | 8/2008 |
| WO | WO 2010/008069 A1 | 1/2010 |
| WO | WO 2010/124188 A1 | 10/2010 |
| WO | WO 2011/054007 A1 | 5/2011 |
| WO | WO 2011/079902 A2 | 7/2011 |
| WO | WO 2012/045085 | 4/2012 |

OTHER PUBLICATIONS

Baskar, Sivasubramanian et al., "Targeting Human B Cell Chronic Lymphocytic Leukemia with a Monoclonal Antibody Specific for the Receptor Tyrosine Kinase ROR1," J. of Immunotherapy, vol. 31, No. 9, p. 969, Jan. 1, 2008.
Broome, H.E., et al., "Detection of Minimal Residual Disease in Chronic Lymphocytic Leukemia with Monoclonal Antibodies Specific for CD5, CD10, CD19 and ROR1," Blood, American Society of Hematology, vol. 112, No. 11, p. 724, Dec. 9, 2008.
Choudhury, A., et al., "Silencing of ROR1 and Fmod with siRNA Results in Apoptosis of CLL Cells," British J. of Haematology, vol. 151, No. 4, p. 327-335, Aug. 31, 2010.
Daneshmanesh, Amir H. et al., "ROR1, a Cell Surface Receptor Tyrosine Kinase is expressed in Chronic Lymphocytic Leukemia and May Serve as a Putative Target for Therapy," Intl. J. of Cancer, vol. 123, No. 5 p. 1190-1195.
Katoh, Masuko, et al., "Comparative Genomics and ROR1 and ROR2 Orthologs," Oncology Reports, vol. 14, No. 5, p. 1381-1384, (Nov. 1, 2005).
Katoh, Masuko, et al., "Transcriptional Mechanisms of WNT5A Based on NG-Kappa B, Hedgehog, TGF Beta, and Notch Signaling Cascades," Intl. J. of Molecular Medicine, vol. 23, No. 6, p. 763-769, (Jun. 2009).
Miller, Carl W. et al., "ROR1 Amplification and Overexpression in Ovarian Cancer," Proc. of the Annual Mtg. of the Amer. Assoc. for Cancer Res., vol. 50, p. 324, (Apr. 22, 2009).
Rabbani, H. et al., "Rori Targeting Monoclonal Antibodies Induced Apoptosis of Chronic Lymphocytic Leukemia Cells—A Potential Novel Therapeutic Approach," Internet Citation, Dec. 7, 2010, p. 1.
Yang, Jiahui et al., "Therapeutic Potential and Challenges of Targeting Receptor Tyrosine Kinase ROR1 with Monoclonal Antibodies in B-Cell Malignancies," PLOS One, vol. 6, No. 6 (Jun. 2011).
Brischwein, Klaus, et al., "Strictly Target Cell-Dependent activiation of T Cells by Bispecific Single-Chain Anti8body Constructs of the BiTE Class", J. Immunother., vol. 30, No. 8, p. 798-807.
Edwards, Bryan M., et al. "The Remarkable Flexibility of the Human Antibody Repertoire; Isolation of Over One Thousand Different Antibodies to a Single Protein, BLyS", J. Mol. Biol. vol. 334, p. 103-118, 2003.
Möller, Susanna A. et al., "Bispecific-Monoclonal-Antibody-Directed Lysis of Ovarian Carcinoma Cells by Activated Human T Lymphocytes", Cancer Immunol Immunother. vol. 33, p. 210-216, 1991.

*Primary Examiner* — Elly-Gerald Stoica
(74) *Attorney, Agent, or Firm* — Morgan, Lewis & Bockius LLP

(57) ABSTRACT

The invention provides antibodies which bind to the extracellular domain of the Tyrosine-protein kinase transmembrane receptor ROR1. Nucleic acid molecules encoding the antibodies, expression vectors, host cells and methods for expressing the antibodies are also provided. The antibodies may be used for the treatment of cancer, including non-small cell lung carcinoma, B-cell chronic lymphocytic leukemia and colon cancer.

102 Claims, 46 Drawing Sheets

VK CDR1 Alignments

A1
SEQ ID No: 181     aaggcgagtcaggacattaatagctatttaaactgg
SEQ ID No: 243     aaggcgagtcaggacattaatagctatttaagctgg
                   ***************************** **

A2
SEQ ID No: 182     aaggcgagtcaggacattaatagctatttaagctgg
SEQ ID No: 243     aaggcgagtcaggacattaatagctatttaagctgg
                   ************************************

A3, A4, A5, A7, A9 and A12
SEQ ID No: 182     aaggcgagtcaggacattaatagctatttaagctgg
SEQ ID No: 243     aaggcgagtcaggacattaatagctatttaagctgg
                   ************************************

A6
SEQ ID No: 183     aaggcgagtcaagacattaatagctatttaagctgg
SEQ ID No: 243     aaggcgagtcaggacattaatagctatttaagctgg
                   ******** ***********************

A10
SEQ ID No: 185     aaggcgagtcaggacatttatagctatttaagctgg
SEQ ID No: 243     aaggcgagtcaggacattaatagctatttaagctgg
                   *************** ****************

A13
SEQ ID No: 187     aagtcgagtcaggacattaatagctatttaagttgg
SEQ ID No: 243     aaggcgagtcaggacattaatagctatttaagctgg
                   * ************************* *

A8
SEQ ID No: 184     ataaccaacactgatattgatgatgctatgaactgg
SEQ ID No: 255     ataaccagcactgatattgatgatgatatgaactgg
                   ***** ************** *******

A11
SEQ ID No: 186     atgaccagcactgatattgatgatgctctgaactgg
SEQ ID No: 255     ataaccagcactgatattgatgatgatatgaactgg
                    ******************** * ********

A14
SEQ ID No: 188     cagagtctgctcaacagtagaacccgaaagaactac
SEQ ID No: 260     cagagtctgctcaacagtagaacccgaaagaactac
                   ************************************

FIGURE 1a

A14
SEQ ID No: 189     aaatccagtcagagtctgctcaacagtagaacccgaaagaactacttggct
SEQ ID No: 261     aaatccagtcagagtctgctcaacagtagaacccgaaagaactacttggct
                   ***************************************************

FIGURE 1b

VK CDR2 Alignments

A1, A2, A9 and A10
```
SEQ ID No: 210     accctgatctatcgtgcaaacagattggta
SEQ ID No: 245     accctgatctatcgtgcaaacagattggta
                   ******************************
```
A3
```
SEQ ID No: 212     accctgatccatcgtgcaaacagattggta
SEQ ID No: 245     accctgatctatcgtgcaaacagattggta
                   ********  ********************
```
A4
```
SEQ ID No: 213     accctgatctatcgtgcaaacaaattggta
SEQ ID No: 245     accctgatctatcgtgcaaacagattggta
                   ********************* ********
```
A5
```
SEQ ID No: 215     accctgatctatcgtgcaaagagattgata
SEQ ID No: 245     accctgatctatcgtgcaaacagattggta
                   ******************** ****** **
```
A6
```
SEQ ID No: 217     accctgacctatcgtgcaaacagattggta
SEQ ID No: 245     accctgatctatcgtgcaaacagattggta
                   *******  *********************
```
A7
```
SEQ ID No: 219     accctgatctatcgtgcaaacagattgata
SEQ ID No: 245     accctgatctatcgtgcaaacagattggta
                   **************************** *
```
A12
```
SEQ ID No: 225     accctgacccatcgtgcaaacagattggta
SEQ ID No: 245     accctgatctatcgtgcaaacagattggta
                   *******  *  ******************
```
A13
```
SEQ ID No: 226     accctgatctttcgtgcaaacagattggta
SEQ ID No: 245     accctgatctatcgtgcaaacagattggta
                   ********** *******************
```
A8
```
SEQ ID No: 221     ctccttatttcagaaggcaatactcttcgt
SEQ ID No: 257     ctccttatttcagaaggcaatactcttcgt
                   ******************************
```
A11
```
SEQ ID No: 223     ctccttatttcagaaggcaatagtcttcgt
SEQ ID No: 257     ctccttatttcagaaggcaatactcttcgt
                   ********************** *******
```
A14
```
SEQ ID No: 227     aaactgctgatctactggacatccactaggaa
SEQ ID No: 262     aaactgctgatctactgggcatccactaggaa
                   ****************** *************
```

FIGURE 2a

VK CDR2 Alignments

A1, A2, A3, A9, A10, A12 and A13
SEQ ID No: 209    cgtgcaaacagattggtagat
SEQ ID No: 244    cgtgcaaacagattggtagat
                  *********************

A4
SEQ ID No: 214    cgtgcaaacaaattggtagat
SEQ ID No: 244    cgtgcaaacagattggtagat
                  ******** ********

A5
SEQ ID No: 216    cgtgcaaagagattgatagat
SEQ ID No: 244    cgtgcaaacagattggtagat
                  ******  **  ***

A6
SEQ ID No: 218    cgtgcaaacagattggtagaa
SEQ ID No: 244    cgtgcaaacagattggtagat
                  ********************

A7
SEQ ID No: 220    cgtgcaaacagattgatagat
SEQ ID No: 244    cgtgcaaacagattggtagat
                  *************  ***

A8
SEQ ID No: 222    gaaggcaatactcttcgtcct
SEQ ID No: 258    gaaggcaatactcttcgtcct
                  *********************

A11
SEQ ID No: 224    gaaggcaatagtcttcgtcct
SEQ ID No: 258    gaaggcaatactcttcgtcct
                  ******** ********

A14
SEQ ID No: 228    tggacatccactagggaatct
SEQ ID No: 263    tgggcatccactagggaatct
                  *  **************

FIGURE 2b

VK CDR3 Alignments

A1, A3, A4, A6, A9, A10, A12 and A13
```
SEQ ID No: 234    ctacagtatgatgagtttccgtacacg
SEQ ID No: 246    ctacagtatgatgagtttcctcccaca
                  *******************   ***
```

A2
```
SEQ ID No: 235    ctacagtatgatgaatttccgtacacg
SEQ ID No: 246    ctacagtatgatgagtttcctcccaca
                  ************** *****   ***
```

A5
```
SEQ ID No: 236    ctacagtatgatgagtttccttacacg
SEQ ID No: 246    ctacagtatgatgagtttcctcccaca
                  ********************   ***
```

A7
```
SEQ ID No: 237    ctacagtatgatgagtttccattcacg
SEQ ID No: 246    ctacagtatgatgagtttcctcccaca
                  *******************   ***
```

A8
```
SEQ ID No: 238    ttgcaaactgataacttgcctctcacg
SEQ ID No: 259    ttgcaaagtgataacttgcctctcaca
                  ******* ******************
```

A11
```
SEQ ID No: 239    ttgcaaagtgataacttgcctctcacg
SEQ ID No: 259    ttgcaaagtgataacttgcctctcaca
                  **************************
```

A14
```
SEQ ID No: 240    aagcaatcttatgatcttccgtggacg
SEQ ID No: 264    aagcaatcttataatcttcccacagtg
                  *********** *******        *
```

FIGURE 3

VH CDR1 Alignments

A14
```
SEQ ID No: 97       gctactggctacacattcagtagttactggatagag
SEQ ID No: 265      gctactggctacacattcactggctactggatagag
                    ****************** * * ***********
```

A2
```
SEQ ID No: 80       gcctctggattcactttcagtacctatgccatgtct
SEQ ID No: 247      gcctctggattcgctttcagtagctatgacatgtct
                    ************ ********* ***** *******
```

A12 and A13
```
SEQ ID No: 82       gcctctggattcactttcagtagctatgccatgtct
SEQ ID No: 247      gcctctggattcgctttcagtagctatgacatgtct
                    ************ *************** *******
```

A10
```
SEQ ID No: 93       gcctctggattcgctttcagtagctatgccatgtct
SEQ ID No: 247      gcctctggattcgctttcagtagctatgacatgtct
                    ***************************** *******
```

A11
```
SEQ ID No: 95       gcctctggattcactttcagtagatatggcatgtct
SEQ ID No: 247      gcctctggattcgctttcagtagctatgacatgtct
                    ************ ********* **** *******
```

A1
```
SEQ ID No: 78       gtctctggattcactttcagtagctatgccatgtct
SEQ ID No: 251      gcctctggattcactttcagtagctattacatgtct
                    * ************************** *******
```

A3 and A8
```
SEQ ID No: 82       gcctctggattcactttcagtagctatgccatgtct
SEQ ID No: 251      gcctctggattcactttcagtagctattacatgtct
                    *************************** *******
```

A4
```
SEQ ID No: 83       gcctctggattcactttcagtaactatggcatgtct
SEQ ID No: 251      gcctctggattcactttcagtagctattacatgtct
                    ********************* **** *******
```

A5
```
SEQ ID No: 85       gcctctggattcactttcagtaactatgacatgtct
SEQ ID No: 251      gcctctggattcactttcagtagctattacatgtct
                    ********************* **** *******
```

A6
```
SEQ ID No: 87       gcctctggattcactttcagtccctatgccatgtct
SEQ ID No: 251      gcctctggattcactttcagtagctattacatgtct
                    ********************  ****  *******
```

A7
```
SEQ ID No: 89       gcctctggattctctttcagtagctatgccatgtct
SEQ ID No: 251      gcctctggattcactttcagtagctattacatgtct
                    ************ ************** *******
```

A9
```
SEQ ID No: 91       gcctctggattcactttcagtagcaatgccatgtcc
SEQ ID No: 251      gcctctggattcactttcagtagctattacatgtct
                    *********************** ** ******
```

FIGURE 4a

VH CDR1 Alignments

A1
```
SEQ ID No: 79      ggattcactttcagtagctatgccatgtct
SEQ ID No: 252     ggattcactttcagtagctattacatgtct
                   ********************  *******
```

A2
```
SEQ ID No: 81      ggattcactttcagtacctatgccatgtct
SEQ ID No: 248     ggattcgctttcagtagctatgacatgtct
                   ****** ********* ***** *******
```

A12 and A13
```
SEQ ID No: 79      ggattcactttcagtagctatgccatgtct
SEQ ID No: 248     ggattcgctttcagtagctatgacatgtct
                   ****** *************** *******
```

A10
```
SEQ ID No: 94      ggattcgctttcagtagctatgccatgtct
SEQ ID No: 248     ggattcgctttcagtagctatgacatgtct
                   ********************* *******
```

A11
```
SEQ ID No: 96      ggattcactttcagtagatatggcatgtct
SEQ ID No: 248     ggattcgctttcagtagctatgacatgtct
                   ****** ********** **** *******
```

A3 and A8
```
SEQ ID No: 79      ggattcactttcagtagctatgccatgtct
SEQ ID No: 252     ggattcactttcagtagctattacatgtct
                   ********************  *******
```

A4
```
SEQ ID No: 84      ggattcactttcagtaactatggcatgtct
SEQ ID No: 252     ggattcactttcagtagctattacatgtct
                   ****************  ****  *******
```

A5
```
SEQ ID No: 86      ggattcactttcagtaactatgacatgtct
SEQ ID No: 252     ggattcactttcagtagctattacatgtct
                   ****************  **** ********
```

A6
```
SEQ ID No: 88      ggattcactttcagtccctatgccatgtct
SEQ ID No: 252     ggattcactttcagtagctattacatgtct
                   ***************  ****  *******
```

A7
```
SEQ ID No: 90      ggattctctttcagtagctatgccatgtct
SEQ ID No: 252     ggattcactttcagtagctattacatgtct
                   ****** **************  *******
```

A9
```
SEQ ID No: 92      ggattcactttcagtagcaatgccatgtcc
SEQ ID No: 252     ggattcactttcagtagctattacatgtct
                   ***************** **  ******
```

A14
```
SEQ ID No: 98      ggctacacattcagtagttactggatagag
SEQ ID No: 256     ggctacacattcactggctactggatagag
                   ************ *  * ***********
```

FIGURE 4b

VH CDR2 Alignments

A14
```
SEQ ID No: 147      gagattttacctggaattggtaatactaac
SEQ ID No: 266      gagattttacctggaagtggtagtactaac
                    ***************** ***** ******
```

A2 and A13
```
SEQ ID No: 126      ggcattaatagtaatcgtggtaccacctac
SEQ ID No: 249      tacattagtagtggtggtggtagcacctac
                    ***** ****  * ****** *******
```

A12
```
SEQ ID No: 135      gccattaatagtaatcgtggtaccacctac
SEQ ID No: 249      tacattagtagtggtggtggtagcacctac
                    ***** ****  * ****** *******
```

A10
```
SEQ ID No: 142      gccattaataatagaggtggtggcacctac
SEQ ID No: 249      tacattagtagtggtggtggtagcacctac
                    ***** ** * * ****** ********
```

A11
```
SEQ ID No: 144      gccattaatcctaatggtggtactacctac
SEQ ID No: 249      tacattagtagtggtggtggtagcacctac
                    ***** * **  ********  ******
```

A1
```
SEQ ID No: 124      gccattaattttaatcgtggtaccacctac
SEQ ID No: 253      gccattaatagtaatggtggtagcacctac
                    ********  **** ****** *******
```

A3
```
SEQ ID No: 128      gccattaatattaatcgtggtaccacctac
SEQ ID No: 253      gccattaatagtaatggtggtagcacctac
                    ********** **** ****** *******
```

A4
```
SEQ ID No: 130      gccatgaataataatggtgctagcacctac
SEQ ID No: 253      gccattaatagtaatggtggtagcacctac
                    ***** **** ******** **********
```

A5
```
SEQ ID No: 132      gccattaatcgtaaaggtcatagtacctac
SEQ ID No: 253      gccattaatagtaatggtggtagcacctac
                    ********  ****  ***   *** ******
```

A6
```
SEQ ID No: 135      gccattaatagtaatcgtggtaccacctac
SEQ ID No: 253      gccattaatagtaatggtggtagcacctac
                    *************** ****** *******
```

A7
```
SEQ ID No: 136      gccattaatattaatcgtggtaccccctat
SEQ ID No: 253      gccattaatagtaatggtggtagcacctac
                    ********** **** ****** * ****
```

A8
```
SEQ ID No: 138      gccattaatcctaatggtggtagtacctac
SEQ ID No: 253      gccattaatagtaatggtggtagcacctac
                    ********  ************* ******
```

A9
```
SEQ ID No: 140      gccattaatagtaaaggtggtggcacctac
SEQ ID No: 253      gccattaatagtaatggtggtagcacctac
                    ************** ****** ********
```

FIGURE 5a

VH CDR2 Alignments

```
A1
SEQ ID No: 125      gccattaattttaatcgtggtaccacctactattcagacactgtgaagggc
SEQ ID No: 254      gccattaatagtaatggtggtagcacctactatccagacactgtgaagggc
                    ********  **** ****** ********** ******************

A2 and A13
SEQ ID No: 127      ggcattaatagtaatcgtggtaccacctactatccagacactgtgaagggc
SEQ ID No: 250      tacattagtagtggtggtggtagcacctactatccagacactgtgaagggc
                    ***** ****  * ****** ******************************

A12
SEQ ID No: 146      gccattaatagtaatcgtggtaccacctactattcagacactgtgaagggc
SEQ ID No: 250      tacattagtagtggtggtggtagcacctactatccagacactgtgaagggc
                    ***** ****  * ****** ********** ******************

A10
SEQ ID No: 143      gccattaataatagaggtggtggcacctactatccagacactgtgaggggc
SEQ ID No: 250      tacattagtagtggtggtggtagcacctactatccagacactgtgaagggc
                    ***** **  * * ****** ********************** *** ****

A11
SEQ ID No: 242      gccattaatcctaatggtggtactacctactatccagacactgtgaagggc
SEQ ID No: 250      tacattagtagtggtggtggtagcacctactatccagacactgtgaagggc
                    ***** *   *    ******** ***************************

A3
SEQ ID No: 129      gccattaatattaatcgtggtaccacctactattcagacactgtgaagggc
SEQ ID No: 254      gccattaatagtaatggtggtagcacctactatccagacactgtgaagggc
                    ********** **** ****** ********** ******************

A4
SEQ ID No: 131      gccatgaataataatggtgctagcacctactatccagacactgtgaagggc
SEQ ID No: 254      gccattaatagtaatggtggtagcacctactatccagacactgtgaagggc
                    ***** **** ******** *******************************

A5
SEQ ID No: 133      gccattaatcgtaaaggtcatagtacctactatccagacactgtgcagggc
SEQ ID No: 254      gccattaatagtaatggtggtagcacctactatccagacactgtgaagggc
                    *********  ***  ***  *** ****************** *****

A6
SEQ ID No: 134      gccattaatagtaatcgtggtaccacctactatccagacactgtgaagggc
SEQ ID No: 254      gccattaatagtaatggtggtagcacctactatccagacactgtgaagggc
                    *************** ***** *****************************

A7
SEQ ID No: 137      gccattaatattaatcgtggtaccccctattatccagacactgtgaagggc
SEQ ID No: 254      gccattaatagtaatggtggtagcacctactatccagacactgtgaagggc
                    ********** **** ****** * ********* *****************

A8
SEQ ID No: 139      gccattaatcctaatggtggtagtacctactatccagacactgtgaagggc
SEQ ID No: 254      gccattaatagtaatggtggtagcacctactatccagacactgtgaagggc
                    *********  ************ ****************************

A9
SEQ ID No: 141      gccattaatagtaaaggtggtggcacctactatccagacactgtgaggggc
SEQ ID No: 254      gccattaatagtaatggtggtagcacctactatccagacactgtgaagggc
                    ************** ****** ********************** *** ****

A14
SEQ ID No: 148      gagatttacctggaattggtaatactaactacaatgagaaattcaagggc
SEQ ID No: 267      gagatttacctggaagtggtagtactaactacaatgagaagttcaagggc
                    *************** ***** ****************** *********
```

| SEQ ID No. | Description | Sequence |
|---|---|---|
| 1 | VH_aa A1 | MKQSTIALALLPLLFTPVAKAEVKLVESGGGLVRPGGSLKLSCAVSGFTFSSYAMSWVRQTPEKRLEWVAAINFNRGTTYYSDTVKGRFTISRDNAKNTLYLQLSSLRSEDTAFYYCSRHRYSDYDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 2 | VH_aa A2 | MKQSTIALALLPLLFTPVAKAEVQLLETGGGLVKPGGSLKLSCAASGFTFSTYAMSWVRQTPEKRLEWVAGINSNRGTTYYPDTVKGRFTISRDNAKNTLSLQMTSLRSEDTALYYCVRHRYTNYDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 3 | VH_aa A3 | MKQSTIALALLPLLFTPVAKADVMLVESGGGLVKPGGSLKLSCAASGFTFSSYAMSWVRQTPEKRLEWVAAININRGTTYYSDTVKGRFTISRDNAKNTLYLQLSSLRSEDTALYYCSRHRYSDYDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 4 | VH_aa A4 | MKQSTIALALLPLLFTPVAKAEVKLVESGGGLVKPGGSLKLSCAASGFTFSNYGMSWVRQTPERRLEWVAAMNNNGASTYYPDTVKGRFTISRDNAKNTLYLQMSSLRSEDTALYFCVRHNNYVDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 5 | VH_aa A5 | MKQSTIALALLPLLFTPVAKAEVKLVESGGGLVKPGGSLKLSCAASGFTFSNYDMSWVRQSPEKRLEWVAAINRKGHSTYYPDTVQGRFTISRDNAKNTLYLQMSSLRSEDTALYYCVRLDDNYYFFDYWGQGTTLTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 6 | VH_aa A6 | MKQSTIALALLPLLFTPVAKAEVMLVESGGGLVKPGGSLKLSCAASGFTFSPYAMSWVRQTPEKRLEWVAAINSNRGTTYYPDTVKGRFTISRDNAKNTLYLQMSSLRSEDTAFYYCVRHRYNNYDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |

FIG 14b

| SEQ ID No. | Description | Sequence |
|---|---|---|
| 7 | VH_aa A7 | MKQSTIALALLPLLFTPVAKAEVMLVESGGGLVKPGGSLKISCAASGFSFSSYAMSWVRQTPEKSLEWVAAININRGTPYYPDTVKGRFTISRDNAKNTLYLQMSSLRSEDTALYYCVRHRNSNNDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 8 | VH_aa A8 | MKQSTIALALLPLLFTPVAKADVQVVESGGGLVKPGGSLKLSCAASGFTFSSYAMSWVRQTPEKRLEWVAAINPNGGSTYYPDTVKGRFTISRDNAKNTLYLQMSGLRSEDTALYYCARLPWSPYTLDYWGQGTSVTVSSAKTTPPSVYPLAPGSAAQTNSMVTLGCLVKGYFPE |
| 9 | VH_aa A9 | MKQSTIALALLPLLFTPVAKAEVQLVETGGDLVKPGGSLKLSCVASGFTFSSNAMSWVRQTPEKRLEWVAAINSKGGGTYYPDTVRGRFTISRDNAKNTLYLQVTSLRSEDTALYYCVSHGDNKYFYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 10 | VH_aa A10 | MKQSTIALALLPLLFTPVAKAEVQLVETGGGLVKPGGSLKLSCAASGFAFSSYAMSWVRQTPEKRLEWVAAINNRGGGTYYPDTVRGRFTISRDNAKNTLYLQMSSLRSADTALYYCVRHDNLNYDYAMDSWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 11 | VH_aa A11 | MKQSTIALALLPLLFTPVPKAEVQLVESGGDLVKPGGSLKLSCAASGFTFSRYGMSWVRQTPEKRLEWVAAINPNGGTYYPDTVKGRFTISRDNAKNTLFLQMTGLRSEDTALYYCARLPWSPYTLDYWGQGTSVIVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 12 | VH_aa A12 | MKQSTIALALLPLLFTPVAKAEVQLVESGGGLVKPGGSLKLSCAASGFTFSSYAMSWVRQTPEKRLEWVAAINSNRGTTYYSDTVKGRFTISRDNAKNTLYLQMSSLRSEDTAFYYCTRHRYSDYDYAMDYWGQGTSVTVSSAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDC |
| 13 | VH_aa A13 | MKQSTIALALLPLLFTPVAKAEVQLVETGGGLVKPGGSLKLSCAASGFTFSSYAMSWIRQTPEKR |

FIG 14c

| SEQ ID No. | Description | Sequence |
|---|---|---|
|  |  | LEWVAGINSNRGTTYYPDTVKGRFTISRDNAKN TLYLQMNSLRSEDSALYYCVRHRYIDYDYAMD YWGQGTSVTVSSAKTTPPSVYPLAPGSAAQTNS MVTLGCLVKGYFPEPVTVTWNSGSLSSGVHTF PAVLQSDLYTLSSSVTVPSSTWPSETVTCNVAHP ASSTKVDKKIVPRDC |
| 14 | VH_aa A14 | MKQSTIALALLPLLFTPVAKAQVQLKQSGAEL VKPGASVKISCKATGYTFSSYWIEWVKERPGH GLEWIGEILPGIGNTNYNEKFKGKATFTADLSS KTAYMQLSSLTSEDSAVYYCASGGYSTVYWYF DVWGAGTTVTVSSAKTTPPSVYPLAPGSAAQTN SMVTLGCLVKGYFPEPVTVTWNSGSLSSGVHT FPAVLQSDLYTLSSSVTVPSSTWPSETVTCNVAH PASSTKVDKKIVPRDC |
| 15 | VH_nt A1 | TTACCCACGCTTTGTACATGGAGAAAATAAA GTGAAACAAAGCACTATTGCACTGGCACTCT TACCGCTCTTATTTACCCCTGTGGCAAAAGCC GAGGTGAAGCTGGTGGAATCTGGGGGAGGC TTAGTGAGGCCTGGAGGGTCCCTGAAACTCT CCTGTGCAGTCTCTGGATTCACTTTCAGTAGC TATGCCATGTCTTGGGTTCGCCAGACTCCGG AGAAGAGGCTGGAATGGGTCGCAGCCATTAA TTTTAATCGTGGTACCACCTACTATTCAGACA CTGTGAAGGGCCGATTCACCATCTCCAGAGA CAATGCCAAGAATACCCTGTACCTGCAACTG AGCAGTCTGAGGTCTGAGGACACAGCCTTTT ATTACTGTTCAAGACACCGCTATAGTGACTAC GACTATGCTATGGACTACTGGGGTCAAGGAA CCTCAGTCACCGTCTCCTCAGCCAAAACGAC ACCCCCATCTGTCTATCCACTGGCCCCTGGA TCTGCTGCCCAAACTAACTCCATGGTGACCC TGGGATGCCTGGTCAAGGGCTATTTCCCTGA GCCAGTGACAGTGACCTGGAACTCTGGATCC CTGTCCAGCGGTGTGCACACCTTCCCAGCTG TCCTGCAGTCTGACCTCTACACTCTGAGCAG CTCAGTGACTGTCCCCTCCAGCACCTGGCCC AGCGAGACCGTCACCTGCAACGTTGCCCACC CGGCCAGCAGCACCAAGGTGGACAAGAAAAT TGTGCCCAGGGATTGTCATCATCACCATCAC CATCACTAAATGGACAGCTTAATCATTTATAA AGCT |
| 16 | VH_nt A2 | AACCCTGGCGTTACCCACGCTTTGTACATGG AGAAAATAAAGTGAAACAAAGCACTATTGCA CTGGCACTCTTACCGCTCTTATTTACCCCTGT GGCAAAAGCCGAAGTGCAGCTGTTGGAGACT GGGGGAGGCTTAGTGAAGCCTGGAGGGTCC CTGAAACTCTCCTGTGCAGCCTCTGGATTCA CTTTCAGTACCTATGCCATGTCTTGGGTTCGC |

FIG 14d

| SEQ ID No. | Description | Sequence |
|---|---|---|
|  |  | CAGACTCCGGAGAAGAGGCTGGAGTGGGTC GCAGGCATTAATAGTAATCGTGGTACCACCT ACTATCCAGACACTGTGAAGGGCCGCTTCAC CATCTCCAGAGACAATGCCAAGAACACCCTG TCCCTGCAAATGACCAGTCTGAGGTCTGAGG ACACAGCCTTGTATTATTGTGTAAGACACCG CTATACTAACTACGACTATGCTATGGACTACT GGGGTCAAGGAACCTCAGTCACCGTCTCCTC AGCCAAAACGACACCCCATCTGTCTATCCA CTGGCCCCTGGATCTGCTGCCCAAACTAACT CCATGGTGACCCTGGGATGCCTGGTCAAGGG CTATTTCCCTGAGCCAGTGACAGTGACCTGG AACTCTGGATCCCTGTCCAGCGGTGTGCACA CCTTCCCAGCTGTCCTGCAGTCTGACCTCTAC ACTCTGAGCAGCTCAGTGACTGTCCCCTCCA GCACCTGGCCCAGCGAGACCGTCACCTGCAA CGTTGCCCACCCGGCCAGCAGCACCAAGGTG GACAAGAAAATTGTGCCCAGGGATTGTCATC ATCACCATCACCATCACTAATTGACAGCTTAT CATCGATAAGCTTTAATGCGGTAGTTTAT |
| 17 | VH_nt A3 | CGTCGTTTTACAACGTCGTGACTGGGAAAAC CCTGGCGTTACCCACGCTTTGTACATGGAGA AAATAAAGTGAAACAAAGCACTATTGCACTG GCACTCTTACCGCTCTTATTTACCCCTGTGGC AAAAGCCGATGTGATGCTGGTGGAGTCTGGG GGAGGCTTAGTGAAGCCTGGAGGGTCCCTGA AACTCTCCTGTGCAGCCTCTGGATTCACTTTC AGTAGCTATGCCATGTCTTGGGTTCGCCAGA CTCCGGAGAAGAGGCTGGAATGGGTCGCAGC CATTAATATTAATCGTGGTACCACCTACTATT CAGACACTGTGAAGGGCCGATTCACCATCTC CAGAGACAATGCCAAGAATACCCTGTACCTG CAACTGAGCAGTCTGAGGTCTGAGGACACAG CCTTGTATTACTGTTCAAGACACCGCTATAGT GACTACGACTATGCTATGGACTACTGGGGTC AAGGAACCTCAGTCACCGTCTCCTCAGCCAA AACGACACCCCATCTGTCTATCCACTGGCC CCTGGATCTGCTGCCCAAACTAACTCCATGG TGACCCTGGGATGCCTGGTCAAGGGCTATTT CCCTGAGCCAGTGACAGTGACCTGGAACTCT GGATCCCTGTCCAGCGGTGTGCACACCTTCC CAGCTGTCCTGCAGTCTGACCTCTACACTCT GAGCAGCTCAGTGACTGTCCCCTCCAGCACC TGGCCCAGCGAGACCGTCACCTGCAACGTTG CCCACCCGGCCAGCAGCACCAAGGTGGACAA GAAAATTGTGCCCAGGGATTGTCATCATCAC CATCACCATCACTAATTGACAGCTTATCATCG ATAAGCTTTAATGCGGTAGTTT |

FIG 14e

| SEQ ID No. | Description | Sequence |
|---|---|---|
| 18 | VH_nt A4 | TTACCCACGCTTTGTACATGGAGAAAATAAAGTGAAACAAAGCACTATTGCACTGGCACTCTTACCGCTCTTATTTACCCCTGTGGCAAAAGCCGAGGTGAAGCTGGTGGAATCTGGGGGAGGCTTAGTGAAGCCTGGAGGGTCCTGAAACTCTCCTGTGCAGCCTCTGGATTCACTTTCAGTAACTATGGCATGTCTTGGGTTCGCCAGACTCCGGAGAGGAGGCTGGAGTGGGTCGCAGCCATGAATAATAATGGTGCTAGCACCTACTATCCAGACACTGTGAAGGGCCGATTCACCATCTCCAGAGACAATGCCAAGAACACCCTGTACCTGCAAATGAGCAGTCTGAGGTCTGAGGACACAGCCTTGTATTTCTGTGTAAGACATAATAACTACGTTGACTATGCTATGGACTATTGGGGTCAAGGAACCTCAGTCACCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCCTGTCCAGCGGTGTGCACACCTTCCCAGCTGTCCTGCAGTCTGACCTCTACACTCTGAGCAGCTCAGTGACTGTCCCCTCCAGCACCTGGCCCAGCGAGACCGTCACCTGCAACGTTGCCCACCCGGCCAGCAGCACCAAGGTGGACAAGAAAATTGTGCCCAGGGATTGTCATCATCACCATCACCATCACTAATTGACAGCTTATCATCGATAAGCTTTAATGCGGTAGTTTATCACAGTTAAATT |
| 19 | VH_nt A5 | ACCCTGGCGTTACCCACGCTTTGTACATGGAGAAAATAAAGTGAAACAAAGCACTATTGCACTGGCACTCTTACCGCTCTTATTTACCCCTGTGGCAAAAGCCGAGGTGAAGCTGGTGGAATCTGGGGGAGGCTTAGTGAAGCCTGGAGGGTCCTGAAACTCTCCTGTGCAGCCTCTGGATTCACTTTCAGTAACTATGACATGTCTTGGGTTCGCCAGAGTCCGGAGAAGAGGCTGGAGTGGGTCGCAGCCATTAATCGTAAAGGTCATAGTACCTACTATCCAGACACTGTGCAGGGCCGATTCACCATCTCCAGAGACAATGCCAAGAACACCCTGTACCTGCAAATGAGCAGTCTGAGGTCTGAGGACACAGCCTTGTATTACTGTGTAAGACTTGACGATAACTACTACTTCTTTGACTACTGGGGCCAAGGCACCACTCTCACAGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCCTGTCCAGCGGTGTGCACACCTTCCCAGCTGTCCTGCAGTCTGACCTCTACACTCTGAG |

FIG 14f

| SEQ ID No. | Description | Sequence |
|---|---|---|
| | | CAGCTCAGTGACTGTCCCCTCCAGCACCTGG CCCAGCGAGACCGTCACCTGCAACGTTGCCC ACCCGGCCAGCAGCACCAAGGTGGACAAGAA AATTGTGCCCAGGGATTGTCATCATCACCAT CACCATCACTAATTGACAGCTTATCATCGATA AGCTTTAATGCGGTAGTTTAT |
| 20 | VH_nt A6 | GGAAAACCCTGGCGTTACCCACGCTTTGTAC ATGGAGAAAATAAAGTGAAACAAAGCACTAT TGCACTGGCACTCTTACCGCTCTTATTTACCC CTGTGGCAAAAGCCGAAGTGATGCTGGTGGA GTCTGGGGGAGGCTTAGTGAAGCCTGGAGG GTCCCTGAAACTCTCCTGCGCAGCCTCTGGA TTCACTTTCAGTCCCTATGCCATGTCTTGGGT TCGCCAGACTCCGGAGAAGAGGCTGGAGTGG GTCGCAGCCATTAATAGTAATCGTGGTACCA CCTACTATCCAGACACTGTGAAGGGCCGATT CACCATCTCCAGAGACAATGCCAAGAACACC CTGTACCTGCAAATGAGCAGTCTGAGGTCTG AGGACACAGCCTTTTATTACTGTGTAAGACA CCGCTATAATAACTACGACTATGCTATGGACT ACTGGGGTCAAGGAACCTCAGTCACCGTCTC CTCAGCCAAAACGACACCCCCATCTGTCTAT CCACTGGCCCCTGGATCTGCTGCCCAAACTA ACTCCATGGTGACCCTGGGATGCCTGGTCAA GGGCTATTTCCCTGAGCCAGTGACAGTGACC TGGAACTCTGGATCCCTGTCCAGCGGTGTGC ACACCTTCCCAGCTGTCCTGCAGTCTGACCT CTACACTCTGAGCAGCTCAGTGACTGTCCCC TCCAGCACCTGGCCCAGCGAGACCGTCACCT GCAACGTTGCCCACCCGGCCAGCAGCACCAA GGTGGACAAGAAAATTGTGCCCAGGGATTGT CATCATCACCATCACCATCACTAATTGACAGC TTATCATCGATAAGCTTTAATGCGGTAGTTTA TCACAGT |
| 21 | VH_nt A7 | CGTTTTACAACGTCGTGACTGGGAAAACCCT GGCGTTACCCACGCTTTGTACATGGAGAAAA TAAAGTGAAACAAAGCACTATTGCACTGGCA CTCTTACCGCTCTTATTTACCCCTGTGGCAAA AGCCGAAGTGATGCTGGTGGAGTCTGGGGGA GGCTTAGTGAAGCCTGGAGGGTCCCTGAAAA TCTCCTGTGCAGCCTCTGGATTCTCTTTCAGT AGCTATGCCATGTCTTGGGTTCGCCAGACTC CGGAGAAGAGCCTGGAATGGGTCGCAGCCAT TAATATTAATCGTGGTACCCCTATTATCCAG ACACTGTGAAGGGCCGATTCACCATCTCCAG AGACAATGCCAAGAACACCCTGTACCTGCAA ATGAGTAGTCTGAGGTCTGAGGACACAGCCT TGTATTACTGTGTAAGACACCGCAATAGTAA |

FIG 14g

| SEQ ID No. | Description | Sequence |
|---|---|---|
| | | CAACGACTATGCTATGGACTACTGGGGTCAAGGAACCTCAGTCACCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCTGTCCAGCGGTGTGCACACCTTCCCAGCTGTCCTGCAGTCTGACCTCTACACTCTGAGCAGCTCAGTGACTGTCCCCTCCAGCACCTGGCCCAGCGAGACCGTCACCTGCAACGTTGCCCACCCGGCCAGCAGCACCAAGGTGGACAAGAAAATTGTGCCCAGGGATTGTCATCATCACCATCACCATCACTAATTGACAGCTTATCATCGATAAGCTTTAAT |
| 22 | VH_nt A8 | TACAACGTCGTGACTGGGAAAACCCTGGCGTTACCCACGCTTTGTACATGGAGAAAATAAAGTGAAACAAAGCACTATTGCACTGGCACTCTTACCGCTCTTATTTACCCCTGTGGCAAAAGCCGACGTGCAGGTGGTGGAGTCTGGGGGAGGCTTAGTGAAGCCTGGAGGGTCCCTGAAACTCTCCTGTGCAGCCTCTGGATTCACTTTCAGTAGCTATGCCATGTCTTGGGTTCGCCAGACTCCGGAGAAGAGGCTGGAGTGGGTCGCAGCCATTAATCCTAATGGTGGTAGTACCTACTATCCAGACACTGTGAAGGGCCGATTCACCATCTCCAGAGACAATGCCAAGAACACCCTATACCTGCAAATGAGCGGTCTGAGGTCTGAGGACACAGCCTTGTATTACTGTGCAAGACTCCCATGGTCCCCCTATACTTTGGACTACTGGGGTCAAGGAACCTCAGTCACCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGC |
| 23 | VH_nt A9 | TTACCCACGCTTTGTACATGGAGAAAATAAAGTGAAACAAAGCACTATTGCACTGGCACTCTTACCGCTCTTATTTACCCCTGTGGCAAAAGCCGAAGTGCAGCTTGTGGAGACTGGGGGAGACTTAGTGAAGCCTGGAGGGTCCCTGAAACTCTCCTGTGTAGCCTCTGGATTCACTTTCAGTAGCAATGCCATGTCCTGGGTTCGCCAGACTCCGGAGAAGAGGCTGGAGTGGGTCGCAGCCATTAATAGTAAAGGTGGTGGCACCTACTATCCAGACACTGTGAGGGGCCGATTCACCATCTCCAGAGACAATGCCAAGAACACCCTGTACCTGCAAGTGACCAGTCTGAGGTCTGAGGACACAGCCTTGTATTACTGTGTAAGCCATGGGATAATAAGTACTTTTATGCTATGGACTACTGGGGTCAAGGAACCTCAGTCACCGTCTCCTCAGCCAAAACGA |

FIG 14h

| SEQ ID No. | Description | Sequence |
|---|---|---|
| | | CACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCCTGTCCAGCGGTGTGCACACCTTCCCAGCTGTCCTGCAGTCTGACCTCTACACTCTGAGCAGCTCAGTGACTGTCCCCTCCAGCACCTGGCCCAGCGAGACCGTCACCTGCAACGTTGCCCACCCGGCCAGCAGCACCAAGGTGGACAAGAAAATTGTGCCCAGGGATTGTCATCATCACCATCACCATCACTAATTGACAGCTTATC |
| 24 | VH_nt A10 | TTACCCACGCTTTGTACATGGAGAAAATAAAGTGAAACAAAGCACTATTGCACTGGCACTCTTACCGCTCTTATTTACCCCTGTGGCAAAAGCCGAAGTGCAGCTTGTGGAGACTGGGGGAGGCTTAGTGAAGCCTGGAGGGTCCCTGAAACTCTCCTGTGCAGCCTCTGGATTCGCTTTCAGTAGCTATGCCATGTCTTGGGTTCGCCAAACTCCGGAGAAGAGGCTGGAGTGGGTCGCAGCCATTAATAATAGAGGTGGTGGCACCTACTATCCAGACACTGTGAGGGGCCGATTCACCATCTCCAGAGACAATGCCAAGAACACCCTGTACCTGCAAATGAGCAGCCTGAGGTCTGCGGACACAGCCTTGTATTACTGTGTGAGACATGACAATCTTAACTATGACTATGCTATGGACTCCTGGGGTCAAGGAACCTCAGTCACCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCCTGTCCAGCGGTGTGCACACCTTCCCAGCTGTCCTGCAGTCTGACCTCTACACTCTGAGCAGCTCAGTGACTGTCCCCTCCAGCACCTGGCCCAGCGAGACCGTCACCTGCAACGTTGCCCACCCGGCCAGCAGCACCAAGGTGGACAAGAAAATTGTGCCCAGGGATTGTCATCATCACCATCACCATCACTAATTGACAGCTTATCATCGATAAGCTTTAA |
| 25 | VH_nt A11 | CGTCGTGACTGGGAAAACCCTGGCGTTACCCACGCTTTGTACATGGAGAAAATAAAGTGAAACAAAGCACTATTGCACTGGCACTCTTACCGCTCTTATTTACCCCTGTGCCAAAAGCCGAAGTGCAGCTGGTGGAGTCTGGGGGAGACTTAGTGAAGCCTGGAGGGTCCCTGAAACTCTCCTGTGCAGCCTCTGGATTCACTTTCAGTAGATATGGCATGTCTTGGGTTCGCCAGACTCCGGAGAAGAGGCTGGAGTGGGTCGCAGCCATTAATCCTAATGGTGGTACTACCTACTATCCAGACACTGT |

FIG 14i

| SEQ ID No. | Description | Sequence |
|---|---|---|
|  |  | GAAGGGCCGATTCACCATCTCCCGAGACAATGCCAAGAACACCCTGTTCCTGCAAATGACCGGTCTGAGGTCTGAGGACACAGCCTTATACTACTGTGCAAGACTCCCATGGTCCCCCTATACTTTGGACTACTGGGGTCAAGGAACCTCAGTCATCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCTGAGCCAGTGACAGTGACCTGGAACTCTGGATCCCTGTCCAGCGGTGTGCACACCTTCCCAGCTGTCCTGCAGTCTGACCTCTACACTCTGAGCAGCTCAGTGACTGTCCCCTCCAGCACCTGGCCCAGCGAGACCGTCACCTGCAACGTTGCCCACCCGGCCAGCAGCACCAAGGTGGACAAGAAAATTGTGCCCAGGGATTGTCATCATCACCATCACCATCACTAATTGACAGCTTATCATCGATAAGCTTTAATGCGGTAGTTTATCACAGTTAAAT |
| 26 | VH_nt A12 | GCGTTACCCACGCTTTGTACATGGAGAAAATAAAGTGAAACAAAGCACTATTGCACTGGCACTCTTACCGCTCTTATTTACCCCTGTGGCAAAAGCCGAAGTGCAGCTGGTGGAGTCTGGGGGAGGCTTAGTGAAGCCTGGAGGGTCCCTGAAACTCTCCTGCGCAGCCTCTGGATTCACTTTCAGTAGCTATGCCATGTCTTGGGTTCGCCAGACTCCGGAGAAGAGGCTAGAGTGGGTCGCAGCCATTAATAGTAATCGTGGTACCACCTACTATTCAGACACTGTGAAGGGCCGATTCACCATCTCCAGAGACAATGCCAAGAACACCCTGTACCTGCAAATGAGCAGTCTGAGGTCTGAGGACACAGCCTTCTATTACTGTACAAGACACCGCTATAGTGACTACGACTATGCTATGGACTACTGGGGTCAAGGAACCTCAGTCACCGTCTCCTCAGCCAAAACGACACCCCCATCTGTCTATCCACTGGCCCCTGGATCTGCTGCCCAAACTAACTCCATGGTGACCCTGGGATGCCTGGTCAAGGGCTATTTCCCTGAGCCAGTGACAGTGACCTGGAACTCTGGATCCCTGTCCAGCGGTGTGCACACCTTCCCAGCTGTCCTGCAGTCTGACCTCTACACTCTGAGCAGCTCAGTGACTGTCCCCTCCAGCACCTGGCCCAGCGAGACCGTCACCTGCAACGTTGCCCACCCGGCCAGCAGCACCAAGGTGGACAAGAAAATTGTGCCCAGGGATTGTCATCATCACCATCACCATCACTAATTGACAGCTTATCATCGATAAGCTTTAATGCGGTAGTTTATCACAGTTAAATTGCTACG |
| 27 | VH_nt A13 | GGCGTTACCCACGCTTTGTACATGGAGAAAATAAAGTGAAACAAAGCACTATTGCACTGGCA |

FIG 14j

| SEQ ID No. | Description | Sequence |
|---|---|---|
|  |  | CTCTTACCGCTCTTATTTACCCCTGTGGCAAA AGCCGAAGTGCAGCTTGTGGAGACTGGGGGA GGCTTAGTGAAGCCTGGAGGGTCCCTGAAAC TCTCCTGTGCAGCCTCTGGATTCACTTTCAGT AGCTATGCCATGTCTTGGATTCGCCAGACTC CGGAGAAGAGGCTGGAGTGGGTCGCAGGCA TTAATAGTAATCGTGGTACCACCTACTATCCA GACACTGTGAAGGGCCGATTCACCATCTCCA GAGACAATGCCAAGAACACCCTGTACCTGCA AATGAACAGTCTGAGGTCTGAGGACTCAGCC TTGTATTACTGTGTAAGACACCGCTATATTGA CTACGACTATGCTATGGACTACTGGGGTCAA GGAACCTCAGTCACCGTCTCCTCAGCCAAAA CGACACCCCCATCTGTCTATCCACTGGCCCC TGGATCTGCTGCCCAAACTAACTCCATGGTG ACCCTGGGATGCCTGGTCAAGGGCTATTTCC CTGAGCCAGTGACAGTGACCTGGAACTCTGG ATCCCTGTCCAGCGGTGTGCACACCTTCCCA GCTGTCCTGCAGTCTGACCTCTACACTCTGA GCAGCTCAGTGACTGTCCCCTCCAGCACCTG GCCCAGCGAGACCGTCACCTGCAACGTTGCC CACCCGGCCAGCAGCACCAAGGTGGACAAGA AAATTGTGCCCAGGGATTGTCATCATCACCA TCACCATCACTAATTGACAGCTTATCATCGAT AAGCTTTAATGCGGTAGTT |
| 28 | VH_nt A14 | GTCGTGACTGGGAAAACCCTGGCGTTACCCA CGCTTTGTACATGGAGAAAATAAAGTGAAAC AAAGCACTATTGCACTGGCACTCTTACCGCT CTTATTTACCCCTGTGGCAAAAGCCCAGGTG CAGCTTAAGCAGTCTGGGGCTGAGCTGGTGA AGCCTGGGGCCTCAGTGAAGATATCCTGCAA GGCTACTGGCTACACATTCAGTAGTTACTGG ATAGAGTGGGTAAAGGAGAGGCCTGGACATG GCCTTGAGTGGATTGGAGAGATTTTACCTGG AATTGGTAATACTAACTACAATGAGAAATTCA AGGGCAAGGCCACATTCACTGCTGATCTATC CTCCAAGACAGCCTACATGCAACTCAGCAGC CTGACATCTGAGGACTCTGCCGTCTATTACT GTGCAAGTGGGGGGTATAGTACCGTCTATTG GTATTTTGATGTCTGGGGCGCAGGGACCACG GTCACCGTCTCCTCAGCCAAAACGACACCCC CATCTGTCTATCCACTGGCCCCTGGATCTGCT GCCCAAACTAACTCCATGGTGACCCTGGGAT GCCTGGTCAAGGGCTATTTCCCTGAGCCAGT GACAGTGACCTGGAACTCTGGATCCCTGTCC AGCGGTGTGCACACCTTCCCAGCTGTCCTGC AGTCTGACCTCTACACTCTGAGCAGCTCAGT GACTGTCCCCTCCAGCACCTGGCCCAGCGAG |

FIG 14k

| SEQ ID No. | Description | Sequence |
|---|---|---|
|  |  | ACCGTCACCTGCAACGTTGCCCACCCGGCCAGCAGCACCAAGGTGGACAAGAAAATTGTGCCCAGGGATTGTCATCATCACCATCACCATCACTAATTTGACAGCTTTAATCATTCAATTAAGCTTTTAAT |
| 29 | VK_aa A1 | MKYLLPTAAAGLLLLAAQPAMADIVMSQSPSSMYASLGERVTITCKASQDINSYLNWFQQKPGKSPKTLIYRANRLVDGVPSRFSGSGSGHDYFLTIRSLEYEDMGIYYCLQYDEFPYTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 30 | VK_aa A2 | MKYLLPTAAAGLLLLAAQPAMADIKMTQSPSSMYASLGERVTITCKASQDINSYLSWFQQKPGKSPKTLIYRANRLVDGVPSRFSGSGSGQDYSLTISSLEYEDMGIYYCLQYDEFPYTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 31 | VK_aa A3 | MKYLLPTAAAGLLLLAAQPAMADIQLTQSPSSMYASLGERVTIACKASQDINSYLSWFQQKPGKSPKTLIHRANRLVDGVPSRFSGSGSGQDYSLTISSLEYEDIGIYYCLQYDEFPYTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 32 | VK_aa A4 | MKYLLPTAAAGLLLLAAQPAMADILLTQSPSSMYTSLGERVTITCKASQDINSYLSWFQQKPGKSPKTLIYRANKLVDGVPSRFSGSGSGQDYSLTISSLESEDMGIYYCLQYDEFPYTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 33 | VK_aa A5 | MKYLLPTAAAGLLLLAAQPAMADIKMTQSPSSMYASLGERVTITCKASQDINSYLSWFQQKPGKSPKTLIYRAKRLIDGVPSRFSGSGSGQDYSLTISSLEYEDMGIYYCLQYDEFPYTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 34 | VK_aa A6 | MKYLLPTAAAGLLLLAAQPAMADIVMSQSPSSMYASLGERVTITCKASQDINSYLSWFQQKPGKSPKTLTYRANRLVEGVPSRFSGSGSGQDYSLTISS |

FIG 14I

| SEQ ID No. | Description | Sequence |
|---|---|---|
| | | LEYEDMGIYYCLQYDEFPYTFGGGTKLEIKRA DAAPTVSIFPPSSEQLTSGGASVVCFLNNFYPKD INVKWKIDGSERQNGVLNSWTDQDSKDSTYSM SSTLTLTKDEYERHNSYTCEATHKTSTSPIVKSF NRNES |
| 35 | VK_aa A7 | MKYLLPTAAAGLLLLAAQPAMADIVMTQSPSS MYTSLGERVTITCKASQDINSYLSWFQQKPGKS PKTLIYRANRLIDGVPSRFSGSGSGQDYSLTISSL EYEDMGIYYCLQYDEFPFTFGSGTKLEIKRADA APTVSIFPPSSEQLTSGGASVVCFLNNFYPKDIN VKWKIDGSERQNGVLNSWTDQDSKDSTYSMSS TLTLTKDEYERHNSYTCEATHKTSTSPIVKSFN RNES |
| 36 | VK_aa A8 | MKYLLPTAAAGLLLLAAQPAMANIVMTQSPVS LSMAIGEKVTIRCITNTDIDDAMNWYQQKPGEP PKLLISEGNTLRPGVPSRFSSSGYGTDFVFTIEN MLSEDVADYYCLQTDNLPLTFGSGTKLAIKRA DAAPTVSIFPPSSEQLTSGGASVVCFLNNFYPKD INVKWKIDGSERQNGVMNSWTDQDSKDSTYSM SSTLTLTKDEYERHNSYTCEATHKTSTSPIVKSF NRNES |
| 37 | VK_aa A9 | MKYLLPTAAAGLLLLAAQPAMANIVMTQSPSS MYASLGERVTITCKASQDINSYLSWFQQKPGKS PKTLIYRANRLVDGVPSRFSGSGSGQDYSLTISS LEYEDMGIYYCLQYDEFPYTFGGGTKLEIKRA DAAPTVSIFPPSSEQLTSGGASVVCFLNNFYPKD INVKWKIDGSERQNGVLNSWTDQDSKDSTYSM SSTLTLTKDEYERHNSYTCEATHKTSTSPIVKSF NRNES |
| 38 | VK_aa A10 | MKYLLPTAAAGLLLLAAQPAMANIVMTQSPSS MYASLGERVTITCKASQDIYSYLSWFQQKPGKS PKTLIYRANRLVDGVPSRFSGSGSGQDYSLTISS LDYEDVGIYYCLQYDEFPYTFGSGTKLEIERAD AAPTVSIFPPSSEQLTSGGASVVCFLNNFYPKDI NVKWKIDGSERQNGVLNSWTDQDSKDSTYSMS STLTLTKDEYERHNSYTCEATHKTSTSPIVKSFN RNES |
| 39 | VK_aa A11 | MKYLLPTAAAGLLLLAAQPAMAETTVTQSPVS LSMAIGEKVTIRCMTSTDIDDALNWYQQKPGE PPKLLISEGNSLRPGVPSRFSSSGNGTDFVFTIEN MLSEDVADYYCLQSDNLPLTFGSGTKLEIKRAD AAPTVSIFPPSSEQLTSGGASVVCFLNNFYPKDI NVKWKIDGSERQNGVLNSWTDQDSKDSTYSMS STLTLTKDEYERHNSYTCEATHKTSTSPIVKSFN RNES |
| 40 | VK_aa A12 | MKYLLPTAAAGLLLLAAQPAMADIKMTQSPSS MYASLGERVTITCKASQDINSYLSWFQQKPGKS PMTLTHRANRLVDGVPSRFSGSGSGQDYSLTIS |

FIG 14m

| SEQ ID No. | Description | Sequence |
|---|---|---|
| | | SLENEDMGIYYCLQYDEFPYTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 41 | VK_aa A13 | MKYLLPTAAAGLLLLAAQPAMANIVMTQSPSSMYASLGERVTIICKSSQDINSYLSWFQQKPGKSPKTLIFRANRLVDGVPSRFSGSGSGQDYSLTISSLEYEDMGIYYCLQYDEFPYTFGGGTKLEVKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 42 | VK_aa A14 | MKYLLPTAAAGLLLLAAQPAMADVVMSQSPSSLAVSTGEKVTLSCKSSQSLLNSRTRKNYLAWYQQKPGQSPKLLIYWTSTRESGVPNRFTGSGSGTDFTLTISSVQAEDLAVYYCKQSYDLPWTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNES |
| 43 | VK_nt A1 | TATCGCAACTCTCTACTGTTTCTCCATACCCGTTTTTTTGGATGGAGTGAAACGATGAAATACCTATTGCCTACGGCAGCCGCTGGATTGTTATTACTCGCTGCCCAACCAGCCATGGCCGACATCGTTATGTCTCAGTCTCCATCTTCCATGTATGCATCTCTAGGAGAGAGAGTCACTATCACTTGCAAGGCGAGTCAGGACATTAATAGCTATTTAAACTGGTTCCAGCAGAAACCAGGCAAATCTCCTAAGACCCTGATCTATCGTGCAAACAGATTGGTAGATGGGGTCCCATCAAGGTTCAGTGGCAGTGGATCTGGGCACGATTATTTTCTTACCATTCGCAGCCTGGAATATGAAGATATGGGAATTTATTATTGTCTACAGTATGATGAGTTTCCGTACACGTTCGGAGGGGGGACCAAGCTGGAAATAAAACGGGCTGATGCTGCACCAACTGTATCCATCTTCCCACCATCCAGTGAGCAGTTAACATCTGGAGGTGCCTCAGTCGTGTGCTTCTTGAACAACTTCTACCCCAAAGACATCAATGTCAAGTGGAAGATTGATGGCAGTGAACGACAAAATGGCGTCCTGAACAGTTGGACTGATCAGGACAGCAAAGACAGCACCTACAGCATGAGCAGCACCCTCACGTTGACCAAGGACGAGTATGAACGACATAACAGCTATACCTGTGAGGCCACTCACAAGACATCAACTTCACCCATTGTCAAGAGCTTCAACAGGAATGAGTCTTAAGTGATTAGCTAATTCTAGAACGCGTCACTTGGCACTGGCCGTCG |
| 44 | VK_nt A2 | TTATCGCAACTCTCTACTGTTTCTCCATACCC |

FIG 14n

| SEQ ID No. | Description | Sequence |
|---|---|---|
| | | GTTTTTTTGGATGGAGTGAAACGATGAAATA CCTATTGCCTACGGCAGCCGCTGGATTGTTA TTACTCGCTGCCCAACCAGCCATGGCCGACA TCAAAATGACCCAGTCTCCATCTTCCATGTAT GCATCTCTAGGAGAGAGTCACTATCACTT GCAAGGCGAGTCAGGACATTAATAGCTATTT AAGCTGGTTCCAGCAGAAACCAGGGAAATCT CCTAAGACCCTGATCTATCGTGCAAACAGAT TGGTAGATGGGGTCCCATCAAGGTTCAGTGG CAGTGGATCTGGGCAAGATTATTCTCTCACC ATCAGCAGCCTGGAGTATGAAGATATGGGAA TTTATTATTGTCTACAGTATGATGAATTTCCG TACACGTTCGGAGGGGGGACCAAGCTGGAAA TAAAACGGGCTGATGCTGCACCAACTGTATC CATCTTCCCACCATCCAGTGAGCAGTTAACAT CTGGAGGTGCCTCAGTCGTGTGCTTCTTGAA CAACTTCTACCCCAAAGACATCAATGTCAAGT GGAAGATTGATGGCAGTGAACGACAAAATGG CGTCCTGAACAGTTGGACTGATCAGGACAGC AAAGACAGCACCTACAGCATGAGCAGCACCC TCACGTTGACCAAGGACGAGTATGAACGACA TAACAGCTATACCTGTGAGGCCACTCACAAG ACATCAACTTCACCCATTGTCAAGAGCTTCAA CAGGAATGAGTCTTAAGTGATTAGCTAATTCT AGAACGCGTCACTTGGCACTGGCCGTCGTTT TACAACGTCGTGACTGGGAAAA |
| 45 | VK_nt A3 | TATCGCAACTCTCTACTGTTTCTCCATACCCG TTTTTTTGGATGGAGTGAAACGATGAAATAC CTATTGCCTACGGCAGCCGCTGGATTGTTAT TACTCGCTGCCCAACCAGCCATGGCCGACAT TCAGCTGACCCAGTCTCCATCTTCCATGTATG CATCTCTAGGAGAGAGTCACTATCGCTTG CAAGGCGAGTCAGGACATTAATAGCTATTTA AGCTGGTTCCAGCAGAAACCAGGGAAATCTC CTAAGACCCTGATCCATCGTGCAAACAGATT GGTAGATGGGGTCCCATCAAGGTTCAGTGGC AGTGGATCTGGGCAAGATTATTCTCTCACCA TCAGCAGCCTGGAGTATGAAGATATCGGAAT TTATTATTGTCTACAGTATGATGAGTTTCCGT ACACGTTCGGAGGGGGGACCAAGCTGGAAAT AAAACGGGCTGATGCTGCACCAACTGTATCC ATCTTCCCACCATCCAGTGAGCAGTTAACATC TGGAGGTGCCTCAGTCGTGTGCTTCTTGAAC AACTTCTACCCCAAAGACATCAATGTCAAGT GGAAGATTGATGGCAGTGAACGACAAAATGG CGTCCTGAACAGTTGGACTGATCAGGACAGC AAAGACAGCACCTACAGCATGAGCAGCACCC TCACGTTGACCAAGGACGAGTATGAACGACA |

FIG 14o

| SEQ ID No. | Description | Sequence |
|---|---|---|
|  |  | TAACAGCTATACCTGTGAGGCCACTCACAAG ACATCAACTTCACCCATTGTCAAGAGCTTCAA CAGGAATGAGTCTTAAGTGATTAGCTAATTCT AGAACGCGTCACTTGGCACTGGCCGTCGTTT TACAACGTCG |
| 46 | VK_nt A4 | TCGCAACTCTCTACTGTTTCTCCATACCCGTT TTTTTGGATGGAGTGAAACGATGAAATACCT ATTGCCTACGGCAGCCGCTGGATTGTTATTA CTCGCTGCCCAACCAGCCATGGCCGACATCT TGCTGACTCAGTCTCCATCTTCCATGTATACA TCTCTAGGAGAGAGTCACTATCACTTGCA AGGCGAGTCAGGACATTAATAGCTATTTAAG CTGGTTCCAGCAGAAACCAGGAAAATCTCCT AAGACCCTGATCTATCGTGCAAACAAATTGG TAGATGGGGTCCCATCAAGATTCAGTGGCAG TGGATCTGGGCAAGATTATTCTCTCACCATCA GCAGCCTGGAGTCTGAAGATATGGGAATTTA TTATTGTCTACAGTATGATGAGTTTCCGTACA CGTTCGGAGGGGGGACCAAGCTGGAAATCAA ACGGGCTGATGCTGCACCAACTGTATCCATC TTCCCACCATCCAGTGAGCAGTTAACATCTG GAGGTGCCTCAGTCGTGTGCTTCTTGAACAA CTTCTACCCCAAAGACATCAATGTCAAGTGG AAGATTGATGGCAGTGAACGACAAAATGGCG TCCTGAACAGTTGGACTGATCAGGACAGCAA AGACAGCACCTACAGCATGAGCAGCACCCTC ACGTTGACCAAGGACGAGTATGAACGACATA ACAGCTATACCTGTGAGGCCACTCACAAGAC ATCAACTTCACCCATTGTCAAGAGCTTCAACA GGAATGAGTCTTAAGTGATTAGCTAATTCTA GAACGCGTCACTTGG |
| 47 | VK_nt A5 | TCGCAACTCTCTACTGTTTCTCCATACCCGTT TTTTTGGATGGAGTGAAACGATGAAATACCT ATTGCCTACGGCAGCCGCTGGATTGTTATTA CTCGCTGCCCAACCAGCCATGGCCGACATCA AAATGACCCAGTCTCCATCTTCCATGTATGCA TCTCTAGGAGAGAGTCACTATCACTTGCA AGGCGAGTCAGGACATTAATAGCTATTTAAG CTGGTTCCAGCAGAAACCAGGGAAATCTCCT AAGACCCTGATCTATCGTGCAAAGAGATTGA TAGATGGGGTCCCATCAAGGTTCAGTGGCAG TGGATCTGGGCAAGATTATTCTCTCACCATCA GCAGCCTGGAGTATGAAGATATGGGAATTTA TTATTGTCTACAGTATGATGAGTTTCCTTACA CGTTCGGAGGGGGGACAAAGTTGGAAATAAA ACGGGCTGATGCTGCACCAACTGTATCCATC TTCCCACCATCCAGTGAGCAGTTAACATCTG GAGGTGCCTCAGTCGTGTGCTTCTTGAACAA |

FIG 14p

| SEQ ID No. | Description | Sequence |
|---|---|---|
|  |  | CTTCTACCCCAAAGACATCAATGTCAAGTGG AAGATTGATGGCAGTGAACGACAAAATGGCG TCCTGAACAGTTGGACTGATCAGGACAGCAA AGACAGCACCTACAGCATGAGCAGCACCCTC ACGTTGACCAAGGACGAGTATGAACGACATA ACAGCTATACCTGTGAGGCCACTCACAAGAC ATCAACTTCACCCATTGTCAAGAGCTTCAACA GGAATGAGTCTTAAGTGATTAGCTAATTCTA GAACGCGTCACTTGGCACTGGCCGTCGTTTT ACAACGTCG |
| 48 | VK_nt A6 | TTTTATCGCAACTCTCTACTGTTTCTCCATAC CCGTTTTTTTGGATGGAGTGAAACGATGAAA TACCTATTGCCTACGGCAGCCGCTGGATTGT TATTACTCGCTGCCCAACCAGCCATGGCCGA CATCGTTATGTCTCAGTCTCCATCTTCCATGT ATGCATCTCTAGGAGAGAGAGTCACTATCAC TTGCAAGGCGAGTCAAGACATTAATAGCTAT TTAAGCTGGTTCCAGCAGAAACCAGGGAAAT CTCCTAAGACCCTGACCTATCGTGCAAACAG ATTGGTAGAAGGGGTCCCATCAAGGTTCAGT GGCAGTGGATCTGGGCAAGATTATTCTCTCA CCATCAGCAGCCTGGAATATGAAGATATGGG AATTTATTATTGTCTACAGTATGATGAGTTTC CGTACACGTTCGGAGGGGGGACCAAGCTGGA AATAAAACGGGCTGATGCTGCACCAACTGTA TCCATCTTCCCACCATCCAGTGAGCAGTTAAC ATCTGGAGGTGCCTCAGTCGTGTGCTTCTTG AACAACTTCTACCCCAAAGACATCAATGTCAA GTGGAAGATTGATGGCAGTGAACGACAAAAT GGCGTCCTGAACAGTTGGACTGATCAGGACA GCAAAGACAGCACCTACAGCATGAGCAGCAC CCTCACGTTGACCAAGGACGAGTATGAACGA CATAACAGCTATACCTGTGAGGCCACTCACA AGACATCAACTTCACCCATTGTCAAGAGCTTC AACAGGAATGAGTCTTAAGTGATTAGCTAAT TCTAGAACGCGTCACTTGGCACTGGCCGTCG TTTTACAACGT |
| 49 | VK_nt A7 | GCAACTCTCTACTGTTTCTCCATACCCGTTTT TTTGGATGGAGTGAAACGATGAAATACCTAT TGCCTACGGCAGCCGCTGGATTGTTATTACT CGCTGCCCAACCAGCCATGGCCGACATTGTG ATGACCCAGTCTCCATCTTCCATGTATACATC TCTAGGAGAGAGAGTCACTATCACTTGCAAG GCGAGTCAGGACATTAATAGCTATTTAAGCT GGTTCCAGCAGAAACCAGGGAAATCTCCTAA GACCCTGATCTATCGTGCAAACAGATTGATA GATGGGGTCCCATCAAGGTTCAGTGGCAGTG GATCTGGGCAAGATTATTCTCTCACCATCAG |

FIG 14q

| SEQ ID No. | Description | Sequence |
|---|---|---|
| | | CAGCCTGGAGTATGAAGATATGGGAATTTAT TATTGTCTACAGTATGATGAGTTTCCATTCAC GTTCGGCTCGGGGACAAAGTTGGAAATAAAA CGGGCTGATGCTGCACCAACTGTATCCATCT TCCCACCATCCAGTGAGCAGTTAACATCTGG AGGTGCCTCAGTCGTGTGCTTCTTGAACAAC TTCTACCCCAAAGACATCAATGTCAAGTGGA AGATTGATGGCAGTGAACGACAAAATGGCGT CCTGAACAGTTGGACTGATCAGGACAGCAAA GACAGCACCTACAGCATGAGCAGCACCCTCA CGTTGACCAAGGACGAGTATGAACGACATAA CAGCTATACCTGTGAGGCCACTCACAAGACA TCAACTTCACCCATTGTCAAGAGCTTCAACAG GAATGAGTCTTAAGTGATTAGCTAATTCTAGA ACGCGTCACTTGGCACTGGCCGTCGTTTTAC AACGTCGTGACTGGGAAAACCCTGGC |
| 50 | VK_nt A8 | GAGTGAAACGATGAAATACCTATTGCCTACG GCAGCCGCTGGATTGTTATTACTCGCTGCCC AACCAGCCATGGCCAACATCGTTATGACCCA GTCTCCAGTATCCTGTCCATGGCTATAGGA GAAAAAGTCACCATCAGATGCATAACCAACA CTGATATTGATGATGCTATGAACTGGTACCA GCAAAAGCCAGGGGAACCTCCTAAGCTCCTT ATTTCAGAAGGCAATACTCTTCGTCCTGGAG TCCCATCCCGATTCTCCAGCAGTGGCTATGG TACAGATTTTGTTTTTACAATTGAAAACATGC TCTCAGAAGATGTTGCAGATTACTACTGTTTG CAAACTGATAACTTGCCTCTCACGTTCGGCTC GGGGACAAAGTTGGCAATAAAACGGGCTGAT GCTGCACCAACTGTATCCATCTTCCCACCATC CAGTGAGCAGTTAACATCTGGAGGTGCCTCA GTCGTGTGCTTCTTGAACAACTTCTACCCCAA AGACATCAATGTCAAGTGGAAGATTGATGGC AGTGAACGACAAAATGGCGTCATGAACAGTT GGACTGATCAGGACAGCAAAGACAGCACCTA CAGCATGAGCAGCACCCTCACGTTGACCAAG GACGAGTATGAACGACATAACAGCTATACCT GTGAGGCCACTCACAAGACATCAACTTCACC CATTGTCAAGAGCTTCAACAGGAATGAGTCT TAAGTGATTAG |
| 51 | VK_nt A9 | TCGCAACTCTCTACTGTTTCTCCATACCCGTT TTTTTGGATGGAGTGAAACGATGAAATACCT ATTGCCTACGGCAGCCGCTGGATTGTTATTA CTCGCTGCCCAACCAGCCATGGCCAACATCG TTATGACCCAGTCTCCATCTTCCATGTATGCA TCTCTAGGAGAGAGTCACTATCACTTGCA AGGCGAGTCAGGACATTAATAGCTATTTAAG CTGGTTCCAGCAGAAACCAGGGAAATCTCCT |

FIG 14r

| SEQ ID No. | Description | Sequence |
|---|---|---|
| | | AAGACCCTGATCTATCGTGCAAACAGATTGG TAGATGGGGTCCCATCAAGGTTCAGTGGCAG TGGATCTGGGCAAGATTATTCTCTCACCATCA GCAGCCTGGAGTATGAAGATATGGGAATTTA TTATTGTCTACAGTATGATGAGTTTCCGTACA CGTTCGGAGGGGGGACCAAACTGGAAATAAA ACGGGCTGATGCTGCACCAACTGTATCCATC TTCCCACCATCCAGTGAGCAGTTAACATCTG GAGGTGCCTCAGTCGTGTGCTTCTTGAACAA CTTCTACCCCAAAGACATCAATGTCAAGTGG AAGATTGATGGCAGTGAACGACAAAATGGCG TCCTGAACAGTTGGACTGATCAGGACAGCAA AGACAGCACCTACAGCATGAGCAGCACCCTC ACGTTGACCAAGGACGAGTATGAACGACATA ACAGCTATACCTGTGAGGCCACTCACAAGAC ATCAACTTCACCCATTGTCAAGAGCTTCAACA GGAATGAGTCTTAAGTGATTAGCTAATTCTA GAACGCGTCACTTGGCACTGGCCGTCGTTTT ACA |
| 52 | VK_nt A10 | GCAACTCTCTACTGTTTCTCCATACCCGTTTT TTTGGATGGAGTGAAACGATGAAATACCTAT TGCCTACGGCAGCCGCTGGATTGTTATTACT CGCTGCCCAACCAGCCATGGCCAACATCGTT ATGACCCAGTCTCCATCTTCCATGTATGCATC TCTAGGAGAGAGGGTCACTATCACTTGCAAG GCGAGTCAGGACATTTATAGCTATTTAAGCT GGTTCCAGCAGAAACCAGGCAAATCTCCTAA GACCCTGATCTATCGTGCAAACAGATTGGTA GATGGGGTCCCATCAAGGTTCAGTGGCAGTG GATCTGGGCAAGATTATTCTCTCACCATCAG CAGCCTGGACTATGAAGATGTGGGAATTTAT TATTGTCTACAGTATGATGAGTTTCCGTACAC GTTCGGCTCGGGGACAAAGTTGGAAATAGAA CGGGCTGATGCTGCACCAACTGTATCCATCT TCCCACCATCCAGTGAGCAGTTAACATCTGG AGGTGCCTCAGTCGTGTGCTTCTTGAACAAC TTCTACCCCAAAGACATCAATGTCAAGTGGA AGATTGATGGCAGTGAACGACAAAATGGCGT CCTGAACAGTTGGACTGATCAGGACAGCAAA GACAGCACCTACAGCATGAGCAGCACCCTCA CGTTGACCAAGGACGAGTATGAACGACATAA CAGCTATACCTGTGAGGCCACTCACAAGACA TCAACTTCACCCATTGTCAAGAGCTTCAACAG GAATGAGTCTTAAGTGATTAGCTAATTCTAGA ACGCGTCACTTGGCACTGGCCGTCGTTTTA |
| 53 | VK_nt A11 | CGCAACTCTCTACTGTTTCTCCATACCCGTTT TTTTGGATGGAGTGAAACGATGAAATACCTA TTGCCTACGGCAGCCGCTGGATTGTTATTAC |

FIG 14s

| SEQ ID No. | Description | Sequence |
|---|---|---|
|  |  | TCGCTGCCCAACCAGCCATGGCCGAAACAAC<br>TGTGACCCAGTCTCCAGTATCCCTGTCCATG<br>GCTATAGGAGAAAAAGTCACCATCAGATGCA<br>TGACCAGCACTGATATTGATGATGCTCTGAA<br>CTGGTACCAGCAAAAGCCAGGGGAACCTCCT<br>AAACTCCTTATTTCAGAAGGCAATAGTCTTCG<br>TCCTGGAGTCCCATCCCGATTCTCCAGCAGT<br>GGCAATGGTACAGATTTTGTTTTTACAATTGA<br>AAACATGCTCTCAGAAGATGTTGCAGATTAC<br>TACTGTTTGCAAAGTGATAACTTGCCTCTCAC<br>GTTCGGCTCGGGGACAAAGTTGGAAATAAAA<br>CGGGCTGATGCTGCACCAACTGTATCCATCT<br>TCCCACCATCCAGTGAGCAGTTAACATCTGG<br>AGGTGCCTCAGTCGTGTGCTTCTTGAACAAC<br>TTCTACCCCAAAGACATCAATGTCAAGTGGA<br>AGATTGATGGCAGTGAACGACAAAATGGCGT<br>CCTGAACAGTTGGACTGATCAGGACAGCAAA<br>GACAGCACCTACAGCATGAGCAGCACCCTCA<br>CGTTGACCAAGGACGAGTATGAACGACATAA<br>CAGCTATACCTGTGAGGCCACTCACAAGACA<br>TCAACTTCACCCATTGTCAAGAGCTTCAACAG<br>GAATGAGTCTTAAGTGATTAGCTAATTCTAGA<br>ATGCGTCACTTGGCACTGGCCGTCGTTTTAC<br>AACGTCGTGAC |
| 54 | VK_nt A12 | TATCGCAACTCTCTACTGTTTCTCCATACCCG<br>TTTTTTTGGATGGAGTGAAACGATGAAATAC<br>CTATTGCCTACGGCAGCCGCTGGATTGTTAT<br>TACTCGCTGCCCAACCAGCCATGGCCGACAT<br>CAAAATGACCCAGTCTCCATCTTCCATGTATG<br>CATCTCTAGGAGAGAGAGTCACTATCACTTG<br>CAAGGCGAGTCAGGACATTAATAGCTATTTA<br>AGCTGGTTCCAGCAGAAACCAGGGAAATCTC<br>CTATGACCCTGACCCATCGTGCAAACAGATT<br>GGTAGATGGGGTCCCATCAAGGTTCAGTGGC<br>AGTGGATCTGGGCAAGATTATTCTCTCACCA<br>TCAGCAGCCTGGAGAATGAAGATATGGGAAT<br>TTATTATTGTCTACAGTATGATGAGTTTCCGT<br>ACACGTTCGGAGGGGGGACCAAGCTGGAAAT<br>AAAACGGGCTGATGCTGCACCAACTGTATCC<br>ATCTTCCCACCATCCAGTGAGCAGTTAACATC<br>TGGAGGTGCCTCAGTCGTGTGCTTCTTGAAC<br>AACTTCTACCCCAAAGACATCAATGTCAAGT<br>GGAAGATTGATGGCAGTGAACGACAAAATGG<br>CGTCCTGAACAGTTGGACTGATCAGGACAGC<br>AAAGACAGCACCTACAGCATGAGCAGCACCC<br>TCACGTTGACCAAGGACGAGTATGAACGACA<br>TAACAGCTATACCTGTGAGGCCACTCACAAG<br>ACATCAACTTCACCCATTGTCAAGAGCTTCAA |

FIG 14t

| SEQ ID No. | Description | Sequence |
|---|---|---|
| | | CAGGAATGAGTCTTAAGTGATTAGCTAATTCT AGAACGCGTCACTTGGCACTGGCCGTCGTTT TACAACGTCGT |
| 55 | VK_nt A13 | CGCAACTCTCTACTGTTTCTCCATACCCGTTT TTTTGGATGGAGTGAAACGATGAAATACCTA TTGCCTACGGCAGCCGCTGGATTGTTATTAC TCGCTGCCCAACCAGCCATGGCCAACATCGT TATGACCCAGTCTCCATCTTCCATGTATGCAT CTCTAGGAGAGAGAGTCACTATCATTTGCAA GTCGAGTCAGGACATTAATAGCTATTTAAGTT GGTTCCAGCAGAAACCAGGGAAGTCTCCTAA GACCCTGATCTTTCGTGCAAACAGATTGGTA GATGGGGTCCCATCAAGGTTCAGTGGCAGTG GATCTGGGCAAGATTATTCTCTCACCATCAG CAGCCTGGAGTATGAAGATATGGGAATTTAT TATTGTCTACAGTATGATGAGTTTCCGTACAC GTTCGGAGGGGGGACCAAGCTGGAAGTAAAA CGGGCTGATGCTGCACCAACCGTATCCATCT TCCCACCATCCAGTGAGCAGTTAACATCTGG AGGTGCCTCAGTCGTGTGCTTCTTGAACAAC TTCTACCCCAAAGACATCAATGTCAAGTGGA AGATTGATGGCAGTGAACGACAAAATGGCGT CCTGAACAGTTGGACTGATCAGGACAGCAAA GACAGCACCTACAGCATGAGCAGCACCCTCA CGTTGACCAAGGACGAGTATGAACGACATAA CAGCTATACCTGTGAGGCCACTCACAAGACA TCAACTTCACCCATTGTCAAGAGCTTCAACAG GAATGAGTCTTAAGTGATTAGCTAATTCTAGA ACGCGTCACTTGGCACTGGCCGTCGTTTTAC AACGTCGTGA |
| 56 | VK_nt A14 | TCGCAACTCTCTACTGTTTCTCCATACCCGTT TTTTGGATGGAGTGAAACGATGAAATACCT ATTGCCTACGGCAGCCGCTGGATTGTTATTA CTCGCTGCCCAACCAGCCATGGCCGACGTTG TGATGTCACAGTCTCCATCCTCCCTGGCTGT GTCAACAGGAGAGAAGGTCACTTTGAGCTGC AAATCCAGTCAGAGTCTGCTCAACAGTAGAA CCCGAAAGAACTACTTGGCTTGGTACCAGCA GAAACCAGGGCAGTCTCCTAAACTGCTGATC TACTGGACATCCACTAGGGAATCTGGGGTCC CTAATCGCTTCACAGGCAGTGGATCTGGGAC AGATTTCACTCTCACCATCAGCAGTGTGCAG GCTGAAGACCTGGCAGTTTATTACTGCAAGC AATCTTATGATCTTCCGTGGACGTTCGGTGG GGGCACCAAACTGGAAATCAAACGGGCTGAT GCTGCACCAACTGTATCCATCTTCCCACCATC CAGTGAGCAGTTAACATCTGGAGGTGCCTCA GTCGTGTGCTTCTTGAACAACTTCTACCCCAA |

FIG 14u

| SEQ ID No. | Description | Sequence |
|---|---|---|
| | | AGACATCAATGTCAAGTGGAAGATTGATGGC AGTGAACGACAAAATGGCGTCCTGAACAGTT GGACTGATCAGGACAGCAAAGACAGCACCTA CAGCATGAGCAGCACCCTCACGTTGACCAAG GACGAGTATGAACGACATAACAGCTATACCT GTGAGGCCACTCACAAGACATCAACTTCACC CATTGTCAAGAGCTTCAACAGGAATGAGTCT TAAGTGATTAGCTAATTCTAGAACGCGTCACT TGGCACTGGCCGTCGT |
| 57 | VH_CDR1_aa A1 | VSGFTFSSYAMS |
| 58 | VH_CDR1_aa A1, A3, A8, A12 and A13 | GFTFSSYAMS |
| 59 | VH_CDR1_aa A2 | ASGFTFSTYAMS |
| 60 | VH_CDR1_aa A2 | GFTFSTYAMS |
| 61 | VH_CDR1_aa A3, A8, A12 and A13 | ASGFTFSSYAMS |
| 62 | VH_CDR1_aa A4 | ASGFTFSNYGMS |
| 63 | VH_CDR1_aa A4 | GFTFSNYGMS |
| 64 | VH_CDR1_aa A5 | ASGFTFSNYDMS |
| 65 | VH_CDR1_aa A5 | GFTFSNYDMS |
| 66 | VH_CDR1_aa A6 | ASGFTFSPYAMS |
| 67 | VH_CDR1_aa A6 | GFTFSPYAMS |
| 68 | VH_CDR1_aa A7 | ASGFSFSSYAMS |
| 69 | VH_CDR1_aa A7 | GFSFSSYAMS |
| 70 | VH_CDR1_aa A9 | ASGFTFSSNAMS |
| 71 | VH_CDR1_aa A9 | GFTFSSNAMS |
| 72 | VH_CDR1_aa A10 | ASGFAFSSYAMS |
| 73 | VH_CDR1_aa A10 | GFAFSSYAMS |
| 74 | VH_CDR1_aa A11 | ASGFTFSRYGMS |
| 75 | VH_CDR1_aa A11 | GFTFSRYGMS |
| 76 | VH_CDR1_aa A14 | ATGYTFSSYWIE |
| 77 | VH_CDR1_aa A14 | GYTFSSYWIE |
| 78 | VH_CDR1_nt A1 | GTCTCTGGATTCACTTTCAGTAGCTATGCCATGTCT |
| 79 | VH_CDR1_nt A1, A3, A8, A12 and A13 | GGATTCACTTTCAGTAGCTATGCCATGTCT |
| 80 | VH_CDR1_nt A2 | GCCTCTGGATTCACTTTCAGTACCTATGCCATGTCT |
| 81 | VH_CDR1_nt A2 | GGATTCACTTTCAGTACCTATGCCATGTCT |
| 82 | VH_CDR1_nt A3, A8, A12 and A13 | GCCTCTGGATTCACTTTCAGTAGCTATGCCATGTCT |
| 83 | VH_CDR1_nt A4 | GCCTCTGGATTCACTTTCAGTAACTATGGCATGTCT |
| 84 | VH_CDR1_nt A4 | GGATTCACTTTCAGTAACTATGGCATGTCT |
| 85 | VH_CDR1_nt A5 | GCCTCTGGATTCACTTTCAGTAACTATGACATGTCT |
| 86 | VH_CDR1_nt A5 | GGATTCACTTTCAGTAACTATGACATGTCT |

FIG. 14v

| SEQ ID No. | Description | Sequence |
|---|---|---|
| 87 | VH_CDR1_nt A6 | GCCTCTGGATTCACTTTCAGTCCCTATGCCATGTCT |
| 88 | VH_CDR1_nt A6 | GGATTCACTTTCAGTCCCTATGCCATGTCT |
| 89 | VH_CDR1_nt A7 | GCCTCTGGATTCTCTTTCAGTAGCTATGCCATGTCT |
| 90 | VH_CDR1_nt A7 | GGATTCTCTTTCAGTAGCTATGCCATGTCT |
| 91 | VH_CDR1_nt A9 | GCCTCTGGATTCACTTTCAGTAGCAATGCCATGTCC |
| 92 | VH_CDR1_nt A9 | GGATTCACTTTCAGTAGCAATGCCATGTCC |
| 93 | VH_CDR1_nt A10 | GCCTCTGGATTCGCTTTCAGTAGCTATGCCATGTCT |
| 94 | VH_CDR1_nt A10 | GGATTCGCTTTCAGTAGCTATGCCATGTCT |
| 95 | VH_CDR1_nt A11 | GCCTCTGGATTCACTTTCAGTAGATATGGCATGTCT |
| 96 | VH_CDR1_nt A11 | GGATTCACTTTCAGTAGATATGGCATGTCT |
| 97 | VH_CDR1_nt A14 | GCTACTGGCTACACATTCAGTAGTTACTGGATAGAG |
| 98 | VH_CDR1_nt A14 | GGCTACACATTCAGTAGTTACTGGATAGAG |
| 99 | VH_CDR2_aa A1 | AINFNRGTTY |
| 100 | VH_CDR2_aa A1 | AINFNRGTTYYSDTVKG |
| 101 | VH_CDR2_aa A2 and A13 | GINSNRGTTY |
| 102 | VH_CDR2_aa A2 and A13 | GINSNRGTTYYPDTVKG |
| 103 | VH_CDR2_aa A3 | AININRGTTY |
| 104 | VH_CDR2_aa A3 | AININRGTTYYSDTVKG |
| 105 | VH_CDR2_aa A4 | AMNNNGASTY |
| 106 | VH_CDR2_aa A4 | AMNNNGASTYYPDTVKG |
| 107 | VH_CDR2_aa A5 | AINRKGHSTY |
| 108 | VH_CDR2_aa A5 | AINRKGHSTYYPDTVQG |
| 109 | VH_CDR2_aa A6 | AINSNRGTTYYPDTVKG |
| 110 | VH_CDR2_aa A6 and A12 | AINSNRGTTY |
| 111 | VH_CDR2_aa A7 | AININRGTPY |
| 112 | VH_CDR2_aa A7 | AININRGTPYYPDTVKG |
| 113 | VH_CDR2_aa A8 | AINPNGGSTY |
| 114 | VH_CDR2_aa A8 | AINPNGGSTYYPDTVKG |
| 115 | VH_CDR2_aa A9 | AINSKGGGTY |
| 116 | VH_CDR2_aa A9 | AINSKGGGTYYPDTVRG |
| 117 | VH_CDR2_aa A10 | AINNRGGGTY |
| 118 | VH_CDR2_aa A10 | AINNRGGGTYYPDTVRG |
| 119 | VH_CDR2_aa A11 | AINPNGGTTY |
| 120 | VH_CDR2_aa A11 | AINPNGGTTYYPDTVKG |
| 121 | VH_CDR2_aa A12 | AINSNRGTTYYSDTVKG |
| 122 | VH_CDR2_aa A14 | EILPGIGNTN |
| 123 | VH_CDR2_aa A14 | EILPGIGNTNYNEKFKG |
| 124 | VH_CDR2_nt A1 | GCCATTAATTTTAATCGTGGTACCACCTAC |

FIG 14w

| SEQ ID No. | Description | Sequence |
|---|---|---|
| 125 | VH_CDR2_nt A1 | GCCATTAATTTTAATCGTGGTACCACCTACTATTCAGACACTGTGAAGGGC |
| 126 | VH_CDR2_nt A2 and A13 | GGCATTAATAGTAATCGTGGTACCACCTAC |
| 127 | VH_CDR2_nt A2 and A13 | GGCATTAATAGTAATCGTGGTACCACCTACTATCCAGACACTGTGAAGGGC |
| 128 | VH_CDR2_nt A3 | GCCATTAATATTAATCGTGGTACCACCTAC |
| 129 | VH_CDR2_nt A3 | GCCATTAATATTAATCGTGGTACCACCTACTATTCAGACACTGTGAAGGGC |
| 130 | VH_CDR2_nt A4 | GCCATGAATAATAATGGTGCTAGCACCTAC |
| 131 | VH_CDR2_nt A4 | GCCATGAATAATAATGGTGCTAGCACCTACTATCCAGACACTGTGAAGGGC |
| 132 | VH_CDR2_nt A5 | GCCATTAATCGTAAAGGTCATAGTACCTAC |
| 133 | VH_CDR2_nt A5 | GCCATTAATCGTAAAGGTCATAGTACCTACTATCCAGACACTGTGCAGGGC |
| 134 | VH_CDR2_nt A6 | GCCATTAATAGTAATCGTGGTACCACCTACTATCCAGACACTGTGAAGGGC |
| 135 | VH_CDR2_nt A6 and A12 | GCCATTAATAGTAATCGTGGTACCACCTAC |
| 136 | VH_CDR2_nt A7 | GCCATTAATATTAATCGTGGTACCCCCTAT |
| 137 | VH_CDR2_nt A7 | GCCATTAATATTAATCGTGGTACCCCCTATTATCCAGACACTGTGAAGGGC |
| 138 | VH_CDR2_nt A8 | GCCATTAATCCTAATGGTGGTAGTACCTAC |
| 139 | VH_CDR2_nt A8 | GCCATTAATCCTAATGGTGGTAGTACCTACTATCCAGACACTGTGAAGGGC |
| 140 | VH_CDR2_nt A9 | GCCATTAATAGTAAAGGTGGTGGCACCTAC |
| 141 | VH_CDR2_nt A9 | GCCATTAATAGTAAAGGTGGTGGCACCTACTATCCAGACACTGTGAGGGGC |
| 142 | VH_CDR2_nt A10 | GCCATTAATAATAGAGGTGGTGGCACCTAC |
| 143 | VH_CDR2_nt A10 | GCCATTAATAATAGAGGTGGTGGCACCTACTATCCAGACACTGTGAGGGGC |
| 144 | VH_CDR2_nt A11 | GCCATTAATCCTAATGGTGGTACTACCTAC |
| 145 | | GCCATTAATCCTAATGGTGGTACTACCTACTACAATGAGAAATTCAAGGGC |
| 146 | VH_CDR2_nt A12 | GCCATTAATAGTAATCGTGGTACCACCTACTATTCAGACACTGTGAAGGGC |
| 147 | VH_CDR2_nt A14 | GAGATTTTACCTGGAATTGGTAATACTAAC |
| 148 | VH_CDR2_nt A14 | GAGATTTTACCTGGAATTGGTAATACTAACTACAATGAGAAATTCAAGGGC |
| 149 | VH_CDR3_aa A1 and A3 | SRHRYSDYDYAMDY |
| 150 | VH_CDR3_aa A2 | VRHRYTNYDYAMDY |
| 151 | VH_CDR3_aa A4 | VRHNNYVDYAMDY |
| 152 | VH_CDR3_aa A5 | VRLDDNYYFFDY |
| 153 | VH_CDR3_aa A6 | VRHRYNNYDYAMDY |
| 154 | VH_CDR3_aa A7 | VRHRNSNNDYAMDY |
| 155 | VH_CDR3_aa A8 and | ARLPWSPYTLDY |

FIG 14x

| SEQ ID No. | Description | Sequence |
|---|---|---|
| | A11 | |
| 156 | VH_CDR3_aa A9 | VSHGDNKYFYAMDY |
| 157 | VH_CDR3_aa A10 | VRHDNLNYDYAMDS |
| 158 | VH_CDR3_aa A12 | TRHRYSDYDYAMDY |
| 159 | VH_CDR3_aa A13 | VRHRYIDYDYAMDY |
| 160 | VH_CDR3_aa A14 | SGGYSTVYWYFDV |
| 161 | VH_CDR3_nt A1 and A3 | TCAAGACACCGCTATAGTGACTACGACTATGCTATGGACTAC |
| 162 | VH_CDR3_nt A2 | GTAAGACACCGCTATACTAACTACGACTATGCTATGGACTAC |
| 163 | VH_CDR3_nt A4 | GTAAGACATAATAACTACGTTGACTATGCTATGGACTAT |
| 164 | VH_CDR3_nt A5 | GTAAGACTTGACGATAACTACTACTTCTTTGACTAC |
| 165 | VH_CDR3_nt A6 | GTAAGACACCGCTATAATAACTACGACTATGCTATGGACTAC |
| 166 | VH_CDR3_nt A7 | GTAAGACACCGCAATAGTAACAACGACTATGCTATGGACTAC |
| 167 | VH_CDR3_nt A8 and A11 | GCAAGACTCCCATGGTCCCCCTATACTTTGGACTAC |
| 168 | VH_CDR3_nt A9 | GTAAGCCATGGGGATAATAAGTACTTTTATGCTATGGACTAC |
| 169 | VH_CDR3_nt A10 | GTGAGACATGACAATCTTAACTATGACTATGCTATGGACTCC |
| 170 | VH_CDR3_nt A12 | ACAAGACACCGCTATAGTGACTACGACTATGCTATGGACTAC |
| 171 | VH_CDR3_nt A13 | GTAAGACACCGCTATATTGACTACGACTATGCTATGGACTAC |
| 172 | VH_CDR3_nt A14 | GCAAGTGGGGGGTATAGTACCGTCTATTGGTATTTTGATGTC |
| 173 | VK_CDR1_aa A1 | KASQDINSYLNW |
| 174 | VK_CDR1_aa A10 | KASQDIYSYLSW |
| 175 | VK_CDR1_aa A11 | MTSTDIDDALNW |
| 176 | VK_CDR1_aa A13 | KSSQDINSYLSW |
| 177 | VK_CDR1_aa A14 | QSLLNSRTRKNY |
| 178 | VK_CDR1_aa A14 | KSSQSLLNSRTRKNYLA |
| 179 | VK_CDR1_aa A2, A3, A4, A5, A6, A7, A9 and A12 | KASQDINSYLSW |
| 180 | VK_CDR1_aa A8 | ITNTDIDDAMNW |
| 181 | VK_CDR1_nt A1 | AAGGCGAGTCAGGACATTAATAGCTATTTAAACTGG |
| 182 | VK_CDR1_nt A2, A3, A4, A5, A7, A9 and A12 | AAGGCGAGTCAGGACATTAATAGCTATTTAAGCTGG |
| 183 | VK_CDR1_nt A6 | AAGGCGAGTCAAGACATTAATAGCTATTTAAGCTGG |

FIG 14y

| SEQ ID No. | Description | Sequence |
|---|---|---|
| 184 | VK_CDR1_nt A8 | ATAACCAACACTGATATTGATGATGCTATGAACTGG |
| 185 | VK_CDR1_nt A10 | AAGGCGAGTCAGGACATTTATAGCTATTTAAGCTGG |
| 186 | VK_CDR1_nt A11 | ATGACCAGCACTGATATTGATGATGCTCTGAACTGG |
| 187 | VK_CDR1_nt A13 | AAGTCGAGTCAGGACATTAATAGCTATTTAAGTTGG |
| 188 | VK_CDR1_nt A14 | CAGAGTCTGCTCAACAGTAGAACCCGAAAGAACTAC |
| 189 | VK_CDR1_nt A14 | AAATCCAGTCAGAGTCTGCTCAACAGTAGAACCCGAAAGAACTACTTGGCT |
| 190 | VK_CDR2_aa A1, A2, A3, A9, A10, A12 and A13 | RANRLVD |
| 191 | VK_CDR2_aa A1, A2, A9 and A10 | TLIYRANRLV |
| 192 | VK_CDR2_aa A3 | TLIHRANRLV |
| 193 | VK_CDR2_aa A4 | TLIYRANKLV |
| 194 | VK_CDR2_aa A4 | RANKLVD |
| 195 | VK_CDR2_aa A5 | TLIYRAKRLI |
| 196 | VK_CDR2_aa A5 | RAKRLID |
| 197 | VK_CDR2_aa A6 | TLTYRANRLV |
| 198 | VK_CDR2_aa A6 | RANRLVE |
| 199 | VK_CDR2_aa A7 | TLIYRANRLI |
| 200 | VK_CDR2_aa A7 | RANRLID |
| 201 | VK_CDR2_aa A8 | LLISEGNTLR |
| 202 | VK_CDR2_aa A8 | EGNTLRP |
| 203 | VK_CDR2_aa A11 | LLISEGNSLR |
| 204 | VK_CDR2_aa A11 | EGNSLRP |
| 205 | VK_CDR2_aa A12 | TLTHRANRLV |
| 206 | VK_CDR2_aa A13 | TLIFRANRLV |
| 207 | VK_CDR2_aa A14 | KLLIYWTSTRE |
| 208 | VK_CDR2_aa A14 | WTSTRES |
| 209 | VK_CDR2_nt A1, A2, A3, A9, A10, A12 and A13 | CGTGCAAACAGATTGGTAGAT |
| 210 | VK_CDR2_nt A1, A2, A9 and A10 | ACCCTGATCTATCGTGCAAACAGATTGGTA |
| 211 | | CCCTCATCTATCCTCCAAACACATTCCTACA |
| 212 | VK_CDR2_nt A3 | ACCCTGATCCATCGTGCAAACAGATTGGTA |
| 213 | VK_CDR2_nt A4 | ACCCTGATCTATCGTGCAAACAAATTGGTA |
| 214 | VK_CDR2_nt A4 | CGTGCAAACAAATTGGTAGAT |
| 215 | VK_CDR2_nt A5 | ACCCTGATCTATCGTGCAAAGAGATTGATA |
| 216 | VK_CDR2_nt A5 | CGTGCAAAGAGATTGATAGAT |
| 217 | VK_CDR2_nt A6 | ACCCTGACCTATCGTGCAAACAGATTGGTA |
| 218 | VK_CDR2_nt A6 | CGTGCAAACAGATTGGTAGAA |

FIG 14z

| SEQ ID No. | Description | Sequence |
|---|---|---|
| 219 | VK_CDR2_nt A7 | ACCCTGATCTATCGTGCAAACAGATTGATA |
| 220 | VK_CDR2_nt A7 | CGTGCAAACAGATTGATAGAT |
| 221 | VK_CDR2_nt A8 | CTCCTTATTTCAGAAGGCAATACTCTTCGT |
| 222 | VK_CDR2_nt A8 | GAAGGCAATACTCTTCGTCCT |
| 223 | VK_CDR2_nt A11 | CTCCTTATTTCAGAAGGCAATAGTCTTCGT |
| 224 | VK_CDR2_nt A11 | GAAGGCAATAGTCTTCGTCCT |
| 225 | VK_CDR2_nt A12 | ACCCTGACCCATCGTGCAAACAGATTGGTA |
| 226 | VK_CDR2_nt A13 | ACCCTGATCTTTCGTGCAAACAGATTGGTA |
| 227 | VK_CDR2_nt A14 | AAACTGCTGATCTACTGGACATCCACTAGGGAA |
| 228 | VK_CDR2_nt A14 | TGGACATCCACTAGGGAATCT |
| 229 | VK_CDR3_aa A1, A2, A3, A4, A5, A6, A9, A10, A12 and A13 | LQYDEFPYT |
| 230 | VK_CDR3_aa A7 | LQYDEFPFT |
| 231 | VK_CDR3_aa A8 | LQTDNLPLT |
| 232 | VK_CDR3_aa A11 | LQSDNLPLT |
| 233 | VK_CDR3_aa A14 | KQSYDLPWT |
| 234 | VK_CDR3_nt A1, A3, A4, A6, A9, A10, A12 and A13 | CTACAGTATGATGAGTTTCCGTACACG |
| 235 | VK_CDR3_nt A2 | CTACAGTATGATGAATTTCCGTACACG |
| 236 | VK_CDR3_nt A5 | CTACAGTATGATGAGTTTCCTTACACG |
| 237 | VK_CDR3_nt A7 | CTACAGTATGATGAGTTTCCATTCACG |
| 238 | VK_CDR3_nt A8 | TTGCAAACTGATAACTTGCCTCTCACG |
| 239 | VK_CDR3_nt A11 | TTGCAAAGTGATAACTTGCCTCTCACG |
| 240 | VK_CDR3_nt A14 | AAGCAATCTTATGATCTTCCGTGGACG |
| 241 | VH_CDR2_aa A12 | AINSNRGTTYYSDTVKG |
| 242 | VH_CDR2_nt A11 | GCCATTAATCCTAATGGTGGTACTACCTACTATCCAGACACTGTGAAGGGC |
| 243 | VK14-111 (GenBank V01563) n.t. 813-848 | AAGGCGAGTCAGGACATTAATAGCTATTTAAGCTGG |
| 244 | VK14-111 (GenBank V01563) n.t. 879-908 | ACCCTGATCTATCGTGCAAACAGATTGGTAGAT |
| 245 | VK14-111 (GenBank V01563) n.t. 879-908 | ACCCTGATCTATCGTGCAAACAGATTGGTA |
| 246 | VK14-111 (GenBank V01563) n.t. 1008-1034 | CTACAGTATGATGAGTTTCCTCCCACA |
| 247 | VH5-12 (GenBank AJ851868) n.t. 926028-926063 | GCCTCTGGATTCGCTTTCAGTAGCTATGACATGTCT |
| 248 | VH5-12 (GenBank AJ851868) n.t. 926022-926063 | GGATTCGCTTTCAGTAGCTATGACATGTCT |
| 249 | VH5-12 (GenBank AJ851868) n.t. 926106-926135 | TACATTAGTAGTGGTGGTGGTAGCACCTAC |

FIG 14aa

| SEQ ID No. | Description | Sequence |
|---|---|---|
| 250 | VH5-12 (GenBank AJ851868) n.t. 926106-926156 | TACATTAGTAGTGGTGGTGGTAGCACCTACTATCCAGACACTGTGAAGGGC |
| 251 | VH5-6 (GenBank AJ851868) n.t. 983326-983361 | GCCTCTGGATTCACTTTCAGTAGCTATTACATGTCT |
| 252 | VH5-6 (GenBank AJ851868) n.t. 983320-983361 | GGATTCACTTTCAGTAGCTATTACATGTCT |
| 253 | VH5-6 (GenBank AJ851868) n.t. 983404-983433 | GCCATTAATAGTAATGGTGGTAGCACCTAC |
| 254 | VH5-6 (GenBank AJ851868) n.t. 983404-983454 | GCCATTAATAGTAATGGTGGTAGCACCTACTATCCAGACACTGTGAAGGGC |
| 255 | VK17-121 (GenBank AJ231258) n.t. 594-629 | ATAACCAGCACTGATATTGATGATGATATGAACTGG |
| 256 | VK17-121 (GenBank AJ231258) n.t. 588-629 | GGCTACACATTCACTGGCTACTGGATAGAG |
| 257 | VK17-121 (GenBank AJ231258) n.t. 660-689 | CTCCTTATTTCAGAAGGCAATACTCTTCGT |
| 258 | VK17-121 (GenBank AJ231258) n.t. 660-692 | CTCCTTATTTCAGAAGGCAATACTCTTCGTCCT |
| 259 | VK17-121 (GenBank AJ231258) n.t. 789-815 | TTGCAAAGTGATAACTTGCCTCTCACA |
| 260 | VK8-21 (GenBank Y15982) n.t. 430-465 | CAGAGTCTGCTCAACAGTAGAACCCGAAAGAACTAC |
| 261 | VK8-21 (GenBank Y15982) n.t. 421-471 | AAATCCAGTCAGAGTCTGCTCAACAGTAGAACCCGAAAGAACTACTTGGCT |
| 262 | VK8-21 (GenBank Y15982) n.t. 502-534 | AAACTGCTGATCTACTGGGCATCCACTAGGGAA |
| 263 | VK8-21 (GenBank Y15982) n.t. 514-537 | TGGGCATCCACTAGGGAATCT |
| 264 | VK8-21 (GenBank Y15982) n.t. 634-658 | AAGCAATCTTATAATCTTCCCACAGTG |
| 265 | VH1-9 (GenBank AC090843) n.t. 86263-86299 | GCTACTGGCTACACATTCACTGGCTACTGGATAGAG |
| 266 | VH1-9 (GenBank AC090843) n.t. 86341-86370 | GAGATTTTACCTGGAAGTGGTAGTACTAAC |
| 267 | VH1-9 (GenBank AC090843) n.t. 86341-86391 | GAGATTTTACCTGGAAGTGGTAGTACTAACTACAATGAGAAGTTCAAGGGC |
| 268 | A1_HuVH_aa | METDTLLLWVLLLWVPGSTGEVQLVESGGGLVQPGGSLRLSCAASGFTFSSYAMSWVRQAPGKGLEWVAAINFNRGTTYYSDTVKGRFTISRDNAK |

FIG 14bb

| SEQ ID No. | Description | Sequence |
|---|---|---|
|  |  | NSLYLQMNSLRAEDTAVYYCSRHRYSDYDYAM DYWGQGTMVTVSSASTKGPSVFPLAPSSKSTSG GTAALGCLVKDYFPEPVTVSWNSGALTSGVHT FPAVLQSSGLYSLSSVVTVPSSSLGTQTYICNVN HKPSNTKVDKRVEPKSCDKTHTCPPCPAPELLG GPSVFLFPPKPKDTLMISRTPEVTCVVVDVSHE DPEVKFNWYVDGVEVHNAKTKPREEQYNSTYR VVSVLTVLHQDWLNGKEYKCKVSNKALPAPIE KTISKAKGQPREPQVYTLPPSREEMTKNQVSLT CLVKGFYPSDIAVEWESNGQPENNYKTTPPVLD SDGSFFLYSKLTVDKSRWQQGNVFSCSVMHEA LHNHYTQKSLSLSPGK |
| 269 | A1_HuVH_nt | ATGGAAACCGACACCCTGCTGCTGTGGGTCC TGCTGCTCTGGGTGCCAGGCTCTACCGGCGA GGTGCAGCTGGTGGAATCCGGCGGAGGCCT GGTCCAGCCTGGCGGATCCCTGAGACTGTCC TGTGCCGCCTCCGGCTTCACCTTCTCCAGCT ACGCCATGTCCTGGGTCCGACAGGCTCCAGG CAAGGGCCTGGAATGGGTGGCCGCCATCAAC TTCAACCGGGGCACCACCTACTACTCCGACA CCGTGAAGGGCCGGTTTACCATCTCCCGGGA CAACGCCAAGAACTCCCTGTACCTGCAGATG AACTCCCTGCGGGCCGAGGACACCGCCGTGT ACTACTGCTCCCGGCACCGGTACTCCGACTA CGACTACGCCATGGACTACTGGGGCCAGGGC ACCATGGTCACCGTGTCCTCCGCCTCCACCA AGGGCCCCTCCGTGTTTCCTCTGGCCCCCTC CAGCAAGTCTACCTCTGGCGGCACCGCCGCA CTGGGCTGCCTGGTCAAGGACTATTTCCCCG AGCCCGTGACCGTGTCCTGGAACTCTGGCGC CCTGACCTCCGGCGTGCACACCTTTCCAGCC GTGCTGCAGTCCTCCGGCCTGTACTCCCTGT CCTCCGTCGTGACCGTGCCCTCCAGCTCTCT GGGCACCCAGACCTACATCTGCAACGTGAAC CACAAGCCCTCCAACACCAAGGTGGACAAGC GGGTGGAACCCAAGTCCTGCGACAAGACCCA CACCTGTCCCCCCTGCCCTGCCCCTGAACTG CTGGGAGGACCTTCCGTGTTCCTGTTCCCTC CAAAGCCCAAGGACACCCTGATGATCTCCCG GACCCCCGAAGTGACCTGCGTGGTGGTGGAC GTGTCCCACGAGGACCCTGAAGTGAAGTTCA ATTGGTACGTGGACGGCGTGGAAGTGCACAA TGCCAAGACCAAGCCCAGAGAGGAACAGTAC AACTCCACCTACCGGGTGGTGTCCGTGCTGA CCGTGCTGCACCAGGACTGGCTGAACGGCAA AGAGTACAAGTGCAAGGTCTCCAACAAGGCT CTGCCTGCCCCCATCGAAAAGACCATCTCCA AGGCCAAGGGGCAGCCTCGCGAGCCTCAGGT |

FIG 14cc

| SEQ ID No. | Description | Sequence |
|---|---|---|
|  |  | GTACACACTGCCCCCTAGCCGGGAAGAGATGACCAAGAACCAGGTGTCCCTGACCTGTCTGGTCAAAGGCTTCTACCCCTCCGATATCGCCGTGGAATGGGAGTCCAACGGCCAGCCCGAGAACAACTACAAGACCACCCCCCCTGTGCTGGACTCCGACGGCTCATTCTTCCTGTACTCCAAGCTGACCGTGGACAAGTCCCGGTGGCAGCAGGGCAACGTGTTCTCCTGCTCCGTGATGCACGAGGCCCTGCACAACCACTACACCCAGAAGTCCCTGTCCCTGAGCCCCGGCAAGTGATAGTCTAGA |
| 270 | A1_HuVK_aa | METDTLLLWVLLLWVPGSTGDIQMTQSPSSLSASVGDRVTITCKASQDINSYLNWFQQKPGKAPKSLIYRANRLVDGVPSKFSGSGSGHDYTLTISSLQPEDFATYYCLQYDEFPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECSARQSTPFVCEYQGQSSDLP |
| 271 | A1_HuVK_nt | ATGGAAACCGACACCCTGCTGCTGTGGGTCCTGCTGCTCTGGGTGCCAGGCTCCACCGGCGACATCCAGATGACCCAGTCCCCCTCCAGCCTGTCCGCCTCTGTGGGCGACAGAGTGACCATCACATGCAAGGCCTCCCAGGACATCAACTCCTACCTGAACTGGTTCCAGCAGAAGCCCGGCAAGGCCCCCAAGTCCCTGATCTACCGGGCCAACCGGCTGGTGGACGGCGTGCCCTCCAAGTTCTCCGGCTCTGGCTCCGGCCACGACTATACCCTGACCATCTCCAGCCTGCAGCCCGAGGACTTCGCCACCTACTACTGCCTGCAGTACGACGAGTTCCCCTACACCTTCGGCCAGGGCACCAAGCTGGAAATCAAGCGGACCGTGGCCGCTCCCTCCGTGTTCATCTTCCCACCCTCCGACGAGCAGCTGAAGTCCGGCACCGCCTCCGTCGTGTGCCTGCTGAACAACTTCTACCCCGCGAGGCCAAGGTGCAGTGGAAGGTGGACAACGCCCTGCAGTCCGGCAACTCCCAGGAATCCGTCACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCCAGCCCCGTGACCAAGTCCTTCAACCGGGGCGAGTGCTCTGCCCGGCAGTCCACCCCTTTCGTGTGCGAGTACCAGGGCCAGTCCTCCGACCTGCCCTGATAGTCTAGAGGGCCCTATTCTATAGTGTCACCTAAATG |
| 272 | Tyrosine-protein kinase transmembrane receptor ROR1 (ECD | QETELSVSAELVPTSSWNISSELNKDSYLTLDEPMNNITTSLGQTAELHCKVSGNPPPTIRWFKNDAPVVQEPRRLSFRSTIYGSRLRIRNLDTTDTGYFQ |

FIG 14dd

| SEQ ID No. | Description | Sequence |
|---|---|---|
| | a.a 30-407) | CVATNGKEVVSSTGVLFVKFGPPPTASPGYSDEYEEDGFCQPYRGIACARFIGNRTVYMESLHMQGEIENQITAAFTMIGTSSHLSDKCSQFAIPSLCHYAFPYCDETSSVPKPRDLCRDECEILENVLCQTEYIFARSNPMILMRLKLPNCEDLPQPESPEAANCIRIGIPMADPINKNHKCYNSTGVDYRGTVSVTKSGRQCQPWNSQYPHTHTFTALRFPELNGGHSYCRNPGNQKEAPWCFTLDENFKSDLCDIPACDSKDSKEKNKMEILYI |
| 273 | | CTACACTATCATCAATTTCCCTACACC |
| 274 | | AACCCCACTCACCACATTAATACCTATTTAACCTCC |
| 275 | Amino acid consensus sequence heavy chain CDR1 | G-(F/Y)-(T/S/A)-F-S-(S/T/N/P/R)-(Y/N)-(A/G/D/W)-(M/I)-(S/E) |
| 276 | Amino acid consensus sequence heavy chain CDR1 without A14 | G-(F/Y)-(T/S/A)-F-S-(S/T/N/P/R)-(Y/N)-(A/G/D)-M-S |
| 277 | Amino acid consensus sequence heavy chain CDR2 | (A/G/E)-(I/M)-(N/L)-(F/S/I/N/R/P)-(N/K/R/G)-(R/G/I)-(G/H/A)-(T/S/G/N)-(T/P)-(Y/N)-Y-(S/P/N)-(D/E)-(T/K)-(V/F)-(K/Q/R)-G |
| 278 | Amino acid consensus sequence heavy chain CDR2 without A14 | (A/G)-(I/M)-(N)-(F/S/I/N/R/P)-(N/K/R)-(R/G)-(G/H/A)-(T/S/G)-(T/P)-Y-Y-(S/P)-D-T-V/-(K/Q/R)-G |
| 279 | Amino acid consensus sequence heavy chain CDR3 | (S/V/T/A)-(R/S)-(H/L/G)-(R/N/D/P/G)-(Y/N/D/W)-(S/T/Y/N/L)-(D/N/V/Y/P/K/T)-(Y/D/N)-(D/Y/F/T)-(Y/F/L/*)-(A/*)-(M/*)-D-(Y/S) |
| 280 | Amino acid consensus sequence heavy chain CDR3 without A14 | (S/V/T/A)-(R/S)-(H/L)-(R/N/D/P/G)-(Y/N/D/W)-(S/T/Y/N/L)-(D/N/V/Y/P/K)-(Y/D)-(D/Y/F/T)-(Y/F/L)-A-M-D-Y |
| 281 | Amino acid consensus sequence light chain CDR1 | (K/I/M)-(A/T/S)-(S/N)-(Q/T)-(D/S)-(I/L)-(N/D/Y/L)-(S/D/N)-(Y/A/S)-(L/M/R)-(N/S/T)-(W/R) |
| 282 | Amino acid consensus sequence light chain CDR1 without A14 | (K/I/M)-(A/T)-(S/N)-(Q/T)-D-I-(N/D/Y)-(S/D)-(Y/A)-(L/M)-(N/S)-W |
| 283 | Amino acid consensus sequence light chain CDR2 | (R/E/P)-(A/G/K)-(N/K/L)-(R/K/T/S/L)-(L/I)-(V/I/R/Y)-(D/E/P/W)-(G/T) |
| 284 | Amino acid consensus sequence light chain CDR2 without A14 | (R/E)-(A/G)-(N/K)-(R/K/T/S)-I-(V/I/R)-(D/E/P)-G |
| 285 | Amino acid consensus sequence light chain CDR3 | (L/K)-Q-(Y/T/S)-D-(E/N/L)-(F/L)-P-(Y/L/F/W)-T |
| 286 | Amino acid consensus sequence light chain | L-Q-(Y/T/S)-D-(E/N)-(F/L)-P-(Y/L/F)-T |

FIG 14ee

| SEQ ID No. | Description | Sequence |
|---|---|---|
| | CDR3 without A14 | |
| 287 | Full length isoform 1 human ROR1 identifier Q01973-1 | MHRPRRRGTR PPLLALLAAL LLAARGAAAQ ETELSVSAEL VPTSSWNISS ELNKDSYLTL DEPMNNITTS LGQTAELHCK VSGNPPPTIR WFKNDAPVVQ EPRRLSFRST IYGSRLRIRN LDTTDTGYFQ CVATNGKEVV SSTGVLFVKF GPPPTASPGY SDEYEEDGFC QPYRGIACAR FIGNRTVYME SLHMQGEIEN QITAAFTMIG TSSHLSDKCS QFAIPSLCHY AFPYCDETSS VPKPRDLCRD ECEILENVLC QTEYIFARSN PMILMRLKLP NCEDLPQPES PEAANCIRIG IPMADPINKN HKCYNSTGVD YRGTVSVTKS GRQCQPWNSQ YPHTHTFTAL RFPELNGGHS YCRNPGNQKE APWCFTLDEN FKSDLCDIPA CDSKDSKEKN KMEILYILVP SVAIPLAIAL LFFFICVCRN NQKSSSAPVQ RQPKHVRGQN VEMSMLNAYK PKSKAKELPL SAVRFMEELG ECAFGKIYKG HLYLPGMDHA QLVAIKTLKD YNNPQQWTEF QQEASLMAEL HHPNIVCLLG AVTQEQPVCM LFEYINQGDL HEFLIMRSPH SDVGCSSDED GTVKSSLDHG DFLHIAIQIA AGMEYLSSHF FVHKDLAARN ILIGEQLHVK ISDLGLSREI YSADYYRVQS KSLLPIRWMP PEAIMYGKFS SDSDIWSFGV VLWEIFSFGL QPYYGFSNQE VIEMVRKRQL LPCSEDCPPR MYSLMTECWN EIPSRRPRFK DIHVRLRSWE GLSSHTSSTT PSGGNATTQT TSLSASPVSN LSNPRYPNYM FPSQGITPQG QIAGFIGPPI PQNQRFIPIN GYPIPPGYAA FPAAHYQPTG PPRVIQHCPP PKSRSPSSAS GSTSTGHVTS LPSSGSNQEA NIPLLPHMSI PNHPGGMGIT VFGNKSQKPY KIDSKQASLL GDANIHGHTE SMISAEL |
| 287 | Human ROR1 isoform 2 identifier Q01973-2 | M LFEYINQGDL HEFLIMRSPH SDVGCSSDED GTVKSSLDHG DFLHIAIQIAAGMEYLSSHF FVHKDLAARN ILIGEQLHVK ISDLGLSREI YSADYYRVQS KSLLPIRWMPPEAIMYGKFS SDSDIWSFGV VLWEIFSFGL QPYYGFSNQE VIEMVRKRQL LPCSEDCPPR MYSLMTECWN EIPSRRPRFK DIHVRLRSWE GLSSHTSSTT PSGGNATTQT TSLSASPVSN LSNPRYPNYM FPSQGITPQG QIAGFIGPPI PQNQRFIPIN GYPIPPGYAA FPAAHYQPTG PPRVIQHCPP PKSRSPSSAS GSTSTGHVTS LPSSGSNQEA NIPLLPHMSI PNHPGGMGIT VFGNKSQKPY KIDSKQASLL GDANIHGHTE SMISAEL |

CDR Sequence List Summary

| Antibody | VH ||||| VK |||||
| --- | --- | --- | --- | --- | --- | --- | --- | --- | --- | --- |
| | aa CDR1 | aa CDR2 | aa CDR3 | nt CDR1 | nt CDR2 | nt CDR3 | aa CDR1 | aa CDR2 | aa CDR3 | nt CDR1 | nt CDR2 | nt CDR3 |
| A1 | 57, 58 | 99, 100 | 149 | 78, 79 | 124, 125 | 161 | 173 | 190, 191 | 229 | 181 | 209, 210 | 234 |
| A2 | 59, 60 | 101, 102 | 150 | 80, 81 | 126, 127 | 162 | 179 | 190, 191 | 229 | 182 | 209, 210 | 235 |
| A3 | 58, 61 | 103, 104 | 149 | 79, 82 | 128, 129 | 161 | 179 | 190, 192 | 229 | 182 | 209, 212 | 234 |
| A4 | 62, 63 | 105, 106 | 151 | 83, 84 | 130, 131 | 163 | 179 | 193, 194 | 229 | 182 | 213, 214 | 234 |
| A5 | 64, 65 | 107, 108 | 152 | 85, 86 | 132, 133 | 164 | 179 | 195, 196 | 229 | 182 | 215, 216 | 236 |
| A6 | 66, 67 | 109, 110 | 153 | 87, 88 | 134, 135 | 165 | 179 | 197, 198 | 229 | 183 | 217, 218 | 234 |
| A7 | 68, 69 | 111, 112 | 154 | 89, 90 | 136, 137 | 166 | 179 | 199, 200 | 230 | 182 | 219, 220 | 237 |
| A8 | 58, 61 | 113, 114 | 155 | 79, 82 | 138, 139 | 167 | 180 | 201, 202 | 231 | 184 | 221, 222 | 238 |
| A9 | 70, 71 | 115, 116 | 156 | 91, 92 | 140, 141 | 168 | 179 | 190, 191 | 229 | 182 | 209, 210 | 234 |
| A10 | 72, 73 | 117, 118 | 157 | 93, 94 | 142, 143 | 169 | 174 | 190, 191 | 229 | 185 | 209, 210 | 234 |
| A11 | 74, 75 | 119, 120 | 155 | 95, 96 | 144, 267 | 167 | 175 | 203, 204 | 232 | 186 | 223, 224 | 239 |
| A12 | 58, 61 | 110, 266 | 158 | 79, 82 | 135, 146 | 170 | 179 | 190, 205 | 229 | 182 | 209, 225 | 234 |
| A13 | 58, 61 | 101, 102 | 159 | 79, 82 | 126, 127 | 171 | 176 | 190, 206 | 229 | 187 | 209, 226 | 234 |
| A14 | 76, 77 | 122, 123 | 160 | 97, 98 | 147, 148 | 172 | 177, 178 | 207, 208 | 233 | 188, 189 | 227, 228 | 240 |

Figure 15

SEQUENCE LISTING

<160> NUMBER OF SEQ ID NOS: 288

<210> SEQ ID NO 1
<211> LENGTH: 244
<212> TYPE: PRT
<213> ORGANISM: Mus musculus

<400> SEQUENCE: 1

Met Lys Gln Ser Thr Ile Ala Leu Ala Leu Leu Pro Leu Leu Phe Thr
1               5                   10                  15

Pro Val Ala Lys Ala Glu Val Lys Leu Val Glu Ser Gly Gly Gly Leu
            20                  25                  30

Val Arg Pro Gly Gly Ser Leu Lys Leu Ser Cys Ala Val Ser Gly Phe
        35                  40                  45

Thr Phe Ser Ser Tyr Ala Met Ser Trp Val Arg Gln Thr Pro Glu Lys
    50                  55                  60

Arg Leu Glu Trp Val Ala Ala Ile Asn Phe Asn Arg Gly Thr Thr Tyr
65                  70                  75                  80

Tyr Ser Asp Thr Val Lys Gly Arg Phe Thr Ile Ser Arg Asp Asn Ala
                85                  90                  95

Lys Asn Thr Leu Tyr Leu Gln Leu Ser Ser Leu Arg Ser Glu Asp Thr
            100                 105                 110

Ala Phe Tyr Tyr Cys Ser Arg His Arg Tyr Ser Asp Tyr Asp Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 2
<211> LENGTH: 244
<212> TYPE: PRT
<213> ORGANISM: Mus musculus

<400> SEQUENCE: 2

Met Lys Gln Ser Thr Ile Ala Leu Ala Leu Leu Pro Leu Leu Phe Thr
1               5                   10                  15

Pro Val Ala Lys Ala Glu Val Gln Leu Leu Glu Thr Gly Gly Gly Leu
            20                  25                  30

Val Lys Pro Gly Gly Ser Leu Lys Leu Ser Cys Ala Ala Ser Gly Phe
        35                  40                  45

Thr Phe Ser Thr Tyr Ala Met Ser Trp Val Arg Gln Thr Pro Glu Lys
    50                  55                  60

Arg Leu Glu Trp Val Ala Gly Ile Asn Ser Asn Arg Gly Thr Thr Tyr
65                  70                  75                  80

```
Tyr Pro Asp Thr Val Lys Gly Arg Phe Thr Ile Ser Arg Asp Asn Ala
                85                  90                  95

Lys Asn Thr Leu Ser Leu Gln Met Thr Ser Leu Arg Ser Glu Asp Thr
            100                 105                 110

Ala Leu Tyr Tyr Cys Val Arg His Arg Tyr Thr Asn Tyr Asp Tyr Ala
        115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 3
<211> LENGTH: 244
<212> TYPE: PRT
<213> ORGANISM: Mus musculus

<400> SEQUENCE: 3

Met Lys Gln Ser Thr Ile Ala Leu Ala Leu Leu Pro Leu Leu Phe Thr
1               5                   10                  15

Pro Val Ala Lys Ala Asp Val Met Leu Val Glu Ser Gly Gly Gly Leu
            20                  25                  30

Val Lys Pro Gly Gly Ser Leu Lys Leu Ser Cys Ala Ala Ser Gly Phe
        35                  40                  45

Thr Phe Ser Ser Tyr Ala Met Ser Trp Val Arg Gln Thr Pro Glu Lys
50                  55                  60

Arg Leu Glu Trp Val Ala Ala Ile Asn Ile Asn Arg Gly Thr Thr Tyr
65                  70                  75                  80

Tyr Ser Asp Thr Val Lys Gly Arg Phe Thr Ile Ser Arg Asp Asn Ala
                85                  90                  95

Lys Asn Thr Leu Tyr Leu Gln Leu Ser Ser Leu Arg Ser Glu Asp Thr
            100                 105                 110

Ala Leu Tyr Tyr Cys Ser Arg His Arg Tyr Ser Asp Tyr Asp Tyr Ala
        115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205
```

```
Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys
```

<210> SEQ ID NO 4
<211> LENGTH: 243
<212> TYPE: PRT
<213> ORGANISM: Mus musculus

<400> SEQUENCE: 4

```
Met Lys Gln Ser Thr Ile Ala Leu Ala Leu Leu Pro Leu Leu Phe Thr
1               5                   10                  15

Pro Val Ala Lys Ala Glu Val Lys Leu Val Glu Ser Gly Gly Gly Leu
            20                  25                  30

Val Lys Pro Gly Gly Ser Leu Lys Leu Ser Cys Ala Ala Ser Gly Phe
        35                  40                  45

Thr Phe Ser Asn Tyr Gly Met Ser Trp Val Arg Gln Thr Pro Glu Arg
    50                  55                  60

Arg Leu Glu Trp Val Ala Met Asn Asn Asn Gly Ala Ser Thr Tyr
65                  70                  75                  80

Tyr Pro Asp Thr Val Lys Gly Arg Phe Thr Ile Ser Arg Asp Asn Ala
                85                  90                  95

Lys Asn Thr Leu Tyr Leu Gln Met Ser Ser Leu Arg Ser Glu Asp Thr
            100                 105                 110

Ala Leu Tyr Phe Cys Val Arg His Asn Asn Tyr Val Asp Tyr Ala Met
        115                 120                 125

Asp Tyr Trp Gly Gln Gly Thr Ser Val Thr Val Ser Ser Ala Lys Thr
    130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
    210                 215                 220

Val Ala His Pro Ala Ser Ser Thr Lys Val Asp Lys Lys Ile Val Pro
225                 230                 235                 240

Arg Asp Cys
```

<210> SEQ ID NO 5
<211> LENGTH: 242
<212> TYPE: PRT
<213> ORGANISM: Mus musculus

<400> SEQUENCE: 5

```
Met Lys Gln Ser Thr Ile Ala Leu Ala Leu Leu Pro Leu Leu Phe Thr
1               5                   10                  15

Pro Val Ala Lys Ala Glu Val Lys Leu Val Glu Ser Gly Gly Gly Leu
            20                  25                  30

Val Lys Pro Gly Gly Ser Leu Lys Leu Ser Cys Ala Ala Ser Gly Phe
```

```
                35                  40                  45
Thr Phe Ser Asn Tyr Asp Met Ser Trp Val Arg Gln Ser Pro Glu Lys
 50                  55                  60

Arg Leu Glu Trp Val Ala Ala Ile Asn Arg Lys Gly His Ser Thr Tyr
 65                  70                  75                  80

Tyr Pro Asp Thr Val Gln Gly Arg Phe Thr Ile Ser Arg Asp Asn Ala
                 85                  90                  95

Lys Asn Thr Leu Tyr Leu Gln Met Ser Ser Leu Arg Ser Glu Asp Thr
                100                 105                 110

Ala Leu Tyr Tyr Cys Val Arg Leu Asp Asp Asn Tyr Tyr Phe Phe Asp
                115                 120                 125

Tyr Trp Gly Gln Gly Thr Thr Leu Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
                195                 200                 205

Thr Val Pro Ser Ser Thr Trp Pro Ser Glu Thr Val Thr Cys Asn Val
                210                 215                 220

Ala His Pro Ala Ser Ser Thr Lys Val Asp Lys Lys Ile Val Pro Arg
225                 230                 235                 240

Asp Cys

<210> SEQ ID NO 6
<211> LENGTH: 244
<212> TYPE: PRT
<213> ORGANISM: Mus musculus

<400> SEQUENCE: 6

Met Lys Gln Ser Thr Ile Ala Leu Ala Leu Leu Pro Leu Leu Phe Thr
 1               5                  10                  15

Pro Val Ala Lys Ala Glu Val Met Leu Val Glu Ser Gly Gly Gly Leu
                20                  25                  30

Val Lys Pro Gly Gly Ser Leu Lys Leu Ser Cys Ala Ala Ser Gly Phe
                35                  40                  45

Thr Phe Ser Pro Tyr Ala Met Ser Trp Val Arg Gln Thr Pro Glu Lys
 50                  55                  60

Arg Leu Glu Trp Val Ala Ala Ile Asn Ser Asn Arg Gly Thr Thr Tyr
 65                  70                  75                  80

Tyr Pro Asp Thr Val Lys Gly Arg Phe Thr Ile Ser Arg Asp Asn Ala
                 85                  90                  95

Lys Asn Thr Leu Tyr Leu Gln Met Ser Ser Leu Arg Ser Glu Asp Thr
                100                 105                 110

Ala Phe Tyr Tyr Cys Val Arg His Arg Tyr Asn Asn Tyr Asp Tyr Ala
                115                 120                 125

Met Asp Tyr Trp Gly Gln Gly Thr Ser Val Thr Val Ser Ser Ala Lys
                130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
```

```
                165                 170                 175
Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
            195                 200                 205

Ser Val Thr Val Pro Ser Ser Thr Trp Pro Ser Glu Thr Val Thr Cys
            210                 215                 220

Asn Val Ala His Pro Ala Ser Ser Thr Lys Val Asp Lys Lys Ile Val
225                 230                 235                 240

Pro Arg Asp Cys

<210> SEQ ID NO 7
<211> LENGTH: 244
<212> TYPE: PRT
<213> ORGANISM: Mus musculus

<400> SEQUENCE: 7

Met Lys Gln Ser Thr Ile Ala Leu Ala Leu Leu Pro Leu Leu Phe Thr
1               5                   10                  15

Pro Val Ala Lys Ala Glu Val Met Leu Val Glu Ser Gly Gly Gly Leu
            20                  25                  30

Val Lys Pro Gly Gly Ser Leu Lys Ile Ser Cys Ala Ala Ser Gly Phe
        35                  40                  45

Ser Phe Ser Ser Tyr Ala Met Ser Trp Val Arg Gln Thr Pro Glu Lys
    50                  55                  60

Ser Leu Glu Trp Val Ala Ala Ile Asn Ile Asn Arg Gly Thr Pro Tyr
65                  70                  75                  80

Tyr Pro Asp Thr Val Lys Gly Arg Phe Thr Ile Ser Arg Asp Asn Ala
                85                  90                  95

Lys Asn Thr Leu Tyr Leu Gln Met Ser Ser Leu Arg Ser Glu Asp Thr
            100                 105                 110

Ala Leu Tyr Tyr Cys Val Arg His Arg Asn Ser Asn Asn Asp Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 8
<211> LENGTH: 175
<212> TYPE: PRT
<213> ORGANISM: Mus musculus

<400> SEQUENCE: 8
```

Met Lys Gln Ser Thr Ile Ala Leu Ala Leu Leu Pro Leu Leu Phe Thr
1               5                   10                  15

Pro Val Ala Lys Ala Asp Val Gln Val Glu Ser Gly Gly Gly Leu
            20                  25                  30

Val Lys Pro Gly Gly Ser Leu Lys Leu Ser Cys Ala Ala Ser Gly Phe
        35                  40                  45

Thr Phe Ser Ser Tyr Ala Met Ser Trp Val Arg Gln Thr Pro Glu Lys
    50                  55                  60

Arg Leu Glu Trp Val Ala Ala Ile Asn Pro Asn Gly Ser Thr Tyr
65                  70                  75                  80

Tyr Pro Asp Thr Val Lys Gly Arg Phe Thr Ile Ser Arg Asp Asn Ala
                85                  90                  95

Lys Asn Thr Leu Tyr Leu Gln Met Ser Gly Leu Arg Ser Glu Asp Thr
            100                 105                 110

Ala Leu Tyr Tyr Cys Ala Arg Leu Pro Trp Ser Pro Tyr Thr Leu Asp
        115                 120                 125

Tyr Trp Gly Gln Gly Thr Ser Val Thr Val Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu
            165                 170                 175

<210> SEQ ID NO 9
<211> LENGTH: 244
<212> TYPE: PRT
<213> ORGANISM: Mus musculus

<400> SEQUENCE: 9

Met Lys Gln Ser Thr Ile Ala Leu Ala Leu Leu Pro Leu Leu Phe Thr
1               5                   10                  15

Pro Val Ala Lys Ala Glu Val Gln Leu Val Glu Thr Gly Gly Asp Leu
            20                  25                  30

Val Lys Pro Gly Gly Ser Leu Lys Leu Ser Cys Val Ala Ser Gly Phe
        35                  40                  45

Thr Phe Ser Ser Asn Ala Met Ser Trp Val Arg Gln Thr Pro Glu Lys
    50                  55                  60

Arg Leu Glu Trp Val Ala Ala Ile Asn Ser Lys Gly Gly Gly Thr Tyr
65                  70                  75                  80

Tyr Pro Asp Thr Val Arg Gly Arg Phe Thr Ile Ser Arg Asp Asn Ala
                85                  90                  95

Lys Asn Thr Leu Tyr Leu Gln Val Thr Ser Leu Arg Ser Glu Asp Thr
            100                 105                 110

Ala Leu Tyr Tyr Cys Val Ser His Gly Asp Asn Lys Tyr Phe Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
            165                 170                 175

Glu Pro Val Thr Val Thr Trp Asn Ser Gly Ser Leu Ser Ser Gly Val
                180                 185                 190

His Thr Phe Pro Ala Val Leu Gln Ser Asp Leu Tyr Thr Leu Ser Ser
            195                 200                 205

```
Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 10
<211> LENGTH: 244
<212> TYPE: PRT
<213> ORGANISM: Mus musculus

<400> SEQUENCE: 10

Met Lys Gln Ser Thr Ile Ala Leu Ala Leu Leu Pro Leu Leu Phe Thr
1               5                   10                  15

Pro Val Ala Lys Ala Glu Val Gln Leu Val Glu Thr Gly Gly Gly Leu
            20                  25                  30

Val Lys Pro Gly Gly Ser Leu Lys Leu Ser Cys Ala Ala Ser Gly Phe
        35                  40                  45

Ala Phe Ser Ser Tyr Ala Met Ser Trp Val Arg Gln Thr Pro Glu Lys
    50                  55                  60

Arg Leu Glu Trp Val Ala Ala Ile Asn Asn Arg Gly Gly Gly Thr Tyr
65                  70                  75                  80

Tyr Pro Asp Thr Val Arg Gly Arg Phe Thr Ile Ser Arg Asp Asn Ala
                85                  90                  95

Lys Asn Thr Leu Tyr Leu Gln Met Ser Ser Leu Arg Ser Ala Asp Thr
            100                 105                 110

Ala Leu Tyr Tyr Cys Val Arg His Asp Asn Leu Asn Tyr Asp Tyr Ala
        115                 120                 125

Met Asp Ser Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 11
<211> LENGTH: 242
<212> TYPE: PRT
<213> ORGANISM: Mus musculus

<400> SEQUENCE: 11

Met Lys Gln Ser Thr Ile Ala Leu Ala Leu Leu Pro Leu Leu Phe Thr
1               5                   10                  15

Pro Val Pro Lys Ala Glu Val Gln Leu Val Glu Ser Gly Gly Asp Leu
            20                  25                  30

Val Lys Pro Gly Gly Ser Leu Lys Leu Ser Cys Ala Ala Ser Gly Phe
```

```
                 35                  40                  45
Thr Phe Ser Arg Tyr Gly Met Ser Trp Val Arg Gln Thr Pro Glu Lys
             50                  55                  60

Arg Leu Glu Trp Val Ala Ala Ile Asn Pro Asn Gly Gly Thr Thr Tyr
 65                  70                  75                  80

Tyr Pro Asp Thr Val Lys Gly Arg Phe Thr Ile Ser Arg Asp Asn Ala
                 85                  90                  95

Lys Asn Thr Leu Phe Leu Gln Met Thr Gly Leu Arg Ser Glu Asp Thr
            100                 105                 110

Ala Leu Tyr Tyr Cys Ala Arg Leu Pro Trp Ser Pro Tyr Thr Leu Asp
            115                 120                 125

Tyr Trp Gly Gln Gly Thr Ser Val Ile Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
            195                 200                 205

Thr Val Pro Ser Ser Thr Trp Pro Ser Glu Thr Val Thr Cys Asn Val
        210                 215                 220

Ala His Pro Ala Ser Ser Thr Lys Val Asp Lys Lys Ile Val Pro Arg
225                 230                 235                 240

Asp Cys

<210> SEQ ID NO 12
<211> LENGTH: 244
<212> TYPE: PRT
<213> ORGANISM: Mus musculus

<400> SEQUENCE: 12

Met Lys Gln Ser Thr Ile Ala Leu Ala Leu Leu Pro Leu Leu Phe Thr
  1               5                  10                  15

Pro Val Ala Lys Ala Glu Val Gln Leu Val Glu Ser Gly Gly Gly Leu
             20                  25                  30

Val Lys Pro Gly Gly Ser Leu Lys Leu Ser Cys Ala Ala Ser Gly Phe
         35                  40                  45

Thr Phe Ser Ser Tyr Ala Met Ser Trp Val Arg Gln Thr Pro Glu Lys
     50                  55                  60

Arg Leu Glu Trp Val Ala Ala Ile Asn Ser Asn Arg Gly Thr Thr Tyr
 65                  70                  75                  80

Tyr Ser Asp Thr Val Lys Gly Arg Phe Thr Ile Ser Arg Asp Asn Ala
                 85                  90                  95

Lys Asn Thr Leu Tyr Leu Gln Met Ser Ser Leu Arg Ser Glu Asp Thr
            100                 105                 110

Ala Phe Tyr Tyr Cys Thr Arg His Arg Tyr Ser Asp Tyr Asp Tyr Ala
            115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
```

```
                        165                 170                 175
Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 13
<211> LENGTH: 244
<212> TYPE: PRT
<213> ORGANISM: Mus musculus

<400> SEQUENCE: 13

Met Lys Gln Ser Thr Ile Ala Leu Ala Leu Leu Pro Leu Leu Phe Thr
1               5                   10                  15

Pro Val Ala Lys Ala Glu Val Gln Leu Val Glu Thr Gly Gly Gly Leu
            20                  25                  30

Val Lys Pro Gly Gly Ser Leu Lys Leu Ser Cys Ala Ala Ser Gly Phe
        35                  40                  45

Thr Phe Ser Ser Tyr Ala Met Ser Trp Ile Arg Gln Thr Pro Glu Lys
    50                  55                  60

Arg Leu Glu Trp Val Ala Gly Ile Asn Ser Asn Arg Gly Thr Thr Tyr
65                  70                  75                  80

Tyr Pro Asp Thr Val Lys Gly Arg Phe Thr Ile Ser Arg Asp Asn Ala
                85                  90                  95

Lys Asn Thr Leu Tyr Leu Gln Met Asn Ser Leu Arg Ser Glu Asp Ser
            100                 105                 110

Ala Leu Tyr Tyr Cys Val Arg His Arg Tyr Ile Asp Tyr Asp Tyr Ala
        115                 120                 125

Met Asp Tyr Trp Gly Gln Gly Thr Ser Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 14
<211> LENGTH: 244
<212> TYPE: PRT
<213> ORGANISM: Mus musculus

<400> SEQUENCE: 14
```

```
Met Lys Gln Ser Thr Ile Ala Leu Ala Leu Leu Pro Leu Leu Phe Thr
1               5                   10                  15

Pro Val Ala Lys Ala Gln Val Gln Leu Lys Gln Ser Gly Ala Glu Leu
            20                  25                  30

Val Lys Pro Gly Ala Ser Val Lys Ile Ser Cys Lys Ala Thr Gly Tyr
        35                  40                  45

Thr Phe Ser Ser Tyr Trp Ile Glu Trp Val Lys Glu Arg Pro Gly His
    50                  55                  60

Gly Leu Glu Trp Ile Gly Glu Ile Leu Pro Ile Gly Asn Thr Asn
65                  70                  75                  80

Tyr Asn Glu Lys Phe Lys Gly Lys Ala Thr Phe Thr Ala Asp Leu Ser
                85                  90                  95

Ser Lys Thr Ala Tyr Met Gln Leu Ser Ser Leu Thr Ser Glu Asp Ser
            100                 105                 110

Ala Val Tyr Tyr Cys Ala Ser Gly Gly Tyr Ser Thr Val Tyr Trp Tyr
        115                 120                 125

Phe Asp Val Trp Gly Ala Gly Thr Thr Val Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys

<210> SEQ ID NO 15
<211> LENGTH: 814
<212> TYPE: DNA
<213> ORGANISM: Mus musculus

<400> SEQUENCE: 15
ttacccacgc tttgtacatg gagaaaataa agtgaaacaa agcactattg cactggcact      60
cttaccgctc ttatttaccc ctgtggcaaa agccgaggtg aagctggtgg aatctggggg     120
aggcttagtg aggcctggag ggtccctgaa actctcctgt gcagtctctg gattcacttt     180
cagtagctat gccatgtctt gggttcgcca gactccggag aagaggctgg aatgggtcgc     240
agccattaat tttaatcgtg gtaccaccta ctattcagac actgtgaagg gccgattcac     300
catctccaga gacaatgcca agaataccct gtacctgcaa ctgagcagtc tgaggtctga     360
ggacacagcc ttttattact gttcaagaca ccgctatagt gactacgact atgctatgga     420
ctactggggt caaggaacct cagtcaccgt ctcctcagcc aaaacgacac cccatctgt      480 ctatccactg gcccctggat ctgctgccca aactaactcc atggtgaccc tgggatgcct     540
ggtcaagggc tatttccctg agccagtgac agtgacctgg aactctggat ccctgtccag     600
cggtgtgcac accttcccag ctgtcctgca gtctgacctc tacactctga gcagctcagt     660
gactgtcccc tccagcacct ggcccagcga gaccgtcacc tgcaacgttg cccacccggc     720
```

| | |
|---|---|
| cagcagcacc aaggtggaca agaaaattgt gcccagggat tgtcatcatc accatcacca | 780 |
| tcactaaatg acagcttaa tcatttataa agct | 814 |

<210> SEQ ID NO 16
<211> LENGTH: 838
<212> TYPE: DNA
<213> ORGANISM: Mus musculus

<400> SEQUENCE: 16

| | |
|---|---|
| aaccctggcg ttacccacgc tttgtacatg gagaaaataa agtgaaacaa agcactattg | 60 |
| cactggcact cttaccgctc ttatttaccc ctgtggcaaa agccgaagtg cagctgttgg | 120 |
| agactggggg aggcttagtg aagcctggag ggtccctgaa actctcctgt gcagcctctg | 180 |
| gattcacttt cagtacctat gccatgtctt gggttcgcca gactccggag aagaggctgg | 240 |
| agtgggtcgc aggcattaat agtaatcgtg gtaccaccta ctatccagac actgtgaagg | 300 |
| gccgcttcac catctccaga gacaatgcca gaacaccct gtccctgcaa atgaccagtc | 360 |
| tgaggtctga ggacacagcc ttgtattatt gtgtaagaca ccgctatact aactacgact | 420 |
| atgctatgga ctactggggt caaggaacct cagtcaccgt ctcctcagcc aaaacgacac | 480 |
| ccccatctgt ctatccactg gcccctggat ctgctgccca aactaactcc atggtgaccc | 540 |
| tgggatgcct ggtcaagggc tatttccctg agccagtgac agtgacctgg aactctggat | 600 |
| ccctgtccag cggtgtgcac accttccag ctgtcctgca gtctgacctc tacactctga | 660 |
| gcagctcagt gactgtcccc tccagcacct ggcccagcga ccgtcacc tgcaacgttg | 720 |
| cccacccggc cagcagcacc aaggtggaca agaaaattgt gcccagggat tgtcatcatc | 780 |
| accatcacca tcactaattg acagcttatc atcgataagc tttaatgcgg tagtttat | 838 |

<210> SEQ ID NO 17
<211> LENGTH: 864
<212> TYPE: DNA
<213> ORGANISM: Mus musculus

<400> SEQUENCE: 17

| | |
|---|---|
| cgtcgtttta caacgtcgtg actgggaaaa ccctggcgtt acccacgctt tgtacatgga | 60 |
| gaaaataaag tgaaacaaag cactattgca ctggcactct taccgctctt atttacccct | 120 |
| gtggcaaaag ccgatgtgat gctggtggag tctgggggag gcttagtgaa gcctggaggg | 180 |
| tccctgaaac tctcctgtgc agcctctgga ttcactttca gtagctatgc catgtcttgg | 240 |
| gttcgccaga ctccggagaa gaggctgaa tgggtcgcag ccattaatat taatcgtggt | 300 |
| accacctact attcagacac tgtgaagggc cgattcacca tctccagaga caatgccaag | 360 |
| aatacccttgt acctgcaact gagcagtctg aggtctgagg acacagcctt gtattactgt | 420 |
| tcaagacacc gctatagtga ctacgactat gctatggact actggggtca aggaacctca | 480 |
| gtcaccgtct cctcagccaa aacgacaccc ccatctgtct atccactggc ccctggatct | 540 |
| gctgcccaaa ctaactccat ggtgaccctg ggatgcctgg tcaagggcta tttccctgag | 600 |
| ccagtgacag tgacctggaa ctctggatcc ctgtccagcg gtgtgcacac cttcccagct | 660 |
| gtcctgcagt ctgacctcta cactctgagc agctcagtga ctgtcccctc cagcacctgg | 720 |
| cccagcgaga ccgtcacctg caacgttgcc cacccggcca gcagccaa ggtggacaag | 780 |
| aaaattgtgc ccagggattg tcatcatcac catcaccatc actaattgac agcttatcat | 840 |
| cgataagctt taatgcggta gttt | 864 |

<210> SEQ ID NO 18
<211> LENGTH: 837
<212> TYPE: DNA
<213> ORGANISM: Mus musculus

<400> SEQUENCE: 18

```
ttacccacgc tttgtacatg gagaaaataa agtgaaacaa agcactattg cactggcact     60
cttaccgctc ttatttaccc ctgtggcaaa agccgaggtg aagctggtgg aatctggggg    120
aggcttagtg aagcctggag ggtccctgaa actctcctgt gcagcctctg gattcacttt    180
cagtaactat ggcatgtctt gggttcgcca gactccggag aggaggctgg agtgggtcgc    240
agccatgaat aataatggtg ctagcaccta ctatccagac actgtgaagg gccgattcac    300
catctccaga gacaatgcca gaacaccct gtacctgcaa atgagcagtc tgaggtctga    360
ggacacagcc ttgtatttct gtgtaagaca taataactac gttgactatg ctatggacta    420
ttggggtcaa ggaacctcag tcaccgtctc ctcagccaaa acgacacccc catctgtcta    480
tccactggcc cctggatctg ctgcccaaac taactccatg gtgaccctgg gatgcctggt    540
caagggctat ttccctgagc cagtgacagt gacctggaac tctggatccc tgtccagcgg    600
tgtgcacacc ttcccagctg tcctgcagtc tgacctctac actctgagca gctcagtgac    660
tgtcccctcc agcacctggc ccagcgagac cgtcacctgc aacgttgccc acccggccag    720
cagcaccaag gtggacaaga aaattgtgcc cagggattgt catcatcacc atcaccatca    780
ctaattgaca gcttatcatc gataagcttt aatgcggtag tttatcacag ttaaatt       837
```

<210> SEQ ID NO 19
<211> LENGTH: 831
<212> TYPE: DNA
<213> ORGANISM: Mus musculus

<400> SEQUENCE: 19

```
accctggcgt tacccacgct ttgtacatgg agaaaataaa gtgaaacaaa gcactattgc     60
actggcactc ttaccgctct tatttacccc tgtggcaaaa gccgaggtga agctggtgga    120
atctggggga ggcttagtga agcctggagg gtccctgaaa ctctcctgtg cagcctctgg    180
attcactttc agtaactatg gcatgtcttg ggttcgccag agtccggaga agaggctgga    240
gtgggtcgca gccattaatc gtaaaggtca tagtacctac tatccagaca ctgtgcaggg    300
ccgattcacc atctccagag acaatgccaa gaacacctg tacctgcaaa tgagcagtct    360
gaggtctgag gacacagcct tgtattactg tgtaagactt gacgataact actacttctt    420
tgactactgg ggccaaggca ccactctcac agtctcctca gccaaaacga caccccatc    480
tgtctatcca ctggccctg atctgctgc ccaaactaac tccatggtga ccctgggatg    540
cctggtcaag ggctatttcc ctgagccagt gacagtgacc tggaactctg gatccctgtc    600
cagcggtgtg cacaccttcc cagctgtcct gcagtctgac ctctacactc tgagcagctc    660
agtgactgtc ccctccagca cctggcccag cgagaccgtc acctgcaacg ttgcccaccc    720
ggccagcagc accaaggtgg acaagaaaat tgtgcccagg gattgtcatc atcaccatca    780
ccatcactaa ttgacagctt atcatcgata agctttaatg cggtagttta t             831
```

<210> SEQ ID NO 20
<211> LENGTH: 848
<212> TYPE: DNA
<213> ORGANISM: Mus musculus

<400> SEQUENCE: 20

-continued

```
ggaaaacccct ggcgttaccc acgctttgta catggagaaa ataaagtgaa acaaagcact    60
attgcactgg cactcttacc gctcttattt acccctgtgg caaaagccga agtgatgctg    120
gtggagtctg ggggaggctt agtgaagcct ggagggtccc tgaaactctc ctgcgcagcc    180
tctggattca ctttcagtcc ctatgccatg tcttgggttc gccagactcc ggagaagagg    240
ctggagtggg tcgcagccat aatagtaat cgtggtacca cctactatcc agacactgtg    300
aagggccgat tcaccatctc cagagacaat gccaagaaca ccctgtacct gcaaatgagc    360
agtctgaggt ctgaggacac agcctttat tactgtgtaa gacaccgcta ataactac    420
gactatgcta tggactactg gggtcaagga acctcagtca ccgtctcctc agccaaaacg    480
acacccccat ctgtctatcc actggcccct ggatctgctg cccaaactaa ctccatggtg    540
accctgggat gcctggtcaa gggctatttc cctgagccag tgacagtgac ctggaactct    600
ggatccctgt ccagcggtgt gcacaccttc ccagctgtcc tgcagtctga cctctacact    660
ctgagcagct cagtgactgt cccctccagc acctggccca gcgagaccgt cacctgcaac    720
gttgcccacc cggccagcag caccaaggtg gacaagaaaa ttgtgcccag ggattgtcat    780
catcaccatc accatcacta attgacagct tatcatcgat aagctttaat gcggtagttt    840
atcacagt                                                            848

<210> SEQ ID NO 21
<211> LENGTH: 851
<212> TYPE: DNA
<213> ORGANISM: Mus musculus

<400> SEQUENCE: 21
cgttttacaa cgtcgtgact gggaaaaccc tggcgttacc cacgctttgt acatggagaa    60
aataaagtga aacaaagcac tattgcactg gcactcttac cgctcttatt acccctgtg   120
gcaaaagccg aagtgatgct ggtggagtct gggggaggct tagtgaagcc tggagggtcc   180
ctgaaaatct cctgtgcagc ctctggattc tctttcagta gctatgccat gtcttgggtt   240
cgccagactc cggagaagag cctggaatgg gtcgcagcca ttaatattaa tcgtggtacc   300
ccctattatc cagacactgt gaagggccga ttcaccatct ccagagacaa tgccaagaac   360
accctgtacc tgcaaatgag tagtctgagg tctgaggaca cagccttgta ttactgtgta   420
agacaccgca atagtaacaa cgactatgct atggactact ggggtcaagg aacctcagtc   480
accgtctcct cagccaaaac gacacccccca tctgtctatc cactggcccc tggatctgct   540
gcccaaacta actccatggt gaccctggga tgcctggtca agggctattt ccctgagcca   600
gtgacagtga cctggaactc tggatccctg tccagcggtg tgcacacctt cccagctgtc   660
ctgcagtctg acctctacac tctgagcagc tcagtgactg tcccctccag cacctggccc   720
agcgagaccg tcacctgcaa cgttgcccac ccggccagca gcaccaaggt ggacaagaaa   780
attgtgccca gggattgtca tcatcaccat caccatcact aattgacagc ttatcatcga   840
taagctttaa t                                                         851

<210> SEQ ID NO 22
<211> LENGTH: 587
<212> TYPE: DNA
<213> ORGANISM: Mus musculus

<400> SEQUENCE: 22
tacaacgtcg tgactgggaa aaccctggcg ttacccacgc tttgtacatg gagaaaataa    60
agtgaaacaa agcactattg cactggcact cttaccgctc ttatttaccc ctgtggcaaa   120
```

```
agccgacgtg caggtggtgg agtctgggggg aggcttagtg aagcctggag ggtccctgaa    180
actctcctgt gcagcctctg gattcacttt cagtagctat gccatgtctt gggttcgcca    240
gactccggag aagaggctgg agtgggtcgc agccattaat cctaatggtg gtagtaccta    300
ctatccagac actgtgaagg gccgattcac catctccaga caatgccaa gaacaccct    360 atacctgcaa atgagcggtc tgaggtctga ggacacagcc ttgtattact gtgcaagact    420
cccatggtcc ccctatactt tggactactg gggtcaagga acctcagtca ccgtctcctc    480
agccaaaacg acaccccat ctgtctatcc actggcccct ggatctgctg cccaaactaa    540
ctccatggtg accctgggat gcctggtcaa gggctatttc cctgagc                  587
```

<210> SEQ ID NO 23
<211> LENGTH: 800
<212> TYPE: DNA
<213> ORGANISM: Mus musculus

<400> SEQUENCE: 23

```
ttacccacgc tttgtacatg gagaaaataa agtgaaacaa agcactattg cactggcact     60
cttaccgctc ttatttaccc ctgtggcaaa agccgaagtg cagcttgtgg agactggggg    120
agacttagtg aagcctggag ggtccctgaa actctcctgt gtagcctctg gattcacttt    180
cagtagcaat gccatgtcct gggttcgcca gactccggag aagaggctgg agtgggtcgc    240
agccattaat agtaaaggtg gtggcaccta ctatccagac actgtgaggg gccgattcac    300
catctccaga caatgccaa gaacaccct gtacctgcaa gtgaccagtc tgaggtctga    360
ggacacagcc ttgtattact gtgtaagcca tggggataat aagtacttt atgctatgga    420 ctactggggt caaggaacct cagtcaccgt ctcctcagcc aaaacgacac cccatctgt    480 ctatccactg gcccctggat ctgctgccca aactaactcc atggtgaccc tgggatgcct    540
ggtcaagggc tatttccctg agccagtgac agtgacctgg aactctggat ccctgtccag    600
cggtgtgcac accttcccag ctgtcctgca gtctgacctc tacactctga gcagctcagt    660
gactgtcccc tccagcacct ggcccagcga accgtcacc tgcaacgttg cccacccggc    720
cagcagcacc aaggtggaca gaaaattgt gcccagggat tgtcatcatc accatcacca    780
tcactaattg acagcttatc                                                800
```

<210> SEQ ID NO 24
<211> LENGTH: 815
<212> TYPE: DNA
<213> ORGANISM: Mus musculus

<400> SEQUENCE: 24

```
ttacccacgc tttgtacatg gagaaaataa agtgaaacaa agcactattg cactggcact     60
cttaccgctc ttatttaccc ctgtggcaaa agccgaagtg cagcttgtgg agactggggg    120
aggcttagtg aagcctggag ggtccctgaa actctcctgt gcagcctctg gattcgcttt    180
cagtagctat gccatgtctt gggttcgcca aactccggag aagaggctgg agtgggtcgc    240
agccattaat aatagaggtg gtggcaccta ctatccagac actgtgaggg gccgattcac    300
catctccaga caatgccaa gaacaccct gtacctgcaa atgagcagcc tgaggtctgc    360
ggacacagcc ttgtattact gtgtgagaca tgacaatctt aactatgact atgctatgga    420
ctcctggggt caaggaacct cagtcaccgt ctcctcagcc aaaacgacac cccatctgt    480 ctatccactg gcccctggat ctgctgccca aactaactcc atggtgaccc tgggatgcct    540
```

| | |
|---|---|
| ggtcaagggc tatttccctg agccagtgac agtgacctgg aactctggat ccctgtccag | 600 |
| cggtgtgcac accttcccag ctgtcctgca gtctgacctc tacactctga gcagctcagt | 660 |
| gactgtcccc tccagcacct ggcccagcga gaccgtcacc tgcaacgttg cccacccggc | 720 |
| cagcagcacc aaggtggaca agaaaattgt gcccagggat tgtcatcatc accatcacca | 780 |
| tcactaattg acagcttatc atcgataagc tttaa | 815 |

<210> SEQ ID NO 25
<211> LENGTH: 858
<212> TYPE: DNA
<213> ORGANISM: Mus musculus

<400> SEQUENCE: 25

| | |
|---|---|
| cgtcgtgact gggaaaaccc tggcgttacc cacgctttgt acatggagaa aataaagtga | 60 |
| aacaaagcac tattgcactg gcactcttac cgctcttatt taccccctgtg ccaaaagccg | 120 |
| aagtgcagct ggtggagtct gggggagact tagtgaagcc tggagggtcc ctgaaactct | 180 |
| cctgtgcagc ctctggattc actttcagta gatatggcat gtcttgggtt cgccagactc | 240 |
| cggagaagag gctggagtgg gtcgcagcca ttaatcctaa tggtggtact acctactatc | 300 |
| cagacactgt gaagggccga ttcaccatct cccgagacaa tgccaagaac ccctgttcc | 360 |
| tgcaaatgac cggtctgagg tctgaggaca cagccttata ctactgtgca agactcccat | 420 |
| ggtcccccta ctttggac tactgggtc aaggaacctc agtcatcgtc tcctcagcca | 480 |
| aaacgacacc cccatctgtc tatccactgg ccctggatc tgctgccaa actaactcca | 540 |
| tggtgaccct gggatgcctg gtcaagggct atttccctga gccagtgaca gtgacctgga | 600 |
| actctggatc cctgtccagc ggtgtgcaca ccttcccagc tgtcctgcag tctgacctct | 660 |
| acactctgag cagctcagtg actgtcccct ccagcacctg gcccagcgag accgtcacct | 720 |
| gcaacgttgc ccacccggcc agcagcacca aggtggacaa gaaaattgtg cccagggatt | 780 |
| gtcatcatca ccatcaccat cactaattga cagcttatca tcgataagct taatgcggt | 840 |
| agtttatcac agttaaat | 858 |

<210> SEQ ID NO 26
<211> LENGTH: 849
<212> TYPE: DNA
<213> ORGANISM: Mus musculus

<400> SEQUENCE: 26

| | |
|---|---|
| gcgttaccca cgctttgtac atggagaaaa taaagtgaaa caaagcacta ttgcactggc | 60 |
| actcttaccg ctcttattta ccccctgtggc aaaagccgaa gtgcagctgg tggagtctgg | 120 |
| gggaggctta gtgaagcctg agggtccct gaaactctcc tgcgcagcct ctggattcac | 180 |
| tttcagtagc tatgccatgt cttgggttcg ccagactccg gagaagaggc tagagtgggt | 240 |
| cgcagccatt aatagtaatc gtggtaccac ctactattca gacactgtga agggccgatt | 300 |
| caccatctcc agagacaatg ccaagaacac cctgtacctg caaatgagca gtctgaggtc | 360 |
| tgaggacaca gccttctatt actgtacaag acaccgctat agtgactacg actatgctat | 420 |
| ggactactgg ggtcaaggaa cctcagtcac cgtctcctca gccaaaacga caccccccatc | 480 |
| tgtctatcca ctggcccctg gatctgctgc ccaaactaac tccatggtga cccctgggatg | 540 |
| cctggtcaag ggctatttcc ctgagccagt gacagtgacc tggaactctg gatccctgtc | 600 |
| cagcggtgtg cacaccttcc cagctgtcct gcagtctgac ctctacactc tgagcagctc | 660 |
| agtgactgtc ccctccagca cctggcccag cgagaccgtc acctgcaacg ttgcccaccc | 720 |

| | |
|---|---|
| ggccagcagc accaaggtgg acaagaaaat tgtgcccagg gattgtcatc atcaccatca | 780 |
| ccatcactaa ttgacagctt atcatcgata agctttaatg cggtagttta tcacagttaa | 840 |
| attgctacg | 849 |

<210> SEQ ID NO 27
<211> LENGTH: 829
<212> TYPE: DNA
<213> ORGANISM: Mus musculus

<400> SEQUENCE: 27

| | |
|---|---|
| ggcgttaccc acgctttgta catggagaaa ataaagtgaa acaaagcact attgcactgg | 60 |
| cactcttacc gctcttattt acccctgtgg caaaagccga agtgcagctt gtggagactg | 120 |
| ggggaggctt agtgaagcct ggagggtccc tgaaactctc ctgtgcagcc tctggattca | 180 |
| ctttcagtag ctatgccatg tcttggattc gccagactcc ggagaagagg ctggagtggg | 240 |
| tcgcaggcat taatagtaat cgtggtacca cctactatcc agacactgtg aagggccgat | 300 |
| tcaccatctc cagagacaat gccaagaaca ccctgtacct gcaaatgaac agtctgaggt | 360 |
| ctgaggactc agccttgtat tactgtgtaa gacaccgcta tattgactac gactatgcta | 420 |
| tggactactg gggtcaagga acctcagtca ccgtctcctc agccaaaacg acacccccat | 480 |
| ctgtctatcc actggcccct ggatctgctg cccaaactaa ctccatggtg acctgggat | 540 |
| gcctggtcaa gggctatttc cctgagccag tgacagtgac ctggaactct ggatccctgt | 600 |
| ccagcggtgt gcacaccttc ccagctgtcc tgcagtctga cctctacact ctgagcagct | 660 |
| cagtgactgt cccctccagc acctggccca gcgagaccgt cacctgcaac gttgcccacc | 720 |
| cggccagcag caccaaggtg gacaagaaaa ttgtgcccag gattgtcat catcaccatc | 780 |
| accatcacta attgacagct tatcatcgat aagctttaat gcggtagtt | 829 |

<210> SEQ ID NO 28
<211> LENGTH: 846
<212> TYPE: DNA
<213> ORGANISM: Mus musculus

<400> SEQUENCE: 28

| | |
|---|---|
| gtcgtgactg ggaaaaccct ggcgttaccc acgctttgta catggagaaa ataaagtgaa | 60 |
| acaaagcact attgcactgg cactcttacc gctcttattt acccctgtgg caaaagccca | 120 |
| ggtgcagctt aagcagtctg ggctgagct ggtgaagcct ggggcctcag tgaagatatc | 180 |
| ctgcaaggct actggctaca cattcagtag ttactggata gagtgggtaa aggagaggcc | 240 |
| tggacatggc cttgagtgga ttggagagat tttacctgga attggtaata ctaactacaa | 300 |
| tgagaaattc aagggcaagg ccacattcac tgctgatcta tcctccaaga cagcctacat | 360 |
| gcaactcagc agcctgacat ctgaggactc tgccgtctat tactgtgcaa gtgggggta | 420 |
| tagtaccgtc tattggtatt ttgatgtctg ggcgcaggg accacggtca ccgtctcctc | 480 |
| agccaaaacg acacccccat ctgtctatcc actggcccct ggatctgctg cccaaactaa | 540 |
| ctccatggtg acctgggat gcctggtcaa gggctatttc cctgagccag tgacagtgac | 600 |
| ctggaactct ggatccctgt ccagcggtgt gcacaccttc ccagctgtcc tgcagtctga | 660 |
| cctctacact ctgagcagct cagtgactgt cccctccagc acctggccca gcgagaccgt | 720 |
| cacctgcaac gttgcccacc cggccagcag caccaaggtg gacaagaaaa ttgtgcccag | 780 |
| gattgtcat catcaccatc accatcacta atttgacagc tttaatcatt caattaagct | 840 |

```
tttaat                                                    846
```

<210> SEQ ID NO 29
<211> LENGTH: 236
<212> TYPE: PRT
<213> ORGANISM: Mus musculus

<400> SEQUENCE: 29

```
Met Lys Tyr Leu Leu Pro Thr Ala Ala Gly Leu Leu Leu Ala
1               5                   10                  15

Ala Gln Pro Ala Met Ala Asp Ile Val Met Ser Gln Ser Pro Ser Ser
                20                  25                  30

Met Tyr Ala Ser Leu Gly Glu Arg Val Thr Ile Thr Cys Lys Ala Ser
            35                  40                  45

Gln Asp Ile Asn Ser Tyr Leu Asn Trp Phe Gln Gln Lys Pro Gly Lys
    50                  55                  60

Ser Pro Lys Thr Leu Ile Tyr Arg Ala Asn Arg Leu Val Asp Gly Val
65                  70                  75                  80

Pro Ser Arg Phe Ser Gly Ser Gly Ser Gly His Asp Tyr Phe Leu Thr
                85                  90                  95

Ile Arg Ser Leu Glu Tyr Glu Asp Met Gly Ile Tyr Tyr Cys Leu Gln
            100                 105                 110

Tyr Asp Glu Phe Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225                 230                 235
```

<210> SEQ ID NO 30
<211> LENGTH: 236
<212> TYPE: PRT
<213> ORGANISM: Mus musculus

<400> SEQUENCE: 30

```
Met Lys Tyr Leu Leu Pro Thr Ala Ala Gly Leu Leu Leu Ala
1               5                   10                  15

Ala Gln Pro Ala Met Ala Asp Ile Lys Met Thr Gln Ser Pro Ser Ser
                20                  25                  30

Met Tyr Ala Ser Leu Gly Glu Arg Val Thr Ile Thr Cys Lys Ala Ser
            35                  40                  45

Gln Asp Ile Asn Ser Tyr Leu Ser Trp Phe Gln Gln Lys Pro Gly Lys
    50                  55                  60

Ser Pro Lys Thr Leu Ile Tyr Arg Ala Asn Arg Leu Val Asp Gly Val
65                  70                  75                  80

Pro Ser Arg Phe Ser Gly Ser Gly Ser Gly Gln Asp Tyr Ser Leu Thr
```

```
                    85                  90                  95

Ile Ser Ser Leu Glu Tyr Glu Asp Met Gly Ile Tyr Tyr Cys Leu Gln
                100                 105                 110

Tyr Asp Glu Phe Pro Tyr Thr Phe Gly Gly Gly Thr Lys Leu Glu Ile
                115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
                180                 185                 190

Ser Thr Tyr Ser Met Ser Ser Thr Leu Thr Leu Thr Lys Asp Glu Tyr
                195                 200                 205

Glu Arg His Asn Ser Tyr Thr Cys Glu Ala Thr His Lys Thr Ser Thr
                210                 215                 220

Ser Pro Ile Val Lys Ser Phe Asn Arg Asn Glu Ser
225                 230                 235

<210> SEQ ID NO 31
<211> LENGTH: 236
<212> TYPE: PRT
<213> ORGANISM: Mus musculus

<400> SEQUENCE: 31

Met Lys Tyr Leu Leu Pro Thr Ala Ala Ala Gly Leu Leu Leu Leu Ala
1               5                   10                  15

Ala Gln Pro Ala Met Ala Asp Ile Gln Leu Thr Gln Ser Pro Ser Ser
                20                  25                  30

Met Tyr Ala Ser Leu Gly Glu Arg Val Thr Ile Ala Cys Lys Ala Ser
                35                  40                  45

Gln Asp Ile Asn Ser Tyr Leu Ser Trp Phe Gln Gln Lys Pro Gly Lys
50                  55                  60

Ser Pro Lys Thr Leu Ile His Arg Ala Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Ile Gly Ile Tyr Tyr Cys Leu Gln
                100                 105                 110

Tyr Asp Glu Phe Pro Tyr Thr Phe Gly Gly Gly Thr Lys Leu Glu Ile
                115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
                180                 185                 190

Ser Thr Tyr Ser Met Ser Ser Thr Leu Thr Leu Thr Lys Asp Glu Tyr
                195                 200                 205

Glu Arg His Asn Ser Tyr Thr Cys Glu Ala Thr His Lys Thr Ser Thr
                210                 215                 220
```

```
Ser Pro Ile Val Lys Ser Phe Asn Arg Asn Glu Ser
225                 230                 235

<210> SEQ ID NO 32
<211> LENGTH: 236
<212> TYPE: PRT
<213> ORGANISM: Mus musculus

<400> SEQUENCE: 32

Met Lys Tyr Leu Leu Pro Thr Ala Ala Gly Leu Leu Leu Ala
1               5                   10                  15

Ala Gln Pro Ala Met Ala Asp Ile Leu Leu Thr Gln Ser Pro Ser Ser
                20                  25                  30

Met Tyr Thr Ser Leu Gly Glu Arg Val Thr Ile Thr Cys Lys Ala Ser
            35                  40                  45

Gln Asp Ile Asn Ser Tyr Leu Ser Trp Phe Gln Gln Lys Pro Gly Lys
    50                  55                  60

Ser Pro Lys Thr Leu Ile Tyr Arg Ala Asn Lys Leu Val Asp Gly Val
65                  70                  75                  80

Pro Ser Arg Phe Ser Gly Ser Gly Ser Gln Asp Tyr Ser Leu Thr
                85                  90                  95

Ile Ser Ser Leu Glu Ser Glu Asp Met Gly Ile Tyr Tyr Cys Leu Gln
                100                 105                 110

Tyr Asp Glu Phe Pro Tyr Thr Phe Gly Gly Gly Thr Lys Leu Glu Ile
            115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
    195                 200                 205

Glu Arg His Asn Ser Tyr Thr Cys Glu Ala Thr His Lys Thr Ser Thr
210                 215                 220

Ser Pro Ile Val Lys Ser Phe Asn Arg Asn Glu Ser
225                 230                 235

<210> SEQ ID NO 33
<211> LENGTH: 236
<212> TYPE: PRT
<213> ORGANISM: Mus musculus

<400> SEQUENCE: 33

Met Lys Tyr Leu Leu Pro Thr Ala Ala Gly Leu Leu Leu Ala
1               5                   10                  15

Ala Gln Pro Ala Met Ala Asp Ile Lys Met Thr Gln Ser Pro Ser Ser
                20                  25                  30

Met Tyr Ala Ser Leu Gly Glu Arg Val Thr Ile Thr Cys Lys Ala Ser
            35                  40                  45

Gln Asp Ile Asn Ser Tyr Leu Ser Trp Phe Gln Gln Lys Pro Gly Lys
    50                  55                  60

Ser Pro Lys Thr Leu Ile Tyr Arg Ala Lys Arg Leu Ile Asp Gly Val
65                  70                  75                  80
```

```
Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225                 230                 235

<210> SEQ ID NO 34
<211> LENGTH: 236
<212> TYPE: PRT
<213> ORGANISM: Mus musculus

<400> SEQUENCE: 34

Met Lys Tyr Leu Leu Pro Thr Ala Ala Ala Gly Leu Leu Leu Leu Ala
1               5                   10                  15

Ala Gln Pro Ala Met Ala Asp Ile Val Met Ser Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Asn Ser Tyr Leu Ser Trp Phe Gln Gln Lys Pro Gly Lys
    50                  55                  60

Ser Pro Lys Thr Leu Thr Tyr Arg Ala Asn Arg Leu Val Glu Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220
```

```
Ser Pro Ile Val Lys Ser Phe Asn Arg Asn Glu Ser
225                 230                 235

<210> SEQ ID NO 35
<211> LENGTH: 236
<212> TYPE: PRT
<213> ORGANISM: Mus musculus

<400> SEQUENCE: 35

Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Ser Ser
            20                  25                  30

Met Tyr Thr Ser Leu Gly Glu Arg Val Thr Ile Thr Cys Lys Ala Ser
        35                  40                  45

Gln Asp Ile Asn Ser Tyr Leu Ser Trp Phe Gln Gln Lys Pro Gly Lys
    50                  55                  60

Ser Pro Lys Thr Leu Ile Tyr Arg Ala Asn Arg Leu Ile Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Phe Thr Phe Gly Ser Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225                 230                 235

<210> SEQ ID NO 36
<211> LENGTH: 236
<212> TYPE: PRT
<213> ORGANISM: Mus musculus

<400> SEQUENCE: 36

Met Lys Tyr Leu Leu Pro Thr Ala Ala Ala Gly Leu Leu Leu Leu Ala
1               5                   10                  15

Ala Gln Pro Ala Met Ala Asn Ile Val Met Thr Gln Ser Pro Val Ser
            20                  25                  30

Leu Ser Met Ala Ile Gly Glu Lys Val Thr Ile Arg Cys Ile Thr Asn
        35                  40                  45

Thr Asp Ile Asp Asp Ala Met Asn Trp Tyr Gln Gln Lys Pro Gly Glu
    50                  55                  60

Pro Pro Lys Leu Leu Ile Ser Glu Gly Asn Thr Leu Arg Pro Gly Val
65                  70                  75                  80
```

```
Pro Ser Arg Phe Ser Ser Gly Tyr Gly Thr Asp Phe Val Phe Thr
            85                  90                  95
Ile Glu Asn Met Leu Ser Glu Asp Val Ala Asp Tyr Tyr Cys Leu Gln
                100                 105                 110
Thr Asp Asn Leu Pro Leu Thr Phe Gly Ser Gly Thr Lys Leu Ala Ile
            115                 120                 125
Lys Arg Ala Asp Ala Ala Pro Thr Val Ser Ile Phe Pro Pro Ser Ser
130                 135                 140
Glu Gln Leu Thr Ser Gly Gly Ala Ser Val Val Cys Phe Leu Asn Asn
145                 150                 155                 160
Phe Tyr Pro Lys Asp Ile Asn Val Lys Trp Lys Ile Asp Gly Ser Glu
                165                 170                 175
Arg Gln Asn Gly Val Met Asn Ser Trp Thr Asp Gln Asp Ser Lys Asp
            180                 185                 190
Ser Thr Tyr Ser Met Ser Ser Thr Leu Thr Leu Thr Lys Asp Glu Tyr
            195                 200                 205
Glu Arg His Asn Ser Tyr Thr Cys Glu Ala Thr His Lys Thr Ser Thr
            210                 215                 220
Ser Pro Ile Val Lys Ser Phe Asn Arg Asn Glu Ser
225                 230                 235

<210> SEQ ID NO 37
<211> LENGTH: 236
<212> TYPE: PRT
<213> ORGANISM: Mus musculus

<400> SEQUENCE: 37

Met Lys Tyr Leu Leu Pro Thr Ala Ala Ala Gly Leu Leu Leu Leu Ala
1               5                   10                  15
Ala Gln Pro Ala Met Ala Asn Ile Val Met Thr Gln Ser Pro Ser Ser
            20                  25                  30
Met Tyr Ala Ser Leu Gly Glu Arg Val Thr Ile Thr Cys Lys Ala Ser
            35                  40                  45
Gln Asp Ile Asn Ser Tyr Leu Ser Trp Phe Gln Gln Lys Pro Gly Lys
50                  55                  60
Ser Pro Lys Thr Leu Ile Tyr Arg Ala Asn Arg Leu Val Asp Gly Val
65                  70                  75                  80
Pro Ser Arg Phe Ser Gly Ser Gly Ser Gly Gln Asp Tyr Ser Leu Thr
            85                  90                  95
Ile Ser Ser Leu Glu Tyr Glu Asp Met Gly Ile Tyr Tyr Cys Leu Gln
                100                 105                 110
Tyr Asp Glu Phe Pro Tyr Thr Phe Gly Gly Gly Thr Lys Leu Glu Ile
            115                 120                 125
Lys Arg Ala Asp Ala Ala Pro Thr Val Ser Ile Phe Pro Pro Ser Ser
130                 135                 140
Glu Gln Leu Thr Ser Gly Gly Ala Ser Val Val Cys Phe Leu Asn Asn
145                 150                 155                 160
Phe Tyr Pro Lys Asp Ile Asn Val Lys Trp Lys Ile Asp Gly Ser Glu
                165                 170                 175
Arg Gln Asn Gly Val Leu Asn Ser Trp Thr Asp Gln Asp Ser Lys Asp
            180                 185                 190
Ser Thr Tyr Ser Met Ser Ser Thr Leu Thr Leu Thr Lys Asp Glu Tyr
            195                 200                 205
Glu Arg His Asn Ser Tyr Thr Cys Glu Ala Thr His Lys Thr Ser Thr
```

Ser Pro Ile Val Lys Ser Phe Asn Arg Asn Glu Ser
225             230             235

<210> SEQ ID NO 38
<211> LENGTH: 236
<212> TYPE: PRT
<213> ORGANISM: Mus musculus

<400> SEQUENCE: 38

Met Lys Tyr Leu Leu Pro Thr Ala Ala Gly Leu Leu Leu Ala
1               5                   10                  15

Ala Gln Pro Ala Met Ala Asn Ile Val Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Tyr Ser Tyr Leu Ser Trp Phe Gln Gln Lys Pro Gly Lys
    50                  55                  60

Ser Pro Lys Thr Leu Ile Tyr Arg Ala Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Asp Tyr Glu Asp Val Gly Ile Tyr Tyr Cys Leu Gln
            100                 105                 110

Tyr Asp Glu Phe Pro Tyr Thr Phe Gly Ser Gly Thr Lys Leu Glu Ile
        115                 120                 125

Glu Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225             230             235

<210> SEQ ID NO 39
<211> LENGTH: 236
<212> TYPE: PRT
<213> ORGANISM: Mus musculus

<400> SEQUENCE: 39

Met Lys Tyr Leu Leu Pro Thr Ala Ala Ala Gly Leu Leu Leu Leu Ala
1               5                   10                  15

Ala Gln Pro Ala Met Ala Glu Thr Thr Val Thr Gln Ser Pro Val Ser
            20                  25                  30

Leu Ser Met Ala Ile Gly Glu Lys Val Thr Ile Arg Cys Met Thr Ser
        35                  40                  45

Thr Asp Ile Asp Asp Ala Leu Asn Trp Tyr Gln Gln Lys Pro Gly Glu
    50                  55                  60

Pro Pro Lys Leu Leu Ile Ser Glu Gly Asn Ser Leu Arg Pro Gly Val

```
                65                  70                  75                  80
Pro Ser Arg Phe Ser Ser Gly Asn Gly Thr Asp Phe Val Phe Thr
                85                  90                  95
Ile Glu Asn Met Leu Ser Glu Asp Val Ala Asp Tyr Tyr Cys Leu Gln
                100                 105                 110
Ser Asp Asn Leu Pro Leu Thr Phe Gly Ser Gly Thr Lys Leu Glu Ile
                115                 120                 125
Lys Arg Ala Asp Ala Ala Pro Thr Val Ser Ile Phe Pro Pro Ser Ser
130                 135                 140
Glu Gln Leu Thr Ser Gly Gly Ala Ser Val Val Cys Phe Leu Asn Asn
145                 150                 155                 160
Phe Tyr Pro Lys Asp Ile Asn Val Lys Trp Lys Ile Asp Gly Ser Glu
                165                 170                 175
Arg Gln Asn Gly Val Leu Asn Ser Trp Thr Asp Gln Asp Ser Lys Asp
                180                 185                 190
Ser Thr Tyr Ser Met Ser Ser Thr Leu Thr Leu Thr Lys Asp Glu Tyr
                195                 200                 205
Glu Arg His Asn Ser Tyr Thr Cys Glu Ala Thr His Lys Thr Ser Thr
                210                 215                 220
Ser Pro Ile Val Lys Ser Phe Asn Arg Asn Glu Ser
225                 230                 235

<210> SEQ ID NO 40
<211> LENGTH: 236
<212> TYPE: PRT
<213> ORGANISM: Mus musculus

<400> SEQUENCE: 40

Met Lys Tyr Leu Leu Pro Thr Ala Ala Ala Gly Leu Leu Leu Leu Ala
1                   5                   10                  15
Ala Gln Pro Ala Met Ala Asp Ile Lys Met Thr Gln Ser Pro Ser Ser
                20                  25                  30
Met Tyr Ala Ser Leu Gly Glu Arg Val Thr Ile Thr Cys Lys Ala Ser
                35                  40                  45
Gln Asp Ile Asn Ser Tyr Leu Ser Trp Phe Gln Gln Lys Pro Gly Lys
                50                  55                  60
Ser Pro Met Thr Leu Thr His Arg Ala Asn Arg Leu Val Asp Gly Val
65                  70                  75                  80
Pro Ser Arg Phe Ser Gly Ser Gly Ser Gly Gln Asp Tyr Ser Leu Thr
                85                  90                  95
Ile Ser Ser Leu Glu Asn Glu Asp Met Gly Ile Tyr Tyr Cys Leu Gln
                100                 105                 110
Tyr Asp Glu Phe Pro Tyr Thr Phe Gly Gly Gly Thr Lys Leu Glu Ile
                115                 120                 125
Lys Arg Ala Asp Ala Ala Pro Thr Val Ser Ile Phe Pro Pro Ser Ser
130                 135                 140
Glu Gln Leu Thr Ser Gly Gly Ala Ser Val Val Cys Phe Leu Asn Asn
145                 150                 155                 160
Phe Tyr Pro Lys Asp Ile Asn Val Lys Trp Lys Ile Asp Gly Ser Glu
                165                 170                 175
Arg Gln Asn Gly Val Leu Asn Ser Trp Thr Asp Gln Asp Ser Lys Asp
                180                 185                 190
Ser Thr Tyr Ser Met Ser Ser Thr Leu Thr Leu Thr Lys Asp Glu Tyr
                195                 200                 205
```

```
Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225                 230                 235

<210> SEQ ID NO 41
<211> LENGTH: 236
<212> TYPE: PRT
<213> ORGANISM: Mus musculus

<400> SEQUENCE: 41

Met Lys Tyr Leu Leu Pro Thr Ala Ala Ala Gly Leu Leu Leu Leu Ala
1               5                   10                  15

Ala Gln Pro Ala Met Ala Asn Ile Val Met Thr Gln Ser Pro Ser Ser
                20                  25                  30

Met Tyr Ala Ser Leu Gly Glu Arg Val Thr Ile Ile Cys Lys Ser Ser
            35                  40                  45

Gln Asp Ile Asn Ser Tyr Leu Ser Trp Phe Gln Gln Lys Pro Gly Lys
    50                  55                  60

Ser Pro Lys Thr Leu Ile Phe Arg Ala Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Glu Asp Met Gly Ile Tyr Tyr Cys Leu Gln
            100                 105                 110

Tyr Asp Glu Phe Pro Tyr Thr Phe Gly Gly Gly Thr Lys Leu Glu Val
            115                 120                 125

Lys Arg Ala Asp Ala Ala Pro Thr Val Ser Ile Phe Pro Pro Ser Ser
130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Ser
225                 230                 235

<210> SEQ ID NO 42
<211> LENGTH: 242
<212> TYPE: PRT
<213> ORGANISM: Mus musculus

<400> SEQUENCE: 42

Met Lys Tyr Leu Leu Pro Thr Ala Ala Ala Gly Leu Leu Leu Leu Ala
1               5                   10                  15

Ala Gln Pro Ala Met Ala Asp Val Val Met Ser Gln Ser Pro Ser Ser
                20                  25                  30

Leu Ala Val Ser Thr Gly Glu Lys Val Thr Leu Ser Cys Lys Ser Ser
            35                  40                  45

Gln Ser Leu Leu Asn Ser Arg Thr Arg Lys Asn Tyr Leu Ala Trp Tyr
    50                  55                  60
```

-continued

```
Gln Gln Lys Pro Gly Gln Ser Pro Lys Leu Leu Ile Tyr Trp Thr Ser
 65                  70                  75                  80
Thr Arg Glu Ser Gly Val Pro Asn Arg Phe Thr Gly Ser Gly Ser Gly
                 85                  90                  95
Thr Asp Phe Thr Leu Thr Ile Ser Ser Val Gln Ala Glu Asp Leu Ala
            100                 105                 110
Val Tyr Tyr Cys Lys Gln Ser Tyr Asp Leu Pro Trp Thr Phe Gly Gly
        115                 120                 125
Gly Thr Lys Leu Glu Ile Lys Arg Ala Asp Ala Ala Pro Thr Val Ser
    130                 135                 140
Ile Phe Pro Pro Ser Ser Glu Gln Leu Thr Ser Gly Gly Ala Ser Val
145                 150                 155                 160
Val Cys Phe Leu Asn Asn Phe Tyr Pro Lys Asp Ile Asn Val Lys Trp
                165                 170                 175
Lys Ile Asp Gly Ser Glu Arg Gln Asn Gly Val Leu Asn Ser Trp Thr
            180                 185                 190
Asp Gln Asp Ser Lys Asp Ser Thr Tyr Ser Met Ser Ser Thr Leu Thr
        195                 200                 205
Leu Thr Lys Asp Glu Tyr Glu Arg His Asn Ser Tyr Thr Cys Glu Ala
    210                 215                 220
Thr His Lys Thr Ser Thr Ser Pro Ile Val Lys Ser Phe Asn Arg Asn
225                 230                 235                 240
Glu Ser
```

```
<210> SEQ ID NO 43
<211> LENGTH: 809
<212> TYPE: DNA
<213> ORGANISM: Mus musculus

<400> SEQUENCE: 43
tatcgcaact ctctactgtt tctccatacc cgttttttg gatggagtga aacgatgaaa        60
tacctattgc ctacggcagc cgctggattg ttattactcg ctgcccaacc agccatggcc      120
gacatcgtta tgtctcagtc tccatcttcc atgtatgcat ctctaggaga gagagtcact      180
atcacttgca aggcgagtca ggacattaat agctatttaa actggttcca gcagaaacca      240
ggcaaatctc ctaagaccct gatctatcgt gcaaacagat tggtagatgg ggtcccatca      300
aggttcagtg gcagtggatc tgggcacgat tattttctta ccattcgcag cctggaatat      360
gaagatatgg gaatttatta ttgtctacag tatgatgagt ttccgtacac gttcggaggg      420
gggaccaagc tggaaataaa acgggctgat gctgcaccaa ctgtatccat cttcccacca      480
tccagtgagc agttaacatc tggaggtgcc tcagtcgtgt gcttcttgaa caacttctac      540
cccaaagaca tcaatgtcaa gtggaagatt gatggcagtg aacgacaaaa tggcgtcctg      600
aacagttgga ctgatcagga cagcaaagac agcacctaca gcatgagcag cacctcacg       660 ttgaccaagg acgagtatga acgacataac agctatacct gtgaggccac tcacaagaca      720
tcaacttcac ccattgtcaa gagcttcaac aggaatgagt cttaagtgat tagctaattc      780
tagaacgcgt cacttggcac tggccgtcg                                         809
```

```
<210> SEQ ID NO 44
<211> LENGTH: 835
<212> TYPE: DNA
<213> ORGANISM: Mus musculus

<400> SEQUENCE: 44
```

```
ttatcgcaac tctctactgt ttctccatac ccgttttttt ggatggagtg aaacgatgaa     60
atacctattg cctacggcag ccgctggatt gttattactc gctgcccaac cagccatggc    120
cgacatcaaa atgacccagt ctccatcttc catgtatgca tctctaggag agagagtcac    180
tatcacttgc aaggcgagtc aggacattaa tagctattta agctggttcc agcagaaacc    240
agggaaatct cctaagaccc tgatctatcg tgcaaacaga ttggtagatg ggtcccatc     300 aaggttcagt ggcagtggat ctgggcaaga ttattctctc accatcagca gcctggagta    360
tgaagatatg ggaatttatt attgtctaca gtatgatgaa tttccgtaca cgttcggagg    420
ggggaccaag ctggaaataa aacgggctga tgctgcacca actgtatcca tcttcccacc    480
atccagtgag cagttaacat ctggaggtgc ctcagtcgtg tgcttcttga acaacttcta    540
cccccaaaga catcaatgtca agtggaagat tgatggcagt gaacgacaaa atggcgtcct    600
gaacagttgg actgatcagg acagcaaaga cagcacctac agcatgagca gcaccctcac    660
gttgaccaag gacgagtatg aacgacataa cagctatacc tgtgaggcca ctcacaagac    720
atcaacttca cccattgtca agagcttcaa caggaatgag tcttaagtga ttagctaatt    780
ctagaacgcg tcacttggca ctggccgtcg ttttacaacg tcgtgactgg gaaaa          835

<210> SEQ ID NO 45
<211> LENGTH: 822
<212> TYPE: DNA
<213> ORGANISM: Mus musculus

<400> SEQUENCE: 45
tatcgcaact ctctactgtt tctccatacc cgttttttg gatggagtga acgatgaaa     60 tacctattgc ctacggcagc cgctggattg ttattactcg ctgcccaacc agccatggcc    120
gacattcagc tgacccagtc tccatcttcc atgtatgcat ctctaggaga gagagtcact    180
atcgcttgca aggcgagtca ggacattaat agctatttaa gctggttcca gcagaaacca    240
gggaaatctc ctaagaccct gatccatcgt gcaaacagat ggtagatgg gtcccatca     300 aggttcagtg gcagtggatc tgggcaagat tattctctca ccatcagcag cctggagtat    360
gaagatatcg gaatttatta ttgtctacag tatgatgagt ttccgtacac gttcggaggg    420
gggaccaagc tggaaataaa acgggctgat gctgcaccaa ctgtatccat cttcccacca    480
tccagtgagc agttaacatc tggaggtgcc tcagtcgtgt gcttcttgaa caacttctac    540
cccaaagaca tcaatgtcaa gtggaagatt gatggcagtg aacgacaaaa tggcgtcctg    600
aacagttgga ctgatcagga cagcaaagac agcacctaca gcatgagcag caccctcacg    660
ttgaccaagg acgagtatga acgacataac agctatacct gtgaggccac tcacaagaca    720
tcaacttcac ccattgtcaa gagcttcaac aggaatgagt cttaagtgat tagctaattc    780
tagaacgcgt cacttggcac tggccgtcgt tttacaacgt cg                       822

<210> SEQ ID NO 46
<211> LENGTH: 795
<212> TYPE: DNA
<213> ORGANISM: Mus musculus

<400> SEQUENCE: 46
tcgcaactct ctactgtttc tccatacccg ttttttgga tggagtgaaa cgatgaaata    60
cctattgcct acggcagccg ctggattgtt attactcgct gcccaaccag ccatggcga    120 catcttgctg actcagtctc catcttccat gtatacatct ctaggagaga gagtcactat    180
cacttgcaag gcgagtcagg acattaatag ctatttaagc tggttccagc agaaaccagg    240
```

```
aaaatctcct aagaccctga tctatcgtgc aaacaaattg gtagatgggg tcccatcaag    300
attcagtggc agtggatctg ggcaagatta ttctctcacc atcagcagcc tggagtctga    360
agatatggga atttattatt gtctacagta tgatgagttt ccgtacacgt tcggaggggg    420
gaccaagctg gaaatcaaac gggctgatgc tgcaccaact gtatccatct tcccaccatc    480
cagtgagcag ttaacatctg gaggtgcctc agtcgtgtgc ttcttgaaca acttctaccc    540
caaagacatc aatgtcaagt ggaagattga tggcagtgaa cgacaaaatg gcgtcctgaa    600
cagttggact gatcaggaca gcaaagacag cacctacagc atgagcagca ccctcacgtt    660
gaccaaggac gagtatgaac gacataacag ctatacctgt gaggccactc acaagacatc    720
aacttcaccc attgtcaaga gcttcaacag gaatgagtct taagtgatta gctaattcta    780
gaacgcgtca cttgg    795
```

```
<210> SEQ ID NO 47
<211> LENGTH: 820
<212> TYPE: DNA
<213> ORGANISM: Mus musculus

<400> SEQUENCE: 47
tcgcaactct ctactgtttc tccatacccg ttttttggat ggagtgaaa cgatgaaata     60 cctattgcct acggcagccg ctggattgtt attactcgct gcccaaccag ccatggccga    120
catcaaaatg acccagtctc catcttccat gtatgcatct ctaggagaga gagtcactat    180
cacttgcaag gcgagtcagg acattaatag ctatttaagc tggttccagc agaaaccagg    240
gaaatctcct aagaccctga tctatcgtgc aaagagattg atagatgggg tcccatcaag    300
gttcagtggc agtggatctg ggcaagatta ttctctcacc atcagcagcc tggagtatga    360
agatatggga atttattatt gtctacagta tgatgagttt ccttacacgt tcggaggggg    420
gacaaagttg gaaataaaac gggctgatgc tgcaccaact gtatccatct tcccaccatc    480
cagtgagcag ttaacatctg gaggtgcctc agtcgtgtgc ttcttgaaca acttctaccc    540
caaagacatc aatgtcaagt ggaagattga tggcagtgaa cgacaaaatg gcgtcctgaa    600
cagttggact gatcaggaca gcaaagacag cacctacagc atgagcagca ccctcacgtt    660
gaccaaggac gagtatgaac gacataacag ctatacctgt gaggccactc acaagacatc    720
aacttcaccc attgtcaaga gcttcaacag gaatgagtct taagtgatta gctaattcta    780
gaacgcgtca cttggcactg gccgtcgttt tacaacgtcg    820
```

```
<210> SEQ ID NO 48
<211> LENGTH: 823
<212> TYPE: DNA
<213> ORGANISM: Mus musculus

<400> SEQUENCE: 48
ttttatcgca actctctact gtttctccat acccgttttt ttggatggag tgaaacgatg     60 aaataccttat tgcctacggc agccgctgga ttgttattac tcgctgccca accagccatg    120
gccgacatcg ttatgtctca gtctccatct tccatgtatg catctctagg agagagagtc    180
actatcactt gcaaggcgag tcaagacatt aatagctatt taagctggtt ccagcagaaa    240
ccagggaaat ctcctaagac cctgacctat cgtgcaaaca gattggtaga agggtccca    300 tcaaggttca gtgcagtgg atctgggcaa gattattctc tcaccatcag cagcctggaa    360
tatgaagata tgggaattta ttattgtcta cagtatgatg agtttccgta cacgttcgga    420
```

```
gggggggacca agctggaaat aaaacgggct gatgctgcac caactgtatc catcttccca      480
ccatccagtg agcagttaac atctggaggt gcctcagtcg tgtgcttctt gaacaacttc      540
taccccaaag acatcaatgt caagtggaag attgatggca gtgaacgaca aaatggcgtc      600
ctgaacagtt ggactgatca ggacagcaaa gacagcacct acagcatgag cagcaccctc      660
acgttgacca aggacgagta tgaacgacat aacagctata cctgtgaggc cactcacaag      720
acatcaactt cacccattgt caagagcttc aacaggaatg agtcttaagt gattagctaa      780
ttctagaacg cgtcacttgg cactggccgt cgttttacaa cgt                        823

<210> SEQ ID NO 49
<211> LENGTH: 837
<212> TYPE: DNA
<213> ORGANISM: Mus musculus

<400> SEQUENCE: 49
gcaactctct actgtttctc catacccgtt tttttggatg gagtgaaacg atgaaatacc       60
tattgcctac ggcagccgct ggattgttat tactcgctgc ccaaccagcc atggccgaca      120
ttgtgatgac ccagtctcca tcttccatgt atacatctct aggagagaga gtcactatca      180
cttgcaaggc gagtcaggac attaatagct atttaagctg gttccagcag aaaccaggga      240
aatctcctaa gaccctgatc tatcgtgcaa acagattgat agatggggtc ccatcaaggt      300
tcagtggcag tggatctggg caagattatt ctctcaccat cagcagcctg gagtatgaag      360
atatgggaat ttattattgt ctacagtatg atgagtttcc attcacgttc ggctcgggga      420
caaagttgga aataaaacgg ctgatgctgc accaactgt atccatcttc ccaccatcca       480
gtgagcagtt aacatctgga ggtgcctcag tcgtgtgctt cttgaacaac ttctacccca      540
aagacatcaa tgtcaagtgg aagattgatg gcagtgaacg acaaaatggc gtcctgaaca      600
gttggactga tcaggacagc aaagacagca cctacagcat gagcagcacc ctcacgttga      660
ccaaggacga gtatgaacga cataacagct atacctgtga ggccactcac aagacatcaa      720
cttcacccat tgtcaagagc ttcaacagga atgagtctta agtgattagc taattctaga      780
acgcgtcact tggcactggc cgtcgtttta caacgtcgtg actgggaaaa ccctggc       837

<210> SEQ ID NO 50
<211> LENGTH: 729
<212> TYPE: DNA
<213> ORGANISM: Mus musculus

<400> SEQUENCE: 50
gagtgaaacg atgaaatacc tattgcctac ggcagccgct ggattgttat tactcgctgc       60
ccaaccagcc atggccaaca tcgttatgac ccagtctcca gtatccctgt ccatggctat      120
aggagaaaaa gtcaccatca gatgcataac caacactgat attgatgatg ctatgaactg      180
gtaccagcaa aagccagggg aacctcctaa gctccttatt tcagaaggca atactcttcg      240
tcctggagtc ccatcccgat tctccagcag tggctatggt acagattttg ttttacaat       300 tgaaaacatg ctctcagaag atgttgcaga ttactactgt ttgcaaactg ataacttgcc      360
tctcacgttc ggctcgggga caaagttggc aataaaacgg ctgatgctgc accaactgt       420 atccatcttc ccaccatcca gtgagcagtt aacatctgga ggtgcctcag tcgtgtgctt      480
cttgaacaac ttctacccca aagacatcaa tgtcaagtgg aagattgatg cagtgaacg       540 acaaaatggc gtcatgaaca gttggactga tcaggacagc aaagacagca cctacagcat      600
gagcagcacc ctcacgttga ccaaggacga gtatgaacga cataacagct atacctgtga      660
```

```
ggccactcac aagacatcaa cttcacccat tgtcaagagc ttcaacagga atgagtctta      720
agtgattag                                                             729

<210> SEQ ID NO 51
<211> LENGTH: 814
<212> TYPE: DNA
<213> ORGANISM: Mus musculus

<400> SEQUENCE: 51
tcgcaactct ctactgtttc tccatacccg ttttttggga tggagtgaaa cgatgaaata      60
cctattgcct acggcagccg ctggattgtt attactcgct gcccaaccag ccatggccaa     120
catcgttatg acccagtctc catcttccat gtatgcatct ctaggagaga gagtcactat     180
cacttgcaag gcgagtcagg acattaatag ctatttaagc tggttccagc agaaaccagg     240
gaaatctcct aagaccctga tctatcgtgc aaacagattg gtagatgggg tcccatcaag     300
gttcagtggc agtggatctg ggcaagatta ttctctcacc atcagcagcc tggagtatga     360
agatatggga atttattatt gtctacagta tgatgagttt ccgtacacgt tcggaggggg     420
gaccaaactg gaaataaaac gggctgatgc tgcaccaact gtatccatct tcccaccatc     480
cagtgagcag ttaacatctg gaggtgcctc agtcgtgtgc ttcttgaaca acttctaccc     540
caaagacatc aatgtcaagt ggaagattga tggcagtgaa cgacaaaatg gcgtcctgaa     600
cagttggact gatcaggaca gcaaagacag cacctacagc atgagcagca ccctcacgtt     660
gaccaaggac gagtatgaac gacataacag ctatacctgt gaggccactc acaagacatc     720
aacttcaccc attgtcaaga gcttcaacag gaatgagtct taagtgatta gctaattcta     780
gaacgcgtca cttggcactg gccgtcgttt taca                                 814

<210> SEQ ID NO 52
<211> LENGTH: 810
<212> TYPE: DNA
<213> ORGANISM: Mus musculus

<400> SEQUENCE: 52
gcaactctct actgtttctc catacccgtt ttttggatgg gagtgaaacg atgaaatacc      60
tattgcctac ggcagccgct ggattgttat tactcgctgc ccaaccagcc atggccaaca     120
tcgttatgac ccagtctcca tcttccatgt atgcatctct aggagagagg gtcactatca     180
cttgcaaggc gagtcaggac atttatagct atttaagctg gttccagcag aaaccaggca     240
aatctcctaa gaccctgatc tatcgtgcaa acagattggt agatgggtc ccatcaaggt     300 tcagtggcag tggatctggg caagattatt ctctcaccat cagcagcctg gactatgaag     360
atgtgggaat ttattattgt ctacagtatg atgagtttcc gtacacgttc ggctcgggga     420
caaagttgga aatagaacgg gctgatgctg caccaactgt atccatcttc ccaccatcca     480
gtgagcagtt aacatctgga ggtgcctcag tcgtgtgctt cttgaacaac ttctacccca     540 agacatcaa tgtcaagtgg aagattgatg gcagtgaacg acaaaatggc gtcctgaaca     600
gttggactga tcaggacagc aaagacagca cctacagcat gagcagcacc ctcacgttga     660
ccaaggacga gtatgaacga cataacagct atacctgtga ggccactcac aagacatcaa     720
cttcacccat tgtcaagagc ttcaacagga atgagtctta agtgattagc taattctaga     780
acgcgtcact tggcactggc cgtcgtttta                                      810

<210> SEQ ID NO 53
```

<210> SEQ ID NO 53
<211> LENGTH: 823
<212> TYPE: DNA
<213> ORGANISM: Mus musculus

<400> SEQUENCE: 53

| | | | | | |
|---|---|---|---|---|---|
| cgcaactctc | tactgtttct | ccatacccgt | ttttttggat | ggagtgaaac | gatgaaatac | 60 |
| ctattgccta | cggcagccgc | tggattgtta | ttactcgctg | cccaaccagc | catggccgaa | 120 |
| acaactgtga | cccagtctcc | agtatccctg | tccatggcta | taggagaaaa | agtcaccatc | 180 |
| agatgcatga | ccagcactga | tattgatgat | gctctgaact | ggtaccagca | aaagccaggg | 240 |
| gaacctccta | aactccttat | ttcagaaggc | aatagtcttc | gtcctggagt | cccatcccga | 300 |
| ttctccagca | gtggcaatgg | tacagatttt | gttttacaa | ttgaaaacat | gctctcagaa | 360 |
| gatgttgcag | attactactg | tttgcaaagt | gataacttgc | ctctcacgtt | cggctcgggg | 420 |
| acaaagttgg | aaataaaacg | ggctgatgct | gcaccaactg | tatccatctt | cccaccatcc | 480 |
| agtgagcagt | taacatctgg | aggtgcctca | gtcgtgtgct | tcttgaacaa | cttctacccc | 540 |
| aaagacatca | atgtcaagtg | gaagattgat | ggcagtgaac | gacaaaatgg | cgtcctgaac | 600 |
| agttggactg | atcaggacag | caaagacagc | acctacagca | tgagcagcac | cctcacgttg | 660 |
| accaaggacg | agtatgaacg | acataacagc | tatacctgtg | aggccactca | caagacatca | 720 |
| acttcaccca | ttgtcaagag | cttcaacagg | aatgagtctt | aagtgattag | ctaattctag | 780 |
| aatgcgtcac | ttggcactgg | ccgtcgtttt | acaacgtcgt | gac | | 823 |

<210> SEQ ID NO 54
<211> LENGTH: 823
<212> TYPE: DNA
<213> ORGANISM: Mus musculus

<400> SEQUENCE: 54

| | | | | | |
|---|---|---|---|---|---|
| tatcgcaact | ctctactgtt | tctccatacc | cgttttttg | gatggagtga | aacgatgaaa | 60 |
| tacctattgc | ctacggcagc | cgctggattg | ttattactcg | ctgcccaacc | agccatggcc | 120 |
| gacatcaaaa | tgacccagtc | tccatcttcc | atgtatgcat | ctctaggaga | gagagtcact | 180 |
| atcacttgca | aggcgagtca | ggacattaat | agctatttaa | gctggttcca | gcagaaacca | 240 |
| gggaaatctc | ctatgaccct | gacccatcgt | gcaaacagat | tggtagatgg | ggtcccatca | 300 |
| aggttcagtg | gcagtggatc | tgggcaagat | tattctctca | ccatcagcag | cctggagaat | 360 |
| gaagatatgg | gaatttatta | ttgtctacag | tatgatgagt | ttccgtacac | gttcggaggg | 420 |
| gggaccaagc | tggaaataaa | acgggctgat | gctgcaccaa | ctgtatccat | cttcccacca | 480 |
| tccagtgagc | agttaacatc | tggaggtgcc | tcagtcgtgt | gcttcttgaa | caacttctac | 540 |
| cccaaagaca | tcaatgtcaa | gtggaagatt | gatggcagtg | aacgacaaaa | tggcgtcctg | 600 |
| aacagttgga | ctgatcagga | cagcaaagac | agcacctaca | gcatgagcag | caccctcacg | 660 |
| ttgaccaagg | acgagtatga | acgacataac | agctatacct | gtgaggccac | tcacaagaca | 720 |
| tcaacttcac | ccattgtcaa | gagcttcaac | aggaatgagt | cttaagtgat | tagctaattc | 780 |
| tagaacgcgt | cacttggcac | tggccgtcgt | tttacaacgt | cgt | | 823 |

<210> SEQ ID NO 55
<211> LENGTH: 822
<212> TYPE: DNA
<213> ORGANISM: Mus musculus

<400> SEQUENCE: 55

| | | | | | |
|---|---|---|---|---|---|
| cgcaactctc | tactgtttct | ccatacccgt | ttttttggat | ggagtgaaac | gatgaaatac | 60 |

```
ctattgccta cggcagccgc tggattgtta ttactcgctg cccaaccagc catggccaac      120
atcgttatga cccagtctcc atcttccatg tatgcatctc taggagagag agtcactatc      180
atttgcaagt cgagtcagga cattaatagc tatttaagtt ggttccagca gaaaccaggg      240
aagtctccta gaccctgat ctttcgtgca aacagattgg tagatggggt cccatcaagg       300
ttcagtggca gtggatctgg gcaagattat tctctcacca tcagcagcct ggagtatgaa      360
gatatgggaa tttattattg tctacagtat gatgagtttc cgtacacgtt cggagggggg      420
accaagctgg aagtaaaacg ggctgatgct gcaccaaccg tatccatctt cccaccatcc      480
agtgagcagt taacatctgg aggtgcctca gtcgtgtgct tcttgaacaa cttctacccc      540
aaagacatca atgtcaagtg aagattgat ggcagtgaac gacaaaatgg cgtcctgaac       600
agttggactg atcaggacag caaagacagc acctacagca tgagcagcac cctcacgttg      660
accaaggacg agtatgaacg acataacagc tatacctgtg aggccactca caagacatca      720 acttcacccca ttgtcaagag cttcaacagg aatgagtctt aagtgattag ctaattctag     780
aacgcgtcac ttggcactgg ccgtcgtttt acaacgtcgt ga                        822
```

```
<210> SEQ ID NO 56
<211> LENGTH: 826
<212> TYPE: DNA
<213> ORGANISM: Mus musculus

<400> SEQUENCE: 56
```

```
tcgcaactct ctactgtttc tccatacccg ttttttgga tggagtgaaa cgatgaaata      60
cctattgcct acggcagccg ctggattgtt attactcgct gcccaaccag ccatggccga    120
cgttgtgatg tcacagtctc catcctccct ggctgtgtca acaggagaga aggtcacttt    180
gagctgcaaa tccagtcaga gtctgctcaa cagtagaacc cgaaagaact acttggcttg    240
gtaccagcag aaaccagggc agtctcctaa actgctgatc tactggacat ccactaggga    300
atctggggtc cctaatcgct tcacaggcag tggatctggg acagatttca ctctcaccat    360
cagcagtgtg caggctgaag acctggcagt ttattactgc aagcaatctt atgatcttcc    420
gtggacgttc ggtggggca ccaaactgga aatcaaacgg gctgatgctg caccaactgt     480
atccatcttc ccaccatcca gtgagcagtt aacatctgga ggtgcctcag tcgtgtgctt    540
cttgaacaac ttctacccca aagacatcaa tgtcaagtgg aagattgatg gcagtgaacg    600
acaaaatggc gtcctgaaca gttggactga tcaggacagc aaagacagca cctacagcat    660
gagcagcacc ctcacgttga ccaaggacga gtatgaacga cataacagct atacctgtga    720
ggccactcac aagacatcaa cttcacccat tgtcaagagc ttcaacagga atgagtctta    780
agtgattagc taattctaga acgcgtcact tggcactggc cgtcgt                   826
```

```
<210> SEQ ID NO 57
<211> LENGTH: 12
<212> TYPE: PRT
<213> ORGANISM: Mus musculus

<400> SEQUENCE: 57
```

```
Val Ser Gly Phe Thr Phe Ser Ser Tyr Ala Met Ser
1               5                   10
```

```
<210> SEQ ID NO 58
<211> LENGTH: 10
<212> TYPE: PRT
<213> ORGANISM: Mus musculus
```

<400> SEQUENCE: 58

Gly Phe Thr Phe Ser Ser Tyr Ala Met Ser
1               5                   10

<210> SEQ ID NO 59
<211> LENGTH: 12
<212> TYPE: PRT
<213> ORGANISM: Mus musculus

<400> SEQUENCE: 59

Ala Ser Gly Phe Thr Phe Ser Thr Tyr Ala Met Ser
1               5                   10

<210> SEQ ID NO 60
<211> LENGTH: 10
<212> TYPE: PRT
<213> ORGANISM: Mus musculus

<400> SEQUENCE: 60

Gly Phe Thr Phe Ser Thr Tyr Ala Met Ser
1               5                   10

<210> SEQ ID NO 61
<211> LENGTH: 12
<212> TYPE: PRT
<213> ORGANISM: Mus musculus

<400> SEQUENCE: 61

Ala Ser Gly Phe Thr Phe Ser Ser Tyr Ala Met Ser
1               5                   10

<210> SEQ ID NO 62
<211> LENGTH: 12
<212> TYPE: PRT
<213> ORGANISM: Mus musculus

<400> SEQUENCE: 62

Ala Ser Gly Phe Thr Phe Ser Asn Tyr Gly Met Ser
1               5                   10

<210> SEQ ID NO 63
<211> LENGTH: 10
<212> TYPE: PRT
<213> ORGANISM: Mus musculus

<400> SEQUENCE: 63

Gly Phe Thr Phe Ser Asn Tyr Gly Met Ser
1               5                   10

<210> SEQ ID NO 64
<211> LENGTH: 12
<212> TYPE: PRT
<213> ORGANISM: Mus musculus

<400> SEQUENCE: 64

Ala Ser Gly Phe Thr Phe Ser Asn Tyr Asp Met Ser
1               5                   10

<210> SEQ ID NO 65
<211> LENGTH: 10
<212> TYPE: PRT
<213> ORGANISM: Mus musculus

<400> SEQUENCE: 65

```
Gly Phe Thr Phe Ser Asn Tyr Asp Met Ser
1               5                   10
```

<210> SEQ ID NO 66
<211> LENGTH: 12
<212> TYPE: PRT
<213> ORGANISM: Mus musculus

<400> SEQUENCE: 66

```
Ala Ser Gly Phe Thr Phe Ser Pro Tyr Ala Met Ser
1               5                   10
```

<210> SEQ ID NO 67
<211> LENGTH: 10
<212> TYPE: PRT
<213> ORGANISM: Mus musculus

<400> SEQUENCE: 67

```
Gly Phe Thr Phe Ser Pro Tyr Ala Met Ser
1               5                   10
```

<210> SEQ ID NO 68
<211> LENGTH: 12
<212> TYPE: PRT
<213> ORGANISM: Mus musculus

<400> SEQUENCE: 68

```
Ala Ser Gly Phe Ser Phe Ser Ser Tyr Ala Met Ser
1               5                   10
```

<210> SEQ ID NO 69
<211> LENGTH: 10
<212> TYPE: PRT
<213> ORGANISM: Mus musculus

<400> SEQUENCE: 69

```
Gly Phe Ser Phe Ser Ser Tyr Ala Met Ser
1               5                   10
```

<210> SEQ ID NO 70
<211> LENGTH: 12
<212> TYPE: PRT
<213> ORGANISM: Mus musculus

<400> SEQUENCE: 70

```
Ala Ser Gly Phe Thr Phe Ser Ser Asn Ala Met Ser
1               5                   10
```

<210> SEQ ID NO 71
<211> LENGTH: 10
<212> TYPE: PRT
<213> ORGANISM: Mus musculus

<400> SEQUENCE: 71

```
Gly Phe Thr Phe Ser Ser Asn Ala Met Ser
1               5                   10
```

<210> SEQ ID NO 72
<211> LENGTH: 12
<212> TYPE: PRT
<213> ORGANISM: Mus musculus

<400> SEQUENCE: 72

Ala Ser Gly Phe Ala Phe Ser Ser Tyr Ala Met Ser

<210> SEQ ID NO 73
<211> LENGTH: 10
<212> TYPE: PRT
<213> ORGANISM: Mus musculus

<400> SEQUENCE: 73

Gly Phe Ala Phe Ser Ser Tyr Ala Met Ser
1               5                   10

<210> SEQ ID NO 74
<211> LENGTH: 12
<212> TYPE: PRT
<213> ORGANISM: Mus musculus

<400> SEQUENCE: 74

Ala Ser Gly Phe Thr Phe Ser Arg Tyr Gly Met Ser
1               5                   10

<210> SEQ ID NO 75
<211> LENGTH: 10
<212> TYPE: PRT
<213> ORGANISM: Mus musculus

<400> SEQUENCE: 75

Gly Phe Thr Phe Ser Arg Tyr Gly Met Ser
1               5                   10

<210> SEQ ID NO 76
<211> LENGTH: 12
<212> TYPE: PRT
<213> ORGANISM: Mus musculus

<400> SEQUENCE: 76

Ala Thr Gly Tyr Thr Phe Ser Ser Tyr Trp Ile Glu
1               5                   10

<210> SEQ ID NO 77
<211> LENGTH: 10
<212> TYPE: PRT
<213> ORGANISM: Mus musculus

<400> SEQUENCE: 77

Gly Tyr Thr Phe Ser Ser Tyr Trp Ile Glu
1               5                   10

<210> SEQ ID NO 78
<211> LENGTH: 36
<212> TYPE: DNA
<213> ORGANISM: Mus musculus

<400> SEQUENCE: 78
gtctctggat tcactttcag tagctatgcc atgtct                              36

<210> SEQ ID NO 79
<211> LENGTH: 30
<212> TYPE: DNA
<213> ORGANISM: Mus musculus

<400> SEQUENCE: 79
ggattcactt tcagtagcta tgccatgtct                                     30

<210> SEQ ID NO 80

```
<211> LENGTH: 36
<212> TYPE: DNA
<213> ORGANISM: Mus musculus

<400> SEQUENCE: 80
gcctctggat tcactttcag tacctatgcc atgtct                        36

<210> SEQ ID NO 81
<211> LENGTH: 30
<212> TYPE: PRT
<213> ORGANISM: Mus musculus

<400> SEQUENCE: 81

Gly Gly Ala Thr Thr Cys Ala Cys Thr Thr Cys Ala Gly Thr Ala
1               5                   10                  15
Cys Cys Thr Ala Thr Gly Cys Cys Ala Thr Gly Thr Cys Thr
            20                  25                  30

<210> SEQ ID NO 82
<211> LENGTH: 36
<212> TYPE: DNA
<213> ORGANISM: Mus musculus

<400> SEQUENCE: 82
gcctctggat tcactttcag tagctatgcc atgtct                        36

<210> SEQ ID NO 83
<211> LENGTH: 36
<212> TYPE: DNA
<213> ORGANISM: Mus musculus

<400> SEQUENCE: 83
gcctctggat tcactttcag taactatggc atgtct                        36

<210> SEQ ID NO 84
<211> LENGTH: 30
<212> TYPE: DNA
<213> ORGANISM: Mus musculus

<400> SEQUENCE: 84
ggattcactt tcagtaacta tggcatgtct                               30

<210> SEQ ID NO 85
<211> LENGTH: 36
<212> TYPE: DNA
<213> ORGANISM: Mus musculus

<400> SEQUENCE: 85
gcctctggat tcactttcag taactatgac atgtct                        36

<210> SEQ ID NO 86
<211> LENGTH: 30
<212> TYPE: DNA
<213> ORGANISM: Mus musculus

<400> SEQUENCE: 86
ggattcactt tcagtaacta tgacatgtct                               30

<210> SEQ ID NO 87
<211> LENGTH: 36
<212> TYPE: DNA
<213> ORGANISM: Mus musculus

<400> SEQUENCE: 87
```

```
gcctctggat tcactttcag tccctatgcc atgtct                    36
```

<210> SEQ ID NO 88
<211> LENGTH: 30
<212> TYPE: DNA
<213> ORGANISM: Mus musculus

<400> SEQUENCE: 88

```
ggattcactt tcagtcccta tgccatgtct                           30
```

<210> SEQ ID NO 89
<211> LENGTH: 36
<212> TYPE: DNA
<213> ORGANISM: Mus musculus

<400> SEQUENCE: 89

```
gcctctggat tctctttcag tagctatgcc atgtct                    36
```

<210> SEQ ID NO 90
<211> LENGTH: 30
<212> TYPE: DNA
<213> ORGANISM: Mus musculus

<400> SEQUENCE: 90

```
ggattctctt tcagtagcta tgccatgtct                           30
```

<210> SEQ ID NO 91
<211> LENGTH: 36
<212> TYPE: DNA
<213> ORGANISM: Mus musculus

<400> SEQUENCE: 91

```
gcctctggat tcactttcag tagcaatgcc atgtcc                    36
```

<210> SEQ ID NO 92
<211> LENGTH: 30
<212> TYPE: DNA
<213> ORGANISM: Mus musculus

<400> SEQUENCE: 92

```
ggattcactt tcagtagcaa tgccatgtcc                           30
```

<210> SEQ ID NO 93
<211> LENGTH: 36
<212> TYPE: DNA
<213> ORGANISM: Mus musculus

<400> SEQUENCE: 93

```
gcctctggat tcgctttcag tagctatgcc atgtct                    36
```

<210> SEQ ID NO 94
<211> LENGTH: 30
<212> TYPE: DNA
<213> ORGANISM: Mus musculus

<400> SEQUENCE: 94

```
ggattcgctt tcagtagcta tgccatgtct                           30
```

<210> SEQ ID NO 95
<211> LENGTH: 36
<212> TYPE: DNA
<213> ORGANISM: Mus musculus

<400> SEQUENCE: 95
gcctctggat tcactttcag tagatatggc atgtct         36

<210> SEQ ID NO 96
<211> LENGTH: 30
<212> TYPE: DNA
<213> ORGANISM: Mus musculus

<400> SEQUENCE: 96
ggattcactt tcagtagata tggcatgtct         30

<210> SEQ ID NO 97
<211> LENGTH: 36
<212> TYPE: DNA
<213> ORGANISM: Mus musculus

<400> SEQUENCE: 97
gctactggct acacattcag tagttactgg atagag         36

<210> SEQ ID NO 98
<211> LENGTH: 30
<212> TYPE: DNA
<213> ORGANISM: Mus musculus

<400> SEQUENCE: 98
ggctacacat tcagtagtta ctggatagag         30

<210> SEQ ID NO 99
<211> LENGTH: 10
<212> TYPE: PRT
<213> ORGANISM: Mus musculus

<400> SEQUENCE: 99

Ala Ile Asn Phe Asn Arg Gly Thr Thr Tyr
1               5                   10

<210> SEQ ID NO 100
<211> LENGTH: 17
<212> TYPE: PRT
<213> ORGANISM: Mus musculus

<400> SEQUENCE: 100

Ala Ile Asn Phe Asn Arg Gly Thr Thr Tyr Tyr Ser Asp Thr Val Lys
1               5                   10                  15
Gly

<210> SEQ ID NO 101
<211> LENGTH: 10
<212> TYPE: PRT
<213> ORGANISM: Mus musculus

<400> SEQUENCE: 101

Gly Ile Asn Ser Asn Arg Gly Thr Thr Tyr
1               5                   10

<210> SEQ ID NO 102
<211> LENGTH: 17
<212> TYPE: PRT
<213> ORGANISM: Mus musculus

<400> SEQUENCE: 102

Gly Ile Asn Ser Asn Arg Gly Thr Thr Tyr Tyr Pro Asp Thr Val Lys
1               5                   10                  15

Gly

<210> SEQ ID NO 103
<211> LENGTH: 10
<212> TYPE: PRT
<213> ORGANISM: Mus musculus

<400> SEQUENCE: 103

Ala Ile Asn Ile Asn Arg Gly Thr Thr Tyr
1               5                   10

<210> SEQ ID NO 104
<211> LENGTH: 17
<212> TYPE: PRT
<213> ORGANISM: Mus musculus

<400> SEQUENCE: 104

Ala Ile Asn Ile Asn Arg Gly Thr Thr Tyr Tyr Ser Asp Thr Val Lys
1               5                   10                  15

Gly

<210> SEQ ID NO 105
<211> LENGTH: 10
<212> TYPE: PRT
<213> ORGANISM: Mus musculus

<400> SEQUENCE: 105

Ala Met Asn Asn Asn Gly Ala Ser Thr Tyr
1               5                   10

<210> SEQ ID NO 106
<211> LENGTH: 17
<212> TYPE: PRT
<213> ORGANISM: Mus musculus

<400> SEQUENCE: 106

Ala Met Asn Asn Asn Gly Ala Ser Thr Tyr Tyr Pro Asp Thr Val Lys
1               5                   10                  15

Gly

<210> SEQ ID NO 107
<211> LENGTH: 10
<212> TYPE: PRT
<213> ORGANISM: Mus musculus

<400> SEQUENCE: 107

Ala Ile Asn Arg Lys Gly His Ser Thr Tyr
1               5                   10

<210> SEQ ID NO 108
<211> LENGTH: 17
<212> TYPE: PRT
<213> ORGANISM: Mus musculus

<400> SEQUENCE: 108

Ala Ile Asn Arg Lys Gly His Ser Thr Tyr Tyr Pro Asp Thr Val Gln
1               5                   10                  15

Gly

<210> SEQ ID NO 109
<211> LENGTH: 17
<212> TYPE: PRT

<213> ORGANISM: Mus musculus

<400> SEQUENCE: 109

Ala Ile Asn Ser Asn Arg Gly Thr Thr Tyr Tyr Pro Asp Thr Val Lys
1               5                   10                  15

Gly

<210> SEQ ID NO 110
<211> LENGTH: 10
<212> TYPE: PRT
<213> ORGANISM: Mus musculus

<400> SEQUENCE: 110

Ala Ile Asn Ser Asn Arg Gly Thr Thr Tyr
1               5                   10

<210> SEQ ID NO 111
<211> LENGTH: 10
<212> TYPE: PRT
<213> ORGANISM: Mus musculus

<400> SEQUENCE: 111

Ala Ile Asn Ile Asn Arg Gly Thr Pro Tyr
1               5                   10

<210> SEQ ID NO 112
<211> LENGTH: 17
<212> TYPE: PRT
<213> ORGANISM: Mus musculus

<400> SEQUENCE: 112

Ala Ile Asn Ile Asn Arg Gly Thr Pro Tyr Tyr Pro Asp Thr Val Lys
1               5                   10                  15

Gly

<210> SEQ ID NO 113
<211> LENGTH: 10
<212> TYPE: PRT
<213> ORGANISM: Mus musculus

<400> SEQUENCE: 113

Ala Ile Asn Pro Asn Gly Gly Ser Thr Tyr
1               5                   10

<210> SEQ ID NO 114
<211> LENGTH: 17
<212> TYPE: PRT
<213> ORGANISM: Mus musculus

<400> SEQUENCE: 114

Ala Ile Asn Pro Asn Gly Gly Ser Thr Tyr Tyr Pro Asp Thr Val Lys
1               5                   10                  15

Gly

<210> SEQ ID NO 115
<211> LENGTH: 10
<212> TYPE: PRT
<213> ORGANISM: Mus musculus

<400> SEQUENCE: 115

Ala Ile Asn Ser Lys Gly Gly Gly Thr Tyr
1               5                   10

<210> SEQ ID NO 116
<211> LENGTH: 17
<212> TYPE: PRT
<213> ORGANISM: Mus musculus

<400> SEQUENCE: 116

Ala Ile Asn Ser Lys Gly Gly Gly Thr Tyr Tyr Pro Asp Thr Val Arg
1               5                   10                  15

Gly

<210> SEQ ID NO 117
<211> LENGTH: 10
<212> TYPE: PRT
<213> ORGANISM: Mus musculus

<400> SEQUENCE: 117

Ala Ile Asn Asn Arg Gly Gly Gly Thr Tyr
1               5                   10

<210> SEQ ID NO 118
<211> LENGTH: 17
<212> TYPE: PRT
<213> ORGANISM: Mus musculus

<400> SEQUENCE: 118

Ala Ile Asn Asn Arg Gly Gly Gly Thr Tyr Tyr Pro Asp Thr Val Arg
1               5                   10                  15

Gly

<210> SEQ ID NO 119
<211> LENGTH: 10
<212> TYPE: PRT
<213> ORGANISM: Mus musculus

<400> SEQUENCE: 119

Ala Ile Asn Pro Asn Gly Gly Thr Thr Tyr
1               5                   10

<210> SEQ ID NO 120
<211> LENGTH: 17
<212> TYPE: PRT
<213> ORGANISM: Mus musculus

<400> SEQUENCE: 120

Ala Ile Asn Pro Asn Gly Gly Thr Thr Tyr Tyr Pro Asp Thr Val Lys
1               5                   10                  15

Gly

<210> SEQ ID NO 121
<211> LENGTH: 17
<212> TYPE: PRT
<213> ORGANISM: Mus musculus

<400> SEQUENCE: 121

Ala Ile Asn Ser Asn Arg Gly Thr Thr Tyr Tyr Ser Asp Thr Val Lys Gly
1               5                   10                  15

<210> SEQ ID NO 122
<211> LENGTH: 10
<212> TYPE: PRT
<213> ORGANISM: Mus musculus

<400> SEQUENCE: 122

Glu Ile Leu Pro Gly Ile Gly Asn Thr Asn
1               5                   10

<210> SEQ ID NO 123
<211> LENGTH: 17
<212> TYPE: PRT
<213> ORGANISM: Mus musculus

<400> SEQUENCE: 123

Glu Ile Leu Pro Gly Ile Gly Asn Thr Asn Tyr Asn Glu Lys Phe Lys
1               5                   10                  15

Gly

<210> SEQ ID NO 124
<211> LENGTH: 30
<212> TYPE: DNA
<213> ORGANISM: Mus musculus

<400> SEQUENCE: 124
gccattaatt ttaatcgtgg taccacctac                                    30

<210> SEQ ID NO 125
<211> LENGTH: 51
<212> TYPE: DNA
<213> ORGANISM: Mus musculus

<400> SEQUENCE: 125
gccattaatt ttaatcgtgg taccacctac tattcagaca ctgtgaaggg c            51

<210> SEQ ID NO 126
<211> LENGTH: 30
<212> TYPE: DNA
<213> ORGANISM: Mus musculus

<400> SEQUENCE: 126
ggcattaata gtaatcgtgg taccacctac                                    30

<210> SEQ ID NO 127
<211> LENGTH: 51
<212> TYPE: DNA
<213> ORGANISM: Mus musculus

<400> SEQUENCE: 127
ggcattaata gtaatcgtgg taccacctac tatccagaca ctgtgaaggg c            51

<210> SEQ ID NO 128
<211> LENGTH: 30
<212> TYPE: DNA
<213> ORGANISM: Mus musculus

<400> SEQUENCE: 128
gccattaata ttaatcgtgg taccacctac                                    30

<210> SEQ ID NO 129
<211> LENGTH: 51
<212> TYPE: DNA
<213> ORGANISM: Mus musculus

<400> SEQUENCE: 129
gccattaata ttaatcgtgg taccacctac tattcagaca ctgtgaaggg c            51

<210> SEQ ID NO 130

<210> SEQ ID NO 130
<211> LENGTH: 30
<212> TYPE: DNA
<213> ORGANISM: Mus musculus

<400> SEQUENCE: 130
gccatgaata ataatggtgc tagcacctac                                    30

<210> SEQ ID NO 131
<211> LENGTH: 51
<212> TYPE: DNA
<213> ORGANISM: Mus musculus

<400> SEQUENCE: 131
gccatgaata ataatggtgc tagcacctac tatccagaca ctgtgaaggg c             51

<210> SEQ ID NO 132
<211> LENGTH: 30
<212> TYPE: DNA
<213> ORGANISM: Mus musculus

<400> SEQUENCE: 132
gccattaatc gtaaaggtca tagtacctac                                    30

<210> SEQ ID NO 133
<211> LENGTH: 51
<212> TYPE: DNA
<213> ORGANISM: Mus musculus

<400> SEQUENCE: 133
gccattaatc gtaaaggtca tagtacctac tatccagaca ctgtgcaggg c             51

<210> SEQ ID NO 134
<211> LENGTH: 51
<212> TYPE: DNA
<213> ORGANISM: Mus musculus

<400> SEQUENCE: 134
gccattaata gtaatcgtgg taccacctac tatccagaca ctgtgaaggg c             51

<210> SEQ ID NO 135
<211> LENGTH: 30
<212> TYPE: DNA
<213> ORGANISM: Mus musculus

<400> SEQUENCE: 135
gccattaata gtaatcgtgg taccacctac                                    30

<210> SEQ ID NO 136
<211> LENGTH: 30
<212> TYPE: DNA
<213> ORGANISM: Mus musculus

<400> SEQUENCE: 136
gccattaata ttaatcgtgg taccccctat                                    30

<210> SEQ ID NO 137
<211> LENGTH: 51
<212> TYPE: DNA
<213> ORGANISM: Mus musculus

<400> SEQUENCE: 137
gccattaata ttaatcgtgg taccccctat tatccagaca ctgtgaaggg c             51

```
<210> SEQ ID NO 138
<211> LENGTH: 30
<212> TYPE: DNA
<213> ORGANISM: Mus musculus

<400> SEQUENCE: 138
gccattaatc ctaatggtgg tagtacctac                                        30

<210> SEQ ID NO 139
<211> LENGTH: 51
<212> TYPE: DNA
<213> ORGANISM: Mus musculus

<400> SEQUENCE: 139
gccattaatc ctaatggtgg tagtacctac tatccagaca ctgtgaaggg c                51

<210> SEQ ID NO 140
<211> LENGTH: 30
<212> TYPE: DNA
<213> ORGANISM: Mus musculus

<400> SEQUENCE: 140
gccattaata gtaaaggtgg tggcacctac                                        30

<210> SEQ ID NO 141
<211> LENGTH: 51
<212> TYPE: DNA
<213> ORGANISM: Mus musculus

<400> SEQUENCE: 141
gccattaata gtaaaggtgg tggcacctac tatccagaca ctgtgagggg c                51

<210> SEQ ID NO 142
<211> LENGTH: 30
<212> TYPE: DNA
<213> ORGANISM: Mus musculus

<400> SEQUENCE: 142
gccattaata atagaggtgg tggcacctac                                        30

<210> SEQ ID NO 143
<211> LENGTH: 51
<212> TYPE: DNA
<213> ORGANISM: Mus musculus

<400> SEQUENCE: 143
gccattaata atagaggtgg tggcacctac tatccagaca ctgtgagggg c                51

<210> SEQ ID NO 144
<211> LENGTH: 30
<212> TYPE: DNA
<213> ORGANISM: Mus musculus

<400> SEQUENCE: 144
gccattaatc ctaatggtgg tactacctac                                        30

<210> SEQ ID NO 145
<211> LENGTH: 51
<212> TYPE: DNA
<213> ORGANISM: Mus musculus

<400> SEQUENCE: 145
gccattaatc ctaatggtgg tactacctac tacaatgaga aattcaaggg c                51
```

<210> SEQ ID NO 146
<211> LENGTH: 51
<212> TYPE: DNA
<213> ORGANISM: Mus musculus

<400> SEQUENCE: 146
gccattaata gtaatcgtgg taccacctac tattcagaca ctgtgaaggg c     51

<210> SEQ ID NO 147
<211> LENGTH: 30
<212> TYPE: DNA
<213> ORGANISM: Mus musculus

<400> SEQUENCE: 147
gagattttac ctggaattgg taatactaac                              30

<210> SEQ ID NO 148
<211> LENGTH: 51
<212> TYPE: DNA
<213> ORGANISM: Mus musculus

<400> SEQUENCE: 148
gagattttac ctggaattgg taatactaac tacaatgaga aattcaaggg c     51

<210> SEQ ID NO 149
<211> LENGTH: 14
<212> TYPE: PRT
<213> ORGANISM: Mus musculus

<400> SEQUENCE: 149

Ser Arg His Arg Tyr Ser Asp Tyr Asp Tyr Ala Met Asp Tyr
1               5                   10

<210> SEQ ID NO 150
<211> LENGTH: 14
<212> TYPE: PRT
<213> ORGANISM: Mus musculus

<400> SEQUENCE: 150

Val Arg His Arg Tyr Thr Asn Tyr Asp Tyr Ala Met Asp Tyr
1               5                   10

<210> SEQ ID NO 151
<211> LENGTH: 13
<212> TYPE: PRT
<213> ORGANISM: Mus musculus

<400> SEQUENCE: 151

Val Arg His Asn Asn Tyr Val Asp Tyr Ala Met Asp Tyr
1               5                   10

<210> SEQ ID NO 152
<211> LENGTH: 12
<212> TYPE: PRT
<213> ORGANISM: Mus musculus

<400> SEQUENCE: 152

Val Arg Leu Asp Asp Asn Tyr Tyr Phe Phe Asp Tyr
1               5                   10

<210> SEQ ID NO 153
<211> LENGTH: 14
<212> TYPE: PRT
<213> ORGANISM: Mus musculus

<400> SEQUENCE: 153

Val Arg His Arg Tyr Asn Asn Tyr Asp Tyr Ala Met Asp Tyr
1               5                   10

<210> SEQ ID NO 154
<211> LENGTH: 14
<212> TYPE: PRT
<213> ORGANISM: Mus musculus

<400> SEQUENCE: 154

Val Arg His Arg Asn Ser Asn Asn Asp Tyr Ala Met Asp Tyr
1               5                   10

<210> SEQ ID NO 155
<211> LENGTH: 12
<212> TYPE: PRT
<213> ORGANISM: Mus musculus

<400> SEQUENCE: 155

Ala Arg Leu Pro Trp Ser Pro Tyr Thr Leu Asp Tyr
1               5                   10

<210> SEQ ID NO 156
<211> LENGTH: 14
<212> TYPE: PRT
<213> ORGANISM: Mus musculus

<400> SEQUENCE: 156

Val Ser His Gly Asp Asn Lys Tyr Phe Tyr Ala Met Asp Tyr
1               5                   10

<210> SEQ ID NO 157
<211> LENGTH: 14
<212> TYPE: PRT
<213> ORGANISM: Mus musculus

<400> SEQUENCE: 157

Val Arg His Asp Asn Leu Asn Tyr Asp Tyr Ala Met Asp Ser
1               5                   10

<210> SEQ ID NO 158
<211> LENGTH: 14
<212> TYPE: PRT
<213> ORGANISM: Mus musculus

<400> SEQUENCE: 158

Thr Arg His Arg Tyr Ser Asp Tyr Asp Tyr Ala Met Asp Tyr
1               5                   10

<210> SEQ ID NO 159
<211> LENGTH: 14
<212> TYPE: PRT
<213> ORGANISM: Mus musculus

<400> SEQUENCE: 159

Val Arg His Arg Tyr Ile Asp Tyr Asp Tyr Ala Met Asp Tyr
1               5                   10

<210> SEQ ID NO 160
<211> LENGTH: 13
<212> TYPE: PRT
<213> ORGANISM: Mus musculus

<400> SEQUENCE: 160

```
Ser Gly Gly Tyr Ser Thr Val Tyr Trp Tyr Phe Asp Val
1               5                   10
```

<210> SEQ ID NO 161
<211> LENGTH: 42
<212> TYPE: DNA
<213> ORGANISM: Mus musculus

<400> SEQUENCE: 161
tcaagacacc gctatagtga ctacgactat gctatggact ac           42

<210> SEQ ID NO 162
<211> LENGTH: 42
<212> TYPE: DNA
<213> ORGANISM: Mus musculus

<400> SEQUENCE: 162
gtaagacacc gctatactaa ctacgactat gctatggact ac           42

<210> SEQ ID NO 163
<211> LENGTH: 39
<212> TYPE: DNA
<213> ORGANISM: Mus musculus

<400> SEQUENCE: 163
gtaagacata ataactacgt tgactatgct atggactat              39

<210> SEQ ID NO 164
<211> LENGTH: 36
<212> TYPE: DNA
<213> ORGANISM: Mus musculus

<400> SEQUENCE: 164
gtaagacttg acgataacta ctacttcttt gactac                 36

<210> SEQ ID NO 165
<211> LENGTH: 42
<212> TYPE: DNA
<213> ORGANISM: Mus musculus

<400> SEQUENCE: 165
gtaagacacc gctataataa ctacgactat gctatggact ac           42

<210> SEQ ID NO 166
<211> LENGTH: 42
<212> TYPE: DNA
<213> ORGANISM: Mus musculus

<400> SEQUENCE: 166
gtaagacacc gcaatagtaa caacgactat gctatggact ac           42

<210> SEQ ID NO 167
<211> LENGTH: 36
<212> TYPE: DNA
<213> ORGANISM: Mus musculus

<400> SEQUENCE: 167
gcaagactcc catggtcccc ctatactttg gactac                 36

<210> SEQ ID NO 168
<211> LENGTH: 42
<212> TYPE: DNA
<213> ORGANISM: Mus musculus

```
<400> SEQUENCE: 168
gtaagccatg gggataataa gtacttttat gctatggact ac                         42

<210> SEQ ID NO 169
<211> LENGTH: 42
<212> TYPE: DNA
<213> ORGANISM: Mus musculus

<400> SEQUENCE: 169
gtgagacatg acaatcttaa ctatgactat gctatggact cc                         42

<210> SEQ ID NO 170
<211> LENGTH: 42
<212> TYPE: DNA
<213> ORGANISM: Mus musculus

<400> SEQUENCE: 170
acaagacacc gctatagtga ctacgactat gctatggact ac                         42

<210> SEQ ID NO 171
<211> LENGTH: 42
<212> TYPE: DNA
<213> ORGANISM: Mus musculus

<400> SEQUENCE: 171
gtaagacacc gctatattga ctacgactat gctatggact ac                         42

<210> SEQ ID NO 172
<211> LENGTH: 42
<212> TYPE: DNA
<213> ORGANISM: Mus musculus

<400> SEQUENCE: 172
gcaagtgggg ggtatagtac cgtctattgg tattttgatg tc                         42

<210> SEQ ID NO 173
<211> LENGTH: 12
<212> TYPE: PRT
<213> ORGANISM: Mus musculus

<400> SEQUENCE: 173

Lys Ala Ser Gln Asp Ile Asn Ser Tyr Leu Asn Trp
1               5                   10

<210> SEQ ID NO 174
<211> LENGTH: 12
<212> TYPE: PRT
<213> ORGANISM: Mus musculus

<400> SEQUENCE: 174

Lys Ala Ser Gln Asp Ile Tyr Ser Tyr Leu Ser Trp
1               5                   10

<210> SEQ ID NO 175
<211> LENGTH: 12
<212> TYPE: PRT
<213> ORGANISM: Mus musculus

<400> SEQUENCE: 175

Met Thr Ser Thr Asp Ile Asp Asp Ala Leu Asn Trp
1               5                   10
```

<210> SEQ ID NO 176
<211> LENGTH: 12
<212> TYPE: PRT
<213> ORGANISM: Mus musculus

<400> SEQUENCE: 176

Lys Ser Ser Gln Asp Ile Asn Ser Tyr Leu Ser Trp
1               5                   10

<210> SEQ ID NO 177
<211> LENGTH: 12
<212> TYPE: PRT
<213> ORGANISM: Mus musculus

<400> SEQUENCE: 177

Gln Ser Leu Leu Asn Ser Arg Thr Arg Lys Asn Tyr
1               5                   10

<210> SEQ ID NO 178
<211> LENGTH: 17
<212> TYPE: PRT
<213> ORGANISM: Mus musculus

<400> SEQUENCE: 178

Lys Ser Ser Gln Ser Leu Leu Asn Ser Arg Thr Arg Lys Asn Tyr Leu
1               5                   10                  15
Ala

<210> SEQ ID NO 179
<211> LENGTH: 12
<212> TYPE: PRT
<213> ORGANISM: Mus musculus

<400> SEQUENCE: 179

Lys Ala Ser Gln Asp Ile Asn Ser Tyr Leu Ser Trp
1               5                   10

<210> SEQ ID NO 180
<211> LENGTH: 12
<212> TYPE: PRT
<213> ORGANISM: Mus musculus

<400> SEQUENCE: 180

Ile Thr Asn Thr Asp Ile Asp Asp Ala Met Asn Trp
1               5                   10

<210> SEQ ID NO 181
<211> LENGTH: 36
<212> TYPE: DNA
<213> ORGANISM: Mus musculus

<400> SEQUENCE: 181
aaggcgagtc aggacattaa tagctattta aactgg                         36

<210> SEQ ID NO 182
<211> LENGTH: 36
<212> TYPE: DNA
<213> ORGANISM: Mus musculus

<400> SEQUENCE: 182
aaggcgagtc aggacattaa tagctattta agctgg                         36

<210> SEQ ID NO 183
<211> LENGTH: 36

```
<212> TYPE: DNA
<213> ORGANISM: Mus musculus

<400> SEQUENCE: 183
aaggcgagtc aagacattaa tagctattta agctgg                              36

<210> SEQ ID NO 184
<211> LENGTH: 36
<212> TYPE: DNA
<213> ORGANISM: Mus musculus

<400> SEQUENCE: 184
ataaccaaca ctgatattga tgatgctatg aactgg                              36

<210> SEQ ID NO 185
<211> LENGTH: 36
<212> TYPE: DNA
<213> ORGANISM: Mus musculus

<400> SEQUENCE: 185
aaggcgagtc aggacattta tagctattta agctgg                              36

<210> SEQ ID NO 186
<211> LENGTH: 36
<212> TYPE: DNA
<213> ORGANISM: Mus musculus

<400> SEQUENCE: 186
atgaccagca ctgatattga tgatgctctg aactgg                              36

<210> SEQ ID NO 187
<211> LENGTH: 36
<212> TYPE: DNA
<213> ORGANISM: Mus musculus

<400> SEQUENCE: 187
aagtcgagtc aggacattaa tagctattta agttgg                              36

<210> SEQ ID NO 188
<211> LENGTH: 36
<212> TYPE: DNA
<213> ORGANISM: Mus musculus

<400> SEQUENCE: 188
cagagtctgc tcaacagtag aacccgaaag aactac                              36

<210> SEQ ID NO 189
<211> LENGTH: 51
<212> TYPE: DNA
<213> ORGANISM: Mus musculus

<400> SEQUENCE: 189
aaatccagtc agagtctgct caacagtaga acccgaaaga actacttggc t             51

<210> SEQ ID NO 190
<211> LENGTH: 7
<212> TYPE: PRT
<213> ORGANISM: Mus musculus

<400> SEQUENCE: 190

Arg Ala Asn Arg Leu Val Asp
1               5
```

```
<210> SEQ ID NO 191
<211> LENGTH: 10
<212> TYPE: PRT
<213> ORGANISM: Mus musculus

<400> SEQUENCE: 191

Thr Leu Ile Tyr Arg Ala Asn Arg Leu Val
1               5                   10

<210> SEQ ID NO 192
<211> LENGTH: 10
<212> TYPE: PRT
<213> ORGANISM: Mus musculus

<400> SEQUENCE: 192

Thr Leu Ile His Arg Ala Asn Arg Leu Val
1               5                   10

<210> SEQ ID NO 193
<211> LENGTH: 10
<212> TYPE: PRT
<213> ORGANISM: Mus musculus

<400> SEQUENCE: 193

Thr Leu Ile Tyr Arg Ala Asn Lys Leu Val
1               5                   10

<210> SEQ ID NO 194
<211> LENGTH: 7
<212> TYPE: PRT
<213> ORGANISM: Mus musculus

<400> SEQUENCE: 194

Arg Ala Asn Lys Leu Val Asp
1               5

<210> SEQ ID NO 195
<211> LENGTH: 10
<212> TYPE: PRT
<213> ORGANISM: Mus musculus

<400> SEQUENCE: 195

Thr Leu Ile Tyr Arg Ala Lys Arg Leu Ile
1               5                   10

<210> SEQ ID NO 196
<211> LENGTH: 7
<212> TYPE: PRT
<213> ORGANISM: Mus musculus

<400> SEQUENCE: 196

Arg Ala Lys Arg Leu Ile Asp
1               5

<210> SEQ ID NO 197
<211> LENGTH: 10
<212> TYPE: PRT
<213> ORGANISM: Mus musculus

<400> SEQUENCE: 197

Thr Leu Thr Tyr Arg Ala Asn Arg Leu Val
1               5                   10

<210> SEQ ID NO 198
<211> LENGTH: 7
```

```
<212> TYPE: PRT
<213> ORGANISM: Mus musculus

<400> SEQUENCE: 198

Arg Ala Asn Arg Leu Val Glu
1               5

<210> SEQ ID NO 199
<211> LENGTH: 10
<212> TYPE: PRT
<213> ORGANISM: Mus musculus

<400> SEQUENCE: 199

Thr Leu Ile Tyr Arg Ala Asn Arg Leu Ile
1               5                   10

<210> SEQ ID NO 200
<211> LENGTH: 7
<212> TYPE: PRT
<213> ORGANISM: Mus musculus

<400> SEQUENCE: 200

Arg Ala Asn Arg Leu Ile Asp
1               5

<210> SEQ ID NO 201
<211> LENGTH: 10
<212> TYPE: PRT
<213> ORGANISM: Mus musculus

<400> SEQUENCE: 201

Leu Leu Ile Ser Glu Gly Asn Thr Leu Arg
1               5                   10

<210> SEQ ID NO 202
<211> LENGTH: 7
<212> TYPE: PRT
<213> ORGANISM: Mus musculus

<400> SEQUENCE: 202

Glu Gly Asn Thr Leu Arg Pro
1               5

<210> SEQ ID NO 203
<211> LENGTH: 10
<212> TYPE: PRT
<213> ORGANISM: Mus musculus

<400> SEQUENCE: 203

Leu Leu Ile Ser Glu Gly Asn Ser Leu Arg
1               5                   10

<210> SEQ ID NO 204
<211> LENGTH: 7
<212> TYPE: PRT
<213> ORGANISM: Mus musculus

<400> SEQUENCE: 204

Glu Gly Asn Ser Leu Arg Pro
1               5

<210> SEQ ID NO 205
<211> LENGTH: 10
<212> TYPE: PRT
<213> ORGANISM: Mus musculus
```

```
<400> SEQUENCE: 205

Thr Leu Thr His Arg Ala Asn Arg Leu Val
1               5                   10

<210> SEQ ID NO 206
<211> LENGTH: 10
<212> TYPE: PRT
<213> ORGANISM: Mus musculus

<400> SEQUENCE: 206

Thr Leu Ile Phe Arg Ala Asn Arg Leu Val
1               5                   10

<210> SEQ ID NO 207
<211> LENGTH: 11
<212> TYPE: PRT
<213> ORGANISM: Mus musculus

<400> SEQUENCE: 207

Lys Leu Leu Ile Tyr Trp Thr Ser Thr Arg Glu
1               5                   10

<210> SEQ ID NO 208
<211> LENGTH: 7
<212> TYPE: PRT
<213> ORGANISM: Mus musculus

<400> SEQUENCE: 208

Trp Thr Ser Thr Arg Glu Ser
1               5

<210> SEQ ID NO 209
<211> LENGTH: 21
<212> TYPE: DNA
<213> ORGANISM: Mus musculus

<400> SEQUENCE: 209
cgtgcaaaca gattggtaga t                                          21

<210> SEQ ID NO 210
<211> LENGTH: 30
<212> TYPE: DNA
<213> ORGANISM: Mus musculus

<400> SEQUENCE: 210
accctgatct atcgtgcaaa cagattggta                                 30

<210> SEQ ID NO 211
<211> LENGTH: 31
<212> TYPE: DNA
<213> ORGANISM: Mus musculus

<400> SEQUENCE: 211
ccctcatcta tcctccaaac acattcctac a                               31

<210> SEQ ID NO 212
<211> LENGTH: 30
<212> TYPE: DNA
<213> ORGANISM: Mus musculus

<400> SEQUENCE: 212
accctgatcc atcgtgcaaa cagattggta                                 30
```

<210> SEQ ID NO 213
<211> LENGTH: 30
<212> TYPE: DNA
<213> ORGANISM: Mus musculus

<400> SEQUENCE: 213
accctgatct atcgtgcaaa caaattggta                              30

<210> SEQ ID NO 214
<211> LENGTH: 21
<212> TYPE: DNA
<213> ORGANISM: Mus musculus

<400> SEQUENCE: 214
cgtgcaaaca aattggtaga t                                       21

<210> SEQ ID NO 215
<211> LENGTH: 30
<212> TYPE: DNA
<213> ORGANISM: Mus musculus

<400> SEQUENCE: 215
accctgatct atcgtgcaaa gagattgata                              30

<210> SEQ ID NO 216
<211> LENGTH: 21
<212> TYPE: DNA
<213> ORGANISM: Mus musculus

<400> SEQUENCE: 216
cgtgcaaaga gattgataga t                                       21

<210> SEQ ID NO 217
<211> LENGTH: 30
<212> TYPE: DNA
<213> ORGANISM: Mus musculus

<400> SEQUENCE: 217
accctgacct atcgtgcaaa cagattggta                              30

<210> SEQ ID NO 218
<211> LENGTH: 21
<212> TYPE: DNA
<213> ORGANISM: Mus musculus

<400> SEQUENCE: 218
cgtgcaaaca gattggtaga a                                       21

<210> SEQ ID NO 219
<211> LENGTH: 30
<212> TYPE: DNA
<213> ORGANISM: Mus musculus

<400> SEQUENCE: 219
accctgatct atcgtgcaaa cagattgata                              30

<210> SEQ ID NO 220
<211> LENGTH: 21
<212> TYPE: DNA
<213> ORGANISM: Mus musculus

<400> SEQUENCE: 220
cgtgcaaaca gattgataga t                                       21

<210> SEQ ID NO 221
<211> LENGTH: 30
<212> TYPE: DNA
<213> ORGANISM: Mus musculus

<400> SEQUENCE: 221
ctccttattt cagaaggcaa tactcttcgt                                    30

<210> SEQ ID NO 222
<211> LENGTH: 21
<212> TYPE: DNA
<213> ORGANISM: Mus musculus

<400> SEQUENCE: 222
gaaggcaata ctcttcgtcc t                                             21

<210> SEQ ID NO 223
<211> LENGTH: 30
<212> TYPE: DNA
<213> ORGANISM: Mus musculus

<400> SEQUENCE: 223
ctccttattt cagaaggcaa tagtcttcgt                                    30

<210> SEQ ID NO 224
<211> LENGTH: 21
<212> TYPE: DNA
<213> ORGANISM: Mus musculus

<400> SEQUENCE: 224
gaaggcaata gtcttcgtcc t                                             21

<210> SEQ ID NO 225
<211> LENGTH: 30
<212> TYPE: DNA
<213> ORGANISM: Mus musculus

<400> SEQUENCE: 225
accctgaccc atcgtgcaaa cagattggta                                    30

<210> SEQ ID NO 226
<211> LENGTH: 30
<212> TYPE: DNA
<213> ORGANISM: Mus musculus

<400> SEQUENCE: 226
accctgatct ttcgtgcaaa cagattggta                                    30

<210> SEQ ID NO 227
<211> LENGTH: 33
<212> TYPE: DNA
<213> ORGANISM: Mus musculus

<400> SEQUENCE: 227
aaactgctga tctactggac atccactagg gaa                                33

<210> SEQ ID NO 228
<211> LENGTH: 21
<212> TYPE: DNA
<213> ORGANISM: Mus musculus

<400> SEQUENCE: 228
tggacatcca ctagggaatc t     21

<210> SEQ ID NO 229
<211> LENGTH: 9
<212> TYPE: PRT
<213> ORGANISM: Mus musculus

<400> SEQUENCE: 229

Leu Gln Tyr Asp Glu Phe Pro Tyr Thr
1               5

<210> SEQ ID NO 230
<211> LENGTH: 9
<212> TYPE: PRT
<213> ORGANISM: Mus musculus

<400> SEQUENCE: 230

Leu Gln Tyr Asp Glu Phe Pro Phe Thr
1               5

<210> SEQ ID NO 231
<211> LENGTH: 9
<212> TYPE: PRT
<213> ORGANISM: Mus musculus

<400> SEQUENCE: 231

Leu Gln Thr Asp Asn Leu Pro Leu Thr
1               5

<210> SEQ ID NO 232
<211> LENGTH: 9
<212> TYPE: PRT
<213> ORGANISM: Mus musculus

<400> SEQUENCE: 232

Leu Gln Ser Asp Asn Leu Pro Leu Thr
1               5

<210> SEQ ID NO 233
<211> LENGTH: 9
<212> TYPE: PRT
<213> ORGANISM: Mus musculus

<400> SEQUENCE: 233

Lys Gln Ser Tyr Asp Leu Pro Trp Thr
1               5

<210> SEQ ID NO 234
<211> LENGTH: 27
<212> TYPE: DNA
<213> ORGANISM: Mus musculus

<400> SEQUENCE: 234
ctacagtatg atgagtttcc gtacacg     27

<210> SEQ ID NO 235
<211> LENGTH: 27
<212> TYPE: DNA
<213> ORGANISM: Mus musculus

<400> SEQUENCE: 235
ctacagtatg atgaatttcc gtacacg     27

<210> SEQ ID NO 236

```
<210> SEQ ID NO 236
<211> LENGTH: 27
<212> TYPE: DNA
<213> ORGANISM: Mus musculus

<400> SEQUENCE: 236
ctacagtatg atgagtttcc ttacacg                                           27

<210> SEQ ID NO 237
<211> LENGTH: 27
<212> TYPE: DNA
<213> ORGANISM: Mus musculus

<400> SEQUENCE: 237
ctacagtatg atgagtttcc attcacg                                           27

<210> SEQ ID NO 238
<211> LENGTH: 27
<212> TYPE: DNA
<213> ORGANISM: Mus musculus

<400> SEQUENCE: 238
ttgcaaactg ataacttgcc tctcacg                                           27

<210> SEQ ID NO 239
<211> LENGTH: 27
<212> TYPE: DNA
<213> ORGANISM: Mus musculus

<400> SEQUENCE: 239
ttgcaaagtg ataacttgcc tctcacg                                           27

<210> SEQ ID NO 240
<211> LENGTH: 27
<212> TYPE: DNA
<213> ORGANISM: Mus musculus

<400> SEQUENCE: 240
aagcaatctt atgatcttcc gtggacg                                           27

<210> SEQ ID NO 241
<211> LENGTH: 17
<212> TYPE: PRT
<213> ORGANISM: Mus musculus

<400> SEQUENCE: 241

Ala Ile Asn Ser Asn Arg Gly Thr Thr Tyr Tyr Ser Asp Thr Val Lys
1               5                   10                  15

Gly

<210> SEQ ID NO 242
<211> LENGTH: 51
<212> TYPE: DNA
<213> ORGANISM: Mus musculus

<400> SEQUENCE: 242
gccattaatc ctaatggtgg tactacctac tatccagaca ctgtgaaggg c                51

<210> SEQ ID NO 243
<211> LENGTH: 36
<212> TYPE: DNA
<213> ORGANISM: Mus musculus

<400> SEQUENCE: 243
```

```
aaggcgagtc aggacattaa tagctattta agctgg                                36
```

<210> SEQ ID NO 244
<211> LENGTH: 33
<212> TYPE: DNA
<213> ORGANISM: Mus musculus

<400> SEQUENCE: 244

```
accctgatct atcgtgcaaa cagattggta gat                                   33
```

<210> SEQ ID NO 245
<211> LENGTH: 30
<212> TYPE: DNA
<213> ORGANISM: Mus musculus

<400> SEQUENCE: 245

```
accctgatct atcgtgcaaa cagattggta                                       30
```

<210> SEQ ID NO 246
<211> LENGTH: 27
<212> TYPE: DNA
<213> ORGANISM: Mus musculus

<400> SEQUENCE: 246

```
ctacagtatg atgagtttcc tcccaca                                          27
```

<210> SEQ ID NO 247
<211> LENGTH: 36
<212> TYPE: DNA
<213> ORGANISM: Mus musculus

<400> SEQUENCE: 247

```
gcctctggat tcgctttcag tagctatgac atgtct                                36
```

<210> SEQ ID NO 248
<211> LENGTH: 30
<212> TYPE: DNA
<213> ORGANISM: Mus musculus

<400> SEQUENCE: 248

```
ggattcgctt tcagtagcta tgacatgtct                                       30
```

<210> SEQ ID NO 249
<211> LENGTH: 30
<212> TYPE: DNA
<213> ORGANISM: Mus musculus

<400> SEQUENCE: 249

```
tacattagta gtggtggtgg tagcacctac                                       30
```

<210> SEQ ID NO 250
<211> LENGTH: 51
<212> TYPE: DNA
<213> ORGANISM: Mus musculus

<400> SEQUENCE: 250

```
tacattagta gtggtggtgg tagcacctac tatccagaca ctgtgaaggg c                51
```

<210> SEQ ID NO 251
<211> LENGTH: 36
<212> TYPE: DNA
<213> ORGANISM: Mus musculus

<400> SEQUENCE: 251

```
gcctctggat tcactttcag tagctattac atgtct                           36

<210> SEQ ID NO 252
<211> LENGTH: 30
<212> TYPE: DNA
<213> ORGANISM: Mus musculus

<400> SEQUENCE: 252
ggattcactt tcagtagcta ttacatgtct                                  30

<210> SEQ ID NO 253
<211> LENGTH: 30
<212> TYPE: DNA
<213> ORGANISM: Mus musculus

<400> SEQUENCE: 253
gccattaata gtaatggtgg tagcacctac                                  30

<210> SEQ ID NO 254
<211> LENGTH: 51
<212> TYPE: DNA
<213> ORGANISM: Mus musculus

<400> SEQUENCE: 254
gccattaata gtaatggtgg tagcacctac tatccagaca ctgtgaaggg c           51

<210> SEQ ID NO 255
<211> LENGTH: 36
<212> TYPE: DNA
<213> ORGANISM: Mus musculus

<400> SEQUENCE: 255
ataaccagca ctgatattga tgatgatatg aactgg                           36

<210> SEQ ID NO 256
<211> LENGTH: 30
<212> TYPE: DNA
<213> ORGANISM: Mus musculus

<400> SEQUENCE: 256
ggctacacat tcactggcta ctggatagag                                  30

<210> SEQ ID NO 257
<211> LENGTH: 30
<212> TYPE: DNA
<213> ORGANISM: Mus musculus

<400> SEQUENCE: 257
ctccttattt cagaaggcaa tactcttcgt                                  30

<210> SEQ ID NO 258
<211> LENGTH: 33
<212> TYPE: DNA
<213> ORGANISM: Mus musculus

<400> SEQUENCE: 258
ctccttattt cagaaggcaa tactcttcgt cct                              33

<210> SEQ ID NO 259
<211> LENGTH: 27
<212> TYPE: DNA
<213> ORGANISM: Mus musculus
```

<400> SEQUENCE: 259
ttgcaaagtg ataacttgcc tctcaca                                              27

<210> SEQ ID NO 260
<211> LENGTH: 36
<212> TYPE: DNA
<213> ORGANISM: Mus musculus

<400> SEQUENCE: 260
cagagtctgc tcaacagtag aacccgaaag aactac                                    36

<210> SEQ ID NO 261
<211> LENGTH: 51
<212> TYPE: DNA
<213> ORGANISM: Mus musculus

<400> SEQUENCE: 261
aaatccagtc agagtctgct caacagtaga acccgaaaga actacttggc t                   51

<210> SEQ ID NO 262
<211> LENGTH: 33
<212> TYPE: DNA
<213> ORGANISM: Mus musculus

<400> SEQUENCE: 262
aaactgctga tctactgggc atccactagg gaa                                       33

<210> SEQ ID NO 263
<211> LENGTH: 21
<212> TYPE: DNA
<213> ORGANISM: Mus musculus

<400> SEQUENCE: 263
tgggcatcca ctagggaatc t                                                    21

<210> SEQ ID NO 264
<211> LENGTH: 27
<212> TYPE: DNA
<213> ORGANISM: Mus musculus

<400> SEQUENCE: 264
aagcaatctt ataatcttcc cacagtg                                              27

<210> SEQ ID NO 265
<211> LENGTH: 36
<212> TYPE: DNA
<213> ORGANISM: Mus musculus

<400> SEQUENCE: 265
gctactggct acacattcac tggctactgg atagag                                    36

<210> SEQ ID NO 266
<211> LENGTH: 30
<212> TYPE: DNA
<213> ORGANISM: Mus musculus

<400> SEQUENCE: 266
gagattttac ctggaagtgg tagtactaac                                           30

<210> SEQ ID NO 267
<211> LENGTH: 51
<212> TYPE: DNA
<213> ORGANISM: Mus musculus

<400> SEQUENCE: 267
gagattttac ctggaagtgg tagtactaac tacaatgaga agttcaaggg c    51

<210> SEQ ID NO 268
<211> LENGTH: 471
<212> TYPE: PRT
<213> ORGANISM: Artificial sequence
<220> FEATURE:
<223> OTHER INFORMATION: Humanised Mus musculus sequence

<400> SEQUENCE: 268

```
Met Glu Thr Asp Thr Leu Leu Leu Trp Val Leu Leu Trp Val Pro
1               5                   10                  15
Gly Ser Thr Gly Glu Val Gln Leu Val Glu Ser Gly Gly Leu Val
                20                  25                  30
Gln Pro Gly Gly Ser Leu Arg Leu Ser Cys Ala Ala Ser Gly Phe Thr
                35                  40                  45
Phe Ser Ser Tyr Ala Met Ser Trp Val Arg Gln Ala Pro Gly Lys Gly
    50                  55                  60
Leu Glu Trp Val Ala Ala Ile Asn Phe Asn Arg Gly Thr Thr Tyr Tyr
65                  70                  75                  80
Ser Asp Thr Val Lys Gly Arg Phe Thr Ile Ser Arg Asp Asn Ala Lys
                85                  90                  95
Asn Ser Leu Tyr Leu Gln Met Asn Ser Leu Arg Ala Glu Asp Thr Ala
                100                 105                 110
Val Tyr Tyr Cys Ser Arg His Arg Tyr Ser Asp Tyr Asp Tyr Ala Met
                115                 120                 125
Asp Tyr Trp Gly Gln Gly Thr Met Val Thr Val Ser Ser Ala Ser Thr
    130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
                195                 200                 205
Val Val Thr Val Pro Ser Ser Ser Leu Gly Thr Gln Thr Tyr Ile Cys
    210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
                245                 250                 255
Glu Leu Leu Gly Gly Pro Ser Val Phe Leu Phe Pro Pro Lys Pro Lys
                260                 265                 270
Asp Thr Leu Met Ile Ser Arg Thr Pro Glu Val Thr Cys Val Val Val
    275                 280                 285
Asp Val Ser His Glu Asp Pro Glu Val Lys Phe Asn Trp Tyr Val Asp
    290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
```

```
            340                 345                 350
Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 269
<211> LENGTH: 1425
<212> TYPE: DNA
<213> ORGANISM: Artificial sequence
<220> FEATURE:
<223> OTHER INFORMATION: Humanised Mus musculus sequence

<400> SEQUENCE: 269
atggaaaccg acaccctgct gctgtgggtc ctgctgctct gggtgccagg ctctaccggc      60
gaggtgcagc tggtggaatc cggcggaggc ctggtccagc ctggcggatc cctgagactg    120
tcctgtgccg cctccggctt caccttctcc agctacgcca tgtcctgggt ccgacaggct    180
ccaggcaagg gcctggaatg ggtggccgcc atcaacttca ccggggcac acctactac     240 tccgacaccg tgaagggccg gtttaccatc tcccgggaca cgccaagaa ctccctgtac    300 ctgcagatga actccctgcg ggccgaggac accgccgtgt actactgctc ccggcaccgg    360
tactccgact acgactacgc catggactac tggggccagg gcaccatggt caccgtgtcc    420
tccgcctcca ccaagggccc ctccgtgttt cctctggccc cctccagcaa gtctacctct    480
ggcggcaccg ccgcactggg ctgcctggtc aaggactatt tccccgagcc cgtgaccgtg    540
tcctggaact ctggcgccct gacctccggc gtgcacacct ttccagccgt gctgcagtcc    600
tccggcctgt actccctgtc ctcgtcgtg accgtgccct ccagctctct gggcacccag    660
acctacatct gcaacgtgaa ccacaagccc tccaacacca aggtggacaa gcgggtggaa    720
cccaagtcct gcgacaagac ccacacctgt ccccccctgcc ctgcccctga actgctggga    780
ggaccttccg tgttcctgtt ccctccaaag cccaaggaca cctgatgat ctccggacc     840 cccgaagtga cctgcgtggt ggtggacgtg tcccacgagg accctgaagt gaagttcaat    900
tggtacgtgg acggcgtgga agtgcacaat gccaagacca gcccagaga ggaacagtac    960 aactccaccct accgggtggt gtccgtgctg accgtgctgc accaggactg gctgaacggc    1020
aaagagtaca gtgcaaggt ctccaacaag gctctgcctg ccccatcga aaagaccatc    1080 tccaaggcca aggggcagcc tcgcgagcct caggtgtaca cactgcccc tagccgggaa    1140 gagatgacca gaaccaggt gtccctgacc tgtctggtca aaggcttcta ccccttccgat    1200 atcgccgtgg aatgggagtc aacggccag ccgagaaca actacaagac cacccccct    1260 gtgctggact ccgacggctc attcttcctg tactccaagc tgaccgtgga caagtcccgg    1320
```
tggcagcagg gcaacgtgtt ctcctgctcc gtgatgcacg aggccctgca caaccactac   1380
acccagaagt ccctgtccct gagccccggc aagtgatagt ctaga   1425

<210> SEQ ID NO 270
<211> LENGTH: 254
<212> TYPE: PRT
<213> ORGANISM: Artificial sequence
<220> FEATURE:
<223> OTHER INFORMATION: Humanised Mus musculus sequence

<400> SEQUENCE: 270

```
Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile Asn Ser Tyr Leu Asn Trp Phe Gln Gln Lys Pro Gly Lys Ala Pro
    50                  55                  60

Lys Ser Leu Ile Tyr Arg Ala Asn Arg Leu Val Asp Gly Val Pro Ser
65                  70                  75                  80

Lys Phe Ser Gly Ser Gly Ser Gly His Asp Tyr Thr Leu Thr Ile Ser
                85                  90                  95

Ser Leu Gln Pro Glu Asp Phe Ala Thr Tyr Tyr Cys Leu Gln Tyr Asp
            100                 105                 110

Glu Phe Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Ser Ala Arg Gln Ser Thr
225                 230                 235                 240

Pro Phe Val Cys Glu Tyr Gln Gly Gln Ser Ser Asp Leu Pro
                245                 250
```

<210> SEQ ID NO 271
<211> LENGTH: 803
<212> TYPE: DNA
<213> ORGANISM: Artificial sequence
<220> FEATURE:
<223> OTHER INFORMATION: Humanised Mus musculus sequence

<400> SEQUENCE: 271
atggaaaccg acaccctgct gctgtgggtc ctgctgctct gggtgccagg ctccaccggc   60
gacatccaga tgacccagtc ccctccagc ctgtccgcct ctgtgggcga cagagtgacc   120
atcacatgca aggcctccca ggacatcaac tcctacctga ctggttccca gcagaagccc   180

```
ggcaaggccc ccaagtccct gatctaccgg gccaaccggc tggtggacgg cgtgccctcc       240
aagttctccg gctctggctc cggccacgac tataccctga ccatctccag cctgcagccc       300
gaggacttcg ccacctacta ctgcctgcag tacgacgagt tccctacac cttcggccag        360 ggcaccaagc tggaaatcaa gcggaccgtg gccgctccct ccgtgttcat cttcccaccc       420
tccgacgagc agctgaagtc cggcaccgcc tccgtcgtgt gcctgctgaa caacttctac       480
ccccgcgagg ccaaggtgca gtggaaggtg gacaacgccc tgcagtccgg caactcccag       540
gaatccgtca ccgagcagga ctccaaggac agcacctact ccctgtcctc caccctgacc       600
ctgtccaagg ccgactacga aagcacaag gtgtacgcct gcgaagtgac ccaccagggc        660
ctgtccagcc ccgtgaccaa gtccttcaac cggggcgagt gctctgcccg cagtccacc        720 cctttcgtgt gcgagtacca gggccagtcc tccgacctgc cctgatagtc tagagggccc       780
tattctatag tgtcacctaa atg                                               803
```

<210> SEQ ID NO 272
<211> LENGTH: 378
<212> TYPE: PRT
<213> ORGANISM: Homo Sapiens

<400> SEQUENCE: 272

```
Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Thr Ala Ser
        115                 120                 125

Pro Gly Tyr Ser Asp Glu Tyr Glu Glu Asp Gly Phe Cys Gln Pro Tyr
        130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
        210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
```

```
                        260                 265                 270
Pro Met Ala Asp Pro Ile Asn Lys Asn His Lys Cys Tyr Asn Ser Thr
            275                 280                 285

Gly Val Asp Tyr Arg Gly Thr Val Ser Val Thr Lys Ser Gly Arg Gln
        290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
                355                 360                 365

Glu Lys Asn Lys Met Glu Ile Leu Tyr Ile
            370                 375
```

<210> SEQ ID NO 273
<211> LENGTH: 27
<212> TYPE: DNA
<213> ORGANISM: Mus musculus

<400> SEQUENCE: 273
ctacactatc atcaatttcc ctacacc                                       27

<210> SEQ ID NO 274
<211> LENGTH: 36
<212> TYPE: DNA
<213> ORGANISM: Mus musculus

<400> SEQUENCE: 274
aaccccactc accacattaa tacctattta acctcc                             36

<210> SEQ ID NO 275
<211> LENGTH: 10
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: X is F or Y
<220> FEATURE:
<221> NAME/KEY: MISC_FEATURE
<222> LOCATION: (3)..(3)
<223> OTHER INFORMATION: X is T, S or A
<220> FEATURE:
<221> NAME/KEY: MISC_FEATURE
<222> LOCATION: (6)..(6)
<223> OTHER INFORMATION: X is S, T, N, P or R
<220> FEATURE:
<221> NAME/KEY: MISC_FEATURE
<222> LOCATION: (7)..(7)
<223> OTHER INFORMATION: X is Y or N
<220> FEATURE:
<221> NAME/KEY: MISC_FEATURE
<222> LOCATION: (8)..(8)
<223> OTHER INFORMATION: X is A, G, D or W
<220> FEATURE:
<221> NAME/KEY: MISC_FEATURE
<222> LOCATION: (9)..(9)
<223> OTHER INFORMATION: X is M or I
<220> FEATURE:
<221> NAME/KEY: MISC_FEATURE
<222> LOCATION: (10)..(10)
<223> OTHER INFORMATION: X is S or E

<400> SEQUENCE: 275

```
Gly Xaa Xaa Phe Ser Xaa Xaa Xaa Xaa Xaa
1               5                   10

<210> SEQ ID NO 276
<211> LENGTH: 10
<212> TYPE: PRT
<213> ORGANISM: Mus musculus
<220> FEATURE:
<221> NAME/KEY: MISC_FEATURE
<222> LOCATION: (2)..(2)
<223> OTHER INFORMATION: X is F or Y
<220> FEATURE:
<221> NAME/KEY: MISC_FEATURE
<222> LOCATION: (3)..(3)
<223> OTHER INFORMATION: X is T, S or A
<220> FEATURE:
<221> NAME/KEY: MISC_FEATURE
<222> LOCATION: (6)..(6)
<223> OTHER INFORMATION: X is S, T, N, P or R
<220> FEATURE:
<221> NAME/KEY: MISC_FEATURE
<222> LOCATION: (7)..(7)
<223> OTHER INFORMATION: X is Y or N
<220> FEATURE:
<221> NAME/KEY: MISC_FEATURE
<222> LOCATION: (8)..(8)
<223> OTHER INFORMATION: X is A, G or D

<400> SEQUENCE: 276

Gly Xaa Xaa Phe Ser Xaa Xaa Xaa Met Ser
1               5                   10

<210> SEQ ID NO 277
<211> LENGTH: 17
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is A, G or E
<220> FEATURE:
<221> NAME/KEY: MISC_FEATURE
<222> LOCATION: (2)..(2)
<223> OTHER INFORMATION: X is I or M
<220> FEATURE:
<221> NAME/KEY: MISC_FEATURE
<222> LOCATION: (3)..(3)
<223> OTHER INFORMATION: X is N or L
<220> FEATURE:
<221> NAME/KEY: MISC_FEATURE
<222> LOCATION: (4)..(4)
<223> OTHER INFORMATION: X is F, S, I, N, R or P
<220> FEATURE:
<221> NAME/KEY: MISC_FEATURE
<222> LOCATION: (5)..(5)
<223> OTHER INFORMATION: X is N, K, R or G
<220> FEATURE:
<221> NAME/KEY: MISC_FEATURE
<222> LOCATION: (6)..(6)
<223> OTHER INFORMATION: X is R, G or I
<220> FEATURE:
<221> NAME/KEY: MISC_FEATURE
<222> LOCATION: (7)..(7)
<223> OTHER INFORMATION: X is G, H or A
<220> FEATURE:
<221> NAME/KEY: MISC_FEATURE
<222> LOCATION: (8)..(8)
<223> OTHER INFORMATION: X is T, S, G or N
<220> FEATURE:
<221> NAME/KEY: MISC_FEATURE
<222> LOCATION: (9)..(9)
<223> OTHER INFORMATION: X is T or P
<220> FEATURE:
<221> NAME/KEY: MISC_FEATURE
<222> LOCATION: (10)..(10)
<223> OTHER INFORMATION: X is Y or N
```

```
<220> FEATURE:
<221> NAME/KEY: MISC_FEATURE
<222> LOCATION: (12)..(12)
<223> OTHER INFORMATION: X is S, P or N
<220> FEATURE:
<221> NAME/KEY: MISC_FEATURE
<222> LOCATION: (13)..(13)
<223> OTHER INFORMATION: X is D or E
<220> FEATURE:
<221> NAME/KEY: MISC_FEATURE
<222> LOCATION: (14)..(14)
<223> OTHER INFORMATION: X is T or K
<220> FEATURE:
<221> NAME/KEY: MISC_FEATURE
<222> LOCATION: (15)..(15)
<223> OTHER INFORMATION: X is V or F
<220> FEATURE:
<221> NAME/KEY: MISC_FEATURE
<222> LOCATION: (16)..(16)
<223> OTHER INFORMATION: X is K, Q or R

<400> SEQUENCE: 277

Xaa Xaa Xaa Xaa Xaa Xaa Xaa Xaa Xaa Xaa Tyr Xaa Xaa Xaa Xaa Xaa
1               5                   10                  15

Gly

<210> SEQ ID NO 278
<211> LENGTH: 17
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (2)..(2)
<223> OTHER INFORMATION: X is I or M
<220> FEATURE:
<221> NAME/KEY: MISC_FEATURE
<222> LOCATION: (4)..(4)
<223> OTHER INFORMATION: X is F, S, I, N, R or P
<220> FEATURE:
<221> NAME/KEY: MISC_FEATURE
<222> LOCATION: (5)..(5)
<223> OTHER INFORMATION: X is N, K or R
<220> FEATURE:
<221> NAME/KEY: MISC_FEATURE
<222> LOCATION: (6)..(6)
<223> OTHER INFORMATION: X is R or G
<220> FEATURE:
<221> NAME/KEY: MISC_FEATURE
<222> LOCATION: (7)..(7)
<223> OTHER INFORMATION: X is G, H or A
<220> FEATURE:
<221> NAME/KEY: MISC_FEATURE
<222> LOCATION: (8)..(8)
<223> OTHER INFORMATION: X is T, S or G
<220> FEATURE:
<221> NAME/KEY: MISC_FEATURE
<222> LOCATION: (9)..(9)
<223> OTHER INFORMATION: X is T or P
<220> FEATURE:
<221> NAME/KEY: MISC_FEATURE
<222> LOCATION: (12)..(12)
<223> OTHER INFORMATION: X is S or P
<220> FEATURE:
<221> NAME/KEY: MISC_FEATURE
<222> LOCATION: (16)..(16)
<223> OTHER INFORMATION: X is K, Q or R

<400> SEQUENCE: 278

Xaa Xaa Asn Xaa Xaa Xaa Xaa Xaa Xaa Tyr Tyr Xaa Asp Thr Val Xaa
1               5                   10                  15
```

Gly

<210> SEQ ID NO 279
<211> LENGTH: 14
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is S, V, T or A
<220> FEATURE:
<221> NAME/KEY: MISC_FEATURE
<222> LOCATION: (2)..(2)
<223> OTHER INFORMATION: X is S or R
<220> FEATURE:
<221> NAME/KEY: MISC_FEATURE
<222> LOCATION: (3)..(3)
<223> OTHER INFORMATION: X is H, L or G
<220> FEATURE:
<221> NAME/KEY: MISC_FEATURE
<222> LOCATION: (4)..(4)
<223> OTHER INFORMATION: X is R, N, D, P or G
<220> FEATURE:
<221> NAME/KEY: MISC_FEATURE
<222> LOCATION: (5)..(5)
<223> OTHER INFORMATION: X is Y, N, D or W
<220> FEATURE:
<221> NAME/KEY: MISC_FEATURE
<222> LOCATION: (6)..(6)
<223> OTHER INFORMATION: X is S, T, Y, N or L
<220> FEATURE:
<221> NAME/KEY: MISC_FEATURE
<222> LOCATION: (7)..(7)
<223> OTHER INFORMATION: X is D, N, V, Y, P, K or T
<220> FEATURE:
<221> NAME/KEY: MISC_FEATURE
<222> LOCATION: (8)..(8)
<223> OTHER INFORMATION: X is Y, D or N
<220> FEATURE:
<221> NAME/KEY: MISC_FEATURE
<222> LOCATION: (9)..(9)
<223> OTHER INFORMATION: X is D, Y, F or T
<220> FEATURE:
<221> NAME/KEY: MISC_FEATURE
<222> LOCATION: (10)..(10)
<223> OTHER INFORMATION: X is Y, F, L or deleted
<220> FEATURE:
<221> NAME/KEY: MISC_FEATURE
<222> LOCATION: (11)..(11)
<223> OTHER INFORMATION: X is A or deleted
<220> FEATURE:
<221> NAME/KEY: MISC_FEATURE
<222> LOCATION: (12)..(12)
<223> OTHER INFORMATION: X is M or deleted
<220> FEATURE:
<221> NAME/KEY: MISC_FEATURE
<222> LOCATION: (14)..(14)
<223> OTHER INFORMATION: X is Y or S

<400> SEQUENCE: 279

Xaa Xaa Xaa Xaa Xaa Xaa Xaa Xaa Xaa Xaa Xaa Xaa Asp Xaa
1               5                   10

<210> SEQ ID NO 280
<211> LENGTH: 14
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is S, V, T or A
<220> FEATURE:
<221> NAME/KEY: MISC_FEATURE
<222> LOCATION: (2)..(2)
<223> OTHER INFORMATION: X is R or S
<220> FEATURE:

```
<221> NAME/KEY: MISC_FEATURE
<222> LOCATION: (3)..(3)
<223> OTHER INFORMATION: X is H or L
<220> FEATURE:
<221> NAME/KEY: MISC_FEATURE
<222> LOCATION: (4)..(4)
<223> OTHER INFORMATION: X is R, N, D, P or G
<220> FEATURE:
<221> NAME/KEY: MISC_FEATURE
<222> LOCATION: (5)..(5)
<223> OTHER INFORMATION: X is Y, N, D or W
<220> FEATURE:
<221> NAME/KEY: MISC_FEATURE
<222> LOCATION: (6)..(6)
<223> OTHER INFORMATION: X is S, T, Y, N or L
<220> FEATURE:
<221> NAME/KEY: MISC_FEATURE
<222> LOCATION: (7)..(7)
<223> OTHER INFORMATION: X is D, N, V, Y, P or K
<220> FEATURE:
<221> NAME/KEY: MISC_FEATURE
<222> LOCATION: (8)..(8)
<223> OTHER INFORMATION: X is Y or D
<220> FEATURE:
<221> NAME/KEY: MISC_FEATURE
<222> LOCATION: (9)..(9)
<223> OTHER INFORMATION: X is D, Y, F or T
<220> FEATURE:
<221> NAME/KEY: MISC_FEATURE
<222> LOCATION: (10)..(10)
<223> OTHER INFORMATION: X is Y, F or L

<400> SEQUENCE: 280

Xaa Xaa Xaa Xaa Xaa Xaa Xaa Xaa Xaa Xaa Ala Met Asp Tyr
1               5                   10

<210> SEQ ID NO 281
<211> LENGTH: 12
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is K, I or M
<220> FEATURE:
<221> NAME/KEY: MISC_FEATURE
<222> LOCATION: (2)..(2)
<223> OTHER INFORMATION: X is A, T or S
<220> FEATURE:
<221> NAME/KEY: MISC_FEATURE
<222> LOCATION: (3)..(3)
<223> OTHER INFORMATION: X is S or N
<220> FEATURE:
<221> NAME/KEY: MISC_FEATURE
<222> LOCATION: (4)..(4)
<223> OTHER INFORMATION: X is Q or T
<220> FEATURE:
<221> NAME/KEY: MISC_FEATURE
<222> LOCATION: (5)..(5)
<223> OTHER INFORMATION: X is D or S
<220> FEATURE:
<221> NAME/KEY: MISC_FEATURE
<222> LOCATION: (6)..(6)
<223> OTHER INFORMATION: X is I or L
<220> FEATURE:
<221> NAME/KEY: MISC_FEATURE
<222> LOCATION: (7)..(7)
<223> OTHER INFORMATION: X is N, D, Y or L
<220> FEATURE:
<221> NAME/KEY: MISC_FEATURE
<222> LOCATION: (8)..(8)
<223> OTHER INFORMATION: X is S, D or N
<220> FEATURE:
<221> NAME/KEY: MISC_FEATURE
<222> LOCATION: (9)..(9)
<223> OTHER INFORMATION: X is Y, A or S
<220> FEATURE:
```

<221> NAME/KEY: MISC_FEATURE
<222> LOCATION: (10)..(10)
<223> OTHER INFORMATION: X is L, M or R
<220> FEATURE:
<221> NAME/KEY: MISC_FEATURE
<222> LOCATION: (11)..(11)
<223> OTHER INFORMATION: X is N, S or T
<220> FEATURE:
<221> NAME/KEY: MISC_FEATURE
<222> LOCATION: (12)..(12)
<223> OTHER INFORMATION: X is W or R

<400> SEQUENCE: 281

Xaa Xaa Xaa Xaa Xaa Xaa Xaa Xaa Xaa Xaa Xaa Xaa
1               5                   10

<210> SEQ ID NO 282
<211> LENGTH: 12
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is K, I or M
<220> FEATURE:
<221> NAME/KEY: MISC_FEATURE
<222> LOCATION: (2)..(2)
<223> OTHER INFORMATION: X is A or T
<220> FEATURE:
<221> NAME/KEY: MISC_FEATURE
<222> LOCATION: (3)..(3)
<223> OTHER INFORMATION: X is S or N
<220> FEATURE:
<221> NAME/KEY: MISC_FEATURE
<222> LOCATION: (4)..(4)
<223> OTHER INFORMATION: X is Q or T
<220> FEATURE:
<221> NAME/KEY: MISC_FEATURE
<222> LOCATION: (7)..(7)
<223> OTHER INFORMATION: X is N, D or Y
<220> FEATURE:
<221> NAME/KEY: MISC_FEATURE
<222> LOCATION: (8)..(8)
<223> OTHER INFORMATION: X is S or D
<220> FEATURE:
<221> NAME/KEY: MISC_FEATURE
<222> LOCATION: (9)..(9)
<223> OTHER INFORMATION: X is Y or A
<220> FEATURE:
<221> NAME/KEY: MISC_FEATURE
<222> LOCATION: (10)..(10)
<223> OTHER INFORMATION: X is L or M
<220> FEATURE:
<221> NAME/KEY: MISC_FEATURE
<222> LOCATION: (11)..(11)
<223> OTHER INFORMATION: X is N or S

<400> SEQUENCE: 282

Xaa Xaa Xaa Xaa Asp Ile Xaa Xaa Xaa Xaa Xaa Trp
1               5                   10

<210> SEQ ID NO 283
<211> LENGTH: 8
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is R, E or P
<220> FEATURE:
<221> NAME/KEY: MISC_FEATURE
<222> LOCATION: (2)..(2)
<223> OTHER INFORMATION: X is A, G or K
<220> FEATURE:
<221> NAME/KEY: MISC_FEATURE

```
<222> LOCATION: (3)..(3)
<223> OTHER INFORMATION: X is N, K or L
<220> FEATURE:
<221> NAME/KEY: MISC_FEATURE
<222> LOCATION: (4)..(4)
<223> OTHER INFORMATION: X is R, K, T, S or L
<220> FEATURE:
<221> NAME/KEY: MISC_FEATURE
<222> LOCATION: (5)..(5)
<223> OTHER INFORMATION: X is L or I
<220> FEATURE:
<221> NAME/KEY: MISC_FEATURE
<222> LOCATION: (6)..(6)
<223> OTHER INFORMATION: X is V, I, R or Y
<220> FEATURE:
<221> NAME/KEY: MISC_FEATURE
<222> LOCATION: (7)..(7)
<223> OTHER INFORMATION: X is D, E, P or W
<220> FEATURE:
<221> NAME/KEY: MISC_FEATURE
<222> LOCATION: (8)..(8)
<223> OTHER INFORMATION: X is G or T

<400> SEQUENCE: 283

Xaa Xaa Xaa Xaa Xaa Xaa Xaa Xaa
1               5

<210> SEQ ID NO 284
<211> LENGTH: 8
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is R or E
<220> FEATURE:
<221> NAME/KEY: MISC_FEATURE
<222> LOCATION: (2)..(2)
<223> OTHER INFORMATION: X is A or G
<220> FEATURE:
<221> NAME/KEY: MISC_FEATURE
<222> LOCATION: (3)..(3)
<223> OTHER INFORMATION: X is N or K
<220> FEATURE:
<221> NAME/KEY: MISC_FEATURE
<222> LOCATION: (4)..(4)
<223> OTHER INFORMATION: X is R, K, T or S
<220> FEATURE:
<221> NAME/KEY: MISC_FEATURE
<222> LOCATION: (6)..(6)
<223> OTHER INFORMATION: X is V, I or R
<220> FEATURE:
<221> NAME/KEY: MISC_FEATURE
<222> LOCATION: (7)..(7)
<223> OTHER INFORMATION: X is D, E or P

<400> SEQUENCE: 284

Xaa Xaa Xaa Xaa Ile Xaa Xaa Gly
1               5

<210> SEQ ID NO 285
<211> LENGTH: 9
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: X is L or K
<220> FEATURE:
<221> NAME/KEY: MISC_FEATURE
<222> LOCATION: (3)..(3)
<223> OTHER INFORMATION: X is Y, T or S
<220> FEATURE:
<221> NAME/KEY: MISC_FEATURE
<222> LOCATION: (5)..(5)
```

```
<223> OTHER INFORMATION: X is E, N or L
<220> FEATURE:
<221> NAME/KEY: MISC_FEATURE
<222> LOCATION: (6)..(6)
<223> OTHER INFORMATION: X is F or L
<220> FEATURE:
<221> NAME/KEY: MISC_FEATURE
<222> LOCATION: (8)..(8)
<223> OTHER INFORMATION: X is Y, L, F or W

<400> SEQUENCE: 285

Xaa Gln Xaa Asp Xaa Xaa Pro Xaa Thr
1               5

<210> SEQ ID NO 286
<211> LENGTH: 9
<212> TYPE: PRT
<213> ORGANISM: Mus musculus
<220> FEATURE:
<221> NAME/KEY: MISC_FEATURE
<222> LOCATION: (3)..(3)
<223> OTHER INFORMATION: X is Y, T or S
<220> FEATURE:
<221> NAME/KEY: MISC_FEATURE
<222> LOCATION: (5)..(5)
<223> OTHER INFORMATION: X is E or N
<220> FEATURE:
<221> NAME/KEY: MISC_FEATURE
<222> LOCATION: (6)..(6)
<223> OTHER INFORMATION: X is F or L
<220> FEATURE:
<221> NAME/KEY: MISC_FEATURE
<222> LOCATION: (8)..(8)
<223> OTHER INFORMATION: X is Y, L or F

<400> SEQUENCE: 286

Leu Gln Xaa Asp Xaa Xaa Pro Xaa Thr
1               5

<210> SEQ ID NO 287
<211> LENGTH: 937
<212> TYPE: PRT
<213> ORGANISM: Homo sapiens

<400> SEQUENCE: 287

Met His Arg Pro Arg Arg Arg Gly Thr Arg Pro Leu Leu Ala Leu
1               5                   10                  15

Leu Ala Leu Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Pro Thr Ala Ser Pro Gly Tyr
145                 150                 155                 160
```

-continued

```
Ser Asp Glu Tyr Glu Glu Asp Gly Phe Cys Gln Pro Tyr Arg Gly Ile
            165                 170                 175

Ala Cys Ala Arg Phe Ile Gly Asn Arg Thr Val Tyr Met Glu Ser Leu
        180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
        290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
        370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
        450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
        530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575
```

```
Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
        610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
        690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
        770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
        850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
        930                 935

<210> SEQ ID NO 288
<211> LENGTH: 388
<212> TYPE: PRT
<213> ORGANISM: Homo sapiens

<400> SEQUENCE: 288

Met Leu Phe Glu Tyr Ile Asn Gln Gly Asp Leu His Glu Phe Leu Ile
1               5                   10                  15
```

```
Met Arg Ser Pro His Ser Asp Val Gly Cys Ser Ser Asp Glu Asp Gly
            20                  25                  30

Thr Val Lys Ser Ser Leu Asp His Gly Asp Phe Leu His Ile Ala Ile
        35                  40                  45

Gln Ile Ala Ala Gly Met Glu Tyr Leu Ser Ser His Phe Phe Val His
    50                  55                  60

Lys Asp Leu Ala Ala Arg Asn Ile Leu Ile Gly Glu Gln Leu His Val
65                  70                  75                  80

Lys Ile Ser Asp Leu Gly Leu Ser Arg Glu Ile Tyr Ser Ala Asp Tyr
                85                  90                  95

Tyr Arg Val Gln Ser Lys Ser Leu Leu Pro Ile Arg Trp Met Pro Pro
                100                 105                 110

Glu Ala Ile Met Tyr Gly Lys Phe Ser Ser Asp Ser Asp Ile Trp Ser
            115                 120                 125

Phe Gly Val Val Leu Trp Glu Ile Phe Ser Phe Gly Leu Gln Pro Tyr
    130                 135                 140

Tyr Gly Phe Ser Asn Gln Glu Val Ile Glu Met Val Arg Lys Arg Gln
145                 150                 155                 160

Leu Leu Pro Cys Ser Glu Asp Cys Pro Pro Arg Met Tyr Ser Leu Met
                165                 170                 175

Thr Glu Cys Trp Asn Glu Ile Pro Ser Arg Arg Pro Arg Phe Lys Asp
            180                 185                 190

Ile His Val Arg Leu Arg Ser Trp Glu Gly Leu Ser Ser His Thr Ser
        195                 200                 205

Ser Thr Thr Pro Ser Gly Gly Asn Ala Thr Thr Gln Thr Thr Ser Leu
        210                 215                 220

Ser Ala Ser Pro Val Ser Asn Leu Ser Asn Pro Arg Tyr Pro Asn Tyr
225                 230                 235                 240

Met Phe Pro Ser Gln Gly Ile Thr Pro Gln Gly Gln Ile Ala Gly Phe
                245                 250                 255

Ile Gly Pro Pro Ile Pro Gln Asn Gln Arg Phe Ile Pro Ile Asn Gly
            260                 265                 270

Tyr Pro Ile Pro Pro Gly Tyr Ala Ala Phe Pro Ala Ala His Tyr Gln
        275                 280                 285

Pro Thr Gly Pro Pro Arg Val Ile Gln His Cys Pro Pro Pro Lys Ser
    290                 295                 300

Arg Ser Pro Ser Ser Ala Ser Gly Ser Thr Ser Thr Gly His Val Thr
305                 310                 315                 320

Ser Leu Pro Ser Ser Gly Ser Asn Gln Glu Ala Asn Ile Pro Leu Leu
                325                 330                 335

Pro His Met Ser Ile Pro Asn His Pro Gly Gly Met Gly Ile Thr Val
            340                 345                 350

Phe Gly Asn Lys Ser Gln Lys Pro Tyr Lys Ile Asp Ser Lys Gln Ala
        355                 360                 365

Ser Leu Leu Gly Asp Ala Asn Ile His Gly His Thr Glu Ser Met Ile
    370                 375                 380

Ser Ala Glu Leu
385
```

ANTI-ROR1 ANTIBODIES AND METHODS OF USE FOR TREATMENT OF CANCER

CROSS-REFERENCE TO RELATED APPLICATIONS

This application is a U.S. National Phase of International Patent Application No. PCT/US2011/054645 filed Oct. 3, 2011 which claims priority to U.S. provisional application Nos. 61/388,694 filed on Oct. 1, 2010 and 61/482,554 filed on May 4, 2011, the disclosures of which are incorporated herein by reference in their entirety for all purposes.

REFERENCE TO SEQUENCE LISTING SUBMITTED ELECTRONICALLY

The sequence listing contained in the file named "13823999seqlist.txt", created on May 30, 2013, and having a size of 144 kilobytes, has been submitted electronically herewith via EFS-Web, and the contents of the txt file are hereby incorporated by reference in their entirety.

INTRODUCTION

The present disclosure relates generally to the fields of immunology and molecular biology. More specifically, provided herein are antibodies and other therapeutic proteins directed against the Tyrosine-protein kinase transmembrane receptor ROR1, nucleic acids encoding such antibodies and therapeutic proteins, methods for preparing monoclonal antibodies and other therapeutic proteins, and methods for the treatment of diseases, such as cancers mediated by the Tyrosine-protein kinase transmembrane receptor ROR1 expression/activity and/or associated with abnormal expression/activity of ligands therefore.

BACKGROUND

The tyrosine-protein kinase transmembrane receptor ROR1 is a cell surface receptor that belongs to the ROR subfamily of cell surface proteins. It shows strong homology to the tyrosine kinase domain of growth factor receptors, in particular the Trk family [Reddy et al. (1997) Genomics 41(2):283-5] and modulates neurite growth in the central nervous system. So far two isoforms have been reported (SWISS-PROT entry; Q01973) and the nucleotide sequence encoding this protein is found at accession number NM_005012.

According to SWISS-PROT, the tyrosine-protein kinase transmembrane receptor ROR1 is expressed strongly in human heart, lung, and kidney, but weakly in the CNS. The short isoform (missing amino acids 1-549 of the long isoform) is strongly expressed in fetal and adult CNS and in a variety of human cancers, including those originating from CNS or PNS neuroectoderm. The tyrosine-protein kinase transmembrane receptor ROR1 (described as ROR1 henceforward) is expressed at high levels during early embryonic development. The expression levels drop strongly around day 16 and there are only very low levels in adult tissues. Overexpression of the ROR1 gene has recently been reported in B-cell chronic lymphocytic leukemia [Basker et al. (2008) Clin Cancer Res. 14(2):396-404].

BRIEF DESCRIPTION OF THE DRAWINGS

FIG. 1a-FIG. 1b depicts (a) the alignment of the nucleotide sequences of the light chain CDR1 regions of A1 (SEQ ID NO:181); A2, A3, A4, A5, A7, A9 and A12 (SEQ ID NO:182); A6 (SEQ ID NO:183); A10 (SEQ ID NO:185) and A13 (SEQ ID NO:187) with nucleotides 813-848 of the mouse germline $V_K$ 14-111 nucleotide sequence (SEQ ID NO: 243); the alignments of the nucleotide sequences of the light chain CDR1 regions of A8 (SEQ ID NO:184) and A11 (SEQ ID NO:186) with nucleotides 594-629 of the mouse germline $V_k$ 17-121 nucleotide sequence (SEQ ID NO:255) and the alignment of the light chain CDR1 region of A14 (SEQ ID NO:188) with nucleotides 430-465 of the mouse germline $V_k$ 8-21 nucleotide sequence (SEQ ID NO:260), while (b) shows the alignment of the light chain CDR1 region of A14 (SEQ ID NO:189) with nucleotides 421-471 of the mouse germline $V_k$ 8-21 nucleotide sequence (SEQ ID NO: 261).

FIG. 2a-FIG. 2b depicts (a) the alignment of the nucleotide sequences of the light chain CDR2 regions of A1, A2, A9 and A10 (SEQ ID NO:210); A3 (SEQ ID NO:212); A4 (SEQ ID NO:213); A5 (SEQ ID NO:215); A6 (SEQ ID NO:217); A7 (SEQ ID NO:219); A12 (SEQ ID NO:225) and A13 (SEQ ID NO:226) with nucleotides 879-908 of the mouse germline $V_K$ 14-111 nucleotide sequence (SEQ ID NO:245); the alignments of the nucleotide sequences of the light chain CDR2 regions of A8 (SEQ ID NO:221) and A11 (SEQ ID NO:223) with nucleotides 660-689 of the mouse germline $V_k$ 17-121 nucleotide sequence (SEQ ID NO:257) and the alignment of the light chain CDR2 region of A14 (SEQ ID NO:227) with nucleotides 502-534 of the mouse germline $V_k$ 8-21 nucleotide sequence (SEQ ID NO:262), while (b) shows the alignment of the nucleotide sequences of the light chain CDR2 regions of A1, A2, A3, A9, A10, A12 and A13 (SEQ ID NO:209); A4 (SEQ ID NO:214); A5 (SEQ ID NO:216); A6 (SEQ ID NO:218) and A7 (SEQ ID NO:220) with nucleotides 879-908 of the mouse germline $V_K$ 14-111 nucleotide sequence (SEQ ID NO:244); the alignments of the nucleotide sequences of the light chain CDR2 regions of A8 (SEQ ID NO:222) and A11 (SEQ ID NO:224) with nucleotides 660-689 of the mouse germline $V_k$ 17-121 nucleotide sequence (SEQ ID NO:258) and the alignment of the light chain CDR2 region of A14 (SEQ ID NO:228) with nucleotides 514-537 of the mouse germline $V_k$ 8-21 nucleotide sequence (SEQ ID NO:263).

FIG. 3 depicts the alignment of the nucleotide sequences of the light chain CDR3 regions of A1, A3, A4, A6, A9, A10, A12 and A13 (SEQ ID NO:234); A2 (SEQ ID NO:235); A5 (SEQ ID NO:236) and A7 (SEQ ID NO:237) with nucleotides 1008-1034 of the mouse germline $V_K$ 14-111 nucleotide sequence (SEQ ID NO:246); the alignments of the nucleotide sequences of the light chain CDR3 regions of A8 (SEQ ID NO:238) and A11 (SEQ ID NO:239) with nucleotides 789-815 of the mouse germline $V_k$ 17-121 nucleotide sequence (SEQ ID NO:259) and the alignment of the light chain CDR2 region of A14 (SEQ ID NO:240) with nucleotides 634-658 of the mouse germline $V_k$ 8-21 nucleotide sequence (SEQ ID NO:264).

FIG. 4a-FIG. 4b depicts (a) the alignment of the nucleotide sequences of the heavy chain CDR1 regions of A14 (SEQ ID NO:97) with nucleotides 86263-86299 of the mouse germline $V_H$ 1-9 nucleotide sequence (SEQ ID NO:265); the alignments of the nucleotide sequences of the heavy chain CDR1 regions of A2 (SEQ ID NO:80); A12 and A13 (SEQ ID NO:82); A10 (SEQ ID NO:93) and A11 (SEQ ID NO:95) with nucleotides 926028-926063 of the mouse germline $V_H$ 5-12 nucleotide sequence (SEQ ID NO:247) and the alignment of the heavy chain CDR1 region of A1 (SEQ ID NO:78); A3 and A8 (SEQ ID NO:81); A4 (SEQ ID NO:83); A5 (SEQ ID NO:85); A6 (SEQ ID NO:87); A7 (SEQ ID NO:89) and A9 (SEQ ID NO:91) with nucleotides 983326-983361 of the mouse germline V$_H$ 5-6 nucleotide sequence (SEQ ID NO:251) while, (b) shows the alignment of the nucleotide sequences of the heavy chain CDR1 regions of A14 (SEQ ID NO:98) with nucleotides 86263-86299 of the mouse germline V$_H$ 1-9 nucleotide sequence (SEQ ID NO:256); the alignments of the nucleotide sequences of the heavy chain CDR1 regions of A2 (SEQ ID NO:81); A12 and A13 (SEQ ID NO:79); A10 (SEQ ID NO:94) and A11 (SEQ ID NO:96) with nucleotides 926022-926063 of the mouse germline V$_H$ 5-12 nucleotide sequence (SEQ ID NO:248) and the alignment of the heavy chain CDR1 region of A1, A3, A8 (SEQ ID NO:79); A4 (SEQ ID NO:84); A5 (SEQ ID NO:86); A6 (SEQ ID NO:88); A7 (SEQ ID NO:90) and A9 (SEQ ID NO:92) with nucleotides 983320-983361 of the mouse germline V$_H$ 5-6 nucleotide sequence (SEQ ID NO:252).

FIG. 5a-FIG. 5b depicts (a) the alignment of the nucleotide sequences of the heavy chain CDR2 regions of A14 (SEQ ID NO:147) with nucleotides 86341-86370 of the mouse germline V$_H$ 1-9 nucleotide sequence (SEQ ID NO:266); the alignments of the nucleotide sequences of the heavy chain CDR2 regions of A2 and A13 (SEQ ID NO:126); A12 (SEQ ID NO:135); A10 (SEQ ID NO:142) and A11 (SEQ ID NO:144) with nucleotides 926106-926135 of the mouse germline V$_H$ 5-12 nucleotide sequence (SEQ ID NO:1249) and the alignment of the heavy chain CDR2 region of A1 (SEQ ID NO:124); A3 (SEQ ID NO:128); A4 (SEQ ID NO:130); A5 (SEQ ID NO:132); A6 (SEQ ID NO:135); A7 (SEQ ID NO:136); A8 (SEQ ID NO:138) and A9 (SEQ ID NO:140) with nucleotides 983404-983433 of the mouse germline V$_H$ 5-6 nucleotide sequence (SEQ ID NO:253), while (b) shows the alignment of the nucleotide sequences of the heavy chain CDR2 regions of A14 (SEQ ID NO:148) with nucleotides 86341-86391 of the mouse germline V$_H$ 1-9 nucleotide sequence (SEQ ID NO:267); the alignments of the nucleotide sequences of the heavy chain CDR2 regions of A2 and A13 (SEQ ID NO:127); A12 (SEQ ID NO:146); A10 (SEQ ID NO:143) and A11 (SEQ ID NO:242) with nucleotides 926106-926156 of the mouse germline V$_H$ 5-12 nucleotide sequence (SEQ ID NO:250) and the alignment of the heavy chain CDR2 region of A1 (SEQ ID NO:125); A3 (SEQ ID NO:129); A4 (SEQ ID NO:131); A5 (SEQ ID NO:133); A6 (SEQ ID NO:134); A7 (SEQ ID NO:137); A8 (SEQ ID NO:139) and A9 (SEQ ID NO:141) with nucleotides 983404-983454 of the mouse germline V$_H$ 5-6 nucleotide sequence (SEQ ID NO:254).

FIG. 14a-FIG. 14ee depicts the amino acid and nucleotide sequences of the variable heavy chain and variable light chain of antibodies of the invention, including CDRs and antigen binding regions, as well as the ROR1 sequence.

FIG. 15 depicts a summary of the amino acids and nucleic acids encoding the antigen binding regions, such as CDRs, of the heavy and light chain variable regions of the invention.

BRIEF SUMMARY OF THE INVENTION

Figure 6:
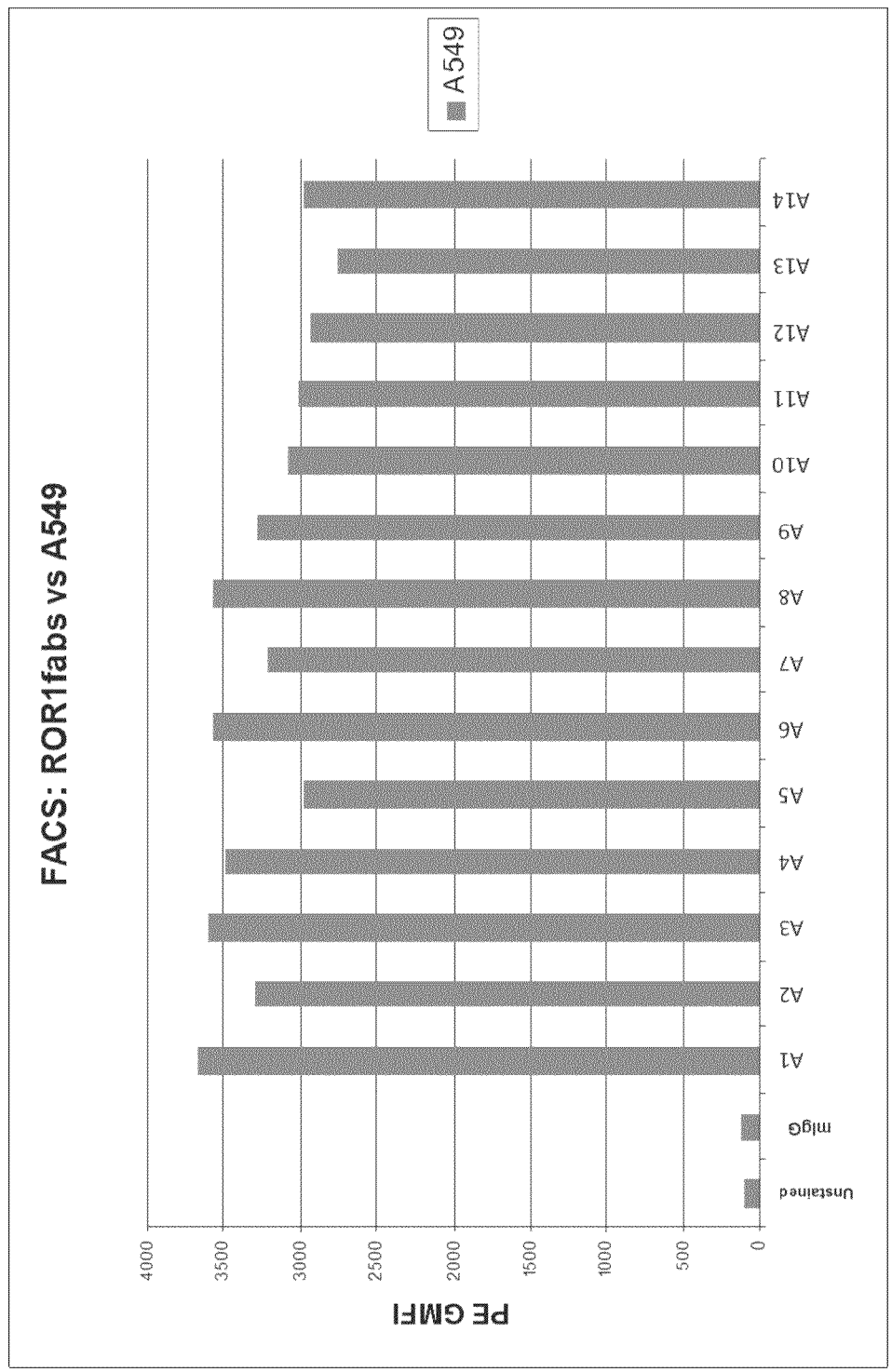
FIG. 6 depicts the flow cytometry analysis of ROR1 monoclonal antibodies, indicating the specific binding of those antibodies to the human lung adenocarcinoma cell line, A549.

The present disclosure provides antibodies directed against the ROR1, nucleic acids encoding such antibodies and therapeutic proteins, host cells comprising such nucleic acids encoding the antibodies of the invention, methods for preparing anti-ROR1, and methods for the treatment of diseases, such as the ROR1 mediated disorders, e.g. human cancers, including non-small cell lung carcinoma, B-cell chronic lymphocytic leukemia and colon cancer.

In some embodiments, an antibody that specifically binds to the extracellular domain of ROR1 (SEQ ID NO:272) and is internalized by a cell expressing ROR1 is provided, the antibody encompassing a heavy chain variable region encompassing a first vhCDR encompassing SEQ ID NO:275; a second vhCDR encompassing SEQ ID NO: 277; and a third vhCDR encompassing SEQ ID NO:279; and a light chain variable region encompassing a first vlCDR encompassing SEQ ID NO:281; a second vlCDR encompassing SEQ ID NO: 283; and a third vlCDR encompassing SEQ ID NO:285.

In some embodiments, the antibodies of the invention further encompass a covalently attached moiety. In some embodiments, the moiety is a drug. In other embodiments, the drug is selected from the group a maytansinoid, a dolastatin, an auristatin, a trichothecene, a calicheamicin, a CC1065 and derivatives thereof.

In some embodiments, a nucleic acid encoding a heavy chain of any of the disclosed antibodies of the invention are provided. In some embodiments a nucleic acid encoding a light chain of the disclosed antibodies of the invention are provided.

In some embodiments a host cell containing the nucleic acid(s) encoding the heavy or light chain or both of the antibodies of the invention are provided wherein the host cell is grown under conditions wherein the nucleic acid(s) is expressed. In other embodiments, a method of recovering one or more antibodies of the invention are provided.

In some embodiments a method of treating cancer is provided, wherein a patient in need thereof is adminstered an antibody or antibodies of the invention which bind to ROR1 (SEQ ID NO:272) and wherein such antibody or antibodies of the invention are internalized, the antibody encompassing a heavy chain variable region encompassing a first vhCDR comprising SEQ ID NO:275; a second vh CDR encompassing SEQ ID NO: 277; and a third vhCDR encompassing SEQ ID NO: 279 and a light chain variable region encompassing a first vlCDR encompassing Seq ID NO: 281, a second vlCDR encompassing SEQ ID NO: 283 and a third vlCDR encompassing SEQ ID NO: 285 and a covalently attached drug conjugate.

In some embodiments, the cancer is selected from the group of non-small cell lung carcinoma, B-cell chronic lymphocytic leukemia and colon cancer.

In some embodiments, an antibody comprising a variable heavy chain region selected from the group consisting of SEQ ID NOs:1-14 or a sequence that is about 90% identical to one of SEQ ID NOs:1-14 is provided. In other embodiments an antibody comprising a variable light chain region selected from the group consisting of SEQ ID NOs:29-42 or a sequence that is about 90% identical to one of SEQ ID NOs: 29-42 is provided.

DETAILED DESCRIPTION OF THE INVENTION

Introduction

The present disclosure relates to isolated antibodies which bind specifically to the extracellular domain of the ROR1 receptor with high affinity as outlined herein. As discussed herein, the ROR1 receptor is reported to have two isoforms, one of which is missing the first 549 amino acids ("the short form") of the "long form". In some embodiments, the antibodies discussed herein bind to the extracellular domain of the short form.

In addition, the ROR1 antibodies of the present invention are internalized when contacted with cells expressing the ROR1 receptor. As discussed herein, the ROR1 receptor is overexpressed and/or differentially expressed on certain cancer cells, including but not limited to, tumors of non-small cell lung carcinoma, B-cell chronic lymphocytic leukemia and colon cancer.

As such, when the ROR1 antibodies of the present invention are conjugated to drugs (sometimes referred to herein as "antibody-drug conjugates" or "ADCs"), the internalization of these ADC molecules into cancer cells results in cell death and thus tumor treatment.

The present invention provides antibodies that possess particular structural features such as CDR regions with particular amino acid sequences. As described herein, 14 different sets of CDRs, e.g. 14 different antibodies, exhibit binding to ROR1. In addition, as described herein, each CDR shows similarity to other identified CDRs, and thus antibodies comprising consensus CDRs are provided, as is more fully described below.

Thus, the disclosure provides isolated antibodies (which, as outlined below, includes a wide variety of well known antibody structures, derivatives, mimetics and conjugates), nucleic acids encoding these antibodies, host cells used to make the antibodies, methods of making the antibodies, and pharmaceutical compositions comprising the antibodies and optionally a pharmaceutical carrier.

ROR1 Proteins

Accordingly, the present invention provides isolated anti-ROR1 antibodies that specifically bind the extracellular domain of a human ROR1 protein. By "human ROR1" or "human ROR1 antigen" refers to the protein of SEQ ID NO:272 or a functional fraction such as the extracellular domain, as defined herein. In general, ROR1 possesses a short intracytoplasmic tail, a transmembrane domain, and an extracellular domain. In specific embodiments, the antibodies of the invention bind to the extracellular part of the ROR1 protein, and in some embodiments, to the extracellular domain of the shorter version of ROR1.

The antibodies of the invention may, in certain cases, cross-react with the ROR1 from species other than human. For example, to facilitate clinical testing, the antibodies of the invention may cross react with murine or primate ROR1 molecules. Alternatively, in certain embodiments, the antibodies may be completely specific for one or more human ROR1 and may not exhibit species or other types of non-human cross-reactivity.

Antibodies

The present invention provides anti-ROR1 antibodies, generally therapeutic and/or diagnostic antibodies as described herein. Antibodies that find use in the present invention can take on a number of formats as described herein, including traditional antibodies as well as antibody derivatives, fragments and mimetics, described below. Essentially, the invention provides antibody structures that contain a set of 6 CDRs as defined herein (including small numbers of amino acid changes as described below).

"Antibody" as used herein includes a wide variety of structures, as will be appreciated by those in the art, that at a minimum contain a set of 6 CDRs as defined herein; including, but not limited to traditional antibodies (including both monoclonal and polyclonal antibodies), humanized and/or chimeric antibodies, antibody fragments, engineered antibodies (e.g. with amino acid modifications as outlined below), multispecific antibodies (including bispecific antibodies), and other analogs known in the art and discussed herein.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Thus, "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. It should be understood that therapeutic antibodies can also comprise hybrids of any combination of isotypes and/or subclasses.

In many embodiments, IgG isotypes are used in the present invention, with IgG1 finding particular use in a number of applications.

The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below In some cases, defining the exact CDR region is difficult. The CDRs of the antibodies of the present invention have been identified in two different ways, in general a "longer" CDR and a "shorter" CDR. For example, as shown in Figure **XX, SEQ ID NO:57 and SEQ ID NO:58 both describe the first CDR of the heavy chain of the first antibody (A1).

Throughout the present specification, the Kabat numbering system is generally used when referring to a residue in the variable domain (approximately, residues 1-107 of the light chain variable region and residues 1-113 of the heavy chain variable region) (e.g., Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. In the present invention, the exact epitope is not determinative; rather, the ability of the antibodies of the invention to bind to the ROR1 receptor and be internalized is important.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

Of particular interest in the present invention are the Fc regions. By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively. Structures that rely on the use of a set of CDRs are included within the definition of "antibody".

In one embodiment, the antibody is an antibody fragment. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242: 423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference).

Chimeric and Humanized Antibodies

In some embodiments, the antibody can be a mixture from different species, e.g. a chimeric antibody and/or a humanized antibody. That is, in the present invention, the CDR sets can be used with framework and constant regions other than those specifically described by sequence herein.

In particular, the A1 antibody herein is shown as both the murine form and the humanized form (huA1).

In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20): 4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16): 10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169: 3076-3084, all entirely incorporated by reference.

In one embodiment, the antibodies of the invention can be multispecific antibodies, and notably bispecific antibodies, also sometimes referred to as "diabodies". These are antibodies that bind to two (or more) different antigens, or different epitopes on the same antigen. Diabodies can be manufactured in a variety of ways known in the art (Holliger and Winter, 1993, Current Opinion Biotechnol. 4:446-449, entirely incorporated by reference), e.g., prepared chemically or from hybrid hybridomas.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region. It should be noted that minibodies are included within the definition of "antibody" despite the fact it does not have a full set of CDRs.

The antibodies of the present invention are generally isolated or recombinant. "Isolated," when used to describe the various polypeptides disclosed herein, means a polypeptide that has been identified and separated and/or recovered from a cell or cell culture from which it was expressed. Thus an isolated antibody is intended to refer to an antibody that is substantially free of other antibodies having different antigenic specificities (e.g. an isolated antibody that specifically binds to the ROR1 is substantially free of antibodies that specifically bind antigens other than the ROR1). Thus, an "isolated" antibody is one found in a form not normally found in nature (e.g. non-naturally occurring).

In some embodiments, the antibodies of the invention are recombinant proteins, isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. In the case of recombinant proteins, the definition includes the production of an antibody in a wide variety of organisms and/or host cells that are known in the art in which it is not naturally produced. Ordinarily, an isolated polypeptide will be prepared by at least one purification step. An "isolated antibody," refers to an antibody which is substantially free of other antibodies having different antigenic specificities. For instance, an isolated antibody that specifically binds to ROR1 is substantially free of antibodies that specifically bind antigens other than ROR1.

Isolated monoclonal antibodies, having different specificities, can be combined in a well defined composition. Thus for example, the A1 to A14 antibodies of the invention can optionally and individually be included or excluded in a formulation, as is further discussed below.

The anti-ROR1 antibodies of the present invention specifically bind ROR1 ligands (e.g. the extracellular domain of the human ROR1 proteins of SEQ ID NO:**ROR1). "Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a $K_D$ for an antigen or epitope of at least about $10^{-4}$ M, at least about $10^{-5}$ M, at least about $10^{-6}$M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where $K_D$ refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope. However, in the present invention, when administering ADCs of the ROR1 antibodies of the invention, what is important is that the KD is sufficient to allow internalization and thus cell death without significant side effects.

Also, specific binding for a particular antigen or an epitope can be exhibited, for example, by an antibody having a $K_A$ or $K_a$ for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

Standard assays to evaluate the binding ability of the antibodies toward the ROR1 can be done on the protein or cellular level and are known in the art, including for example, ELISAs, Western blots, RIAs, BIAcore® assays and flow cytometry analysis. Suitable assays are described in detail in the Examples. The binding kinetics (e.g. binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

ROR1 Antibodies

The present invention provides ROR1 antibodies that specifically bind the extracellular domain human ROR1 (SEQ ID NO:*xx) and are internalized when contacted with cells expressing ROR1 on the cell surface. These antibodies are referred to herein either as "anti-ROR1" antibodies or, for ease of description, "ROR1 antibodies".

The ROR1 antibodies are internalized upon contact with cells, particularly tumor cells, that express ROR1 on the surface. That is, ROR1 antibodies as defined herein that also comprise drug conjugates are internalized by tumor cells, resulting in the release of the drug and subsequent cell death, allowing for treatment of cancers that exhibit ROR1 expression. Internalization in this context can be measured in several ways. In one embodiment, the ROR1 antibodies of the invention are contacted with cells, such as a cell line as outlined herein, using standard assays such as MAbZap and HuZap. In these in vitro assay embodiments, the ROR1 antibodies of the invention are added, along with an anti-ROR1 antibody comprising a toxin; for example, the ROR1 antibody may be murine or humanized and the anti-ROR1 antibody can be anti-murine or anti-humanized and contain a toxin such as saporin. Upon formation of the [ROR1 antibody of the invention]-[anti-ROR1 antibody-drug conjugate] complex, the complex is internalized and the drug (e.g. saporin) is released, resulting in cell death. Only upon internalization does the drug get released, and thus cells remain viable in the absence of internalization. As outlined below, without being bound by theory, in therapeutic applications, the anti-ROR1 antibody contains the toxin, and upon internalization, the bond between the antibody and the toxin is cleaved, releasing the toxin and killing the cell.

In one embodiment, the antibody of the invention is an A1 antibody. By "A1 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A1 | SEQ ID NOs |
|---|---|
| variable heavy CDR1 | 57, 58 |
| variable heavy CDR2 | 99, 100 |
| variable heavy CDR3 | 149 |
| variable light CDR1 | 173 |
| variable light CDR2 | 190, 191 |
| variable light CDR3 | 229 |

In addition, the A1 antibody has been "humanized"; the humanized antibody is referred to herein as "huA1" or equivalents. Thus, included within the definition of "A1" antibody is the huA1 antibody.

As will be appreciated by those in the art, given a set of CDRs, any number of antibodies can be generated, using different framework and Fc regions, as is more fully described herein for each of A1 to A14.

In one embodiment, the antibody of the invention is an A2 antibody. By "A2 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A2 | SEQ ID NOs |
|---|---|
| variable heavy CDR1 | 59, 60 |
| variable heavy CDR2 | 101, 102 |
| variable heavy CDR3 | 150 |
| variable light CDR1 | 179 |
| variable light CDR2 | 190, 191 |
| variable light CDR3 | 229 |

In one embodiment, the antibody of the invention is an A3 antibody. By "A3 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A3 | SEQ ID NOs |
|---|---|
| variable heavy CDR1 | 58, 61 |
| variable heavy CDR2 | 103, 104 |
| variable heavy CDR3 | 149 |
| variable light CDR1 | 179 |
| variable light CDR2 | 190, 192 |
| variable light CDR3 | 229 |

In one embodiment, the antibody of the invention is an A4 antibody. By "A4 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A4 | SEQ ID NOs |
|---|---|
| variable heavy CDR1 | 62, 63 |
| variable heavy CDR2 | 105, 106 |
| variable heavy CDR3 | 151 |
| variable light CDR1 | 179 |
| variable light CDR2 | 193, 194 |
| variable light CDR3 | 229 |

In one embodiment, the antibody of the invention is an A5 antibody. By "A5 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A5 | SEQ ID NOs |
|---|---|
| variable heavy CDR1 | 64, 65 |
| variable heavy CDR2 | 107, 108 |
| variable heavy CDR3 | 152 |
| variable light CDR1 | 179 |
| variable light CDR2 | 195, 196 |
| variable light CDR3 | 229 |

In one embodiment, the antibody of the invention is an A6 antibody. By "A6 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A6 | SEQ ID NOs |
|---|---|
| variable heavy CDR1 | 66, 67 |
| variable heavy CDR2 | 109, 110 |
| variable heavy CDR3 | 153 |
| variable light CDR1 | 179 |
| variable light CDR2 | 197, 198 |
| variable light CDR3 | 229 |

In one embodiment, the antibody of the invention is an A7 antibody. By "A7 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A7 | SEQ ID NOs |
|---|---|
| variable heavy CDR1 | 68, 69 |
| variable heavy CDR2 | 111, 112 |
| variable heavy CDR3 | 154 |
| variable light CDR1 | 179 |
| variable light CDR2 | 199, 200 |
| variable light CDR3 | 230 |

In one embodiment, the antibody of the invention is an A8 antibody. By "A8 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A8 | SEQ ID NOs |
|---|---|
| variable heavy CDR1 | 58, 61 |
| variable heavy CDR2 | 113, 114 |
| variable heavy CDR3 | 155 |
| variable light CDR1 | 180 |
| variable light CDR2 | 201, 202 |
| variable light CDR3 | 231 |

In one embodiment, the antibody of the invention is an A9 antibody. By "A9 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A9 | SEQ ID NOs |
|---|---|
| variable heavy CDR1 | 70, 71 |
| variable heavy CDR2 | 115, 116 |
| variable heavy CDR3 | 156 |
| variable light CDR1 | 179 |
| variable light CDR2 | 190, 191 |
| variable light CDR3 | 229 |

In one embodiment, the antibody of the invention is an A10 antibody. By "A10 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A10 | SEQ ID NOs |
|---|---|
| variable heavy CDR1 | 72, 73 |
| variable heavy CDR2 | 117, 118 |
| variable heavy CDR3 | 157 |
| variable light CDR1 | 174 |
| variable light CDR2 | 190, 191 |
| variable light CDR3 | 229 |

In one embodiment, the antibody of the invention is an A11 antibody. By "A11 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A11 | SEQ ID NOs |
|---|---|
| variable heavy CDR1 | 74, 75 |
| variable heavy CDR2 | 119, 120 |
| variable heavy CDR3 | 155 |
| variable light CDR1 | 175 |
| variable light CDR2 | 203, 204 |
| variable light CDR3 | 232 |

In one embodiment, the antibody of the invention is an A12 antibody. By "A12 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A12 | SEQ ID NOs |
|---|---|
| variable heavy CDR1 | 58, 61 |
| variable heavy CDR2 | 110 |
| variable heavy CDR3 | 158 |
| variable light CDR1 | 179 |
| variable light CDR2 | 190, 205 |
| variable light CDR3 | 229 |

In one embodiment, the antibody of the invention is an A13 antibody. By "A13 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A13 | SEQ ID NOs |
|---|---|
| variable heavy CDR1 | 58, 61 |
| variable heavy CDR2 | 101, 102 |
| variable heavy CDR3 | 159 |
| variable light CDR1 | 176 |
| variable light CDR2 | 190, 206 |
| variable light CDR3 | 229 |

In one embodiment, the antibody of the invention is an A14 antibody. By "A14 antibody" herein is meant an antibody comprising the following CDRs; as described herein, the first SEQ ID listed in the chart below has been defined more broadly to include a few additional amino acids; in addition, as discussed below, these CDR sequences can also contain a limited number of amino acid variants:

| A14 | SEQ ID NOs |
|---|---|
| variable heavy CDR1 | 76, 77 |
| variable heavy CDR2 | 122, 123 |
| variable heavy CDR3 | 160 |
| variable light CDR1 | 177, 178 |
| variable light CDR2 | 207, 208 |
| variable light CDR3 | 223 |

As discussed herein, in addition, the identification of the CDRs of the A1 to A14 antibodies shows that these CDRs fall into consensus sequences. Thus, "ROR1 antibodies" of the invention also include CDRs that have the following sequences. As it appears from sequence identities, the A14 CDRs are more dissimilar than the A1-A13 CDR sets. As such, the consensus sequences discussed below include both a consensus sequence based on all of the CDRs of A1-A14, and a consensus sequence based on A1-A13:

| Consensus sequence | SEQ ID NO |
|---|---|
| variable heavy CDR1 (A1-A14) | 275 |
| variable heavy CDR1 (A1-A13) | 276 |
| variable heavy CDR2 (A1-A14) | 277 |
| variable heavy CDR2 (A1-A13) | 278 |
| variable heavy CDR3 (A1-A14) | 279 |
| variable heavy CDR3 (A1-A13) | 280 |
| variable light CDR1 (A1-A14) | 281 |
| variable light CDR1 (A1-A13) | 282 |
| variable light CDR2 (A1-A14) | 283 |
| variable light CDR2 (A1-A13) | 284 |
| variable light CDR3 (A1-A14) | 285 |
| variable light CDR3 (A1-A13) | 286 |

Thus, at a minimum, an A1-A14 antibody is defined by the set of CDRs it contains. In addition, given that each of these antibodies can bind to the ROR1 and there is significant identity between the CDRs as outlined herein, the CDRs as well as the $V_H$ and $V_K$ sequences can be "mixed and matched" to create other anti-ROR1 binding molecules of the invention. The ROR1 binding of such "mixed and matched" antibodies can be tested using the binding assays described above and in the Examples (e.g. ELISAs or Biacore® assays). Preferably, when $V_H$ and $V_K$ chains are mixed and matched, a $V_H$ sequence from a particular $V_H/V_K$ pairing is replaced with a structurally similar $V_H$ sequence. Likewise, preferably a $V_K$ sequence from a particular $V_H/V_K$ pairing is replaced with a structurally similar $V_K$ sequence. Accordingly, the invention specifically includes every possible combination of CDRs of the heavy and light chains of each of A1-A14.

Thus, at a minimum, an A1-A14 antibody is defined by the set of CDRs it contains. In addition to including the CDRs, the A1-A14 antibodies can include additional sequences, including framework and constant regions. As for the CDRs, as outlined below, the variable heavy and light chains, the Fc regions and/or the framework regions can comprise variants from the parent antibody sequence as outlined herein.

Disclosed herein are also variable heavy and light chains that comprise the CDR sets of the invention, as well as full length heavy and light chains (e.g. comprising constant regions as well). As will be appreciated by those in the art, the CDR sets of the invention can be incorporated into murine, humanized or human constant regions (including framework regions). As shown for A1 and huA1, the amino acid identity between the murine and human sequences is about 90%. Accordingly, the present invention provides variable heavy and light chains that are at least about 90%-99% identical to the SEQ IDs disclosed herein, with 90, 91, 92, 93, 94, 95, 96, 97, 98 and 99% all finding use in the present invention.

Antibodies that Bind to the Same Epitope as the ROR1 Antibodies of the Invention In another embodiment, the invention provides antibodies that bind to the same epitope on the human ROR1 as any of the ROR1 monoclonal antibodies of the invention (i.e. antibodies that have the ability to cross-compete for binding to the ROR1 with any of the monoclonal antibodies of the invention). In preferred embodiments, the reference antibody for cross-competition studies can be any or all of the A1-A14 ROR1 antibodies as defined herein. Such cross-competing antibodies can be identified based on their ability to cross-compete with any or all of the A1-A14 antibodies, Antibody Modifications The present invention further provides variant antibodies, sometimes referred to as "antibody derivatives" or "antibody analogs" as well. That is, there are a number of modifications that can be made to the antibodies of the invention, including, but not limited to, amino acid modifications in the CDRs (affinity maturation), amino acid modifications in the Fc region, glycosylation variants, covalent modifications of other types (e.g. for attachment of drug conjugates, etc.

By "variant" herein is meant a polypeptide sequence that differs from that of a parent polypeptide by virtue of at least one amino acid modification. In this case, the parent polypeptide is either the full length variable heavy or light chains, listed in Figure ****. Amino acid modifications can include substitutions, insertions and deletions, with the former being preferred in many cases.

In general, variants can include any number of modifications, as long as the function of the antibody is still present, as described herein. That is, any of antibodies A1-A14, for example, the antibody should still specifically bind to human ROR1. Similarly, if amino acid variants are generated with the Fc region, for example, the variant antibodies should maintain the required receptor binding functions for the particular application or indication of the antibody.

"Variants" in this case can be made in either the listed CDR sequences, the framework or Fc regions of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications (e.g. individual amino acid substitutions, insertions or deletions), with from 1-2, 1-3 and 1-4 also finding use in many embodiments. The number of modifications can depend on the size of the region being modified; for example, in general, fewer modifications are desired in CDR regions. However, as shown herein, the CDRs of the A1-A14 antibodies herein are similar, such that a number of amino acid changes can be made and preserve binding.

It should be noted that the number of amino acid modifications may be within functional domains: for example, it may be desirable to have from 1-5 modifications in the Fc region of wild-type or engineered proteins, as well as from 1 to 5 modifications in the Fv region, for example. A variant polypeptide sequence will preferably possess at least about 80%, 85%, 90%, 95% or up to 98 or 99% identity to the parent sequences (e.g. the variable regions, the constant regions, and/or the heavy and light chain sequences A1-A14). It should be noted that depending on the size of the sequence, the percent identity will depend on the number of amino acids.

By "amino acid substitution" or "substitution" herein is meant the replacement of an amino acid at a particular position in a parent polypeptide sequence with another amino acid. For example, the substitution S100A refers to a variant polypeptide in which the serine at position 100 is replaced with alanine. By "amino acid insertion" or "insertion" as used herein is meant the addition of an amino acid at a particular position in a parent polypeptide sequence. By "amino acid deletion" or "deletion" as used herein is meant the removal of an amino acid at a particular position in a parent polypeptide sequence.

By "parent polypeptide", "parent protein", "precursor polypeptide", or "precursor protein" as used herein is meant an unmodified polypeptide that is subsequently modified to generate a variant. In general, the parent polypeptides herein are A1-A14 (including huA1) Accordingly, by "parent antibody" as used herein is meant an antibody that is modified to generate a variant antibody.

By "wild type" or "WT" or "native" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

By "variant Fc region" herein is meant an Fc sequence that differs from that of a wild-type Fc sequence by virtue of at least one amino acid modification. Fc variant may refer to the Fc polypeptide itself, compositions comprising the Fc variant polypeptide, or the amino acid sequence.

In some embodiments, one or more amino acid modifications are made in one or more of the CDRs of the antibody (any of A1 to A14, including huA1). In general, only 1 or 2 or 3 amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR can be independently and optionally combined with any other substitution. In addition, as is shown herein, the A1-A13 CDRs share strong identity; for example, as shown in Figure ***, the vh CDR1 region of A1 and A2 only differ by 1 amino acid; similarly, the A1 and A11 vh CDR regions differ by 3 amino acids.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of A1-A14. In addition, as outlined below, amino acid modifications can also independently and optionally be made in any region outside the CDRs, including framework and constant regions as described herein.

In some embodiments, the anti-ROR1 antibodies of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in U.S. patent application Ser. No. 11/841,654 and references cited therein, US 2004/013210, US 2005/0054832, US 2006/0024298, US 2006/0121032, US 2006/0235208, US 2007/0148170, U.S. Ser. No. 12/341,769, U.S. Pat. No. 6,737,056, U.S. Pat. No. 7,670,600, U.S. Pat. No. 6,086,875 all of which are expressly incorporated by reference in their entirety, and in particular for specific amino acid substitutions that increase binding to Fc receptors.

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference).

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Glycosylation

Another type of covalent modification is alterations in glycosylation. In some embodiments, the antibodies disclosed herein can be modified to include one or more engineered glycoforms. By "engineered glycoform" as used herein is meant a carbohydrate composition that is covalently attached to the antibody, wherein the carbohydrate composition differs chemically from that of a parent antibody. Engineered glycoforms may be useful for a variety of purposes, including but not limited to enhancing or reducing effector function. For example, an aglycoslated antibody can be made (i.e. the antibody that lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al., and can be accomplished by removing the asparagine at position 297.

A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (POTELLIGENT® technology [Biowa, Inc., Princeton, N.J.]; GlycoMAb® glycosylation engineering technology [Glycart Biotechnology AG, Zürich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example US/2009/0317869, hereby incorporated by reference in its entirety. "Engineered glycoform" typically refers to the different carbohydrate or oligosaccharide as compared to the antibody made in the absence of the glycosylation technology; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference, including removal of fucose residues using a fucosidase enzyme as is known in the art. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

In additional embodiments, for example in the use of the antibodies of the invention for diagnostic or detection purposes, the antibodies may comprise a label. By "labeled"

herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include, but are not limited to, fluorescent lanthanide complexes (including those of Europium and Terbium), and fluorescent labels including, but not limited to, quantum dots, fluorescein, rhodamine, tetramethylrhodamine, eosin, erythrosin, coumarin, methyl-coumarins, pyrene, Malacite green, stilbene, Lucifer Yellow, Cascade Blue, Texas Red, the Alexa dyes, the Cy dyes, and others described in the 6th Edition of the Molecular Probes Handbook by Richard P. Haugland, hereby expressly incorporated by reference.

Antibody-Drug Conjugates

In some embodiments, the anti-ROR1 antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety.

Thus the invention provides anti-ROR1 antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug:antibody. As will be appreciated by those in the art, the actual number is an average.

Thus the invention provides anti-ROR1 antibodies conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, taxol, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of an anti-ROR1 antibody and one or more small molecule toxins, such as a maytansinoids, dolastatins, auristatins, a trichothecene, calicheamicin, and CC1065, and the derivatives of these toxins that have toxin activity, are contemplated.

Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/–C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/–dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, U.S. Pat. Nos. 7,303,749, 7,601,354, U.S. Ser. No. 12/631,508, WO02/

098883, U.S. Pat. Nos. 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Auristatins and Dolastatins

In some embodiments, the ADC comprises an anti-ROR1 antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety.

Figure 10:
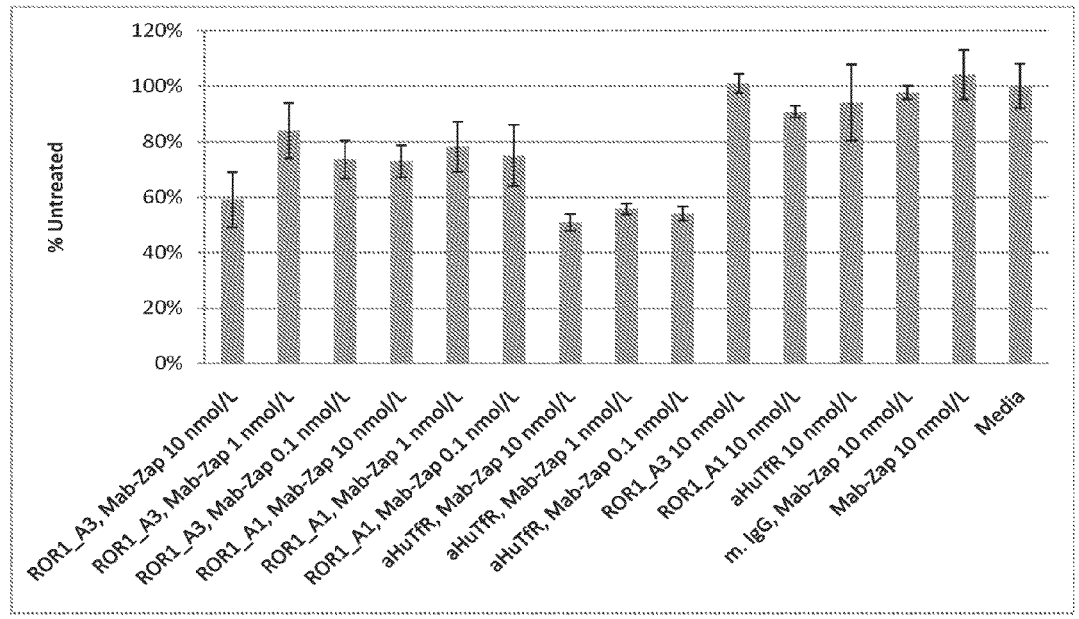
FIG. 10 depicts the internalisation of ROR1_A1 and ROR1_A3 monoclonal antibodies by the ZAP assay to the human epidermoid lung carcinoma cell line, CALU1.

An exemplary auristatin embodiment is MMAE (shown in FIG. 10 wherein the wavy line indicates the covalent attachment to a linker (L) of an antibody drug conjugate; see U.S. Pat. No. 6,884,869 expressly incorporated by reference in its entirety).

Another exemplary auristatin embodiment is MMAF, shown in FIG. 10 wherein the wavy line indicates the covalent attachment to a linker (L) of an antibody drug conjugate (US 2005/0238649, U.S. Pat. Nos. 5,767,237 and 6,124,431, expressly incorporated by reference in their entirety):

Additional exemplary embodiments comprising MMAE or MMAF and various linker components (described further herein) have the following structures and abbreviations (wherein Ab means antibody and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

In other embodiments, the ADC comprises an antibody of the invention conjugated to one or more calicheamicin molecules. For example, Mylotarg is the first commercial ADC drug and utilizes calicheamicin γ1 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773, 001, 5,767,285 and 5,877,296, all expressly incorporated by reference. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α2I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Duocarmycins

CC-1065 (see U.S. Pat. No. 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis.

Important members of the duocarmycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468, 5,475,092, 5,585,499, 5,846,545, WO2007/ 089149, WO2009/017394A1, U.S. Pat. Nos. 5,703,080, 6,989,452, 7,087,600, 7,129,261, 7,498,302, and 7,507,420, all of which are expressly incorporated by reference.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun 80: 49-57 can be used to incorporate Iodine-123. "Monoclonal Antibodies in Immunoscintigraphy" (Chatal, CRC Press 1989) describes other methods in detail.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof The generation of Antibody-drug conjugate compounds can be accomplished by any technique known to the skilled artisan. Briefly, the Antibody-drug conjugate compounds can include an anti-ROR1 antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with an anti-ROR1 antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug.

Linker Units

Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in ROR1-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: X)). Other examples of such linkers are described, e.g., in U.S. Pat. No. 6,214,345, incorporated herein by reference in its entirety and for all purposes In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007059404A2, WO06110476A2, WO05112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the anti-ROR1 antibodies of the invention.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Drug Loading

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachements (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 μCi of $^3$H-thymidine during the final 8 hours of the 72-hour period. The incorporation of $^3$H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the anti-ROR1 antibody of the invention can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). Efficacy can be measured using assays that measure inhibition of tumor formation, tumor regression or metastasis, and the like.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Methods for Producing the Antibodies of the Invention

The present invention further provides methods for producing the disclosed anti-ROR1 antibodies. These methods encompass culturing a host cell containing isolated nucleic acid(s) encoding the antibodies of the invention. As will be appreciated by those in the art, this can be done in a variety of ways, depending on the nature of the antibody. In some embodiments, in the case where the antibodies of the invention are full length traditional antibodies, for example, a heavy chain variable region and a light chain variable region under conditions such that an antibody is produced and can be isolated.

The variable heavy and light chains of antibodies A1-A14 are disclosed herein (both protein and nucleic acid sequences); as will be appreciated in the art, these can be easily augmented to produce full length heavy and light chains. That is, having provided the DNA fragments encoding $V_H$ and $V_K$ segments as outlined herein, these DNA fragments can be further manipulated by standard recombinant DNA techniques, for example, to convert the variable region genes to full-length antibody chain genes, to Fab fragment genes, or to a scFv gene. In these manipulations, a $V_K$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_H1$, $C_H2$ and $C_H3$). The sequences of murine heavy chain constant region genes are known in the art [see e.g. Kabat, E.A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_H1$ constant region.

The isolated DNA encoding the VL/VK region can be converted to a full-length light chain gene (as well as a Fab light chain gene) by operatively linking the $V_L$-encoding DNA to another DNA molecule encoding the light chain constant region, $C_L$. The sequences of murine light chain constant region genes are known in the art [see, e.g. Kabat, E. A., et al. (1991) Sequences of Proteins of Immunological Interest, Fifth Edition, US Department of Health and Human Services, NIH Publication No. 91-3242] and DNA fragments encompassing these regions can be obtained by standard PCR amplification. In preferred embodiments, the light chain constant region can be a kappa or lambda constant region.

To create a scFv gene, the $V_H$- and $V_L/V_K$-encoding DNA fragments are operatively linked to another fragment encoding a flexible linker, e.g. encoding the amino acid sequence $(Gly_4$-$Ser)_3$, such that the $V_H$ and $V_L/V_K$ sequences can be expressed as a contiguous single-chain protein, with the $V_L/V_K$ and $V_H$ regions joined by the flexible linker [see e.g. Bird et al. (1988) Science 242:423-426; Huston et al. (1988) Proc. Natl. Acad. Sci. USA 85:5879-5883; McCafferty et al., (1990) Nature 348:552-554].

In general, nucleic acids are provided which encode the antibodies of the invention. Such polynucleotides encode for both the variable and constant regions of each of the heavy and light chains, although other combinations are also contemplated by the present invention in accordance with the compositions described herein. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the antibodies of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector (s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

General methods for antibody molecular biology, expression, purification, and screening are well known, for example, see U.S. Pat. Nos. 4,816,567, 4,816,397, 6,331,415 and 7,923,221, as well as Antibody Engineering, edited by Kontermann & Dubel, Springer, Heidelberg, 2001 and 2010 Hayhurst & Georgiou, 2001, Curr Opin Chem Biol 5:683-689; Maynard & Georgiou, 2000, Annu Rev Biomed Eng 2:339-76; and Morrison, S. (1985) Science 229:1202.

Pharmaceutical Compositions

In another aspect, the present invention provides a composition, e.g. a pharmaceutical composition, containing one or a combination of ROR1 antibodies, or antigen-binding portion(s) thereof, of the present invention, formulated together with a pharmaceutically acceptable carrier. Such compositions may include one or a combination of (e.g. two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e. combined with other agents. For example, the combination therapy can include an anti-antibody of the present invention combined with at least one other anti-tumor agent, or an anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). Depending on the route of administration, the active compound, i.e. antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects [see, e.g. Berge, S. M., et al. (1977) *J. Pharm. Sci.* 66:1-19]. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of 100 per cent, this amount will range from about 0.01 per cent to about 99 per cent of active ingredient, preferably from about 0.1 per cent to about 70 per cent, most preferably from about 1 per cent to about 30 per cent of active ingredient in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-ROR1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-ROR1 antibody of the invention preferably results in a decrease in severity of disease symptoms, an increase in frequency and duration of disease symptom-free periods, or a prevention of impairment or disability due to the disease affliction. For example, for the treatment of the ROR1 mediated tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art [see, e.g. *Sustained and Controlled Release Drug Delivery Systems* (1978) J. R. Robinson, ed., Marcel Dekker, Inc., N.Y].

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery [see, e.g. V. V. Ranade (1989) *J. Clin. Pharmacol.* 29:685]. Exemplary targeting moieties include folate or biotin (see, e.g. U.S. Pat. No. 5,416,016.); mannosides [Umezawa et al. (1988) *Biochem. Biophys. Res. Commun.* 153:1038]; antibodies [P. G. Bloeman et al. (1995) *FEBS Lett.* 357:140; M. Owais et al. (1995) *Antimicrob. Agents Chemother.* 39:180]; surfactant protein A receptor [Briscoe et al. (1995) *Am. J. Physiol.* 1233:134]; p 120 [Schreier et al. (1994)*J. Biol. Chem.* 269:9090]; see also K. Keinanen; M. L. Laukkanen (1994) *FEBS Lett.* 346:123; J. J. Killion; I. J. Fidler (1994) *Immunomethods* 4:273.

Uses and Methods

The antibodies, antibody compositions and methods of the present invention have numerous in vitro and in vivo diagnostic and therapeutic utilities involving the diagnosis and treatment of ROR1 mediated disorders.

In some embodiments, these molecules can be administered to cells in culture, in vitro or ex vivo, or to human subjects, e.g. in vivo, to treat, prevent and to diagnose a variety of disorders. As used herein, the term "subject" is intended to include human and non-human animals. Non-human animals include all vertebrates, e.g. mammals and non-mammals, such as non-human primates, sheep, dogs, cats, cows, horses, chickens, amphibians, and reptiles. Preferred subjects include human patients having disorders mediated by ROR1 activity. The methods are particularly suitable for treating human patients having a disorder associated with the aberrant ROR1 expression. When antibodies to ROR1 are administered together with another agent, the two can be administered in either order or simultaneously.

Given the specific binding of the antibodies of the invention for ROR1, the antibodies of the invention can be used to specifically detect ROR1 expression on the surface of cells and, moreover, can be used to purify ROR1 via immunoaffinity purification.

Furthermore, given the expression of ROR1 on tumor cells, the antibodies, antibody compositions and methods of the present invention can be used to treat a subject with a tumorigenic disorder, e.g. a disorder characterized by the presence of tumor cells expressing ROR1 including, for example non-small cell lung carcinoma, B-cell chronic lymphocytic leukemia and colon cancer. ROR1 has been demonstrated to be internalised on antibody binding as illustrated in Examples 5 and 7 below, thus enabling the antibodies of the invention to be used in any payload mechanism of action e.g. an ADC approach, radioimmunoconjugate, or ADEPT approach.

In one embodiment, the antibodies (e.g. monoclonal antibodies, antibody fragments, Nanobodies, multispecific and bispecific molecules and compositions, etc.) of the invention can be used to detect levels of ROR1, or levels of cells which contain ROR1 on their membrane surface, which levels can then be linked to certain disease symptoms. Alternatively, the antibodies, generally administered as ADCs, can be used to inhibit or block ROR1 function which, in turn, can be linked to the prevention or amelioration of certain disease symptoms, thereby implicating the ROR1 as a mediator of the disease. This can be achieved by contacting a sample and a control sample with the anti-ROR1 antibody under conditions that allow for the formation of a complex between the antibody and ROR1. Any complexes formed between the antibody and the ROR1 are detected and compared in the sample and the control.

In another embodiment, the antibodies (e.g. monoclonal antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g. monoclonal antibodies, multispecific and bispecific molecules, immunoconjugates and compositions) of the invention have additional utility in therapy and diagnosis of ROR1 related diseases. For example, the monoclonal antibodies, the multispecific or bispecific molecules and the immunoconjugates can be used to elicit in vivo or in vitro one or more of the following biological activities: to inhibit the growth of and/or kill a cell expressing ROR1; to mediate phagocytosis or ADCC of a cell expressing ROR1 in the presence of human effector cells, or to block ROR1 ligand binding to ROR1.

In a particular embodiment, the antibodies (e.g. monoclonal antibodies, multispecific and bispecific molecules and compositions) are used in vivo to treat, prevent or diagnose a variety of ROR1-related diseases. Examples of ROR1-related diseases include, among others, human cancer tissues representing non-small cell lung carcinoma, B-cell chronic lymphocytic leukemia and colon cancer.

Suitable routes of administering the antibody compositions (e.g. monoclonal antibodies, multispecific and bispecific molecules and immunoconjugates) of the invention in vivo and in vitro are well known in the art and can be selected by those of ordinary skill. For example, the antibody compositions can be administered by injection (e.g. intravenous or subcutaneous). Suitable dosages of the molecules used will depend on the age and weight of the subject and the concentration and/or formulation of the antibody composition.

As previously described, the anti-ROR1 antibodies of the invention can be co-administered with one or more therapeutic agents, e.g. a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g. an anti-cancer therapy, e.g. radiation. Such therapeutic agents include, among others, antineoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Other agents suitable for co-administration with the antibodies of the invention include other agents used for the treatment of cancers, e.g. non-small cell lung carcinoma, B-cell chronic lymphocytic leukemia or colon cancer, such as Avastin®, 5FU and gemcitabine. Co-administration of the anti-ROR1 antibodies or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g. effector cells linked to compositions (e.g. monoclonal antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$, but will vary depending on the therapeutic purpose. In general, the amount will be sufficient to obtain localization at the target cell, e.g. a tumor cell expressing ROR1, and to affect cell killing by, e.g. phagocytosis. Routes of administration can also vary.

Therapy with target-specific effector cells can be performed in conjunction with other techniques for removal of targeted cells. For example, anti-tumor therapy using the compositions (e.g. monoclonal antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-ROR1 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g. monoclonal antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g. monoclonal antibodies, multispecific and bispecific molecules) of the invention can also be lysed by complement. In yet another embodiment, the compositions of the invention do not activate complement.

The compositions (e.g. monoclonal antibodies, multispecific and bispecific molecules and immunoconjugates) of the invention can also be administered together with complement. In certain embodiments, the instant disclosure provides compositions comprising antibodies, multispecific or bispecific molecules and serum or complement. These compositions can be advantageous when the complement is located in close proximity to the antibodies, multispecific or bispecific molecules. Alternatively, the antibodies, multispecific or bispecific molecules of the invention and the complement or serum can be administered separately.

Also within the scope of the present invention are kits comprising the antibody compositions of the invention (e.g. monoclonal antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional antibodies of the invention (e.g. an antibody having a complementary activity which binds to an epitope in the ROR1 antigen distinct from the first antibody).

Accordingly, patients treated with antibody compositions of the invention can be additionally administered (prior to, simultaneously with, or following administration of an antibody of the invention) with another therapeutic agent, such as a cytotoxic or radiotoxic agent, which enhances or augments the therapeutic effect of the antibodies.

In other embodiments, the subject can be additionally treated with an agent that modulates, e.g. enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g. antibodies, multispecific and bispecific molecules) of the invention can also be used to target cells expressing FcγR or ROR1, for example, for labeling such cells. For such use, the binding agent can be linked to a molecule that can be detected. Thus, the invention provides methods for localizing ex vivo or in vitro cells expressing Fc receptors, such as FcγR, or ROR1. The detectable label can be, e.g. a radioisotope, a fluorescent compound, an enzyme, or an enzyme co-factor.

In a particular embodiment, the invention provides methods for detecting the presence of the ROR1 antigen in a sample, or measuring the amount of the ROR1 antigen, comprising contacting the sample, and a control sample, with a monoclonal antibody, or an antigen binding portion thereof, which specifically binds to ROR1, under conditions that allow for formation of a complex between the antibody or portion thereof and ROR1. The formation of a complex is then detected, wherein a difference complex formation between the sample compared to the control sample is indicative the presence of the ROR1 antigen in the sample.

In other embodiments, the invention provides methods for treating an ROR1 mediated disorder in a subject, e.g. human cancers, including non-small cell lung carcinoma, B-cell chronic lymphocytic leukemia and colon cancer.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependant claims.

The present invention is further illustrated by the following examples which should not be construed as further limiting.

EXAMPLES

Example 1

Construction of a Phage-Display Library

A recombinant protein composed of the extracellular domain of ROR1 (SEQ ID NO: 272) was eukaryotically synthesized by standard recombinant methods and used as antigen for immunization.
Immunization and mRNA Isolation A phage display library for identification of the ROR1-binding molecules was constructed as follows. A/J mice (Jackson Laboratories, Bar Harbor, Me.) were immunized intraperitoneally with the recombinant ROR1 antigen (the extracellular domain), using 100 µg protein in Freund's complete adjuvant, on day 0, and with 100 µg antigen on day 28. Test bleeds of mice were obtained through puncture of the retro-orbital sinus. If, by testing the titers, they were deemed high by ELISA using the biotinylated ROR1 antigen immobilized via neutravidin (Reacti-Bind™) NeutrAvidin™-Coated Polystyrene Plates, Pierce, Rockford, Ill.), the mice were boosted with 100 µg of protein on day 70, 71 and 72, with subsequent sacrifice and splenectomy on day 77. If titers of antibody were not deemed satisfactory, mice were boosted with 100 µg antigen on day 56 and a test bleed taken on day 63. If satisfactory titers were obtained, the animals were boosted with 100 µg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.). This spleen suspension was pulled through an 18 gauge needle until all cells were lysed and the viscous solution was transferred to a microcentrifuge tube. The petri dish was washed with 100 µl of solution D to recover any remaining spleen. This suspension was then pulled through a 22 gauge needle an additional 5-10 times.

The sample was divided evenly between two microcentrifuge tubes and the following added, in order, with mixing by inversion after each addition: 50 µl 2 M sodium acetate pH 4.0, 0.5 ml water-saturated phenol (Fisher Scientific, Pittsburgh, Pa.), 100 µl chloroform/isoamyl alcohol 49:1 (Fisher Scientific, Pittsburgh, Pa.). The solution was vortexed for 10 sec and incubated on ice for 15 min. Following centrifugation at 14 krpm for 20 min at 2-8° C., the aqueous phase was transferred to a fresh tube. An equal volume of water saturated phenol:chloroform:isoamyl alcohol (50:49:1) was added, and the tube vortexed for ten seconds. After 15 min incubation on ice, the sample was centrifuged for 20 min at 2-8° C., and the aqueous phase transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile diethyl pyrocarbonate-treated water. The concentration was determined by A260 using an absorbance of 1.0 for a concentration of 40 µg/ml. The RNAs were stored at −80° C.
Preparation of Complementary DNA (cDNA)

The total RNA purified from mouse spleens as described above was used directly as template for cDNA preparation. RNA (50 µg) was diluted to 100 µL with sterile water, and 10 of 130 ng/µL oligo dT12 (synthesized on Applied Biosystems Model 392 DNA synthesizer) was added. The sample was heated for 10 min at 70° C., then cooled on ice. Forty µL 5* first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten reverse transcriptase (Superscript™ II, Gibco/BRL, Gaithersburg, Md.) was added and incubation was continued at 37° C. for 1 hr. The cDNA products were used directly for polymerase chain reaction (PCR).
Amplification of Antibody Genes by PCR To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. Pat. No. 6,555,310. The constant region nucleotide sequences for each chain required only one 3' primer for the H chains and one 3' primer for the kappa L chains.

A 50 µL reaction was performed for each primer pair with 50 µmol of 5' primer, 50 µmol of 3' primer, 0.25 µL Taq DNA Polymerase (5 units/µL, Boehringer Mannheim, Indianapolis, Ind.), 3 µL cDNA (prepared as described), 5 µL 2 mM dNTP's, 5 µL 10*Taq DNA polymerase buffer with MgCl2 (Boehringer Mannheim, Indianapolis, Ind.), and $H_2O$ to 50 µL. Amplification was done using a GeneAmp® 9600 thermal cycler (Perkin Elmer, Foster City, Calif.) with the following thermocycle program: 94° C. for 1 min; 30 cycles of 94° C. for 20 sec, 55° C. for 30 sec, and 72° C. for 30 sec, 72° C. for 6 min; 4° C.

The dsDNA products of the PCR process were then subjected to asymmetric PCR using only a 3' primer to generate substantially only the anti-sense strand of the target genes. A 100 µL reaction was done for each dsDNA product with 200 µmol of 3' primer, 2 µL of ds-DNA product, 0.5 µL Taq DNA Polymerase, 10 µL 2 mM dNTP's, 10 µL 10*Taq DNA polymerase buffer with $MgCl_2$ (Boehringer Mannheim, Indianapolis, Ind.), and $H_2O$ to 100 µL. The same PCR program as that described above was used to amplify the single-stranded (ss)-DNA.
Purification of Single-Stranded DNA by High Performance Liquid Chromatography and Kinasing Single-Stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2-8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 µL water and the L chain products were pooled separately in 210 μL water. The single-stranded DNA was purified by high performance liquid chromatography (HPLC) using a Hewlett Packard 1090 HPLC and a Gen-Pak™ FAX anion exchange column (Millipore Corp., Milford, Mass.). The gradient used to purify the single-stranded DNA is shown in Table 1, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above. The dried DNA pellets were pooled in 200 μL sterile water.

TABLE 1

HPLC gradient for purification of ss-DNA

| Time (min) | % A | % B | % C | Flow (ml/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1M NaCl, pH 8.0
Buffer C is 40 mM phosphoric acid The single-stranded DNA was 5'-phosphorylated in preparation for mutagenesis. Twenty-four μL 10* kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of Tris equilibrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/ml for an absorbance of 1.0. Samples were stored at −20° C.

Preparation of Uracil Templates Used in Generation of Spleen Antibody Phage Libraries One ml of E. coli CJ236 (BioRAD, Hercules, Calif.) overnight culture was added to 50 ml 2*YT in a 250 ml baffled shake flask. The culture was grown at 37° C. to OD600=0.6, inoculated with 10 μl of a 1/100 dilution of BS45 vector phage stock (described in U.S. Pat. No. 6,555,310) and growth continued for 6 hr. Approximately 40 ml of the culture was centrifuged at 12 krpm for 15 min at 4° C. The supernatant (30 ml) was transferred to a fresh centrifuge tube and incubated at room temperature for 15 min after the addition of 15 μl of 10 mg/ml RNaseA (Boehringer Mannheim, Indianapolis, Ind.). The phages were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2-8° C. The supernatant was carefully discarded, and the tube briefly spun to remove all traces of supernatant. The pellet was resuspended in 400 μl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 μl sterile water and the concentration determined by A260 using an absorbance of 1.0 for a concentration of 40 μg/ml. The template was diluted to 250 ng/μL with sterile water, aliquoted and stored at −20° C.

Mutagenesis of Uracil Template with ss-DNA and Electroporation into E. coli to Generate Antibody Phage Libraries Antibody phage display libraries were generated by simultaneously introducing single-stranded heavy and light chain genes onto a phage display vector uracil template. A typical mutagenesis was performed on a 2 μg scale by mixing the following in a 0.2 ml PCR reaction tube: 8 μl of (250 ng/μL) uracil template, 8 μL of 10* annealing buffer (200 mM Tris pH 7.0, 20 mM MgCl2, 500 mM NaCl), 3.33 μl of kinased single-stranded heavy chain insert (100 ng/μL), 3.1 μl of kinased single-stranded light chain insert (100 ng/μL), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10* synthesis buffer (5 mM each dNTP, 10 mM ATP, 100 mM Tris pH 7.4, 50 mM MgCl2, 20 mM DTT), 8 μL T4 DNA ligase (1 U/μL, Boehringer Mannheim, Indianapolis, Ind.), 8 μL diluted T7 DNA polymerase (1 U/μL, New England BioLabs, Beverly, Mass.) and incubating at 37° C. for 30 min. The reaction was stopped with 300 μL of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl, of sterile water.

One μL of mutagenesis DNA (500 ng) was transferred into 40 μl electrocompetent E. coli DH12S (Gibco/BRL, Gaithersburg, Md.) using electroporation. The transformed cells were mixed with approximately 1.0 ml of overnight XL-1 cells which were diluted with 2*YT broth to 60% the original volume. This mixture was then transferred to a 15-ml sterile culture tube and 9 ml of top agar added for plating on a 150-mm LB agar plate. Plates were incubated for 4 hr at 37° C. and then transferred to 20° C. overnight. First round antibody phage were made by eluting phage off these plates in 10 ml of 2*YT, spinning out debris, and taking the supernatant. These samples are the antibody phage display libraries used for selecting antibodies against the ROR1. Efficiency of the electroporations was measured by plating 10 μl of a $10^{-4}$ dilution of suspended cells on LB agar plates, follow by overnight incubation of plates at 37° C. The efficiency was calculated by multiplying the number of plaques on the $10^{-4}$ dilution plate by 106. Library electroporation efficiencies are typically greater than $1*10^7$ phages under these conditions.

Transformation of *E. coli* by Electroporation

Electrocompetent *E. coli* cells were thawed on ice. DNA was mixed with 40 L of these cells by gently pipetting the cells up and down 2-3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the *E. coli* Pulser (BioRAD, Hercules, Calif.) and electroporated with the voltage set at 1.88 kV according to the manufacturer's recommendation. The transformed sample was immediately resuspended in 1 ml of 2*YT broth or 1 ml of a mixture of 400 µl 2*YT/600 overnight XL-1 cells and processed as procedures dictated.

Plating M13 Phage or Cells Transformed with Antibody Phage-Display Vector Mutagenesis Reaction Phage samples were added to 200 µL of an overnight culture of *E. coli* XL1-Blue when plating on 100 mm LB agar plates or to 600 µL of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.-55° C.) to remove any excess moisture on the agar surface. The plates were cooled at room temperature until the top agar solidified. The plates were inverted and incubated at 37° C. as indicated.

Example 2

Preparation of Biotinylated Tyrosine-Protein Kinase Transmembrane Receptor ROR1 and Biotinylated Antibodies The concentrated recombinant ROR1 antigen (full length extracellular domain) was extensively dialyzed into BBS (20 mM borate, 150 mM NaCl, 0.1% $NaN_3$, pH 8.0). After dialysis, 1 mg of the ROR1 (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylation reaction mixture was then dialyzed against BBS at 2-8° C. After dialysis, the biotinylated ROR1 was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2-8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 sec. This mixture was incubated at 45° C. for 2 hr, shaking every 30 min. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 µl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 3

Selection of Recombinant Polyclonal Antibodies to Tyrosine-Protein Kinase Transmembrane Receptor ROR1 Antigen Binding reagents that specifically bind to the ROR1 were selected from the phage display libraries created from hyper-immunized mice as described in Example 1.

Panning

First round antibody phage were prepared as described in Example 1 using BS45 uracil template. Electroporations of mutagenesis DNA were performed yielding phage samples derived from different immunized mice. To create more diversity in the recombinant polyclonal library, each phage sample was panned separately.

Before the first round of functional panning with the biotinylated ROR1 antigen, antibody phage libraries were selected for phage displaying both heavy and light chains on their surface by panning with 7F11-magnetic latex (as described in Examples 21 and 22 of U.S. Pat. No. 6,555,310). Functional panning of these enriched libraries was performed in principle as described in Example 16 of U.S. Pat. No. 6,555,310. Specifically, 10 µL of $1*10^{-6}$ M biotinylated ROR1 antigen was added to the phage samples (approximately $1*10^{-8}$ M final concentration of the ROR1), and the mixture allowed to come to equilibrium overnight at 2-8° C.

After reaching equilibrium, samples were panned with avidin magnetic latex to capture antibody phage bound to the ROR1. Equilibrated avidin magnetic latex (Example 1), 200 µL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 µl 2*YT and plated on 150 mm LB plates as described in Example 1 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2*YT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 µL of each phage stock into 900 µL of panning buffer in 15 ml disposable sterile centrifuge tubes. The biotinylated ROR1 antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6-7 hr, after which the plates were transferred to room temperature and nitrocellulose filters (pore size 0.45 mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F11-magnetic latex before performing a third functional round of panning overnight at 2-8° C. using the biotinylated ROR1 antigen at approximately $2*10^{-9}$ M. This round of panning was also monitored for kappa positives. Individual phage samples that had kappa positive percentages greater than 80% were pooled and subjected to a final round of panning overnight at 2-8° C. at $5*10^{-9}$ M. The ROR1 antibody genes contained within the eluted phage from this fourth round of functional panning were subcloned into the expression vector, pBRncoH3.

The subcloning process was done generally as described in Example 18 of U.S. Pat. No. 6,555,310. After subcloning, the expression vector was electroporated into DH10B cells and the mixture grown overnight in 2*YT containing 1% glycerol and 10 µg/ml tetracycline. After a second round of growth and selection in tetracycline, aliquots of cells were frozen at −80° C. as the source for the ROR1 polyclonal antibody production. Monoclonal antibodies were selected from these polyclonal mixtures by plating a sample of the mixture on LB agar plates containing 10 µg/ml tetracycline and screening for antibodies that recognized the ROR1.

Expression and Purification of Recombinant Antibodies Against Tyrosine-Protein Kinase Transmembrane Receptor ROR1

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium [Pack et al. (1993) Bio/Technology 11: 1271-1277] supplemented with 3 g/L L-leucine, 3 g/L L-isoleucine, 12 g/L casein digest (Difco, Detroit, Mich.), 12.5 g/L glycerol and 10 µg/ml tetracycline. The temperature, pH and dissolved oxygen in the fermentor were controlled at 26° C., 6.0-6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5-200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

Example 4

Structural Characterization of Monoclonal Antibodies to Tyrosine-Protein Kinase Transmembrane Receptor ROR1

The cDNA sequences encoding the heavy and light chain variable regions of the ROR1_A1, ROR1_A2, ROR1_A3, ROR1_A4, ROR1_A5, ROR1_A6, ROR1_A7, ROR1_A8, ROR1_A9, ROR1_A10, ROR1_A11, ROR1_A12, ROR1_A13 and ROR1_A14 monoclonal antibodies were obtained using standard PCR techniques and were sequenced using standard DNA sequencing techniques.

The antibody sequences may be mutagenized to revert back to germline residues at one or more residues.

The nucleotide and amino acid sequences of the light chain variable region of ROR1_A1 are shown in SEQ ID NO:43 and 29, respectively.

The nucleotide and amino acid sequences of the heavy chain variable region of ROR1_A1 are shown in SEQ ID NO:15 and 1, respectively.

The nucleotide and amino acid sequences of the light chain variable region of humanized ROR1_A1 are shown in SEQ ID NO:271 and 270, respectively.

The nucleotide and amino acid sequences of the heavy chain variable region of humanized ROR1_A1 are shown in SEQ ID NO:269 and 268, respectively.

Comparison of the ROR1_A1 light chain immunoglobulin sequence to the known murine germline immunoglobulin light chain sequences demonstrated that the ROR1_A1 light chain utilizes a $V_K$ segment from murine germline $V_K$ 14-111. Further analysis of the ROR1_A1 $V_K$ sequence using the Kabat system of CDR region determination led to the delineation of the light chain CDR1, CDR2 and CDR3 regions as shown in SEQ ID NOs:173, 190 or 191 and 229, respectively. The alignments of the ROR1_A1 CDR1, CDR2 and CDR3 $V_K$ sequences to the germline $V_K$ 14-111 sequences are shown in FIGS. 1a, 1b, 2a, 2b and 3, respectively.

Comparison of the ROR1_A1 heavy chain immunoglobulin sequence to the known murine germline immunoglobulin heavy chain sequences demonstrated that the ROR1_A1 heavy chain utilizes a $V_H$ segment from murine germline $V_H$ 5-6. Further analysis of the ROR1_A1 $V_H$ sequence using the Kabat system of CDR region determination led to the delineation of the heavy chain CDR1, CDR2 and CDR3 regions as shown in SEQ ID NOs: 57 or 58, 99 or 100 and 149, respectively. The alignments of the ROR1_A1 CDR1 and CDR2 $V_H$ sequences to the germline $V_H$ 5-6 sequence are shown in FIGS. 4a, 4b, 5a and 5b.

The nucleotide and amino acid sequences of the light chain variable region of ROR1_A2 are shown in SEQ ID NO:44 and 30, respectively.

The nucleotide and amino acid sequences of the heavy chain variable region of ROR1_A2 are shown in SEQ ID NO:16 and 2, respectively.

Comparison of the ROR1_A2 light chain immunoglobulin sequence to the known murine germline immunoglobulin light chain sequences demonstrated that the ROR1_A2 light chain utilizes a $V_K$ segment from murine germline $V_K$ 14-111. Further analysis of the ROR1_A2 $V_K$ sequence using the Kabat system of CDR region determination led to the delineation of the light chain CDR1, CDR2 and CDR3 regions shown in SEQ ID NOs: 179, 190 or 191 and 229, respectively. The alignments of the ROR1_A2 CDR1, CDR2 and CDR3 $V_K$ sequences to the germline $V_K$ 14-111 sequence are shown in FIGS. 1a, 1b, 2a, 2b and 3, respectively.

Comparison of the ROR1_A2 heavy chain immunoglobulin sequence to the known murine germline immunoglobulin heavy chain sequences demonstrated that the ROR1_A2 heavy chain utilizes a $V_H$ segment from murine germline $V_H$ 5-12. Further analysis of the ROR1_A2 $V_H$ sequence using the Kabat system of CDR region determination led to the delineation of the heavy chain CDR1, CDR2 and CDR3 regions as shown in SEQ ID NOs: 59 or 60, 101 or 102 and 150, respectively. The alignments of the ROR1_A2 CDR1 and CDR2 $V_H$ sequence to the germline $V_H$ 5-12 sequence are shown in FIGS. 4a, 4b, 5a and 5b.

The nucleotide and amino acid sequences of the light chain variable region of ROR1_A3 are shown in SEQ ID NO:45 and 31, respectively.

The nucleotide and amino acid sequences of the heavy chain variable region of ROR1_A3 are shown in SEQ ID NO:17 and 3, respectively.

Comparison of the ROR1_A3 light chain immunoglobulin sequence to the known murine germline immunoglobulin light chain sequences demonstrated that the ROR1_A3 light chain utilizes a $V_K$ segment from murine germline $V_K$ 14-111. Further analysis of the ROR1_A3 $V_K$ sequence using the Kabat system of CDR region determination led to the delineation of the light chain CDR1, CDR2 and CDR3 regions as shown in SEQ ID NOs: 179, 190 or 192 and 229, respectively. The alignments of the ROR1_A3 CDR1, CDR2 and CDR3 $V_K$ sequences to the germline $V_K$ 14-111 sequence are shown in FIGS. 1a, 1b, 2a, 2b and 3, respectively.

Comparison of the ROR1_A3 heavy chain immunoglobulin sequence to the known murine germline immunoglobulin heavy chain sequences demonstrated that the ROR1_A3 heavy chain utilizes a $V_H$ segment from murine germline $V_H$ 5-6 Further analysis of the ROR1_A3 $V_H$ sequence using the Kabat system of CDR region determination led to the delineation of the heavy chain CDR1, CDR2 and CDR3 regions as shown in SEQ ID NOs: 58 or 61, 103 or 104 and 149, respectively. The alignments of the ROR1_A3 CDR1 and CDR2 $V_H$ sequence to the germline $V_H$ 5-6 sequence are shown in FIGS. 4a, 4b, 5a and 5b.

The nucleotide and amino acid sequences of the light chain variable region of ROR1_A4 are shown in SEQ ID NO:46 and 32, respectively.

The nucleotide and amino acid sequences of the heavy chain variable region of ROR1_A4 are shown in SEQ ID NO:18 and 4, respectively.

Comparison of the ROR1_A4 light chain immunoglobulin sequence to the known murine germline immunoglobulin light chain sequences demonstrated that the ROR1_A4 light chain utilizes a $V_K$ segment from murine germline $V_K$ 14-111. Further analysis of the ROR1_A4 $V_K$ sequence using the Kabat system of CDR region determination led to the delineation of the light chain CDR1, CDR2 and CDR3 regions as shown in SEQ ID NOs: 179, 193 or 194 and 229, respectively. The alignments of the ROR1_A4 CDR1, CDR2 and CDR3 $V_K$ sequences to the germline $V_K$ 14-111 sequence are shown in FIGS. 1a, 1b, 2a, 2b and 3, respectively.

Comparison of the ROR1_A4 heavy chain immunoglobulin sequence to the known murine germline immunoglobulin heavy chain sequences demonstrated that the ROR1_A4 heavy chain utilizes a $V_H$ segment from murine germline $V_H$ 5-6 Further analysis of the ROR1_A4 $V_H$ sequence using the Kabat system of CDR region determination led to the delineation of the heavy chain CDR1, CDR2 and CDR3 regions as shown in SEQ ID NOs: 62 or 63, 105 or 106 and 151, respectively. The alignment ofs the ROR1_A4 CDR1 and CDR2 $V_H$ sequence to the germline $V_H$ 5-6 sequence are shown in FIGS. 4a, 4b, 5a and 5b.

The nucleotide and amino acid sequences of the light chain variable region of ROR1_A5 are shown in SEQ ID NO:47 and 33, respectively.

The nucleotide and amino acid sequences of the heavy chain variable region of ROR1_A5 are shown in SEQ ID NO:19 and 5, respectively.

Comparison of the ROR1_A5 light chain immunoglobulin sequence to the known murine germline immunoglobulin light chain sequences demonstrated that the ROR1_A5 light chain utilizes a $V_K$ segment from murine germline $V_K$ 14-111. Further analysis of the ROR1_A5 $V_K$ sequence using the Kabat system of CDR region determination led to the delineation of the light chain CDR1, CDR2 and CDR3 regions as shown in SEQ ID NOs: 179, 195 or 196 and 229, respectively. The alignments of the ROR1_A5 CDR1, CDR2 and CDR3 $V_K$ sequences to the germline $V_K$ 14-111 sequence are shown in FIGS. 1a, 1b, 2a, 2b and 3, respectively.

Comparison of the ROR1_A5 heavy chain immunoglobulin sequence to the known murine germline immunoglobulin heavy chain sequences demonstrated that the ROR1_A5 heavy chain utilizes a $V_H$ segment from murine germline $V_H$ 5-6. Further analysis of the ROR1_A5 $V_H$ sequence using the Kabat system of CDR region determination led to the delineation of the heavy chain CDR1, CDR2 and CDR3 regions as shown in SEQ ID NOs: 64 or 65, 107 or 108 and 152, respectively. The alignments of the ROR1_A5 CDR1 and CDR2 $V_H$ sequence to the germline $V_H$ 5-6 sequence are shown in FIGS. 4a, 4b, 5a and 5b.

The nucleotide and amino acid sequences of the light chain variable region of ROR1_A6 are shown in SEQ ID NO:48 and 34, respectively.

The nucleotide and amino acid sequences of the heavy chain variable region of ROR1_A6 are shown in SEQ ID NO:20 and 6, respectively.

Comparison of the ROR1_A6 light chain immunoglobulin sequence to the known murine germline immunoglobulin light chain sequences demonstrated that the ROR1_A6 light chain utilizes a $V_K$ segment from murine germline $V_K$ 14-111. Further analysis of the ROR1_A6 $V_K$ sequence using the Kabat system of CDR region determination led to the delineation of the light chain CDR1, CDR2 and CDR3 regions as shown in SEQ ID NOs: 179, 197 or 198 and 229, respectively. The alignments of the ROR1_A6 CDR1, CDR2 and CDR3 $V_K$ sequences to the germline $V_K$ 14-111 sequence are shown in FIGS. 1a, 1b, 2a, 2b and 3, respectively.

Comparison of the ROR1_A6 heavy chain immunoglobulin sequence to the known murine germline immunoglobulin heavy chain sequences demonstrated that the ROR1_A6 heavy chain utilizes a $V_H$ segment from murine germline $V_H$ 5-6. Further analysis of the ROR1_A6 $V_H$ sequence using the Kabat system of CDR region determination led to the delineation of the heavy chain CDR1, CDR2 and CDR3 regions as shown in SEQ ID NOs: 66 or 67, 109 or 110 and 153, respectively. The alignments of the ROR1_A6 CDR1 and CDR2 $V_H$ sequence to the germline $V_H$ 5-6 sequence are shown in FIGS. 4a, 4b, 5a and 5b.

The nucleotide and amino acid sequences of the light chain variable region of ROR1_A7 are shown in SEQ ID NO:49 and 35, respectively.

The nucleotide and amino acid sequences of the heavy chain variable region of ROR1_A7 are shown in SEQ ID NO:21 and 7, respectively.

Comparison of the ROR1_A7 light chain immunoglobulin sequence to the known murine germline immunoglobulin light chain sequences demonstrated that the ROR1_A7 light chain utilizes a $V_K$ segment from murine germline $V_K$ 14-111 Further analysis of the ROR1_A7 $V_K$ sequence using the Kabat system of CDR region determination led to the delineation of the light chain CDR1, CDR2 and CDR3 regions as shown in SEQ ID NOs: 179, 199 or 200 and 230, respectively. The alignments of the ROR1_A7 CDR1, CDR2 and CDR3 $V_K$ sequences to the germline $V_K$ 14-111 sequence are shown in FIGS. 1a, 1b, 2a, 2b and 3, respectively.

Comparison of the ROR1_A7 heavy chain immunoglobulin sequence to the known murine germline immunoglobulin heavy chain sequences demonstrated that the ROR1_A7 heavy chain utilizes a $V_H$ segment from murine germline $V_H$ 5-6. Further analysis of the ROR1_A7 $V_H$ sequence using the Kabat system of CDR region determination led to the delineation of the heavy chain CDR1, CDR2 and CDR3 regions as shown in SEQ ID NOs: 68 or 69, 111 or 112 and 154, respectively. The alignments of the ROR1_A7 CDR1 and CDR2 $V_H$ sequence to the germline $V_H$ 5-6 sequence are shown in FIGS. 4a, 4b, 5a and 5b.

The nucleotide and amino acid sequences of the light chain variable region of ROR1_A8 are shown in SEQ ID NO:50 and 36, respectively.

The nucleotide and amino acid sequences of the heavy chain variable region of ROR1_A8 are shown in SEQ ID NO:22 and 8, respectively.

Comparison of the ROR1_A8 light chain immunoglobulin sequence to the known murine germline immunoglobulin light chain sequences demonstrated that the ROR1_A8 light chain utilizes a $V_K$ segment from murine germline $V_K$ 17-121 Further analysis of the ROR1_A8 $V_K$ sequence using the Kabat system of CDR region determination led to the delineation of the light chain CDR1, CDR2 and CDR3 regions as shown in SEQ ID NOs: 180, 201 or 202 and 231, respectively. The alignments of the ROR1_A8 CDR1, CDR2 and CDR3 $V_k$ sequences to the germline $V_K$ 17-121 sequence are shown in FIGS. 1a, 1b, 2a, 2b and 3, respectively.

Comparison of the ROR1_A8 heavy chain immunoglobulin sequence to the known murine germline immunoglobulin heavy chain sequences demonstrated that the ROR1_A8 heavy chain utilizes a $V_H$ segment from murine germline $V_H$ 5-6. Further analysis of the ROR1_A8 $V_H$ sequence using the Kabat system of CDR region determination led to the delineation of the heavy chain CDR1, CDR2 and CDR3 regions as shown in SEQ ID NOs: 58 or 61, 113 or 114 and 155, respectively. The alignments of the ROR1_A8 CDR1 and CDR2 $V_H$ sequence to the germline $V_H$ 5-6 sequence are shown in FIGS. 4a, 4b, 5a and 5b.

The nucleotide and amino acid sequences of the light chain variable region of ROR1_A9 are shown in SEQ ID NO:51 and 37, respectively.

The nucleotide and amino acid sequences of the heavy chain variable region of ROR1_A9 are shown in SEQ ID NO:23 and 9, respectively.

Comparison of the ROR1_A9 light chain immunoglobulin sequence to the known murine germline immunoglobulin light chain sequences demonstrated that the ROR1_A9 light chain utilizes a $V_K$ segment from murine germline $V_K$ 14-111 Further analysis of the ROR1_A9 $V_K$ sequence using the Kabat system of CDR region determination led to the delineation of the light chain CDR1, CDR2 and CDR3 regions as shown in SEQ ID NOs: 179, 190 or 191 and 229, respectively. The alignments of the ROR1_A9 CDR1, CDR2 and CDR3 $V_K$ sequences to the germline $V_K$ 14-111 sequence are shown in FIGS. 1a, 1b, 2a, 2b and 3, respectively.

Comparison of the ROR1_A9 heavy chain immunoglobulin sequence to the known murine germline immunoglobulin heavy chain sequences demonstrated that the ROR1_A9 heavy chain utilizes a $V_H$ segment from murine germline $V_H$ 5-6. Further analysis of the ROR1_A9 $V_H$ sequence using the Kabat system of CDR region determination led to the delineation of the heavy chain CDR1, CDR2 and CDR3 regions as shown in SEQ ID NOs: 70 or 71, 115 or 116 and 156, respectively. The alignments of the ROR1_A9 CDR1 and CDR2 $V_H$ sequence to the germline $V_H$ 5-6 sequence is shown in FIGS. 4a, 4b, 5a and 5b.

The nucleotide and amino acid sequences of the light chain variable region of ROR1_A10 are shown in SEQ ID NO:52 and 38, respectively.

The nucleotide and amino acid sequences of the heavy chain variable region of ROR1_A10 are shown in SEQ ID NO:24 and 10, respectively.

Comparison of the ROR1_A10 light chain immunoglobulin sequence to the known murine germline immunoglobulin light chain sequences demonstrated that the ROR1_A10 light chain utilizes a $V_K$ segment from murine germline $V_K$ 14-111. Further analysis of the ROR1_A10 $V_K$ sequence using the Kabat system of CDR region determination led to the delineation of the light chain CDR1, CDR2 and CDR3 regions as shown in SEQ ID NOs: 174, 190 or 191 and 229, respectively. The alignments of the ROR1_A10 CDR1, CDR2 and CDR3 $V_K$ sequences to the 1 germline $V_K$ 14-111 sequence are shown in FIGS. 1a, 1b, 2a, 2b and 3, respectively.

Comparison of the ROR1_A10 heavy chain immunoglobulin sequence to the known murine germline immunoglobulin heavy chain sequences demonstrated that the ROR1_A10 heavy chain utilizes a $V_H$ segment from murine germline $V_H$ 5-12. Further analysis of the ROR1_A10 $V_H$ sequence using the Kabat system of CDR region determination led to the delineation of the heavy chain CDR1, CDR2 and CDR3 regions as shown in SEQ ID NOs: 72 or 73, 117 or 118 and 157, respectively. The alignments of the ROR1_A10 CDR1 and CDR2 $V_H$ sequence to the germline $V_H$ II gene H17 sequence are shown in FIGS. 4a, 4b, 5a and 5b.

The nucleotide and amino acid sequences of the light chain variable region of ROR1_A11 are shown in SEQ ID NO:53 and 39, respectively.

The nucleotide and amino acid sequences of the heavy chain variable region of ROR1_A11 are shown in SEQ ID NO:25 and 11, respectively.

Comparison of the ROR1_A11 light chain immunoglobulin sequence to the known murine germline immunoglobulin light chain sequences demonstrated that the ROR1_A11 light chain utilizes a $V_K$ segment from murine germline $V_K$ 17-121 Further analysis of the ROR1_A11 $V_K$ sequence using the Kabat system of CDR region determination led to the delineation of the light chain CDR1, CDR2 and CDR3 regions as shown in SEQ ID NOs: 175, 203 or 204 and 232, respectively. The alignments of the ROR1_A11 CDR1, CDR2 and CDR3 $V_K$ sequences to the germline $V_K$ 17-121 sequence are shown in FIGS. 1a, 1b, 2a, 2b and 3, respectively.

Comparison of the ROR1_A11 heavy chain immunoglobulin sequence to the known murine germline immunoglobulin heavy chain sequences demonstrated that the ROR1_A11 heavy chain utilizes a $V_H$ segment from murine germline $V_H$ 5-12. Further analysis of the ROR1_A11 $V_H$ sequence using the Kabat system of CDR region determination led to the delineation of the heavy chain CDR1, CDR2 and CDR3 regions as shown in SEQ ID NOs: 74 or 75, 119 or 120 and 155, respectively. The alignments of the ROR1_A11 CDR1 and CDR2 $V_H$ sequence to the germline $V_H$ 5-12 sequence are shown in FIGS. 4a, 4b, 5a and 5b.

The nucleotide and amino acid sequences of the light chain variable region of ROR1_A12 are shown in SEQ ID NO:54 and 40, respectively.

The nucleotide and amino acid sequences of the heavy chain variable region of ROR1_A12 are shown in SEQ ID NO:26 and 12, respectively.

Comparison of the ROR1_A12 light chain immunoglobulin sequence to the known murine germline immunoglobulin light chain sequences demonstrated that the ROR1_A12 light chain utilizes a $V_K$ segment from murine germline $V_K$ 14-111 Further analysis of the ROR1_A12 $V_K$ sequence using the Kabat system of CDR region determination led to the delineation of the light chain CDR1, CDR2 and CDR3 regions as shown in SEQ ID NOs: 179, 190 or 205 and 229, respectively. The alignments of the ROR1_A12 CDR1, CDR2 and CDR3 $V_K$ sequences to the germline $V_K$ 14-111 sequence are shown in FIGS. 1a, 1b, 2a, 2b and 3, respectively.

Comparison of the ROR1_A12 heavy chain immunoglobulin sequence to the known murine germline immunoglobulin heavy chain sequences demonstrated that the ROR1_A12 heavy chain utilizes a $V_H$ segment from murine germline $V_H$ 5-12. Further analysis of the ROR1_A12 $V_H$ sequence using the Kabat system of CDR region determination led to the delineation of the heavy chain CDR1, CDR2 and CDR3 regions as shown in SEQ ID NOs: 58 or 61, 110 or 266 and 158, respectively. The alignments of the ROR1_A12 CDR1 and CDR2 $V_H$ sequence to the germline $V_H$ 5-12 sequence are shown in FIGS. 4a, 4b, 5a and 5b.

The nucleotide and amino acid sequences of the light chain variable region of ROR1_A13 are shown in SEQ ID NO:55 and 41, respectively.

The nucleotide and amino acid sequences of the heavy chain variable region of ROR1_A13 are shown in SEQ ID NO:27 and 13, respectively.

Comparison of the ROR1_A13 light chain immunoglobulin sequence to the known murine germline immunoglobulin light chain sequences demonstrated that the ROR1_A13 light chain utilizes a $V_K$ segment from murine germline $V_K$ 14-111. Further analysis of the ROR1_A13 $V_K$ sequence using the Kabat system of CDR region determination led to the delineation of the light chain CDR1, CDR2 and CDR3 regions as shown in SEQ ID NOs: 176, 190 or 206 and 229, respectively. The alignments of the ROR1_A13 CDR1, CDR2 and CDR3 $V_K$ sequences to the germline $V_K$ 14-111 sequence are shown in FIGS. 1a, 1b, 2a, 2b and 3, respectively.

Comparison of the ROR1_A13 heavy chain immunoglobulin sequence to the known murine germline immunoglobulin heavy chain sequences demonstrated that the ROR1_A13 heavy chain utilizes a $V_H$ segment from murine germline $V_H$ 5-12. Further analysis of the ROR1_A13 $V_H$ sequence using the Kabat system of CDR region determination led to the delineation of the heavy chain CDR1, CDR2 and CDR3 regions as shown in SEQ ID NOs: 58 or 61, 101 or 102 and 159, respectively. The alignments of the ROR1_A13 CDR1 and CDR2 $V_H$ sequence to the germline $V_H$ 5-12 sequence are shown in FIGS. 4a, 4b, 5a and 5b.

The nucleotide and amino acid sequences of the light chain variable region of ROR1_A14 are shown in SEQ ID NO: 56 and 42, respectively.

The nucleotide and amino acid sequences of the heavy chain variable region of ROR1_A14 are shown in SEQ ID NO:28 and 14, respectively.

Comparison of the ROR1_A14 light chain immunoglobulin sequence to the known murine germline immunoglobulin light chain sequences demonstrated that the ROR1_A14 light chain utilizes a $V_K$ segment from murine germline $V_K$ 8-21. Further analysis of the ROR1_A14 $V_K$ sequence using the Kabat system of CDR region determination led to the delineation of the light chain CDR1, CDR2 and CDR3 regions as shown in SEQ ID NOs: 177 or 178, 207 or 208 and 233, respectively. The alignments of the ROR1_A14 CDR1, CDR2 and CDR3 $V_K$ sequences to the germline $V_K$ 8-21 sequence are shown in FIGS. 1a, 1b, 2a, 2b and 3, respectively.

Comparison of the ROR1_A14 heavy chain immunoglobulin sequence to the known murine germline immunoglobulin heavy chain sequences demonstrated that the ROR1_A14 heavy chain utilizes a $V_H$ segment from murine germline $V_H$ 1-9. Further analysis of the ROR1_A14 $V_H$ sequence using the Kabat system of CDR region determination led to the delineation of the heavy chain CDR1, CDR2 and CDR3 regions as shown in SEQ ID NOs: 76 or 77, 122 or 123 and 160, respectively. The alignments of the ROR1_A14 CDR1 and CDR2 $V_H$ sequence to the germline $V_H$ 1-9 sequence are shown in FIGS. 4a, 4b, 5a and 5b.

Example 5

Immunohistochemistry Using Monoclonal Antibodies to Tyrosine-Protein Kinase Transmembrane Receptor ROR1

Using the following Reference Protocol, ROR_A1 was used in IHC experiments at 20 ug/ml. Under these conditions significant staining was observed in pancreatic cancer and lung cancer for tissue sections prepared as FFPE or frozen formats. The same conditions were used to test binding of ROR1_A1 and ROR1_A8 on normal human tissues Deparaffinisation and Rehydration Slides were heated for 2 hr at 60° C. in 50 ml Falcons in a water bath with no buffer. Each Falcon had one slide or two slides back-to-back with long gel loading tip between them to prevent slides from sticking to each other. Slides were deparaffinised in EZ-DeWax (BioGenex, CA, USA) for 5 min in black slide rack, then rinsed well with the same DeWax solution using 1 ml pipette, then washed with water. Slides were placed in a coplin jar filled with water until the pressure cooker was ready; the water was changed a couple of times.

Antigen Retrieval

Water was exchanged for antigen retrieval solution=1× citrate buffer, pH 6 (DAKO). Antigen was retrieved by the pressure cooker method. The slides in the plastic coplin jar in antigen retrieval solution were placed into a pressure cooker which was then heated up to position 6 (the highest setting). 15-20 min into the incubation, the temperature was reduced to position 3 and left at that (when the temperature inside the pressure cooker was 117° C.) for another 20-25 min. Then the hob was switched off and the cooker was placed onto the cold hob and the pressure was released by carefully moving the handle into the position between "open" and "closed". The whole system was left to release the pressure and to cool down for another 20 min. The lid was opened and samples taken out to rest on the bench. The slides were washed 1×5 min with PBS-3T (0.5 L PBS+3 drops of Tween-20) and the slides were placed in PBS.

Staining

After antigen retrieval, slides were mounted in the Shandon Coverplate system. Trapping of air bubbles between the slide and plastic coverplate was prevented by placing the coverplate into the coplin jar filled with PBS and gently sliding the slide with tissue sections into the coverplate. The slide was pulled out of the coplin jar while holding it tightly together with the coverplate. The assembled slide was placed into the rack, letting PBS trapped in the funnel and between the slide and coverplate to run through. Slides were washed with 2×2 ml (or 4×1 ml) PBS-3T and 1×2 ml PBS, waiting until all PBS had gone through the slide and virtually no PBS was left in the funnel Endogenous peroxide blockade was performed using peroxidase blocking reagent (S2001, DAKO). 1-4 drops of peroxide solution was used per slide and incubated for 5 minutes. The slides were rinsed with water and then once with 2 ml PBS-3T and once with 2 ml PBS; it was important to wait until virtually no liquid was left in the funnel before adding a new portion of wash buffer.

The primary antibody was diluted with an Antibody diluent reagent (DAKO). Optimal dilution was determined to be 0.5 µg/ml. 50-200 µl of diluted primary antibody was applied to each section and/or tissue microarray; taking care to cover the whole tissue. The slide was gently tapped to distribute the antibody evenly over the section or a pipette tip was used over the top of the section. The slide was incubated for 45 min in a moist chamber at room temperature. Slides were washed with 2×2 ml (or 4×1 ml) PBS-3T and then 1×2 ml PBS, waiting until all PBS had gone through the slide and virtually no PBS was left in the funnel. The corresponding donkey anti-goat IgG:HRP (OBT1500P, 1 mg/ml, Serotec) was applied at 1:1000 and incubated for 35 min at room temperature. The slides were washed as above. The DAB substrate was made up in dilution buffer; 2 ml containing 2 drops of substrate was enough for 10 slides. The DAB reagent was applied to the slides by applying a few drops at a time. All of the DAB was distributed between the slides. The slides were incubated for 10 min. The slides were washed 1×2 ml (or 2×1 ml) with PBS-3T and 1×2 ml (or 2×1 ml) with PBS, waiting until all PBS had gone through the slide and virtually no PBS was left in the funnel. Hematoxylin (DAKO) was applied; 1 ml was enough for 10 slides and slides were incubated for 1 min at room temperature. The funnels of the Shandon Coverplate system were filled with 2 ml of water and let to run through. When slides were clear of the excess of hematoxylin, the system was disassembled, tissue sections and/or arrays were washed with water from the wash bottle and placed into a black slide rack. Tissues were rehydrated by incubating in EZ-DeWax for 5 min and then in 95% ethanol for 2-5 min. Slides were left to dry on the bench at room temperature and then mounted in mounting media and covered with coverslip.

The following normal tissues showed no evidence of specific staining with ROR1_A1, in correlation with proteomics and mRNA analyses: Lung, pancreas, liver, heart, lymph node, spleen, colon, skin, brain, kidney, stomach, bladder, skeletal muscle, breast, ovary, prostate, cervix, tonsil, spinal cord, retina (N=2 for each tissue). However, the other antibody, ROR1_A8 showed staining in multiple normal tissues, particularly on endothelial cells and fibroblasts in discordance with other analysis methods, suggesting that this antibody has cross reactivity to another protein/s.

Example 6

Specificity of Monoclonal Antibodies to Tyrosine-Protein Kinase Transmembrane Receptor ROR1. Determined by Flow Cytometry Analysis The specificity of antibodies against the ROR1 selected in Example 2 was tested by flow cytometry. To test the ability of the antibodies to bind to the cell surface ROR1 protein, the antibodies were incubated with the ROR1-expressing cells. Cells were washed in FACS buffer (DPBS, 2% FBS), centrifuged and resuspended in 100 µl of the diluted primary ROR1 antibody (also diluted in FACS buffer). The antibody-cell line complex was incubated on ice for 60 min and then washed twice with FACS buffer as described above. The cell-antibody pellet was resuspended in 100 µl of the diluted secondary antibody (also diluted in FACS buffer) and incubated on ice for 60 min on ice. The pellet was washed as before and resuspended in 200 µl FACS buffer. The samples were loaded onto the BD FACScanto II flow sytometer and the data analyzed using the BD FACSdiva software.

The results of the flow cytometry analysis demonstrated that 14 monoclonal antibodies designated ROR1_A1, ROR1_A2, ROR1_A3, ROR1_A4, ROR1_A5, ROR1_A6, ROR1_A7, ROR1_A8, ROR1_A9, ROR1_A10, ROR1_A11, ROR1_A12, ROR1_A13 and ROR1_A14 bound effectively to the cell-surface human ROR1 expressed in A549 cells, from human lung adenocarinoma (FIG. 6). Further analysis using the above procedure demonstrated ROR1_A1, ROR1_A3, ROR1_A8 and ROR1_A14 bound effectively to the cell-surface human ROR1 expressed in CALU1, H358, PANC-1, H226, H69 and HT-29 cells (FIG. 7).

Example 7

Specificity of Chimeric and Humanised Monoclonal Antibodies to Tyrosine-Protein Kinase Transmembrane Receptor ROR1. Determined by Flow Cytometry Analysis The specificity of chimeric and humanised ROR1_A1 antibody was tested by flow cytometry. To test the ability of the antibodies to bind to the cell surface ROR1 protein, the antibodies were incubated with the ROR1-expressing cells, A549 from human lung adenocarcinoma and HT-29, from human colon adenocarcinoma. Cells were washed in FACS buffer (DPBS, 2% FBS), centrifuged and resuspended in 100 µl of the diluted primary ROR1 antibody (also diluted in FACS buffer). The antibody-cell line complex was incubated on ice for 60 min and then washed twice with FACS buffer as described above. The cell-antibody pellet was resuspended in 100 µl of the diluted secondary antibody (also diluted in FACS buffer) and incubated on ice for 60 min on ice. The pellet was washed as before and resuspended in 200 µl FACS buffer. The samples were loaded onto the BD FACScanto II flow sytometer and the data analyzed using the BD FACSdiva software.

Figure 7:
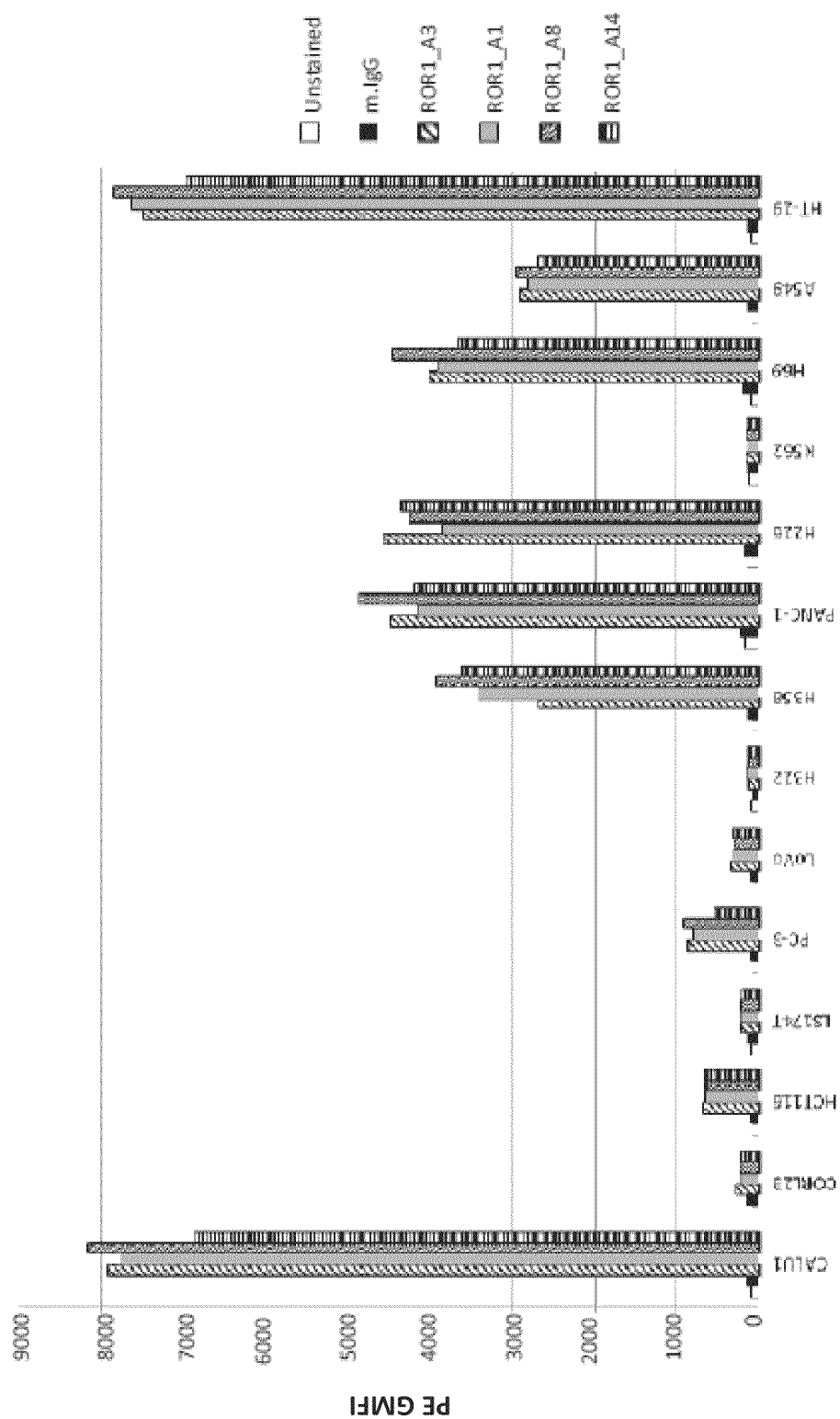
FIG. 7 depicts the flow cytometry analysis of ROR1_A1, ROR1_A3, ROR1_A8 and ROR1_A14 monoclonal antibodies, indicating the specific binding of those antibodies to the human cancer cell lines including CALU1, H358, PANC-1, H226, H69, A549 and HT-29.
Figure 8A:
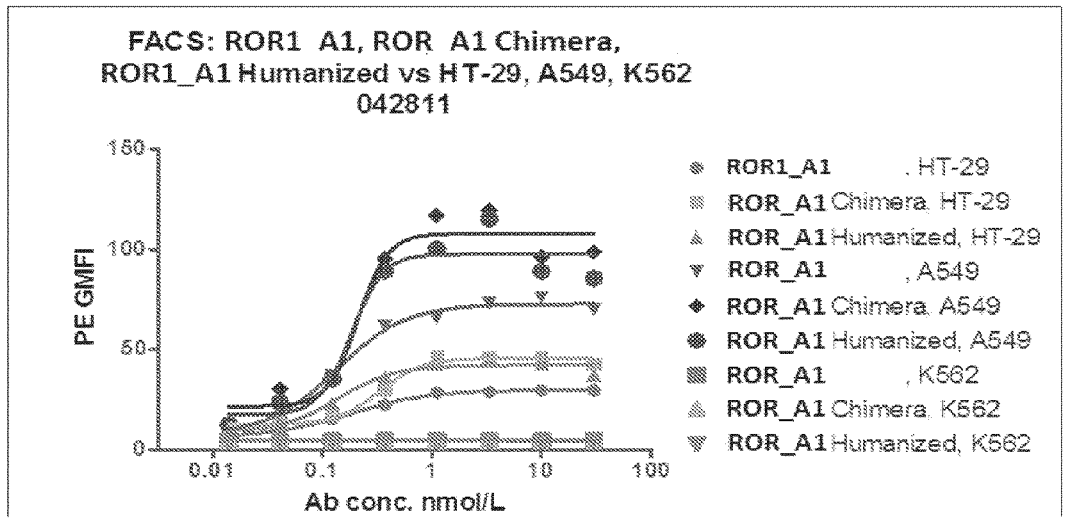
FIG. 8a-FIG. 8b depicts the flow cytometry analysis of ROR1 chimeric and humanised monoclonal antibodies, indicating the specific binding of those antibodies to the human lung adenocarcinoma cell line, A549 (a) and human colon adenocarcinoma cell line, HT-29 (b).
Figure 8B:
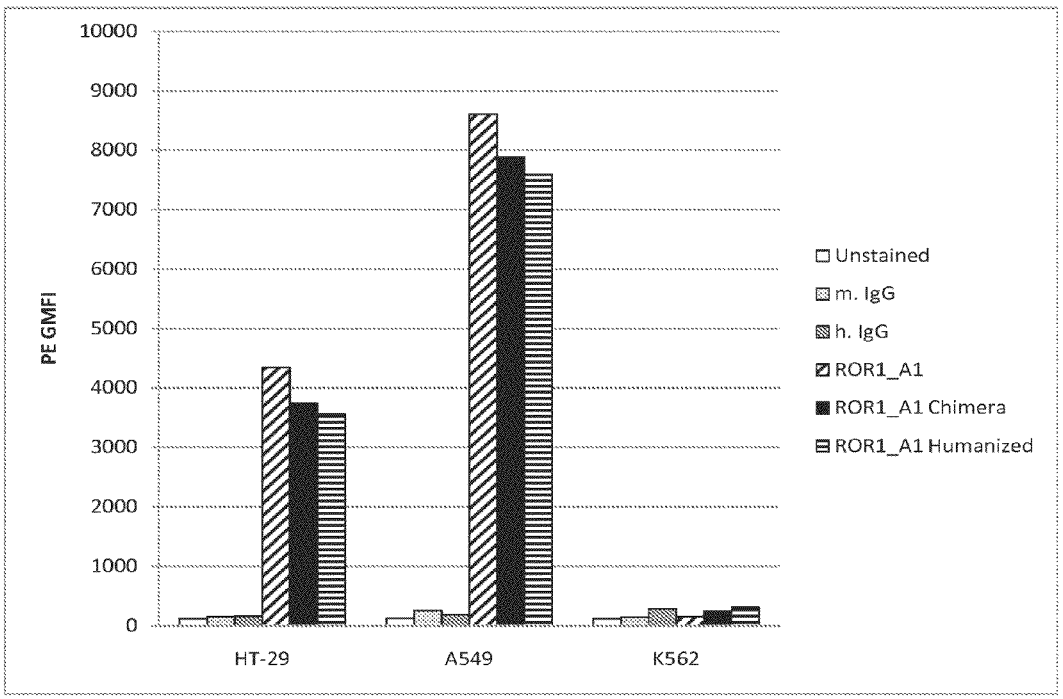
Figure 9:
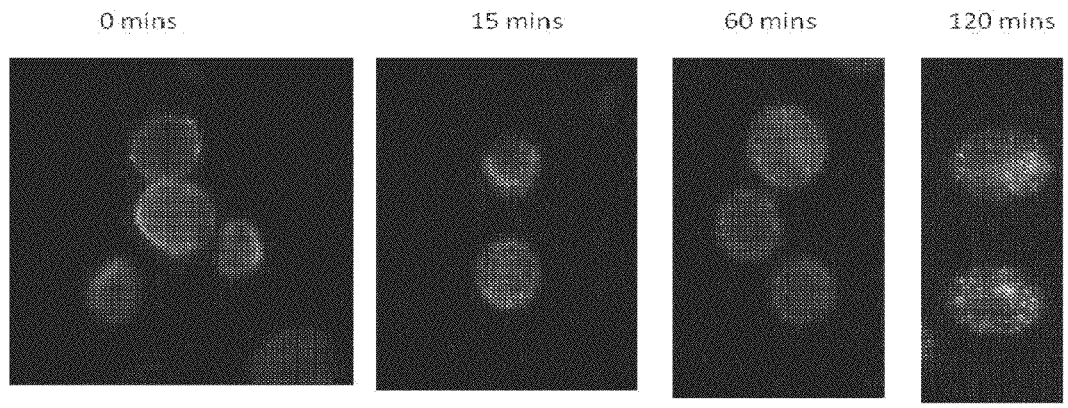
FIG. 9 depicts the internalization of ROR1_A11 by the human colon adenocarcinoma cell line, HT29, at intervals 0 min, 15 min, 60 min and 120 min.

The results of the flow cytometry analysis demonstrated that chimeric and humanized ROR1_A1 antibodies bound effectively to the cell-surface human ROR1 (FIGS. 6 and 7).

Example 8

Internalization of ROR1_A11 by HT29 Cells

ROR1_A11 was shown to be internalized by HT29 cells (human colon adenocarcinoma cell line) upon binding to the cells using an immunofluorescence microscopy assay. The immunofluorescence microscopy assay showed internalization of ROR1_A11 through binding of an anti-human IgG secondary antibody conjugated to fluorescein isothiocyanate (GamK-FITC).

The immunofluorescence microscopy assay was conducted as follows HT29 cells were incubated at 37° C. for 12 hr for cells to adhere to each other. ROR1_A11 and secondary antibody conjugated to fluorescein isothiocyanate were serially diluted, washed with FACS buffer (PBS, 2% FBS) and then added to the culture media. The media was then washed again with FACS buffer (PBS, 2% FBS) and incubated at 37° C., after which 200 µl 2% PFA was added. Coverslips were mounted using a 9 µl aqeous mountaing media and the cells were then visualized at regular time intervals using Leica fluorescent microscope. FIG. 37 shows surface binding of ROR1_A11/secondary antibody FITC conjugate complex to HT29 cells after 0 min, 15 min, 60 min and 120 min. The complete internalization of ROR1_A11 was observed after 120 min.

Example 9

Figure 11:
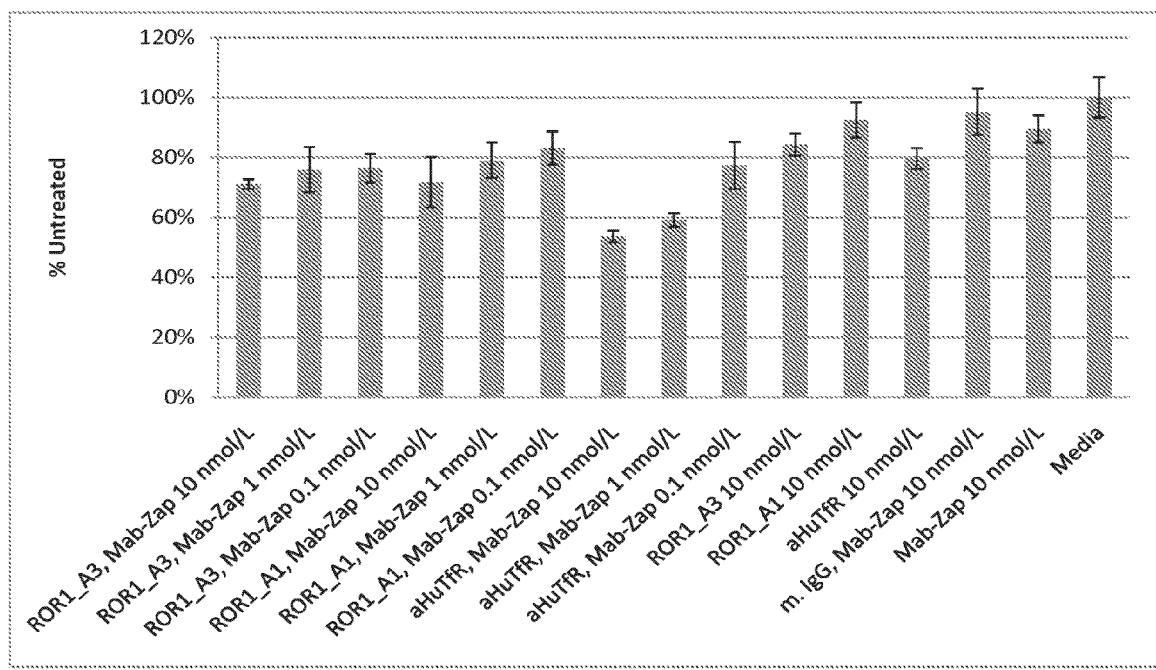
FIG. 11 depicts the internalisation of ROR1_A1 and ROR1_A3 monoclonal antibodies by the ZAP assay to the human pancreatic carcinoma cell line, PANC1.

Internalization of ROR1_A1 and ROR1_A3 Monoclonal Antibodies by CALU1 and PANC1 Cells ROR1_A1 and ROR1_A3 antibodies were shown to be internalized by CALU1 cells (human epidermoid lung carcinoma cell line) and PANC1 cells (human pancreatic carcinoma cell line) upon binding to the cells using MabZAP assays. The MabZAP antibodies were bound to the primary antibodies. Next, the MabZAP complex was internalized by the cells. The entrance of Saporin into the cells resulted in protein synthesis inhibition and eventual cell death The MabZAP assay was conducted as follows. Each of the cells was seeded at a density of 5×103 cells per well. The anti-ROR1 monoclonal antibodies or an isotype control human IgG were serially diluted then added to the cells. The MabZAP were then added at a concentration of 50 µg/ml and the plates allowed to incubate for 48 and 72 hours. Cell viability in the plates was detected by CellTiter-Glo® Luminescent Cell Viability Assay kit (Promega, G7571) and the plates were read at 490 nM by a Luminomitor (Tuner BioSystems, Sunnyvale, Calif.). The data was analyzed by Prism (Graphpad). Cell death was proportional to the concentration of ROR1_A1 and ROR1_A3 antibodies. FIGS. 10 and 11 show that the anti-ROR1 monoclonal antibodies were efficiently internalized by both CALU1 and PANC1 cells, as compared to the anti-human IgG isotype control antibody.

Example 10

Internalization of Chimeric and Humanised ROR1_A1 by A549 and HT-29 Cells

Chimeric and humanised ROR1_A1 antibodies were shown to be internalized by A549 cells (human lung adenocarcinoma cell line) and HT29 cells (human colon adenocarcinoma cell line) upon binding to the cells using MabZAP and HuZAP assays. The MabZAP/HuZAP antibodies were bound to the primary antibodies. Next, the MabZAP/HuZAP complex was internalized by the cells. The entrance of Saporin into the cells resulted in protein synthesis inhibition and eventual cell death.

Figure 12:
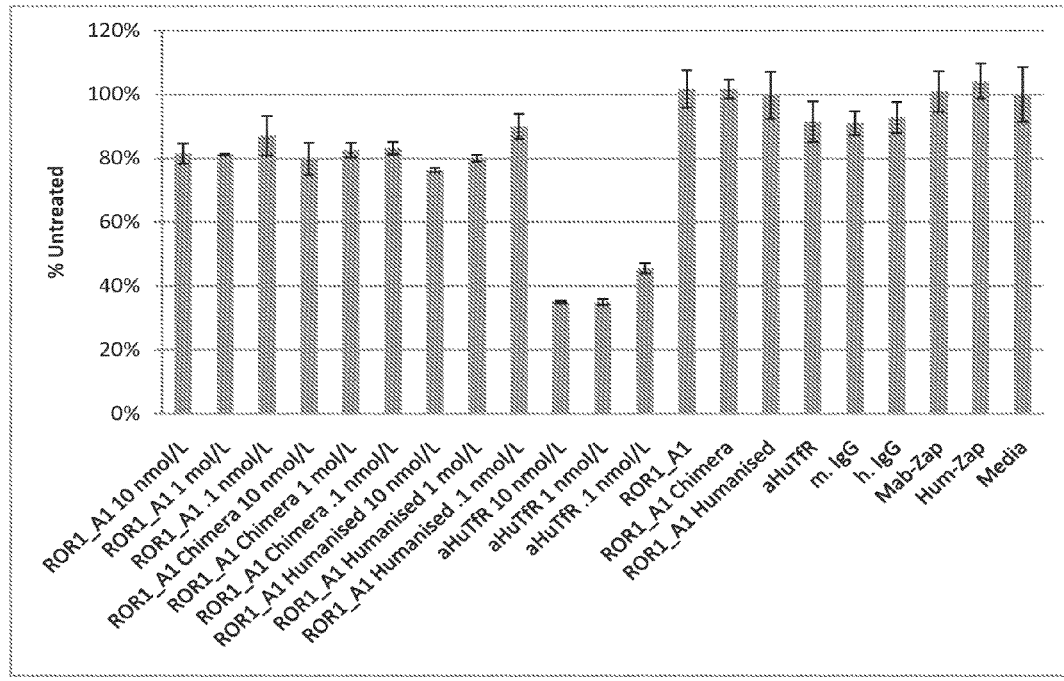
FIG. 12 depicts the internalisation of ROR1_A1 chimeric and humanised monoclonal antibodies by the ZAP assay to the human lung adenocarcinoma cell line, A549.
Figure 13:
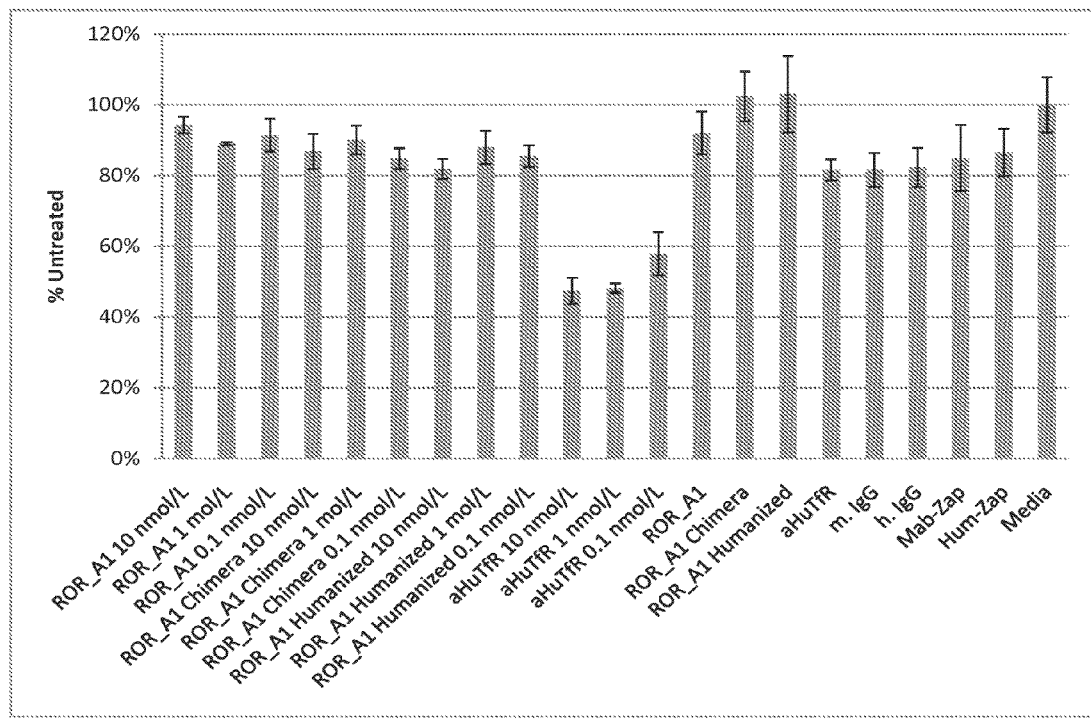
FIG. 13 depicts the internalisation of ROR1_A1 chimeric and humanised monoclonal antibodies by the ZAP assay to the human colon adenocarcinoma cell line, HT29.

The MabZAP/HuZAP assay was conducted as follows. Each of the cells was seeded at a density of 5×103 cells per well. The anti-ROR1 chimeric and humanised monoclonal antibodies or an isotype control human IgG were serially diluted then added to the cells. The MabZAP/HuZAP were then added at a concentration of 50 µg/ml and the plates allowed to incubate for 48 and 72 hours. Cell viability in the plates was detected by CellTiter-Glo® Luminescent Cell Viability Assay kit (Promega, G7571) and the plates were read at 490 nM by a Luminomitor (Tuner BioSystems, Sunnyvale, Calif.). The data was analyzed by Prism (Graphpad). Cell death was proportional to the concentration of chimeric and humanised ROR1_A1 antibodies. FIGS. 12 and 13 show that the anti-ROR1 chimeric and humanised monoclonal antibodies were efficiently internalized by both A549 and HT-29 cells, as compared to the anti-human IgG isotype control antibody.

We claim:

1. An antibody that specifically binds to the extracellular domain of ROR1, comprising:
   a) a heavy chain comprising:
      i) a first vhCDR comprising SEQ ID NO:58;
      ii) a second vhCDR comprising SEQ ID NO:99;
      iii) a third vhCDR comprising SEQ ID NO:149; and
   b) a light chain comprising:
      i) a first vlCDR comprising SEQ ID NO:173;
      ii) a second vlCDR comprising SEQ ID NO:190; and
      iii) a third vlCDR comprising SEQ ID NO:229.

2. An antibody that specifically binds to the extracellular domain of ROR1, comprising:
   a) a heavy chain variable region of SEQ ID NO: 268, comprising amino acids 22-144 and
   b) a light chain variable region of SEQ ID NO: 270, comprising amino acids 23-124.

3. An antibody that specifically binds to the extracellular domain of ROR1, comprising:
   a) a heavy chain at least 95% identical to amino acids 22-144 of SEQ ID NO: 268 and
   b) a light chain at least 95% identical to amino acids 23-124 of SEQ ID NO: 270.

4. An antibody according to claim 1 further comprising a covalently attached moiety.

5. An antibody according to claim 4 wherein said moiety is a drug.

6. An antibody according to claim 5 wherein said drug is selected from the group consisting of a maytansinoid, a dolastatin, an auristatin, a trichothecene, a calicheamicin, a CC1065 and derivatives thereof.

7. A nucleic acid composition encoding:
   a) a heavy chain comprising a heavy chain variable region of the antibody of claim 1; and
   b) a light chain comprising a light chain variable region of the antibody of claim 1.

8. A host cell containing the nucleic acid composition of claim 7.

9. A method of making an antibody of claim 1 comprising i) culturing a host cell according to claim 8 under conditions where the antibody is expressed and ii) recovering said antibody.

10. A method of treating cancer comprising administering to a patient in need thereof an antibody according to claim 5 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

11. A method according to claim 10 wherein said cancer is selected from the group consisting of non-small cell lung carcinoma, B-cell chronic lymphocytic leukemia and colon cancer.

12. An antibody that specifically binds to the extracellular domain of ROR1, comprising:
   a) a heavy chain comprising:
      i) a first vhCDR comprising SEQ ID NO:60;
      ii) a second vhCDR comprising SEQ ID NO:101;
      iii) a third vhCDR comprising SEQ ID NO:150; and
   b) a light chain comprising:
      i) a first vlCDR comprising SEQ ID NO:179;
      ii) a second vlCDR comprising SEQ ID NO:190;
      iii) a third vlCDR comprising SEQ ID NO:229.

13. The antibody of claim 12, wherein said antibody is covalently attached to a drug.

14. A nucleic acid composition encoding:
   a) a heavy chain comprising a heavy chain variable region of the antibody of claim 12; and
   b) a light chain comprising a light chain variable region of the antibody of claim 12.

15. A host cell containing the nucleic acid composition of claim 14.

16. A method of making an antibody of claim 12 comprising i) culturing a host cell according to claim 15 under conditions where the antibody is expressed and ii) recovering said antibody.

17. A method of treating cancer comprising administering to a patient in need thereof an antibody according to claim 13 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

18. A method according to claim 17 wherein said cancer is selected from the group consisting of non-small cell lung carcinoma, B-cell chronic lymphocytic leukemia and colon cancer.

19. An antibody that specifically binds to the extracellular domain of ROR1, comprising:
   a) a heavy chain comprising:
      i) a first vhCDR comprising SEQ ID NO:58;
      ii) a second vhCDR comprising SEQ ID NO:103;
      iii) a third vhCDR comprising SEQ ID NO:149; and
   b) a light chain comprising:
      i) a first vlCDR comprising SEQ ID NO:179;
      ii) a second vlCDR comprising SEQ ID NO:190;
      iii) a third vlCDR comprising SEQ ID NO:229.

20. The antibody of claim 17, wherein said antibody is covalently attached to a drug.

21. A nucleic acid composition encoding:
   a) a heavy chain comprising a heavy chain variable region of the antibody of claim 19; and
   b) a light chain comprising a light chain variable region of the antibody of claim 19.

22. A host cell containing the nucleic acid composition of claim 21.

23. A method of making an antibody of claim 19 comprising i) culturing a host cell according to claim 22 under conditions where the antibody is expressed and ii) recovering said antibody.

24. A method of treating cancer comprising administering to a patient in need thereof an antibody according to claim 20 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

25. A method according to claim 24 wherein said cancer is selected from the group consisting of non-small cell lung carcinoma, B-cell chronic lymphocytic leukemia and colon cancer.

26. An antibody that specifically binds to the extracellular domain of ROR1, comprising:
   a) a heavy chain comprising:
      i) a first vhCDR comprising SEQ ID NO:63;
      ii) a second vhCDR comprising SEQ ID NO:105;
      iii) a third vhCDR comprising SEQ ID NO:151; and
   b) a light chain comprising:
      i) a first vlCDR comprising SEQ ID NO:179;
      ii) a second vlCDR comprising SEQ ID NO:194;
      iii) a third vlCDR comprising SEQ ID NO:229.

27. The antibody of claim 26, wherein said antibody is covalently attached to a drug.

28. A nucleic acid composition encoding:
   a) a heavy chain comprising a heavy chain variable region of the antibody of claim 26; and b) a light chain comprising a light chain variable region of the antibody of claim 26.

29. A host cell containing the nucleic acid composition of claim 28.

30. A method of making an antibody of claim 26 comprising i) culturing a host cell according to claim 29 under conditions where the antibody is expressed and ii) recovering said antibody.

31. A method of treating cancer comprising administering to a patient in need thereof an antibody according to claim 27 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

32. A method according to claim 31 wherein said cancer is selected from the group consisting of non-small cell lung carcinoma, B-cell chronic lymphocytic leukemia and colon cancer.

33. An antibody that specifically binds to the extracellular domain of ROR1, comprising:
　a) a heavy chain comprising:
　　i) a first vhCDR comprising SEQ ID NO:65;
　　ii) a second vhCDR comprising SEQ ID NO:107;
　　iii) a third vhCDR comprising SEQ ID NO:152; and
　b) a light chain comprising:
　　i) a first vlCDR comprising SEQ ID NO:179;
　　ii) a second vlCDR comprising SEQ ID NO:196;
　　iii) a third vlCDR comprising SEQ ID NO:229.

34. The antibody of claim 33, wherein said antibody is covalently attached to a drug.

35. A nucleic acid composition encoding:
　a) a heavy chain comprising a heavy chain variable region of the antibody of claim 33; and
　b) a light chain comprising a light chain variable region of the antibody of claim 33.

36. A host cell containing the nucleic acid composition of claim 35.

37. A method of making an antibody of claim 33 comprising i) culturing a host cell according to claim 36 under conditions where the antibody is expressed and ii) recovering said antibody.

38. A method of treating cancer comprising administering to a patient in need thereof an antibody according to claim 34 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

39. A method according to claim 38 wherein said cancer is selected from the group consisting of non-small cell lung carcinoma, B-cell chronic lymphocytic leukemia and colon cancer.

40. An antibody that specifically binds to the extracellular domain of ROR1, comprising:
　a) a heavy chain comprising:
　　i) a first vhCDR comprising SEQ ID NO:67;
　　ii) a second vhCDR comprising SEQ ID NO:110;
　　iii) a third vhCDR comprising SEQ ID NO:153; and
　b) a light chain comprising:
　　i) a first vlCDR comprising SEQ ID NO:179;
　　ii) a second vlCDR comprising SEQ ID NO:198;
　　iii) a third vlCDR comprising SEQ ID NO:229.

41. The antibody of claim 40, wherein said antibody is covalently attached to a drug.

42. A nucleic acid composition encoding:
　a) a heavy chain comprising a heavy chain variable region of the antibody of claim 40; and
　b) a light chain comprising a light chain variable region of the antibody of claim 40.

43. A host cell containing the nucleic acid composition of claim 42.

44. A method of making an antibody of claim 40 comprising i) culturing a host cell according to claim 43 under conditions where the antibody is expressed and ii) recovering said antibody.

45. A method of treating cancer comprising administering to a patient in need thereof an antibody according to claim 41 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

46. A method according to claim 45 wherein said cancer is selected from the group consisting of non-small cell lung carcinoma, B-cell chronic lymphocytic leukemia and colon cancer.

47. An antibody that specifically binds to the extracellular domain of ROR1, comprising:
　a) a heavy chain comprising:
　　i) a first vhCDR comprising SEQ ID NO:69;
　　ii) a second vhCDR comprising SEQ ID NO:111;
　　iii) a third vhCDR comprising SEQ ID NO:154; and
　b) a light chain comprising:
　　i) a first vlCDR comprising SEQ ID NO:179;
　　ii) a second vlCDR comprising SEQ ID NO:200;
　　iii) a third vlCDR comprising SEQ ID NO:230.

48. The antibody of claim 47, wherein said antibody is covalently attached to a drug.

49. A nucleic acid composition encoding:
　a) a heavy chain comprising a heavy chain variable region of the antibody of claim 47; and
　b) a light chain comprising a light chain variable region of the antibody of claim 47.

50. A host cell containing the nucleic acid composition of claim 49.

51. A method of making an antibody of claim 47 comprising i) culturing a host cell according to claim 50 under conditions where the antibody is expressed and ii) recovering said antibody.

52. A method of treating cancer comprising administering to a patient in need thereof an antibody according to claim 48 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

53. A method according to claim 52 wherein said cancer is selected from the group consisting of non-small cell lung carcinoma, B-cell chronic lymphocytic leukemia and colon cancer.

54. An antibody that specifically binds to the extracellular domain of ROR1, comprising:
　a) a heavy chain comprising:
　　i) a first vhCDR comprising SEQ ID NO:58;
　　ii) a second vhCDR comprising SEQ ID NO:113;
　　iii) a third vhCDR comprising SEQ ID NO:155; and
　b) a light chain comprising:
　　i) a first vlCDR comprising SEQ ID NO:180;
　　ii) a second vlCDR comprising SEQ ID NO:202;
　　iii) a third vlCDR comprising SEQ ID NO:231.

55. The antibody of claim 54, wherein said antibody is covalently attached to a drug.

56. A nucleic acid composition encoding:
　a) a heavy chain comprising a heavy chain variable region of the antibody of claim 54; and b) a light chain comprising a light chain variable region of the antibody of claim 54.

57. A host cell containing the nucleic acid composition of claim 56.

58. A method of making an antibody of claim 54 comprising i) culturing a host cell according to claim 57 under conditions where the antibody is expressed and ii) recovering said antibody.

59. A method of treating cancer comprising administering to a patient in need thereof an antibody according to claim 55 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

60. A method according to claim 59 wherein said cancer is selected from the group consisting of non-small cell lung carcinoma, B-cell chronic lymphocytic leukemia and colon cancer.

61. An antibody that specifically binds to the extracellular domain of ROR1, comprising:
   a) a heavy chain comprising:
      i) a first vhCDR comprising SEQ ID NO:71;
      ii) a second vhCDR comprising SEQ ID NO:115;
      iii) a third vhCDR comprising SEQ ID NO:156; and
   b) a light chain comprising:
      i) a first vlCDR comprising SEQ ID NO:179;
      ii) a second vlCDR comprising SEQ ID NO:190;
      iii) a third vlCDR comprising SEQ ID NO:229.

62. The antibody of claim 61, wherein said antibody is covalently attached to a drug.

63. A nucleic acid composition encoding:
   a) a heavy chain comprising a heavy chain variable region of the antibody of claim 61; and
   b) a light chain comprising a light chain variable region of the antibody of claim 61.

64. A host cell containing the nucleic acid composition of claim 63.

65. A method of making an antibody of claim 61 comprising i) culturing a host cell according to claim 64 under conditions where the antibody is expressed and ii) recovering said antibody.

66. A method of treating cancer comprising administering to a patient in need thereof an antibody according to claim 62 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

67. A method according to claim 66 wherein said cancer is selected from the group consisting of non-small cell lung carcinoma, B-cell chronic lymphocytic leukemia and colon cancer.

68. An antibody that specifically binds to the extracellular domain of ROR1, comprising:
   a) a heavy chain comprising:
      i) a first vhCDR comprising SEQ ID NO:73;
      ii) a second vhCDR comprising SEQ ID NO:117;
      iii) a third vhCDR comprising SEQ ID NO:157; and
   b) a light chain comprising:
      i) a first vlCDR comprising SEQ ID NO:174;
      ii) a second vlCDR comprising SEQ ID NO:190;
      iii) a third vlCDR comprising SEQ ID NO:229.

69. The antibody of claim 68, wherein said antibody is covalently attached to a drug.

70. A nucleic acid composition encoding:
   a) a heavy chain comprising a heavy chain variable region of the antibody of claim 68; and
   b) a light chain comprising a light chain variable region of the antibody of claim 68.

71. A host cell containing the nucleic acid composition of claim 70.

72. A method of making an antibody of claim 68 comprising i) culturing a host cell according to claim 71 under conditions where the antibody is expressed and ii) recovering said antibody.

73. A method of treating cancer comprising administering to a patient in need thereof an antibody according to claim 69 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

74. A method according to claim 73 wherein said cancer is selected from the group consisting of non-small cell lung carcinoma, B-cell chronic lymphocytic leukemia and colon cancer.

75. An antibody that specifically binds to the extracellular domain of ROR1, comprising:
   a) a heavy chain comprising:
      i) a first vhCDR comprising SEQ ID NO:75;
      ii) a second vhCDR comprising SEQ ID NO:119;
      iii) a third vhCDR comprising SEQ ID NO:155; and
   b) a light chain comprising:
      i) a first vlCDR comprising SEQ ID NO:175;
      ii) a second vlCDR comprising SEQ ID NO:204;
      iii) a third vlCDR comprising SEQ ID NO:232.

76. The antibody of claim 75, wherein said antibody is covalently attached to a drug.

77. A nucleic acid composition encoding:
   a) a heavy chain comprising a heavy chain variable region of the antibody of claim 75; and
   b) a light chain comprising a light chain variable region of the antibody of claim 75.

78. A host cell containing the nucleic acid composition of claim 77.

79. A method of making an antibody of claim 75 comprising i) culturing a host cell according to claim 78 under conditions where the antibody is expressed and recovering said antibody.

80. A method of treating cancer comprising administering to a patient in need thereof an antibody according to claim 76 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

81. A method according to claim 80 wherein said cancer is selected from the group consisting of non-small cell lung carcinoma, B-cell chronic lymphocytic leukemia and colon cancer.

82. An antibody that specifically binds to the extracellular domain of ROR1, comprising:
   a) a heavy chain comprising:
      i) a first vhCDR comprising SEQ ID NO:58;
      ii) a second vhCDR comprising SEQ ID NO:110;
      iii) a third vhCDR comprising SEQ ID NO:158; and
   b) a light chain comprising:
      i) a first vlCDR comprising SEQ ID NO:179;
      ii) a second vlCDR comprising SEQ ID NO:190;
      iii) a third vlCDR comprising SEQ ID NO:229.

83. The antibody of claim 82, wherein said antibody is covalently attached to a drug.

84. A nucleic acid composition encoding:
   a) a heavy chain comprising a heavy chain variable region of the antibody of claim 82; and b) a light chain comprising a light chain variable region of the antibody of claim 82.

85. A host cell containing the nucleic acid composition of claim 84.

86. A method of making an antibody of claim 82 comprising i) culturing a host cell according to claim 85 under conditions where the antibody is expressed and ii) recovering said antibody.

87. A method of treating cancer comprising administering to a patient in need thereof an antibody according to claim 83 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

88. A method according to claim 87 wherein said cancer is selected from the group consisting of non-small cell lung carcinoma, B-cell chronic lymphocytic leukemia and colon cancer.

89. An antibody that specifically binds to the extracellular domain of ROR1, comprising:
a) a heavy chain comprising:
  i) a first vhCDR comprising SEQ ID NO:58;
  ii) a second vhCDR comprising SEQ ID NO:101;
  iii) a third vhCDR comprising SEQ ID NO:159; and
b) a light chain comprising:
  i) a first vlCDR comprising SEQ ID NO:176;
  ii) a second vlCDR comprising SEQ ID NO:190;
  iii) a third vlCDR comprising SEQ ID NO:229.

90. The antibody of claim 89, wherein said antibody is covalently attached to a drug.

91. A nucleic acid composition encoding:
a) a heavy chain comprising a heavy chain variable region of the antibody of claim 89; and
b) a light chain comprising a light chain variable region of the antibody of claim 89.

92. A host cell containing the nucleic acid composition of claim 91.

93. A method of making an antibody of claim 89 comprising i) culturing a host cell according to claim 92 under conditions where the antibody is expressed and ii) recovering said antibody.

94. A method of treating cancer comprising administering to a patient in need thereof an antibody according to claim 90 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

95. A method according to claim 94 wherein said cancer is selected from the group consisting of non-small cell lung carcinoma, B-cell chronic lymphocytic leukemia and colon cancer.

96. An antibody that specifically binds to the extracellular domain of ROR1, comprising:
a) a heavy chain comprising:
  i) a first vhCDR comprising SEQ ID NO:77;
  ii) a second vhCDR comprising SEQ ID NO:122;
  iii) a third vhCDR comprising SEQ ID NO:160; and
b) a light chain comprising:
  i) a first vlCDR comprising SEQ ID NO:177;
  ii) a second vlCDR comprising SEQ ID NO:208;
  iii) a third vlCDR comprising SEQ ID NO:233.

97. The antibody of claim 96, wherein said antibody is covalently attached to a drug.

98. A nucleic acid composition encoding:
a) a heavy chain comprising a heavy chain variable region of the antibody of claim 96; and
b) a light chain comprising a light chain variable region of the antibody of claim 96.

99. A host cell containing the nucleic acid composition of claim 98.

100. A method of making an antibody of claim 96 comprising i) culturing a host cell according to claim 99 under conditions where the antibody is expressed and ii) recovering said antibody.

101. A method of treating cancer comprising administering to a patient in need thereof an antibody according to claim 97 that specifically binds to the extracellular domain of ROR1 (SEQ ID NO:272) and induces antibody-dependent cell-mediated cytotoxicity (ADCC) and/or complement dependent cytotoxicity (CDC) and/or T-cell cytotoxicity.

102. A method according to claim 101 wherein said cancer is selected from the group consisting of non-small cell lung carcinoma, B-cell chronic lymphocytic leukemia and colon cancer.

\* \* \* \* \*